United States Patent
Wang et al.

(10) Patent No.: US 10,246,512 B2
(45) Date of Patent: *Apr. 2, 2019

(54) IL-2R BETA/COMMON GAMMA CHAIN ANTIBODIES

(71) Applicant: AGENCY FOR SCIENCE, TECHNOLOGY AND RESEARCH, Singapore (SG)

(72) Inventors: Cheng-I Wang, Singapore (SG); Peter Brauer, Singapore (SG); Siok Ping Yeo, Singapore (SG); Hwee Ching Tan, Singapore (SG); John Edward Connolly, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,921

(22) Filed: Mar. 16, 2018

(65) Prior Publication Data

US 2018/0208663 A1 Jul. 26, 2018

Related U.S. Application Data

(63) Continuation of application No. 15/750,425, filed as application No. PCT/EP2016/068780 on Aug. 5, 2016.

(30) Foreign Application Priority Data

Aug. 6, 2015 (SG) .......................... 10201506227V

(51) Int. Cl.
| | |
|---|---|
| *A61K 39/395* | (2006.01) |
| *C07K 16/28* | (2006.01) |
| *C07K 16/46* | (2006.01) |
| *A61K 47/68* | (2017.01) |
| *C07K 16/10* | (2006.01) |
| *A61K 39/00* | (2006.01) |
| *A61K 38/17* | (2006.01) |

(52) U.S. Cl.
CPC ...... *C07K 16/2866* (2013.01); *A61K 39/3955* (2013.01); *A61K 47/6849* (2017.08); *C07K 16/1036* (2013.01); *C07K 16/468* (2013.01); *A61K 38/1709* (2013.01); *A61K 2039/505* (2013.01); *A61K 2039/57* (2013.01); *C07K 2317/31* (2013.01); *C07K 2317/33* (2013.01); *C07K 2317/51* (2013.01); *C07K 2317/515* (2013.01); *C07K 2317/524* (2013.01); *C07K 2317/526* (2013.01); *C07K 2317/565* (2013.01); *C07K 2317/60* (2013.01); *C07K 2317/622* (2013.01); *C07K 2317/64* (2013.01); *C07K 2317/75* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

FOREIGN PATENT DOCUMENTS

| | | |
|---|---|---|
| WO | WO 96/21732 | 7/1996 |
| WO | WO 97/43416 | 11/1997 |
| WO | WO 2007/084651 | 7/2007 |
| WO | WO 2008/003473 | 1/2008 |
| WO | WO 2011/127324 | 10/2011 |

OTHER PUBLICATIONS

Arruvito et al. (2014) J Immunol 193:4469-4476 "Identification and Clinical Relevance of Naturally Occurring Human CD8 + HLA-DR+ Regulatory T Cells".
Chaput et al. (2009) Gut 58(4):520-529 "Identification of CD8+CD25+Foxp3+ suppressive T cells in colorectal cancer tissue".
Dai et al. (2010) J Immunol 185:803-807 "Cutting Edge: Programmed Death-1 Defines CD8 +CD122+ T Cells as Regulatory versus Memory T Cells".
Dutcher et al. (2014) Journal for ImmunoTherapy of Cancer 2:26 "High dose interleukin-2 (Aldesleukin)—expert consensus on best management practices—2014".
Ellery et al. (2000) Cellular Signalling 12:367-373 "Activation of the interleukin 2 receptor: a possible role for tyrosine phosphatases".
Hechinger et al. (2015) Blood 125(3):570-580 "Therapeutic activity of multiple common γ-chain cytokine inhibition in acute and chronic GVHD".
International Search Report and Written Opinion for PCT/EP2016/068780, dated Jan. 18, 2017, 21 pages.
Kiniwa et al. (2007) Clin Cancer Res 13:23:6947-6958 "CD8+ Foxp3+ Regulatory T Cells Mediate Immunosuppression in Prostate Cancer".
Letourneau et al. (2010) PNAS, 107(5):2171-2176, IL-2/anti-IL-2 antibody complexes show strong biological activity by avoiding interaction with IL-2 receptor α subunit CD25.
Nakamura et al. (1994) Nature 369:330-333 "Heterodimerization of the IL-2 receptor β- and γ-chain cytoplasmic domains is required for signaling".
Nelson et al. (1994) Nature 369:333-336 "Cytoplasmic domains of the interleukin-2 receptor β and γ chains mediate the signal for T-cell proliferation".
Rosenberg (2014) J Immunol 192:5451-5458 "IL-2: The First Effective Immunotherapy for Human Cancer".
Rudikoff et al. (1982) Proc. Natl. Acad. Sci. USA 79:1979-1983 "Single amino acid substitution altering antigen-binding specificity".
Skrombolas et al. (2014) Expert Rev Clin Immunol 10(2):207-217 "Challenges and developing solutions for increasing the benefits of IL-2 treatment in tumor therapy".
Spiess et al. (2015) Molecular Immunology 67:95-106 "Alternative molecular formats and therapeutic applications for bispecific antibodies".

(Continued)

*Primary Examiner* — Dong Jiang
(74) *Attorney, Agent, or Firm* — Adsero IP

(57) ABSTRACT

Anti-CD122 and/or γc antibodies and fragments thereof are disclosed. Also disclosed are compositions comprising such antibodies and fragments, and uses and methods using the same.

6 Claims, 67 Drawing Sheets

Specification includes a Sequence Listing.

(56) References Cited

OTHER PUBLICATIONS

Wang (2015) Cambridge Healthtech Institute's 2nd Annual PEGS Korea, Next-Generation Antibody Therapeutics, Seoul, Korea, Cancer Immunotherapies, "IL-2 Receptor (IL-2R) Agonist Antibody by Engineering".
Zhang et al. (2015) Cellular & Molecular Immunology 12:580-591 "Analysis of CD8+ Treg cells in patients with ovarian cancer: a possible mechanism for immune impairment".
Chang et al. (2009) Transplantation Proceedings 41(9):3913-3915 "Anti-γ Chain and Anti-IL-2Rβ mAbs in Combination With Donor Splenocyte Transfusion Induce H-Y Skin Graft Acceptance in Murine Model".
Meghnem et al. (2017) J Immunol 198(12):4563-4568 Cutting Edge: Differential Fine-Tuning of IL-2-- and IL-15-Dependent Functions by Targeting Their Common IL-2/15R β/γc Receptor.

P2C4, P2C4_A9

QSALTQPASVSGSPGQSIAISC<u>TGTSSDIGHYDFVS</u>WYQQHPGTAPKLIIY<u>DINNRPS</u>GISNR
FSGSKSDNMASLTISGLQPEDEADYYC<u>SAYTSSDTLV</u>FGGGTKLT (SEQ ID NO:1)

LC-CDR1:    TGTSSDIGHYDFVS  (SEQ ID NO:2)
    LC-CDR2:    DINNRPS  (SEQ ID NO:3)
    LC-CDR3:    SAYTSSDTLV  (SEQ ID NO:4)

P2H7

DIQMTQSPSTLSASVGDRVTLSC<u>RAGQAISSWLA</u>WYQQKPGKAPKLLIY<u>KASNLES</u>GVPSR
FSGGGSGAEFTLTISSLQPDDFATYYC<u>QQYQSYPYT</u>FGQGTKLEIR (SEQ ID NO:5)

LC-CDR1:    RAGQAISSWLA  (SEQ ID NO:6)
    LC-CDR2:    KASNLES  (SEQ ID NO:7)
    LC-CDR3:    QQYQSYPYT  (SEQ ID NO:8)

P2D12

DIQLTQSPSSLSASVGDRVTITC<u>QASQDIGNYLN</u>WYQLKPGKAPKLLIY<u>DASNLET</u>GVPSRF
SGSGSGTDFTFTISSLQPEDIATYYC<u>LQLYDYPLT</u>FGGGTKVEIK (SEQ ID NO:9)

LC-CDR1:    QASQDIGNYLN  (SEQ ID NO:10)
    LC-CDR2:    DASNLET  (SEQ ID NO:11)
    LC-CDR3:    LQLYDYPLT  (SEQ ID NO:12)

P1G11

NFMLTQPHSVSESPGKTVTISC<u>TRSSGSIASNYVQ</u>WYQQRPGSSPTTVIF<u>DDNQRPT</u>GVPD
RFSAAIDTSSSSASLTISGLTAEDEADYYC<u>QSSHSTAVV</u>FGGGTKLTVL (SEQ ID NO:13)

LC-CDR1:    TRSSGSIASNYVQ  (SEQ ID NO:14)
    LC-CDR2:    DDNQRPT  (SEQ ID NO:15)
    LC-CDR3:    QSSHSTAVV  (SEQ ID NO:16)

QSALTQPASVSGSPGQSIAISC<u>TGTSSDIGDYDFVS</u>WYQQHPGTAPKLIIY<u>DINNRPS</u>GISNR
FSGSKSDNMASLTISGLQPEDEADYYC<u>SAYTSSDTLV</u>FGGGTKLT (SEQ ID NO:17)

LC-CDR1:    TGTSSDIGDYDFVS  (SEQ ID NO:18)
       LC-CDR2:    DINNRPS  (SEQ ID NO:3)
       LC-CDR3:    SAYTSSDTLV  (SEQ ID NO:4)

P2C4 B1

QSALTQPASVSGSPGQSIAISC<u>TGTSSDIGHYDFVS</u>WYQQHPGTAPKLIIY<u>DNNNRPS</u>GISN
RFSGSKSDNMASLTISGLQPEDEADYYC<u>SAYTSSDTLV</u>FGGGTKLT (SEQ ID NO:19)

LC-CDR1:    TGTSSDIGHYDFVS  (SEQ ID NO:2)
       LC-CDR2:    DNNNRPS  (SEQ ID NO:20)
       LC-CDR3:    SAYTSSDTLV  (SEQ ID NO:4)

P2C4 B5

QSALTQPASVSGSPGQSITISC<u>TGTSSDIGHYDFVS</u>WYQQHPGTAPKLIIY<u>DINNRPS</u>GISNR
FSGSKSDNMASLTISGLQPEDEADYYC<u>SAYTSSDTVV</u>FGGGTKLT (SEQ ID NO:21)

LC-CDR1:    TGTSSDIGHYDFVS  (SEQ ID NO:2)
       LC-CDR2:    DINNRPS  (SEQ ID NO:3)
       LC-CDR3:    SAYTSSDTVV  (SEQ ID NO:22)

P2C4 B6, P2C4 B8, P2C4 C12, P2C4 D10, P2C4 E2, P2C4 E3, P2C4 E8, P2C4 G2, P2C4 G11, P2C4 H1, P2C4 H2, P2C4 H3

QSALTQPASVSGSPGQSIAISC<u>TGTSSDIGHYDFVS</u>WYQQHPGTAPKLIIY<u>DINNRPS</u>GISNR
FSGSKSDNMASLTISGLQPEDEADYYC<u>SAYTSSDTVV</u>FGGGTKLT (SEQ ID NO:23)

LC-CDR1:    TGTSSDIGHYDFVS  (SEQ ID NO:2)
       LC-CDR2:    DINNRPS  (SEQ ID NO:3)
       LC-CDR3:    SAYTSSDTVV  (SEQ ID NO:22)

QSALTQPASVSGSPGQSIAISC<u>TGTSSDIGHYDFIS</u>WYQQHPGTAPKLIIY<u>DFNNRPS</u>GISNRFSGSKSDNMASLTISGLQPEDEADYYC<u>SAYTSSDTLV</u>FGGGTKLT (SEQ ID NO:24)

| | | |
|---|---|---|
| LC-CDR1: | TGTSSDIGHYDFIS | (SEQ ID NO:25) |
| LC-CDR2: | DFNNRPS | (SEQ ID NO:26) |
| LC-CDR3: | SAYTSSDTLV | (SEQ ID NO:4) |

P2C4_C4

QSALTQPASVSGSPGQSIAISC<u>TGTSSDIGHYDFVS</u>WYQQHPGTAPKLIIY<u>DNNRPS</u>GISNRFSGSKSDNMASLTISGLQPEDEADYYC<u>SAYTSSDTVV</u>FGGGTKLT (SEQ ID NO:27)

| | | |
|---|---|---|
| LC-CDR1: | TGTSSDIGHYDFVS | (SEQ ID NO:2) |
| LC-CDR2: | DNNNRPS | (SEQ ID NO:20) |
| LC-CDR3: | SAYTSSDTVV | (SEQ ID NO:22) |

P2C4_C7

QSALTQPASVSGSPGQSIVISC<u>TGTSSDIGHYDFVS</u>WYQQHPGTAPKLIIY<u>DINNRPS</u>GISNRFSGSKSDNMASLTISGLQPEDEADYYC<u>SAYTSSDTVV</u>FGGGTKLT (SEQ ID NO:28)

| | | |
|---|---|---|
| LC-CDR1: | TGTSSDIGHYDFVS | (SEQ ID NO:2) |
| LC-CDR2: | DINNRPS | (SEQ ID NO:3) |
| LC-CDR3: | SAYTSSDTVV | (SEQ ID NO:22) |

P2C4_E6

QSALTQPASVSGSPGQSIAISC<u>TGTSSDIGDYDFVS</u>WYQQHPGTAPKLIIY<u>DINNRPS</u>GISNRFSGSKSDNMASLIISGLQPEDEADYYC<u>SAYTSSDTLV</u>FGGGTKLT (SEQ ID NO:29)

| | | |
|---|---|---|
| LC-CDR1: | TGTSSDIGDYDFVS | (SEQ ID NO:18) |
| LC-CDR2: | DINNRPS | (SEQ ID NO:3) |
| LC-CDR3: | SAYTSSDTLV | (SEQ ID NO:4) |

QSALTQPASVSGSPGQSIAISC<u>TGTSSDIGHYDFVS</u>WYQQHPGTAPKLIIY<u>DINNRPS</u>GISNR
FSGSKSDDMASLTISGLQPEDEADYYC<u>SAYTSSDTVV</u>FGGGTKLT (SEQ ID NO:30)

LC-CDR1:    TGTSSDIGHYDFVS  (SEQ ID NO:2)
    LC-CDR2:    DINNRPS  (SEQ ID NO:3)
    LC-CDR3:    SAYTSSDTVV  (SEQ ID NO:22)

P2C4_E9

QSALTQPASVSGSPGQSIAISC<u>TGTSSDIGHYDFVS</u>WYQQHPGTAPKLIIY<u>DINNRAS</u>GISNR
FSGSKSDNMASLTISGLQPEDEADYYC<u>SAYTSSDTVV</u>FGGGTKLT (SEQ ID NO:31)

LC-CDR1:    TGTSSDIGHYDFVS  (SEQ ID NO:2)
    LC-CDR2:    DINNRAS  (SEQ ID NO:32)
    LC-CDR3:    SAYTSSDTVV  (SEQ ID NO:22)

P2C4_F8

QSALTQPASVSGNPGQSIAISC<u>TGTSSDIGHYDFVS</u>WYQQHPGTAPKLIIY<u>DINNRPS</u>GISNR
FSGSKSDNMASLTISGLQPEDEADYYC<u>SAYTSSDTVV</u>FGGGTKLT (SEQ ID NO:33)

LC-CDR1:    TGTSSDIGHYDFVS  (SEQ ID NO:2)
    LC-CDR2:    DINNRPS  (SEQ ID NO:3)
    LC-CDR3:    SAYTSSDTVV  (SEQ ID NO:22)

P2C4_F11

QSTLTQPASVSGSPGQSITISC<u>TGTSSDIGHYDFVS</u>WYQQHPGTAPKLIIY<u>DINNRPS</u>GISNR
FSGSKSDNMASLTISGLQPEDEADYYC<u>SAYTSSDTVV</u>FGGGTKLT (SEQ ID NO:34)

LC-CDR1:    TGTSSDIGHYDFVS  (SEQ ID NO:2)
    LC-CDR2:    DINNRPS  (SEQ ID NO:3)
    LC-CDR3:    SAYTSSDTVV  (SEQ ID NO:22)

QSALTQPASVSGSPGQSIAISC<u>TGTSSDIGDYDFVS</u>WYQQHPGTAPKLIIY<u>DINNRPS</u>GISNR
FSGSKSDNMASLTISGLQPEDEADYYC<u>SAYTSSDTVV</u>FGGGTKLT (SEQ ID NO:148)

LC-CDR1:    TGTSSDIGDYDFVS  (SEQ ID NO:18)
    LC-CDR2:    DINNRPS  (SEQ ID NO:3)
    LC-CDR3:    SAYTSSDTVV  (SEQ ID NO:22)

P2C4_FW2

QSVLTQPPSVSGAPGQRVTISC<u>TGTSSDIGHYDFVS</u>WYQQLPGTAPKLLIY<u>DINNRPS</u>GVP
DRFSGSKSGTSASLAITGLQAEDEADYYC<u>SAYTSSDTLV</u>FGGGTKLT (SEQ ID NO:149)

LC-CDR1:    TGTSSDIGHYDFVS  (SEQ ID NO:2)
    LC-CDR2:    DINNRPS  (SEQ ID NO:3)
    LC-CDR3:    SAYTSSDTLV  (SEQ ID NO:4)

EVQLVQSGAEVKKPGSSVKVSCKASGYTFT<u>NYYMH</u>WVRQAPGQGLEWMG<u>AIMPSRGGT SYPQKFQG</u>RVTMTGDTSTSTVYMELSSLRSEDTAVYYCAR<u>GEYYYDSSGYYY</u>WGQGTLV TVSS (SEQ ID NO:35)

|  |  |  |
|---|---|---|
| HC-CDR1: | NYYMH | (SEQ ID NO:36) |
| HC-CDR2: | AIMPSRGGTSYPQKFQG | (SEQ ID NO:37) |
| HC-CDR3: | GEYYYDSSGYYY | (SEQ ID NO:38) |

P2H7

EVQLVQSGTEVKKPGASVKVSCKASGYTFT<u>TYAMH</u>WVRQAPGQSLEWMG<u>WINTGNGNT KYSQNFQG</u>RVTMTRDTSISTAYMELSRLRSDDTAVYYCAR<u>DLGQLERLYFW</u>GQGTLVTVS S (SEQ ID NO:39)

|  |  |  |
|---|---|---|
| HC-CDR1: | TYAMH | (SEQ ID NO:40) |
| HC-CDR2: | WINTGNGNTKYSQNFQG | (SEQ ID NO:41) |
| HC-CDR3: | DLGQLERLYFW | (SEQ ID NO:42) |

P2D12

HVQLVETGGGLVQPGGSLRLSCAASGFTFS<u>SYAMS</u>WVRQAPGKGLEWVS<u>AISGSGGSTY YADSVKG</u>RFTISRDNSKNTLYLQMNSLRAEDTAVYYCAR<u>DLGD</u>YWGQGTLVTVSS (SEQ ID NO:43)

|  |  |  |
|---|---|---|
| HC-CDR1: | SYAMS | (SEQ ID NO:44) |
| HC-CDR2: | AISGSGGSTYYADSVKG | (SEQ ID NO:45) |
| HC-CDR3: | DLGDY | (SEQ ID NO:46) |

P1G11

QVQLQQWGAGLLKPSETLSLTCAVYGGSFS<u>GYYWS</u>WIRQPPGKGLEWIG<u>EINHSGSTNYN PSLKS</u>RVTISVDTSKNQFSLKLSSVTAADTAVYYCAR<u>SSSGDAFD</u>IWGQGTMVTVSS (SEQ ID NO:47)

|  |  |  |
|---|---|---|
| HC-CDR1: | GYYWS | (SEQ ID NO:48) |
| HC-CDR2: | EINHSGSTNYNPSLKS | (SEQ ID NO:49) |
| HC-CDR3: | SSSGDAFD | (SEQ ID NO:50) |

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYN</u>WGQGTLV
TVSS (SEQ ID NO:51)

HC-CDR1:   NYYMH                 (SEQ ID NO:36)
    HC-CDR2:   AIMPSRGGTSYPQKFQG   (SEQ ID NO:37)
    HC-CDR3:   GEYYYDSSGYYN        (SEQ ID NO:52)

P2C4_B6, P2C4_E9

EVQLVQSGAEVKKPGSSVKVSCKASGYTFT<u>NYYIH</u>WVRQAPGQGLEWMG<u>AIMPSRGGTS
YPQKFQG</u>RVTMTGDTSTSTVYMELSSLRSEDTAVYYCAR<u>GEYYYDSSGYYY</u>WGQGTLVT
VSS (SEQ ID NO:53)

HC-CDR1:   NYYIH                 (SEQ ID NO:54)
    HC-CDR2:   AIMPSRGGTSYPQKFQG   (SEQ ID NO:37)
    HC-CDR3:   GEYYYDSSGYYY        (SEQ ID NO:38)

P2C4_B8

EVQLVQSGAEVKKPGSSVKVSCKASGYTFT<u>NYYMH</u>WVRQPPGQGLEWMG<u>AIMPSRGGT
SYPQKFQG</u>RVTMTGDTSTSTVYMELSSLRSEDTAVYYCAR<u>GEYYYDSSGYYY</u>WGQGTLV
TVSS (SEQ ID NO:55)

HC-CDR1:   NYYMH                 (SEQ ID NO:36)
    HC-CDR2:   AIMPSRGGTSYPQKFQG   (SEQ ID NO:37)
    HC-CDR3:   GEYYYDSSGYYY        (SEQ ID NO:38)

P2C4_B12

EVQLVQSGAEVKKPGSTVKVSCKASGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYY</u>WGQGTLV
TVSS (SEQ ID NO:56)

HC-CDR1:   NYYMH                 (SEQ ID NO:36)
    HC-CDR2:   AIMPSRGGTSYPQKFQG   (SEQ ID NO:37)
    HC-CDR3:   GEYYYDSSGYYY        (SEQ ID NO:38)

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSNLRSEDTAVYYCAR<u>GEYYYDSSGYYY</u>WGQGTLV
TVSN (SEQ ID NO:57)

HC-CDR1:    NYYMH    (SEQ ID NO:36)
    HC-CDR2:    AIMPSRGGTSYPQKFQG    (SEQ ID NO:37)
    HC-CDR3:    GEYYYDSSGYYY    (SEQ ID NO:38)

P2C4_E2

EVQLVQSGAEVKEPGSSVKVSCKASGYTFT<u>NYYMH</u>WVRQAPGQGLEWMG<u>AIMPSRGGT
SYPQKFQG</u>RVTMTGDISTSTVYMELSSLRSEDTAVYYCAR<u>GEYYYDSSGYYY</u>WGQGTLVT
VSS (SEQ ID NO:58)

HC-CDR1:    NYYMH    (SEQ ID NO:36)
    HC-CDR2:    AIMPSRGGTSYPQKFQG    (SEQ ID NO:37)
    HC-CDR3:    GEYYYDSSGYYY    (SEQ ID NO:38)

P2C4_E3

EVQLVQSGAEVKKPGSSVKVSCKASGYTFT<u>NYYIH</u>WVRQAPGQGLEWMG<u>AIMPSRGGTS
YPQKFQG</u>RVTMTGDTSTSTVYMELNSLRSEDTAVYYCAR<u>GEYYYDSSGYYY</u>WGQGTLVT
VSS (SEQ ID NO:59)

HC-CDR1:    NYYIH    (SEQ ID NO:54)
    HC-CDR2:    AIMPSRGGTSYPQKFQG    (SEQ ID NO:37)
    HC-CDR3:    GEYYYDSSGYYY    (SEQ ID NO:38)

P2C4_E8

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYY</u>WGPGTLV
TVSS (SEQ ID NO:60)

HC-CDR1:    NYYMH    (SEQ ID NO:36)
    HC-CDR2:    AIMPSRGGTSYPQKFQG    (SEQ ID NO:37)
    HC-CDR3:    GEYYYDSSGYYY    (SEQ ID NO:38)

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRSEDTAMYYCAR<u>GEYYYDSSGYYY</u>WGQGTLV
TVSS (SEQ ID NO:61)

HC-CDR1:   NYYMH                    (SEQ ID NO:36)
    HC-CDR2:   AIMPSRGGTSYPQKFQG   (SEQ ID NO:37)
    HC-CDR3:   GEYYYDSSGYYY       (SEQ ID NO:38)

P2C4_G2

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRTEDTAVYYCAR<u>GEYYYDSSGYYY</u>WGQGTLV
TVSS (SEQ ID NO:62)

HC-CDR1:   NYYMH                    (SEQ ID NO:36)
    HC-CDR2:   AIMPSRGGTSYPQKFQG   (SEQ ID NO:37)
    HC-CDR3:   GEYYYDSSGYYY       (SEQ ID NO:38)

P2C4_G11

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSNLRSEDTAVYYCAR<u>GEYYYDSSGYYY</u>WGQGTLV
TVSS (SEQ ID NO:63)

HC-CDR1:   NYYMH                    (SEQ ID NO:36)
    HC-CDR2:   AIMPSRGGTSYPQKFQG   (SEQ ID NO:37)
    HC-CDR3:   GEYYYDSSGYYY       (SEQ ID NO:38)

P2C4_H1

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYY</u>WGQGTLV
NVSS (SEQ ID NO:64)

HC-CDR1:   NYYMH                    (SEQ ID NO:36)
    HC-CDR2:   AIMPSRGGTSYPQKFQG   (SEQ ID NO:37)
    HC-CDR3:   GEYYYDSSGYYY       (SEQ ID NO:38)

EVQLVQSGAEVKKPGSSVKVSCKASGYTFS<u>NYYMH</u>WVRQAPGQGLEWIG<u>AIMPSRGGTS
YPQKFQG</u>RVTMTGDTSTSTVYMELSSLRSEDTAVYYCAR<u>GEYYYDSSGYYY</u>WGQGTLVT
VSS (SEQ ID NO:65)

HC-CDR1:  NYYMH      (SEQ ID NO:36)
   HC-CDR2:  AIMPSRGGTSYPQKFQG (SEQ ID NO:37)
   HC-CDR3:  GEYYYDSSGYYY   (SEQ ID NO:38)

P2C4 H3

EVQLVQSGAEVKKPGSSVKVSCKATGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYY</u>WGQGTLV
TVSS (SEQ ID NO:66)

HC-CDR1:  NYYMH      (SEQ ID NO:36)
   HC-CDR2:  AIMPSRGGTSYPQKFQG (SEQ ID NO:37)
   HC-CDR3:  GEYYYDSSGYYY   (SEQ ID NO:38)

P2C4 C1D10

EVQLVQSGAEVKKPGSSVKVSCKASGYTFT<u>NYYMH</u>WVRQAPGQGLEWMG<u>AIMPSRGGT
SYPQKFQG</u>RVTMTGDTSTSTVYMELSSLRSEDTAVYYCAR<u>GEYYYDSSGYYY</u>WGQGTPV
TVSS (SEQ ID NO:150)

HC-CDR1:  NYYMH      (SEQ ID NO:36)
   HC-CDR2:  AIMPSRGGTSYPQKFQG (SEQ ID NO:37)
   HC-CDR3:  GEYYYDSSGYYY   (SEQ ID NO:38)

P2C4 FW2

EVQLVQSGAEVKKPGASVKVSCKASGYTFT<u>NYYMH</u>WVRQAPGQGLEWMG<u>AIMPSRGGT
SYPQKFQG</u>RVTITADKSTSTAYMELSSLRSEDTAVYYCAR<u>GEYYYDSSGYYY</u>WGQGTLVT
VSS (SEQ ID NO:151)

HC-CDR1:  NYYMH      (SEQ ID NO:36)
   HC-CDR2:  AIMPSRGGTSYPQKFQG (SEQ ID NO:37)
   HC-CDR3:  GEYYYDSSGYYY   (SEQ ID NO:38)

DVVMTQSPLSLPVTPGEPASISC<u>RSSQSLLHSNGYNYLD</u>WYLQKPGQSPQLLIY<u>LGSNRDS</u>
GVPDRFSGSGSGTDFTLKISRVEAEDVGVYYC<u>MQGTHWPWT</u>FGQGTKVEIK (SEQ ID
NO:67)

LC-CDR1:    RSSQSLLHSNGYNYLD    (SEQ ID NO:68)
    LC-CDR2:    LGSNRDS    (SEQ ID NO:69)
    LC-CDR3:    MQGTHWPWT    (SEQ ID NO:70)

P2B9

SYELTQPPSMSVSPGQTARITC<u>SGDALPKQFAF</u>WYQQKPGQAPVLVIY<u>KDTERPS</u>GIPERF
SGSSSGTTVTLTITGVQAEDEADYYC<u>QSPDSSGTVEV</u>FGGGTKLTVL (SEQ ID NO:71)

LC-CDR1:    SGDALPKQFAF    (SEQ ID NO:72)
    LC-CDR2:    KDTERPS    (SEQ ID NO:73)
    LC-CDR3:    QSPDSSGTVEV    (SEQ ID NO:74)

P1A3_B4

DVVMTQSPLSLPVTPGESVSISC<u>RSSQSLLHSNGYNYLD</u>WYLQKPGQSPQLLIY<u>LGSNRDS</u>
GVPDRFSGSGSGTDFTLKISRVEAEDVGVYYC<u>MQGTHWPWT</u>FGQGTKVEIK (SEQ ID
NO:75)

LC-CDR1:    RSSQSLLHSNGYNYLD    (SEQ ID NO:68)
    LC-CDR2:    LGSNRDS    (SEQ ID NO:69)
    LC-CDR3:    MQGTHWPWT    (SEQ ID NO:70)

P1A3_FW2

DIQMTQSPSSLSASVGDRVTITC<u>RSSQSLLHSNGYNYLD</u>WYQQKPGKAPKLLIY<u>LGSNRDS</u>
GVPSRFSGSGSGTDFTLTISSLQPEDFATYYC<u>MQGTHWPWT</u>FGQGTKVEIK (SEQ ID NO:
152)

LC-CDR1:    RSSQSLLHSNGYNYLD    (SEQ ID NO:68)
    LC-CDR2:    LGSNRDS    (SEQ ID NO:69)
    LC-CDR3:    MQGTHWPWT    (SEQ ID NO:70)

QVQLQQWGAGLLKPSETLSLTCAVYGGSFS<u>GYYWS</u>WIRQPPGKGLEWIG<u>EINHSGSTNYN
PSLKS</u>RATISVDTSKNQFSLKLSSVTAADTAVYYCAT<u>SPGGYSGGYFQH</u>WGQGTLVTVSS
(SEQ ID NO:76)

HC-CDR1:    GYYWS    (SEQ ID NO:48)
    HC-CDR2:    EINHSGSTNYNPSLKS    (SEQ ID NO:49)
    HC-CDR3:    SPGGYSGGYFQH    (SEQ ID NO:77)

P2B9

QVQLQESGPGLVKPSETLSLTCTVSGGSIS<u>SSSYYWG</u>WIRQPPGKGLEWIG<u>SIYYSGSTYY
NPSLKS</u>RVTISVDTSKNQFSLKLSSVTAADTAVYYCAG<u>DILTGYALDY</u>WGQGTLVTVSS
(SEQ ID NO:78)

HC-CDR1:    SSSYYWG    (SEQ ID NO:79)
    HC-CDR2:    SIYYSGSTYYNPSLK    (SEQ ID NO:80)
    HC-CDR3:    DILTGYALDY    (SEQ ID NO:81)

P1A3_B3, P1A3_B4, P1A3_E9

QVQLQQWGAGLLKPSETLSLTCAVYGGSFS<u>GYYWS</u>WIRQPPGKGLEWIG<u>EINHFGSTNYN
PSLKS</u>RATISVDTSKNQFSLKLSSVTAADTAVYYCAT<u>SPGGYSGGYFQH</u>WGQGTLVTVSS
(SEQ ID NO:82)

HC-CDR1:    GYYWS    (SEQ ID NO:48)
    HC-CDR2:    EINHFGSTNYNPSLKS    (SEQ ID NO:83)
    HC-CDR3:    SPGGYSGGYFQH    (SEQ ID NO:77)

P1A3_E8

QVQLQQWGAGMLKPSETLSLTCAVYGGSFS<u>GYYWS</u>WIRQPPGKGLEWIG<u>EINHFGSTNY
NPSLKS</u>RATISVDTSKNQFSLKLSSVTAADTAVYYCAT<u>SPGGYSGGYFQH</u>WGQGTLVTVSS
(SEQ ID NO:84)

HC-CDR1:    GYYWS    (SEQ ID NO:48)
    HC-CDR2:    EINHFGSTNYNPSLKS    (SEQ ID NO:83)
    HC-CDR3:    SPGGYSGGYFQH    (SEQ ID NO:77)

EVQLVESGGGLVQPGGSLRLSCAASGGSFS<u>GYYWS</u>WVRQAPGKGLEWVS<u>EINHSGSTNY
NPSLKS</u>RFTISRDNSKNTLYLQMNSLRAEDTAVYYCAR<u>SPGGYSGGYFQH</u>WGQGTLVTVS
S (SEQ ID NO: 153)

HC-CDR1:   GYYWS              (SEQ ID NO:48)
    HC-CDR2:   EINHSGSTNYNPSLKS  (SEQ ID NO:49)
    HC-CDR3:   SPGGYSGGYFQH     (SEQ ID NO:77)

Figure 4 (cont.)

| Clone | CDR 1 | CDR 2 | CDR 3 |
|---|---|---|---|
| Light Chain | | | |
| P2C4<br>P2C4_A9<br>P2C4_FW2 | TGTSSDIGHYDFVS<br>(SEQ ID NO:2) | DINNRPS<br>(SEQ ID NO:3) | SAYTSSDTLV<br>(SEQ ID NO:4) |
| P2H7 | RAGQAISSWLA<br>(SEQ ID NO:6) | KASNLES<br>(SEQ ID NO:7) | QQYQSYPYT<br>(SEQ ID NO:8) |
| P2D12 | QASQDIGNYLN<br>(SEQ ID NO:10) | DASNLET<br>(SEQ ID NO:11) | LQLYDYPLT<br>(SEQ ID NO:12) |
| P1G11 | TRSSGSIASNYVQ<br>(SEQ ID NO:14) | DDNQRPT<br>(SEQ ID NO:15) | QSSHSTAVV<br>(SEQ ID NO:16) |
| P2C4_A4<br>P2C4_C1<br>P2C4_E6 | TGTSSDIGDYDFVS<br>(SEQ ID NO:18) | DINNRPS<br>(SEQ ID NO:3) | SAYTSSDTLV<br>(SEQ ID NO:4) |
| P2C4_B1 | TGTSSDIGHYDFVS<br>(SEQ ID NO:2) | DNNNRPS<br>(SEQ ID NO:20) | SAYTSSDTLV<br>(SEQ ID NO:4) |
| P2C4_B5<br>P2C4_B6<br>P2C4_B8<br>P2C4_C7<br>P2C4_C12<br>P2C4_D10<br>P2C4_E2<br>P2C4_E3<br>P2C4_E7<br>P2C4_E8<br>P2C4_F8<br>P2C4_F11<br>P2C4_G2<br>P2C4_G11<br>P2C4_H1<br>P2C4_H2<br>P2C4_H3 | TGTSSDIGHYDFVS<br>(SEQ ID NO:2) | DINNRPS<br>(SEQ ID NO:3) | SAYTSSDTVV<br>(SEQ ID NO:22) |
| P2C4_B12 | TGTSSDIGHYDFIS<br>(SEQ ID NO:25) | DFNNRPS<br>(SEQ ID NO:26) | SAYTSSDTLV<br>(SEQ ID NO:4) |
| P2C4_C4 | TGTSSDIGHYDFVS<br>(SEQ ID NO:2) | DNNNRPS<br>(SEQ ID NO:20) | SAYTSSDTVV<br>(SEQ ID NO:22) |
| P2C4_E9 | TGTSSDIGHYDFVS<br>(SEQ ID NO:2) | DINNRAS<br>(SEQ ID NO:32) | SAYTSSDTVV<br>(SEQ ID NO:22) |
| P2C4_C1D10 | TGTSSDIGDYDFVS<br>(SEQ ID NO:18) | DINNRPS<br>(SEQ ID NO:3) | SAYTSSDTVV<br>(SEQ ID NO:22) |

Figure 5

| Clone | CDR 1 | CDR 2 | CDR 3 |
|---|---|---|---|
| Heavy Chain | | | |
| P2C4<br>P2C4_A4<br>P2C4_B1<br>P2C4_B5<br>P2C4_B8<br>P2C4_B12<br>P2C4_C1<br>P2C4_C4<br>P2C4_C7<br>P2C4_C12<br>P2C4_D10<br>P2C4_E2<br>P2C4_E6<br>P2C4_E7<br>P2C4_E8<br>P2C4_F8<br>P2C4_F11<br>P2C4_G2<br>P2C4_G11<br>P2C4_H1<br>P2C4_H2<br>P2C4_H3<br>P2C4_C1D10<br>P2C4_FW2 | NYYMH<br>(SEQ ID NO:36) | AIMPSRGGTSYPQKFQG<br>(SEQ ID NO:37) | GEYYYDSSGYYY<br>(SEQ ID NO:38) |
| P2H7 | TYAMH<br>(SEQ ID NO:40) | WINTGNGNTKYSQNFQG<br>(SEQ ID NO:41) | DLGQLERLYFW<br>(SEQ ID NO:42) |
| P2D12 | SYAMS<br>(SEQ ID NO:44) | AISGSGGSTYYADSVKG<br>(SEQ ID NO:45) | DLGDY<br>(SEQ ID NO:46) |
| P1G11 | GYYWS<br>(SEQ ID NO:48) | EINHSGSTNYNPSLKS<br>(SEQ ID NO:49) | SSSGDAFD<br>(SEQ ID NO:50) |
| P2C4_A9 | NYYMH<br>(SEQ ID NO:36) | AIMPSRGGTSYPQKFQG<br>(SEQ ID NO:37) | GEYYYDSSGYYN<br>(SEQ ID NO:52) |
| P2C4_B6<br>P2C4_E3<br>P2C4_E9 | NYYIH<br>(SEQ ID NO:54) | AIMPSRGGTSYPQKFQG<br>(SEQ ID NO:37) | GEYYYDSSGYYY<br>(SEQ ID NO:38) |

Figure 6

| Clone | CDR 1 | CDR 2 | CDR 3 |
|---|---|---|---|
| Light Chain | | | |
| P1A3<br>P1A3_B3<br>P1A3_E8<br>P1A3_E9<br>P1A3_B4<br>P1A3_FW2 | RSSQSLLHSNGYNYLD<br>(SEQ ID NO:68) | LGSNRDS<br>(SEQ ID NO:69) | MQGTHWPWT<br>(SEQ ID NO:70) |
| P2B9 | SGDALPKQFAF<br>(SEQ ID NO:72) | KDTERPS<br>(SEQ ID NO:73) | QSPDSSGTVEV<br>(SEQ ID NO:74) |

Figure 7

| Clone | CDR 1 | CDR 2 | CDR 3 |
|---|---|---|---|
| Heavy Chain | | | |
| P1A3<br>P1A3_FW2 | GYYWS<br>(SEQ ID NO:48) | EINHSGSTNYNPSLKS<br>(SEQ ID NO:49) | SPGGYSGGYFQH<br>(SEQ ID NO:77) |
| P2B9 | SSSYYWG<br>(SEQ ID NO:79) | SIYYSGSTYYNPSLK<br>(SEQ ID NO:80) | DILTGYALDY<br>(SEQ ID NO:81) |
| P1A3_B3<br>P1A3_B4<br>P1A3_E8<br>P1A3_E9 | GYYWS<br>(SEQ ID NO:48) | EINHFGSTNYNPSLKS<br>(SEQ ID NO:83) | SPGGYSGGYFQH<br>(SEQ ID NO:77) |

Figure 8

| Clone | CDR 1 | CDR 2 | CDR 3 |
|---|---|---|---|
| Light Chain | | | |
| P2C4<br>P2C4_A9<br>P2C4_FW2 | TGTSSDIGHYDFVS<br>(SEQ ID NO:2) | DINNRPS<br>(SEQ ID NO:3) | SAYTSSDTLV<br>(SEQ ID NO:4) |
| P2C4_A4<br>P2C4_C1<br>P2C4_E6 | TGTSSDIGDYDFVS<br>(SEQ ID NO:18) | DINNRPS<br>(SEQ ID NO:3) | SAYTSSDTLV<br>(SEQ ID NO:4) |
| P2C4_B1 | TGTSSDIGHYDFVS<br>(SEQ ID NO:2) | DNNNRPS<br>(SEQ ID NO:20) | SAYTSSDTLV<br>(SEQ ID NO:4) |
| P2C4_B5<br>P2C4_B6<br>P2C4_B8<br>P2C4_C7<br>P2C4_C12<br>P2C4_D10<br>P2C4_E2<br>P2C4_E3<br>P2C4_E7<br>P2C4_E8<br>P2C4_F8<br>P2C4_F11<br>P2C4_G2<br>P2C4_G11<br>P2C4_H1<br>P2C4_H2<br>P2C4_H3 | TGTSSDIGHYDFVS<br>(SEQ ID NO:2) | DINNRPS<br>(SEQ ID NO:3) | SAYTSSDTVV<br>(SEQ ID NO:22) |
| P2C4_B12 | TGTSSDIGHYDFIS<br>(SEQ ID NO:25) | DFNNRPS<br>(SEQ ID NO:26) | SAYTSSDTLV<br>(SEQ ID NO:4) |
| P2C4_C4 | TGTSSDIGHYDFVS<br>(SEQ ID NO:2) | DNNNRPS<br>(SEQ ID NO:20) | SAYTSSDTVV<br>(SEQ ID NO:22) |
| P2C4_E9 | TGTSSDIGHYDFVS<br>(SEQ ID NO:2) | DINNRAS<br>(SEQ ID NO:32) | SAYTSSDTVV<br>(SEQ ID NO:22) |
| P2C4_C1D10 | TGTSSDIGDYDFVS<br>(SEQ ID NO:18) | DINNRPS<br>(SEQ ID NO:3) | SAYTSSDTVV<br>(SEQ ID NO:22) |
| CONSENSUS | TGTSSDIGX$_1$YDFX$_2$S<br>(SEQ ID NO:85)<br><br>wherein X$_1$ = H or D, and X$_2$ = V or I | DX$_3$NNRX$_4$S<br>(SEQ ID NO:86)<br><br>wherein X$_3$ = I, N or F, and X$_4$ = P or A | SAYTSSDTX$_5$V<br>(SEQ ID NO:87)<br><br>wherein X$_5$ = L or V |

Figure 9

| Clone | CDR 1 | CDR 2 | CDR 3 |
|---|---|---|---|
| Heavy Chain | | | |
| P2C4<br>P2C4_A4<br>P2C4_B1<br>P2C4_B5<br>P2C4_B8<br>P2C4_B12<br>P2C4_C1<br>P2C4_C4<br>P2C4_C7<br>P2C4_C12<br>2C4_D10<br>P2C4_E2<br>P2C4_E6<br>P2C4_E7<br>P2C4_E8<br>P2C4_F8<br>P2C4_F11<br>P2C4_G2<br>P2C4_G11<br>P2C4_H1<br>P2C4_H2<br>P2C4_H3<br>P2C4_H3<br>P2C4_C1D10<br>P2C4_FW2 | NYYMH<br>(SEQ ID NO:36) | AIMPSRGGTSYPQKFQG<br>(SEQ ID NO:37) | GEYYYDSSGYYY<br>(SEQ ID NO:38) |
| P2C4_A9 | NYYMH<br>(SEQ ID NO:36) | AIMPSRGGTSYPQKFQG<br>(SEQ ID NO:37) | GEYYYDSSGYYN<br>(SEQ ID NO:52) |
| P2C4_B6<br>P2C4_E3<br>P2C4_E9 | NYYIH<br>(SEQ ID NO:54) | AIMPSRGGTSYPQKFQG<br>(SEQ ID NO:37) | GEYYYDSSGYYY<br>(SEQ ID NO:38) |
| CONSENSUS | NYYX$_6$H<br>(SEQ ID NO:88)<br><br>wherein X$_6$ = M or I | AIMPSRGGTSYPQKFQG<br>(SEQ ID NO:37) | GEYYYDSSGYYX$_7$<br>(SEQ ID NO:89)<br><br>wherein X$_7$ = Y or N |

Figure 10

| Clone | CDR 1 | CDR 2 | CDR 3 |
|---|---|---|---|
| Light Chain | | | |
| P1A3<br>P1A3_B3<br>P1A3_E8<br>P1A3_E9<br>P1A3_B4<br>P1A3_FW2 | RSSQSLLHSNGYNYLD<br>(SEQ ID NO:68) | LGSNRDS<br>(SEQ ID NO:69) | MQGTHWPWT<br>(SEQ ID NO:70) |
| CONSENSUS | RSSQSLLHSNGYNYLD<br>(SEQ ID NO:68) | LGSNRDS<br>(SEQ ID NO:69) | MQGTHWPWT<br>(SEQ ID NO:70) |

Figure 11

| Clone | CDR 1 | CDR 2 | CDR 3 |
|---|---|---|---|
| Heavy Chain | | | |
| P1A3<br>P1A3_FW2 | GYYWS<br>(SEQ ID NO:48) | EINHSGSTNYNPSLKS<br>(SEQ ID NO:49) | SPGGYSGGYFQH<br>(SEQ ID NO:77) |
| P1A3_B3<br>P1A3_B4<br>P1A3_E8<br>P1A3_E9 | GYYWS<br>(SEQ ID NO:48) | EINHFGSTNYNPSLKS<br>(SEQ ID NO:83) | SPGGYSGGYFQH<br>(SEQ ID NO:77) |
| CONSENSUS | GYYWS<br>(SEQ ID NO:48) | EINHX$_8$GSTNYNPSLKS<br>(SEQ ID NO:90)<br><br>wherein X$_8$ = S or F | SPGGYSGGYFQH<br>(SEQ ID NO:77) |

PCPAPEAAGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAK (SEQ ID
NO:91)

P2C4 CH3

GQPREPQVYTLPPCRDELTKNQVSLWCLVKGFYPSDIAVEWESNGQPENNYKTTPPVLDS
DGSFFLYSKLTVDKSRWQQGNVFSCSVMHEALHNHYTQKSLSLSPGK (SEQ ID NO:92)

PCPAPEAAGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAK (SEQ ID
NO:93)

P1A3 CH3

GQPREPQVCTLPPSRDELTKNQVSLSCAVKGFYPSDIAVEWESNGQPENNYKTTPPVLDS
DGSFFLCVSKLTVDKSRWQQGNVFSCSVMHEALHNHYTQKSLSLSPGK (SEQ ID NO:94)

Figure 14

P2C4
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTLVFGG
GTKLTVL*NSGAGTAAA**THTCP*PCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKVSNK
ALPAPIEKTISKAKGQPREPQVYTLPPCRDELTKNQVSLWCLVKGFYPSDIAVEWESNGQP
ENNYKTTPPVLDSDGSFFLYSKLTVDKSRWQQGNVFSCSVMHEALHNHYTQKSLSLSPGK
(SEQ ID NO:95)

P2H7
EVQLVQSGTEVKKPGASVKVSCKASGYTFTTYAMHWVRQAPGQSLEWMGWINTGNGNT
KYSQNFQGRVTMTRDTSISTAYMELSRLRSDDTAVYYCARDLGQLERLYFWGQGTLVTVS
SGGGGSGGGGSGGGGSDIQMTQSPSTLSASVGDRVTLSCRAGQAISSWLAWYQQKPGK
APKLLIYKASNLESGVPSRFSGGGSGAEFTLTISSLQPDDFATYYCQQYQSYPYTFGQGTKL
EIR (SEQ ID NO:96)

P2D12
HVQLVETGGGLVQPGGSLRLSCAASGFTFSSYAMSWVRQAPGKGLEWVSAISGSGGSTY
YADSVKGRFTISRDNSKNTLYLQMNSLRAEDTAVYYCARDLGDYWGQGTLVTVSS**GGGGS
GGGGSGGGGS**DIQLTQSPSSLSASVGDRVTITCQASQDIGNYLNWYQLKPGKAPKLLIYDA
SNLETGVPSRFSGSGSGTDFTFTISSLQPEDIATYYCLQLYDYPLTFGGGTKVEIK (SEQ ID
NO:97)

P1G11
QVQLQQWGAGLLKPSETLSLTCAVYGGSFSGYYWSWIRQPPGKGLEWIGEINHSGSTNYN
PSLKSRVTISVDTSKNQFSLKLSSVTAADTAVYYCARSSSGDAFDIWGQGTMVTVSS**GGGG
SGGGGSGGGGS**NFMLTQPHSVSESPGKTVTISCTRSSGSIASNYVQWYQQRPGSSPTTVI
FDDNQRPTGVPDRFSAAIDTSSSSASLTISGLTAEDEADYYCQSSHSTAVVFGGGTKLTVL
(SEQ ID NO:98)

P2C4_A4
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGDYDFVSWYQQ
HPGTAPKLIIYDINNRPSGISNRFSGSKSDNMASLTISGLQPEDEADYYCSAYTSSDTLVFGG
GTKLTVLAAAHHHHHH (SEQ ID NO:99)

P2C4_A9
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYNWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:100)

Figure 15

P2C4_B1
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDNNNRPSGISNRFSGSKSDNMASLTISGLQPEDEADYYCSAYTSSDTLVFG
GGTKLTVLAAAHHHHHH (SEQ ID NO:101)

P2C4_B5
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSITISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:102)

P2C4_B6
EVQLVQSGAEVKKPGSSVKVSCKASGYTFTNYYIHWVRQAPGQGLEWMGAIMPSRGGTS
YPQKFQGRVTMTGDTSTSTVYMELSSLRSEDTAVYYCARGEYYYDSSGYYYWGQGTLVT
VSSGGGGSGGGGSGGGGSQSALTQPASVSGSPGQSIAISCTGTSSDIGHYDFVSWYQQH
PGTAPKLIIYDINNRPSGISNRFSGSKSDNMASLTISGLQPEDEADYYCSAYTSSDTVVFGG
GTKLTVLAAAHHHHHH (SEQ ID NO103)

P2C4_B8
EVQLVQSGAEVKKPGSSVKVSCKASGYTFTNYYMHWVRQPPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:104)

P2C4_B12
EVQLVQSGAEVKKPGSTVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFISWYQQH
PGTAPKLIIYDFNNRPSGISNRFSGSKSDNMASLTISGLQPEDEADYYCSAYTSSDTLVFGG
GTKLTVLAAAHHHHHH (SEQ ID NO:105)

P2C4_C1
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTPV
TVSSGGGGSGGGGSGGGGSQSALTQPASVSGSPGQSIAISCTGTSSDIGDYDFVSWYQQ
HPGTAPKLIIYDINNRPSGISNRFSGSKSDNMASLTISGLQPEDEADYYCSAYTSSDTLVFGG
GTKLTVLAAAHHHHHH (SEQ ID NO:106)

P2C4_C4
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDNNNRPSGISNRFSGSKSDNMASLTISGLQPEDEADYYCSAYTSSDTVVFG
GGTKLTVLAAAHHHHHH (SEQ ID NO:107)

Figure 15 (Cont.)

P2C4_C7
EVQLVQSGAEVKKPGSSVKVSCKASGYTFTNYYMHWVRQAPGQGLEWMGAIMPSRGGT
SYPQKFQGRVTMGDTSTSTVYMELSSLRSEDTAVYYCARGEYYYDSSGYYYWGQGTLV
TVSSGGGGSGGGGSGGGGSQSALTQPASVSGSPGQSIVISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHH (SEQ ID NO:108)

P2C4_C12
EVQLVQSGAEVKKPGSSVKVSCKASGYTFTNYYMHWVRQAPGQGLEWMGAIMPSRGGT
SYPQKFQGRVTMGDTSTSTVYMELSNLRSEDTAVYYCARGEYYYDSSGYYYWGQGTLV
TVSNGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:109)

P2C4_D10
EVQLVQSGAEVKKPGSSVKVSCKASGYTFTNYYMHWVRQAPGQGLEWMGAIMPSRGGT
SYPQKFQGRVTMGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:110)

P2C4_E2
EVQLVQSGAEVKEPGSSVKVSCKASGYTFTNYYMHWVRQAPGQGLEWMGAIMPSRGGT
SYPQKFQGRVTMGDISTSTVYMELSSLRSEDTAVYYCARGEYYYDSSGYYYWGQGTLVT
VSSGGGGSGGGGSGGGGSQSALTQPASVSGSPGQSIAISCTGTSSDIGHYDFVSWYQQH
PGTAPKLIIYDINNRPSGISNRFSGSKSDNMASLTISGLQPEDEADYYCSAYTSSDTVVFGG
GTKLTVLAAAHHHHHH (SEQ ID NO:111)

P2C4_E3
EVQLVQSGAEVKKPGSSVKVSCKASGYTFTNYYIHWVRQAPGQGLEWMGAIMPSRGGTS
YPQKFQGRVTMGDTSTSTVYMELNSLRSEDTAVYYCARGEYYYDSSGYYYWGQGTLVT
VSSGGGGSGGGGSGGGGSQSALTQPASVSGSPGQSIAISCTGTSSDIGHYDFVSWYQQH
PGTAPKLIIYDINNRPSGISNRFSGSKSDNMASLTISGLQPEDEADYYCSAYTSSDTVVFGG
GTKLTVLAAAHHHHHH (SEQ ID NO:112)

P2C4_E6
EVQLVQSGAEVKKPGSSVKVSCKASGYTFTNYYMHWVRQAPGQGLEWMGAIMPSRGGT
SYPQKFQGRVTMGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGDYDFVSWYQQ
HPGTAPKLIIYDINNRPSGISNRFSGSKSDNMASLIISGLQPEDEADYYCSAYTSSDTLVFGG
GTKLTVLAAAHHHHHH (SEQ ID NO:113)

P2C4_E7
EVQLVQSGAEVKKPGSSVKVSCKASGYTFTNYYMHWVRQAPGQGLEWMGAIMPSRGGT
SYPQKFQGRVTMGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDDMASLTISGLQPEDEADYYCSAYTSSDTVVFG
GGTKLTVLAAAHHHHHH (SEQ ID NO:114)

Figure 15 (Cont.)

P2C4_E8
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGPGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:115)

P2C4_E9
EVQLVQSGAEVKKPGSSVKVSCKASGYTFTNYYIHWVRQAPGQGLEWMGAIMPSRGGTS
YPQKFQGRVTMTGDTSTSTVYMELSSLRSEDTAVYYCARGEYYYDSSGYYYWGQGTLVT
VSSGGGGSGGGGSGGGGSQSALTQPASVSGSPGQSIAISCTGTSSDIGHYDFVSWYQQH
PGTAPKLIIYDINNRASGISNRFSGSKSDNMASLTISGLQPEDEADYYCSAYTSSDTVVFGG
GTKLTVLAAAHHHHHH (SEQ ID NO:116)

P2C4_F8
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGNPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:117)

P2C4_F11
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAMYYCARGEYYYDSSGYYYWGQGTLV
TVSSGGGGSGGGGSGGGGSQSTLTQPASVSGSPGQSITISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:118)

P2C4_G2
EVQLVQSGAEVKKPGSSVKVSCKASGYTFTNYYMHWVRQAPGQGLEWMGAIMPSRGGT
SYPQKFQGRVTMTGDTSTSTVYMELSSLRTEDTAVYYCARGEYYYDSSGYYYWGQGTLV
TVSSGGGGSGGGGSGGVGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:119)

P2C4_G11
EVQLVQSGAEVKKPGSSVKVSCKASGYTFTNYYMHWVRQAPGQGLEWMGAIMPSRGGT
SYPQKFQGRVTMTGDTSTSTVYMELSNLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:120)

P2C4_H1
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
NVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:121)

Figure 15 (Cont.)

P2C4 H2
EVQLVQSGAEVKKPGSSVKVSCKASGYTFSNYYMHWVRQAPGQGLEWIGAIMPSRGGTS
YPQKFQGRVTMTGDTSTSTVYMELSSLRSEDTAVYYCARGEYYYDSSGYYYWGQGTLVT
VSSGGGGSGGGGSGGGGSQSALTQPASVSGSPGQSIAISCTGTSSDIGHYDFVSWYQQH
PGTAPKLIIYDINNRPSGISNRFSGSKSDNMASLTISGLQPEDEADYYCSAYTSSDTVVFGG
GTKLTVLAAAHHHHHH (SEQ ID NO:122)

P2C4 H3
EVQLVQSGAEVKKPGSSVKVSCKATGYTFTNYYMHWVRQAPGQGLEWMGAIMPSRGGT
SYPQKFQGRVTMTGDTSTSTVYMELSSLRSEDTAVYYCARGEYYYDSSGYYYWGQGTLV
TVSSGGGGSGGGGSGGGGSQSALTQPASVSGSPGQSIAISCTGTSSDIGHYDFVSWYQQ
HPGTAPKLIIYDINNRPSGISNRFSGSKSDNMASLTISGLQPEDEADYYCSAYTSSDTVVFG
GGTKLTVLAAAHHHHHH (SEQ ID NO:123)

P2C4 C1D10
EVQLVQSGAEVKKPGSSVKVSCKASGYTFTNYYMHWVRQAPGQGLEWMGAIMPSRGGT
SYPQKFQGRVTMTGDTSTSTVYMELSSLRSEDTAVYYCARGEYYYDSSGYYYWGQGTPV
TVSSGGGGSGGGGSGGGGSQSALTQPASVSGSPGQSIAISCTGTSSDIGDYDFVSWYQQ
HPGTAPKLIIYDINNRPSGISNRFSGSKSDNMASLTISGLQPEDEADYYCSAYTSSDTVVFG
GGTKLTVL (SEQ ID NO:154)

P2C4 FW2
EVQLVQSGAEVKKPGASVKVSCKASGYTFTNYYMHWVRQAPGQGLEWMGAIMPSRGGT
SYPQKFQGRVTITADKSTSTAYMELSSLRSEDTAVYYCARGEYYYDSSGYYYWGQGTLVT
VSSGGGGSGGGGSGGGGSQSVLTQPPSVSGAPGQRVTISCTGTSSDIGHYDFVSWYQQL
PGTAPKLLIYDINNRPSGVPDRFSGSKSGTSASLAITGLQAEDEADYYCSAYTSSDTLVFGG
GTKLTVL (SEQ ID NO:155)

Figure 15 (Cont.)

P1A3
QVQLQQWGAGLLKPSETLSLTCAVYGGSFSGYYWSWIRQPPGKGLEWIGEINHSGSTNYN
PSLKSRATISVDTSKNQFSLKLSSVTAADTAVYYCATSPGGYSGGYFQHWGQGTLVTVSS
GGGGSGGGGSGGGGSDVVMTQSPLSLPVTPGEPASISCRSSQSLLHSNGYNYLDWYLQK
PGQSPQLLIYLGSNRDSGVPDRFSGSGSGTDFTLKISRVEAEDVGVYYCMQGTHWPWTFG
QGTKVEIK*NSGAGTAAA*THTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSN
KALPAPIEKTISKAKGQPREPQVCTLPPSRDELTKNQVSLSCAVKGFYPSDIAVEWESNGQP
ENNYKTTPPVLDSDGSFFLCVSKLTVDKSRWQQGNVFSCSVMHEALHNHYTQKSLSLSPG
K (SEQ ID NO:124)

P2B9
QVQLQESGPGLVKPSETLSLTCTVSGGSISSSSYYWGWIRQPPGKGLEWIGSIYYSGSTYY
NPSLKSRVTISVDTSKNQFSLKLSSVTAADTAVYYCAGDILTGYALDYWGQGTLVTVSSGG
GGSGGGGSGGGGSSYELTQPPSMSVSPGQTARITCSGDALPKQFAFWYQQKPGQAPVL
VIYKDTERPSGIPERFSGSSSGTTVTLTITGVQAEDEADYYCQSPDSSGTVEVFGGGTKLTV
L (SEQ ID NO:125)

P1A3_B3
QVQLQQWGAGLLKPSETLSLTCAVYGGSFSGYYWSWIRQPPGKGLEWIGEINHFGSTNYN
PSLKSRATISVDTSKNQFSLKLSSVTAADTAVYYCATSPGGYSGGYFQHWGQGTLVTVSS
GGGGSGGGGSGGGGSDVVMTQSPLSLPVTPGEPASISCRSSQSLLHSNGYNYLDWYLQK
PGQSPQLLIYLGSNRDSGVPDRFSGSGSGTDFTLKISRVEAEDVGVYYCMQGTHWPWTFG
QGTKVEIKAAAHHHHHH (SEQ ID NO:126)

P1A3_B4
QVQLQQWGAGLLKPSETLSLTCAVYGGSFSGYYWSWIRQPPGKGLEWIGEINHFGSTNYN
PSLKSRATISVDTSKNQFSLKLSSVTAADTAVYYCATSPGGYSGGYFQHWGQGTLVTVSS
GGGGSGGGGSGGGGSDVVMTQSPLSLPVTPGESVSISCRSSQSLLHSNGYNYLDWYLQK
PGQSPQLLIYLGSNRDSGVPDRFSGSGSGTDFTLKISRVEAEDVGVYYCMQGTHWPWTFG
QGTKVEIKAAAHHHHHH (SEQ ID NO:127)

P1A3_E8
QVQLQQWGAGMLKPSETLSLTCAVYGGSFSGYYWSWIRQPPGKGLEWIGEINHFGSTNY
NPSLKSRATISVDTSKNQFSLKLSSVTAADTAVYYCATSPGGYSGGYFQHWGQGTLVTVSS
GGGGSGGGGSGGGGSDVVMTQSPLSLPVTPGEPASISCRSSQSLLHSNGYNYLDWYLQK
PGQSPQLLIYLGSNRDSGVPDRFSGSGSGTDFTLKISRVEAEDVGVYYCMQGTHWPWTFG
QGTKVEIKAAAHHHHHH (SEQ ID NO:128)

Figure 16

P1A3_E9
QVQLQQWGAGLLKPSETLSLTCAVYGGSFSGYYWSWIRQPPGKGLEWIGEINHFGSTNYN
PSLKSRATISVDTSKNQFSLKLSSVTAADTAVYYCATSPGGYSGGYFQHWGQGTLVTVSS
GGGGSGEGGSGGGGSDVVMTQSPLSLPVTPGEPASISCRSSQSLLHSNGYNYLDWYLQK
PGQSPQLLIYLGSNRDSGVPDRFSGSGSGTDFTLKISRVEAEDVGVYYCMQGTHWPWTFG
QGTKVEIKAAAHHHHH (SEQ ID NO:129)

P1A3_FW2
EVQLVESGGGLVQPGGSLRLSCAASGGSFSGYYWSWVRQAPGKGLEWVSEINHSGSTNY
NPSLKSRFTISRDNSKNTLYLQMNSLRAEDTAVYYCARSPGGYSGGYFQHWGQGTLVTVS
SGGGGSGGGGSGGGGSDIQMTQSPSSLSASVGDRVTITCRSSQSLLHSNGYNYLDWYQQ
KPGKAPKLLIYLGSNRDSGVPSRFSGSGSGTDFTLTISSLQPEDFATYYCMQGTHWPWTF
GQGTKVEIK (SEQ ID NO:156)

Figure 16 (cont.)

P2C4 Fab Light Chain ntd (VL, joint, CL):
CAGTCTGCCCTGACTCAGCCTGCCTCCGTGTCTGGGTCTCCTGGACAGTCGATCGCCA
TTTCCTGCACTGGAACCAGCAGTGACATTGGTCATTATGACTTTGTCTCCTGGTACCAA
CAGCACCCAGGCACAGCCCCCAAACTCATAATTTATGATATCAATAATCGGCCCTCAGG
GATTTCTAATCGCTTCTCTGGCTCCAAGTCTGACAATATGGCCTCCCTGACCATCTCTG
GGCTCCAGCCTGAGGACGAGGCTGATTATTACTGCAGTGCATATACAAGCAGCGACAC
TCTGGTCTTCGGCGGAGGGACCAAGTTGACCGTCCTCAGTCAGCCCAAGGCTGCCCC
CTCGGTCACTCTGTTCCCACCCTCCTCTGAGGAGCTTCAAGCCAACAAGGCCACACTG
GTGTGTCTCATAAGTGACTTCTACCCGGGAGCCGTGACAGTGGCCTGGAAGGCAGATA
GCAGCCCCGTCAAGGCGGGAGTGGAGACCACCACACCCTCCAAACAAAGCAACAACA
AGTACGCGGCCAGCAGCTACCTGAGCCTGACGCCTGAGCAGTGGAAGTCCCACAAAA
GCTACAGCTGCCAGGTCACGCATGAAGGGAGCACCGTGGAGAAGACAGTGGCCCCTA
CAGAATGTTCA (SEQ ID NO:130)

P2C4 Fab Heavy Chain ntd (VH, joint, CH):
GAGGTCCAGCTGGTACAGTCTGGGGCTGAGGTGAAGAAGCCTGGGTCCTCAGTGAAG
GTTTCCTGCAAGGCATCTGGATACACCTTCACCAACTACTATATGCACTGGGTGCGACA
GGCCCCTGGACAAGGGCTTGAGTGGATGGGGGCAATCATGCCTAGTCGTGGTGGCAC
AAGTTACCCACAGAAGTTCCAGGGCAGAGTCACCATGACCGGGGACACGTCCACGAG
CACAGTCTACATGGAGCTGAGCAGCCTGAGATCTGAGGACACGGCCGTGTATTACTGT
GCGAGAGGGGAGTATTACTATGATAGTAGTGGTTATTACTACTGGGGCCAGGGCACCC
TGGTCACCGTCTCAAGCGCCTCCACCAAGGGCCCATCGGTCTTCCCCCTGGCACCCTC
CTCCAAGAGCACCTCTGGGGGCACAGCGGCCCTGGGCTGCCTGGTCAAGGACTACTT
CCCCGAACCGGTGACGGTGTCGTGGAACTCAGGCGCCCTGACCAGCGGCGTCCACAC
CTTCCCGGCTGTCCTACAGTCCTCAGGACTCTACTCCCTCAGCAGCGTAGTGACCGTG
CCCTCCAGCAGCTTGGGCACCCAGACCTACATCTGCAACGTGAATCACAAGCCCAGCA
ACACCAAGGTGGACAAGAAAGTTGAGCCCAAATCTTGT (SEQ ID NO:131)

Figure 17

P2C4 scFv ntd (scFv and Fc with knob modification):
GAAGTGCAGCTGGTGCAGAGCGGGGCAGAAGTGAAAAAGCCTGGGTCAAGCGTGAAG
GTCTCCTGTAAAGCAAGCGGATACACATTCACAAACTACTATATGCACTGGGTGCGGCA
GGCCCCCGGACAGGGCCTGGAGTGGATGGGCGCTATCATGCCTTCCCGAGGCGGGA
CTTCTTACCCACAGAAGTTCCAGGGAAGAGTGACCATGACAGGCGACACTAGCACCTC
CACAGTCTATATGGAGCTGAGCAGCCTGAGGAGCGAAGACACTGCCGTGTACTATTGC
GCTCGCGGAGAATACTATTACGATTCTAGTGGCTATTACTATTGGGGCAGGGAACACT
GGTGACTGTCTCAAGCGGAGGAGGAGGAAGTGGCGGAGGAGGCTCCGGAGGAGGCG
GTCTCAGAGTGCACTGACCCAGCCAGCATCAGTGAGCGGCAGCCCCGGCCAGTCTA
TCGCAATTAGTTGTACTGGGACCTCCTCTGACATCGGACACTACGATTTCGTCTCTTGG
TATCAGCAGCACCCCGGCACCGCTCCTAAGCTGATCATCTACGACATCAACAATCGGC
CCAGCGGCATTTCCAACAGATTTTCTGGGAGTAAATCAGATAATATGGCCTCACTGACA
ATTAGCGGCCTCCAGCCTGAGGACGAAGCTGATTACTATTGCTCCGCATACACTAGTTC
AGATACCCTGGTGTTTGGAGGCGGGACCAAACTGACAGTCCTGAACAGCGGCGCGGG
CACCGCGGCCGCGACTCACACATGCCCACCGTGCCCAGCACCTGAAGCCGCGGGGG
GACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGA
GCAGTACAACAGCACGTACCGTGTGGTCAGCGTCCTCACCGTCCTGCACCAGGACTGG
CTGAATGGCAAGGAGTACAAGTGCAAGGTCTCCAACAAAGCCCTCCCAGCCCCCATCG
AGAAAACCATCTCCAAAGCCAAAGGGCAGCCCCGAGAACCACAGGTGTACACCCTGCC
CCCATGCCGGGATGAGCTGACCAAGAACCAGGTCAGCCTGTGGTGCCTGGTCAAAGG
CTTCTATCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTACAGCAAG
CTCACCGTGGACAAGAGCAGGTGGCAGCAGGGGAACGTCTTCTCATGCTCCGTGATG
CATGAGGCTCTGCACAACCACTACACGCAGAAGAGCCTCTCCCTGTCTCCGGGTAAA
(SEQ ID NO:132)

P2H7 Fab Light Chain ntd (VL, joint, CL):
GACATCCAGATGACCCAGTCTCCTTCCACATTGTCTGCATCTGTAGGAGACAGAGTCAC
ACTCTCTTGCCGGGCCGGTCAGGCTATTAGTAGTTGGTTGGCCTGGTATCAACAGAAA
CCAGGTAAAGCCCCAAAGCTTCTGATCTATAAGGCATCTAATTTAGAAAGTGGAGTCCC
ATCAAGGTTCAGCGGCGGTGGATCTGGGCAGAATTCACTCTCACCATCAGCAGCCTG
CAGCCTGATGATTTTGCAACTTATTACTGCCAACAGTATCAGAGCTACCCTTACACTTTT
GGCCAGGGGACCAAGCTGGAGATCAGACGAACTGTGGCTGCACCATCTGTCTTCATCT
TCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAGAGTGT
(SEQ ID NO:133)

Figure 17 (Cont.)

P2H7 Fab Heavy Chain ntd (VH, joint, CH):
GAGGTGCAGCTGGTGCAGTCTGGGACTGAGGTGAAGAAGCCTGGGGCCTCAGTGAAG
GTTTCCTGCAAGGCTTCTGGATACACCTTCACTACCTATGCTATGCATTGGGTGCGCCA
GGCCCCCGGACAAAGCCTTGAGTGGATGGGATGGATCAACACTGGCAATGGTAACACA
AAATATTCACAGAACTTCCAGGGCAGAGTCACCATGACCAGGGACACGTCCATCAGCA
CAGCCTACATGGAGCTGAGCAGGCTGAGATCTGACGACACGGCCGTGTATTACTGTGC
GAGAGATCTCGGGCAACTGGAACGACTCTACTTCTGGGGCCAGGGCACCCTGGTCAC
CGTCTCAGCGCCTCCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTCCACACCTTCCCG
GCTGTCCTACAGTCCTCAGGACTCTACTCCCTCAGCAGCGTAGTGACCGTGCCCTCCA
GCAGCTTGGGCACCCAGACCTACATCTGCAACGTGAATCACAAGCCCAGCAACACCAA
GGTGGACAAGAAAGTTGAGCCCAAATCTTGT (SEQ ID NO:134)

P2H7 scFv ntd (scFv and Fc with knob modification):
GAGGTGCAGCTGGTGCAGTCTGGGACTGAGGTGAAGAAGCCTGGGGCCTCAGTGAAG
GTTTCCTGCAAGGCTTCTGGATACACCTTCACTACCTATGCTATGCATTGGGTGCGCCA
GGCCCCCGGACAAAGCCTTGAGTGGATGGGATGGATCAACACTGGCAATGGTAACACA
AAATATTCACAGAACTTCCAGGGCAGAGTCACCATGACCAGGGACACGTCCATCAGCA
CAGCCTACATGGAGCTGAGCAGGCTGAGATCTGACGACACGGCCGTGTATTACTGTGC
GAGAGATCTCGGGCAACTGGAACGACTCTACTTCTGGGGCCAGGGCACCCTGGTCAC
CGTCTCAAGCGGAGGAGGAGGATCTGGCGGAGGAGGCAGTGGAGGAGGAGGGTCAC
TTGACATCCAGATGACCCAGTCTCCTTCCACATTGTCTGCATCTGTAGGAGACAGAGTC
ACACTCTCTTGCCGGGCCGGTCAGGCTATTAGTAGTTGGTTGGCCTGGTATCAACAGA
AACCAGGTAAAGCCCCAAAGCTTCTGATCTATAAGGCATCTAATTTAGAAAGTGGAGTC
CCATCAAGGTTCAGCGGCGGTGGATCTGGGGCAGAATTCACTCTCACCATCAGCAGCC
TGCAGCCTGATGATTTTGCAACTTATTACTGCCAACAGTATCAGAGCTACCCTTACACTT
TTGGCCAGGGGACCAAGCTGGAGATCAGAAACAGCGGCGCGGGCACCGCGGCCGCG
ACTCACACATGCCCACCGTGCCCAGCACCTGAAGCCGCGGGGGGACCGTCAGTCTTC
CTCTTCCCCCCAAAACCCAAGGACACCCTCATGATCTCCCGGACCCCTGAGGTCACAT
GCGTGGTGGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTACAACAGCA
CGTACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTC
CAAAGCCAAAGGGCAGCCCCGAGAACCACAGGTGTACACCCTGCCCCCATGCCGGGA
TGAGCTGACCAAGAACCAGGTCAGCCTGTGGTGCCTGGTCAAAGGCTTCTATCCCAGC
GACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGCA
CAACCACTACACGCAGAAGAGCCTCTCCCTGTCTCCGGGTAAA (SEQ ID NO:135)

Figure 17 (Cont.)

P2D12 Fab Light Chain ntd (VL, joint, CL):
GACATCCAGTTGACCCAGTCTCCATCCTCCCTGTCTGCATCTGTAGGAGACAGAGTCAC
CATCACTTGCCAGGCGAGTCAGGACATTGGCAACTATTTAAATTGGTATCAGCTTAAAC
CAGGGAAAGCCCCTAAGCTCCTGATCTACGATGCATCCAATTTGGAAACAGGGGTCCC
ATCAAGGTTCAGTGGAAGTGGATCTGGGACAGATTTTACTTTCACCATCAGCAGCCTGC
AGCCTGAAGATATTGCAACATATTACTGTCTACAACTTTATGATTACCCCTCACTTTCG
GCGGAGGGACCAAGGTGGAGATCAAACGAACTGTGGCTGCACCATCTGTCTTCATCTT
CCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGG
TAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGT
(SEQ ID NO:136)

P2D12 Fab Heavy Chain ntd (VH, joint, CH):
CACGTGCAGCTGGTGGAGACTGGGGGAGGCTTGGTGCAGCCTGGGGGGTCCCTGAG
ACTCTCCTGTGCAGCCTCTGGATTCACCTTTAGCAGCTATGCCATGAGCTGGGTCCGC
CAGGCTCCAGGGAAGGGGCTGGAGTGGGTCTCAGCTATTAGTGGTAGTGGTGGTAGC
ACATACTACGCAGACTCCGTGAAGGGCCGGTTCACCATCTCCAGAGACAATTCCAAGA
ACACGCTGTATCTGCAAATGAACAGCCTGAGAGCCGAGGACACGGCCGTATATTACTG
TGCGAGAGATCTCGGGGATTATTGGGGCCAGGGAACCCTGGTCACCGTCTCAGCGC
CTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTG
TCGTGGAACTCAGGCGCCCTGACCAGCGGCGTCCACACCTTCCCGGCTGTCCTACAGT
CCTCAGGACTCTACTCCCTCAGCAGCGTAGTGACCGTGCCCTCCAGCAGCTTGGGCAC
CCAGACCTACATCTGCAACGTGAATCACAAGCCCAGCAACACCAAGGTGGACAAGAAA
GTTGAGCCCAAATCTTGT (SEQ ID NO:137)

Figure 17 (Cont.)

P2D12 scFv ntd (scFv and Fc with knob modification):
CAGGTCCAGCTGCAGGAGTCCGGGCCAGGGCTGGTGAAACCAAGCGAAACACTGAGT
CTGACATGTACCGTGAGTGGGGGGTCCATTAACAATAGTAACTACTATTGGTCATGGAT
CAGACAGAGCCCTGGAAGAGGCCTGGAGTGGATCGGCGGGATCTACTTCAGCGGCAC
CACATACTATAACCCATCACTGCAGAGCCGGGTGACTATCTCCATTGACACCTCTAAGA
ATCAGTTCAGCCTGAAGCTGAGCAGCGTGACCGCCGCTGATACAGCCATCTACTATTG
CGTCCGGCAGATGAATTACTATCACCTGGGCTCTAGTGTGGGGTTCGACCCCTGGGGA
CAGGGAGCACTGGCCACCGTGTCAAGCGTCCTCTGGAGGAGGAGGCAGCGGCGG
AGGAGGCTCTGGAGGAGGCGGGAGTGATGTGGTCATGACACAGAGCCCAGCTACTCT
GTCTGTGAGTCCCGGCGAAAGGGCCACACTGAGCTGTCGCGCTTCACAGAGCGTCAG
TTCAAACCTGGCATGGTACCAGCAGAAGCCAGGACAGGCACCTTCCCTGCTGATCTAT
GAGGCTTCTACACGAGCAACTGGCATTCCTGCTAGATTCTCCGGCTCTGGGAGTGGAA
CCGACTTTACTCTGACCATCAGCTCCCTGCAGAGCGAAGATTTTGCAATCTACTATTGT
CAGCAGTATAACGATTGGCTGTGGACCTTCGGGCAGGGGACTAAAGTGGAGATTCGGA
ACAGCGGCGCGGGCACCGCGGCCGCGACTCACACATGCCCACCGTGCCCAGCACCT
GAAGCCGCGGGGGGACCGTCAGTCTTCCTCTTCCCCCCAAAACCCAAGGACACCCTCA
TGATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCT
GCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAG
GTGTACACCCTGCCCCCATGCCGGGATGAGCTGACCAAGAACCAGGTCAGCCTGTGG
TGCCTGGTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTG
TCTCCGGGTAAA (SEQ ID NO:138)

P1G11 Fab Light Chain ntd (VL, joint, CL):
AATTTTATGCTGACTCAGCCCCACTCTGTGTCGGAGTCTCCGGGGAAGACGGTAACCA
TCTCCTGCACCCGCAGCAGTGGCAGCATTGCCAGCAACTATGTGCAGTGGTACCAGCA
GCGCCCGGGCAGTTCCCCCACCACGGTCATTTTTGACGACAATCAAAGACCCACTGGT
GTCCCTGATCGCTTCTCTGCCGCCATCGACACCTCCTCCAGTTCTGCCTCCCTCACCAT
CTCTGGACTGACGGCTGAGGACGAGGCCGATTACTATTGTCAGTCGTCTCATAGCACC
GCTGTCGTCTTTGGCGGAGGGACCAAGCTGACCGTCCTAAGTCAGCCCAAGGCTGCC
CCCTCGGTCACTCTGTTCCCGCCCTCCTCTGAGGAGCTTCAAGCCAACAAGGCCACAC
TGGTGTGTCTCATAAGTGACTTCTACCCGGGAGCCGTGACAGTGGCCTGGAAGGCAGA
TAGCAGCCCCGTCAAGGCGGGAGTGGAGACCACCACACCCTCCAAACAAAGCAACAA
CAAGTACGCGGCCAGCAGCTACCTGAGCCTGACGCCTGAGCAGTGGAAGTCCCACAA
AAGCTACAGCTGCCAGGTCACGCATGAAGGGAGCACCGTGGAGAAGACAGTGGCCCC
TACAGAATGTTCA (SEQ ID NO:139)

Figure 17 (Cont.)

P1G11 Fab Heavy Chain ntd (VH, joint, CH):
CAGGTGCAGCTACAGCAGTGGGGCGCAGGACTGTTGAAGCCTTCGGAGACCCTGTCC
CTCACCTGCGCTGTCTATGGTGGGTCCTTCAGTGGTTACTACTGGAGCTGGATCCGCC
AGCCCCCAGGGAAGGGGCTGGAGTGGATTGGGGAAATCAATCATAGTGGAAGCACCA
ACTACAACCCGTCCCTCAAGAGTCGAGTCACCATATCAGTAGACACGTCCAAGAACCA
GTTCTCCCTGAAGCTGAGCTCTGTGACCGCCGCGGACACGGCTGTGTATTACTGTGCG
AGAAGCTCGTCCGGGGATGCTTTTGATATCTGGGGCCAAGGGACAATGGTCACCGTCT
CAAGCGCCTCCACCAAGGGCCCATCGGTCTTCCCCCTGGCACCCTCCTCCAAGAGCAC
CTCTGGGGGCACAGCGGCCCTGGGCTGCCTGGTCAAGGACTACTTCCCCGAACCGGT
GACGGTGTCGTGGAACTCAGGCGCCCTGACCAGCGGCGTCCACACCTTCCCGGCTGT
CCTACAGTCCTCAGGACTCTACTCCCTCAGCAGCGTAGTGACCGTGCCCTCCAGCAGC
TTGGGCACCCAGACCTACATCTGCAACGTGAATCACAAGCCCAGCAACACCAAGGTGG
ACAAGAAAGTTGAGCCCAAATCTTGT (SEQ ID NO:140)

P1G11 scFv ntd (scFv and Fc with knob modification):
CAGGTGCAGCTACAGCAGTGGGGCGCAGGACTGTTGAAGCCTTCGGAGACCCTGTCC
CTCACCTGCGCTGTCTATGGTGGGTCCTTCAGTGGTTACTACTGGAGCTGGATCCGCC
AGCCCCCAGGGAAGGGGCTGGAGTGGATTGGGGAAATCAATCATAGTGGAAGCACCA
ACTACAACCCGTCCCTCAAGAGTCGAGTCACCATATCAGTAGACACGTCCAAGAACCA
GTTCTCCCTGAAGCTGAGCTCTGTGACCGCCGCGGACACGGCTGTGTATTACTGTGCG
AGAAGCTCGTCCGGGGATGCTTTTGATATCTGGGGCCAAGGGACAATGGTCACCGTCT
CAAGCGGAGGAGGAGGATCTGGCGGAGGAGGCAGTGGAGGAGGAGGGTCACTTAATT
TTATGCTGACTCAGCCCCACTCTGTGTCGGAGTCTCCGGGGAAGACGGTAACCATCTC
CTGCACCCGCAGCAGTGGCAGCATTGCCAGCAACTATGTGCAGTGGTACCAGCAGCG
CCCGGGCAGTTCCCCACCACGGTCATTTTTGACGACAATCAAAGACCCACTGGTGTC
CCTGATCGCTTCTCTGCCGCCATCGACACCTCCTCCAGTTCTGCCTCCCTCACCATCTC
TGGACTGACGGCTGAGGACGAGGCCGATTACTATTGTCAGTCGTCTCATAGCACCGCT
GTCGTCTTTGGCGGAGGGACCAAGCTGACCGTCCTAAACAGCGGCGCGGGCACCGCG
GCCGCGACTCACACATGCCCACCGTGCCCAGCACCTGAAGCCGCGGGGGGACCGTCA
GTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCCCCATGCC
GGGATGAGCTGACCAAGAACCAGGTCAGCCTGTGGTGCCTGGTCAAAGGCTTCTATCC
CAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAA (SEQ ID
NO:141)

Figure 17 (Cont.)

P1A3 Fab Light Chain ntd (VL, joint, CL):
GATGTTGTGATGACTCAGTCTCCACTCTCCCTGCCCGTCACCCCTGGAGAGCCGGCCT
CCATCTCCTGCAGGTCTAGTCAGAGCCTCCTGCATAGTAATGGATACAACTATTTGGAT
TGGTACCTGCAGAAGCCAGGGCAGTCTCCACAGCTCCTGATCTATTTGGGTTCTAACC
GGGACTCTGGGGTCCCAGACAGATTCAGCGGCAGTGGGTCAGGCACTGATTTCACACT
GAAAATCAGCAGGGTGGAGGCTGAGGATGTTGGGGTTTATTACTGCATGCAAGGTACA
CACTGGCCGTGGACGTTCGGCCAAGGGACCAAGGTGGAAATCAAACGAACTGTGGCT
GCACCATCTGTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAAC
ACAAAGTCTACGCCTGCGAAGTCACCCATCAGGGCCTGAGCTCGCCCGTCACAAAGAG
CTTCAACAGGGGAGAGTGT (SEQ ID NO:142)

P1A3 Fab Heavy Chain ntd (VH, joint, CH):
CAGGTGCAGCTACAGCAGTGGGGCGCAGGACTGTTGAAGCCTTCGGAGACCCTGTCC
CTCACCTGCGCTGTCTATGGTGGGTCCTTCAGTGGTTACTACTGGAGCTGGATCCGCC
AGCCCCCAGGGAAGGGGCTGGAGTGGATTGGGGAAATCAATCATAGTGGAAGCACCA
ACTACAACCCGTCCCTCAAGAGTCGAGCCACCATATCAGTAGACACGTCCAAGAACCA
GTTCTCCCTGAAGCTGAGCTCTGTGACCGCCGCGGACACGGCTGTGTATTACTGTGCG
ACCAGCCCGGGAGGCTATTCCGGGGGATACTTCCAGCACTGGGGCCAGGGAACCCTG
GTCACCGTCTCAAGCGCCTCCACCAAGGGCCCATCGGTCTTCCCCCTGGCACCCTCCT
CCAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTCCACACCT
TCCCGGCTGTCCTACAGTCCTCAGGACTCTACTCCCTCAGCAGCGTAGTGACCGTGCC
CTCCAGCAGCTTGGGCACCCAGACCTACATCTGCAACGTGAATCACAAGCCCAGCAAC
ACCAAGGTGGACAAGAAAGTTGAGCCCAAATCTTGT (SEQ ID NO:143)

Figure 18

P1A3 scFv ntd (scFv and Fc with hole modification):
CAGGTCCAGCTGCAGCAGTGGGGAGCCGGCCTGCTGAAACCATCTGAAACTCTGAGC
CTGACTTGCGCTGTCTACGGGGGGTCCTTCAGTGGCTACTATTGGTCATGGATCAGGC
AGCCCCCTGGGAAGGGACTGGAGTGGATCGGGGAAATTAACCACTCCGGATCTACAAA
CTACAATCCCAGTCTGAAATCACGCGCCACCATTTCTGTGGACACCAGTAAGAATCAGT
TCAGCCTGAAGCTGAGCAGCGTGACAGCCGCTGATACCGCCGTGTACTATTGCGCAAC
CAGCCCTGGCGGATACTCCGGAGGCTATTTTCAGCATTGGGGCCAGGGGACCCTGGT
GACAGTCTCTAGTGGGGGAGGAGGGTCTGGAGGAGGAGGAAGTGGAGGAGGAGGCT
CCGACGTGGTCATGACTCAGAGCCCACTGTCCCTGCCAGTGACCCCCGGCGAGCCTG
CTAGTATCTCATGTCGATCAAGCCAGTCACTGCTGCACAGCAACGGGTACAATTATCTG
GATTGGTACTTGCAGAAGCCAGGCCAGTCTCCCCAGCTGCTGATCTATCTGGGCTCCA
ACCGGGACTCTGGGGTGCCTGATAGATTCAGCGGCAGCGGCTCTGGGACTGACTTTAC
CCTGAAAATTTCCAGAGTCGAGGCAGAAGATGTGGGAGTCTACTATTGCATGCAGGGC
ACTCATTGGCCCTGGACCTTCGGACAGGGCACAAAGGTGGAGATCAAGAACAGCGGC
GCGGGCACCGCGGCCGCGACTCACACATGCCCACCGTGCCCAGCACCTGAACTCCTG
GGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCA
AGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTGCACCC
TGCCCCCATCCCGGGATGAGCTGACCAAGAACCAGGTCAGCCTGTCCTGCGCCGTCA
AAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCGTGAG
CAAGCTCACCGTGGACAAGAGCAGGTGGCAGCAGGGGAACGTCTTCTCATGCTCCGT
GATGCATGAGGCTCTGCACAACCACTACACGCAGAAGAGCCTCTCCCTGTCTCCGGGT
AAA (SEQ ID NO:144)

P2B9 Fab Light Chain ntd (VL, joint, CL):
TCCTATGAGCTGACTCAGCCACCCTCGATGTCAGTGTCCCCAGGACAGACGGCCAGGA
TCACCTGCTCTGGAGATGCATTGCCAAAACAATTTGCTTTTTGGTACCAGCAGAAGCCA
GGCCAGGCCCCTGTGTTGGTGATTTATAAAGACACTGAGAGGCCCTCAGGGATCCCTG
AGCGATTCTCTGGCTCCAGCTCAGGGACAACAGTCACGTTGACCATCACTGGAGTCCA
GGCAGAAGATGAGGCTGACTATTACTGTCAATCTCCAGACAGCAGTGGTACCGTCGAA
GTGTTCGGCGGAGGGACCAAGCTGACCGTCCTAGGTCAGCCCAAGGCTGCCCCCTCG
GTCACTCTGTTCCCGCCCTCCTCTGAGGAGCTTCAAGCCAACAAGGCCACACTGGTGT
GTCTCATAAGTGACTTCTACCCGGGAGCCGTGACAGTGGCCTGGAAGGCAGATAGCAG
CCCCGTCAAGGCGGGAGTGGAGACCACCACACCCTCCAAACAAAGCAACAACAAGTAC
GCGGCCAGCAGCTACCTGAGCCTGACGCCTGAGCAGTGGAAGTCCCACAGAAGCTAC
AGCTGCCAGGTCACGCATGAAGGGAGCACCGTGGAGAAGACAGTGGCCCCTGCAGAA
TGTTCA (SEQ ID NO:145)

Figure 18 (Cont.)

P2B9 Fab Heavy Chain ntd (VH, joint, CH):
CAGGTGCAGCTGCAGGAGTCGGGCCCAGGACTGGTGAAGCCTTCGGAGACCCTGTCC
CTCACCTGCACTGTCTCTGGTGGCTCCATCAGCAGTAGTAGTTACTACTGGGGCTGGA
TCCGCCAGCCCCCAGGGAAGGGGCTGGAGTGGATTGGGAGTATCTATTATAGTGGGA
GCACCTACTACAACCCGTCCCTCAAGAGTCGAGTCACCATATCCGTAGACACGTCCAA
GAACCAGTTCTCCCTGAAGCTGAGCTCTGTGACCGCCGCAGACACGGCTGTGTATTAC
TGTGCGGGCGATATTTTGACTGGTTATGCCCTTGACTACTGGGGCCAGGGAACCCTGG
TCACCGTCTCAAGCGCCTCCACCAAGGGCCCATCGGTCTTCCCCCTGGCACCCTCCTC
CAAGAGCACCTCTGGGGGCACAGCGGCCCTGGGCTGCCTGGTCAAGGACTACTTCCC
CGAACCGGTGACGGTGTCGTGGAACTCAGGCGCCCTGACCAGCGGCGTCCACACCTT
CCCGGCTGTCCTACAGTCCTCAGGACTCTACTCCCTCAGCAGCGTAGTGACCGTGCCC
TCCAGCAGCTTGGGCACCCAGACCTACATCTGCAACGTGAATCACAAGCCCAGCAACA
CCAAGGTGGACAAGAAAGTTGAGCCCAAATCTTGT (SEQ ID NO:146)

P2B9 scFv ntd (scFv and Fc with hole modification):
CAGGTGCAGCTGCAGGAAAGCGGACCCGGACTGGTGAAGCCATCTGAAACACTGAGC
CTGACTTGTACCGTGAGCGGCGGAAGCATCAGCTCCTCTAGTTACTATTGGGGATGGA
TCAGGCAGCCCCCTGGCAAGGGGCTGGAGTGGATCGGCAGCATCTACTATAGCGGCT
CCACATACTATAACCCTAGCCTGAAATCCCGCGTGACAATCTCTGTGGACACTAGTAAG
AATCAGTTCTCTCTGAAACTGTCAAGCGTGACCGCCGCTGATACAGCTGTCTACTATTG
CGCAGGCGACATTCTGACCGGGTACGCCCTGGATTATTGGGGACAGGGCACTCTGGT
GACCGTCTCCTCTGGAGGAGGAGGCTCAGGAGGAGGAGGGTCCGGAGGCGGGGGAA
GTTCATACGAACTGACACAGCCACCCTCTATGAGTGTGTCACCAGGGCAGACTGCACG
AATCACCTGTAGCGGAGACGCCCTGCCCAAGCAGTTCGCTTTTTGGTATCAGCAGAAA
CCTGGCCAGGCTCCAGTGCTGGTCATCTATAAGGATACTGAGCGGCCCTCTGGGATTC
CTGAAAGATTCAGTGGCAGCAGCAGCGGAACCACAGTGACTCTGACCATTACAGGCGT
GCAGGCAGAGGACGAAGCCGATTACTATTGCCAGTCCCCCGACAGTTCAGGCACCGT
GGAGGTCTTTGGCGGGGGAACAAAACTGACTGTGCTGAACAGCGGCGCGGGCACCGC
GGCCGCGACTCACACATGCCCACCGTGCCCAGCACCTGAACTCCTGGGGGGACCGTC
AGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTGCACCCTGCCCCCATCC
CGGGATGAGCTGACCAAGAACCAGGTCAGCCTGTCCTGCGCCGTCAAAGGCTTCTATC
CCAGCGACATCGCCGTGGAGTGGGAGAGCAATGGGCAGCCGGAGAACAACTACAAGA
CCACGCCTCCCGTGCTGGACTCCGACGGCTCCTTCTTCCTCGTGAGCAAGCTCACCGT
GGACAAGAGCAGGTGGCAGCAGGGGAACGTCTTCTCATGCTCCGTGATGCATGAGGC
TCTGCACAACCACTACACGCAGAAGAGCCTCTCCCTGTCTCCGGGTAAA (SEQ ID
NO:147)

IL-2R BETA/COMMON GAMMA CHAIN ANTIBODIES

RELATED APPLICATIONS

This application is a continuation of U.S. application Ser. No. 15/750,425, filed Feb. 5, 2018, entitled "IL2RBETA/COMMON GAMMA CHAIN ANTIBODIES", which is a 35 U.S.C. § 371 national phase application of International Application Serial No. PCT/EP2016/068780, filed Aug. 5, 2016, entitled "IL2RBETA/COMMON GAMMA CHAIN ANTIBODIES", which claims priority to SG 10201506227V, filed Aug. 6, 2015, all of which are incorporated herein by reference in their entirety.

REFERENCE TO A "SEQUENCE LISTING"

Incorporated by reference herein in its entirety is the Sequence Listing entitled "PCT_EP21016_068780_Sequence_Listing.txt", created Feb. 28, 2018, size of 177 kilobytes.

FIELD OF THE INVENTION

The present invention relates to antibodies that bind to interleukin 2 receptor β (IL-2Rβ; CD122) and common γ chain (γc; CD132).

BACKGROUND TO THE INVENTION

IL-2 is an essential cytokine that plays a central role in maintaining T cell homeostasis and mediating proper immune responses. Its high potency as an immune stimulator has led to clinical uses to treat a range of conditions, including cancers and AIDS; it is also widely used as an adjuvant for vaccination to stimulate activation and proliferation of various effector cells.

However, the high dose of IL-2 that is required for effective treatment of certain diseases is highly toxic. Major adverse effects of such therapy include vascular leak syndrome (VLS), which results in accumulation of the intravascular fluid in organs such as lung and liver with subsequent pulmonary edema and liver damage. There is no treatment for VLS except withdrawing the therapy.

IL-2 exerts its pleiotropic functions by binding to different combinations of receptor components expressed on different cell types: the alpha chain (IL-2Rα, also known as CD25), the beta chain (IL-2Rβ, or CD122), and the common cytokine receptor gamma chain (IL-2Rγ, γc, or CD132).

Isolated IL-2Rα has been termed the "low affinity" IL-2 receptor (binding affinity $K_D$~10 nM) and is not involved in signal transduction. A complex of IL-2Rβ and γc binds IL-2 with intermediate affinity ($K_D$~1 nM), although IL-2Rβ alone has very low affinity ($K_D$~100 nM) and γc alone has virtually no detectable binding affinity for IL-2. A complex with all three subunits, IL-2Rα, IL-2Rβ, and γc, binds IL-2 with high affinity ($K_D$~10 μM).

Heterodimerization of IL-2Rβ and γc is necessary and sufficient for effective signal transduction through the interaction of their cytoplasmic domains and subsequent kinase activation of multiple signaling pathways; IL-2Rα plays no role in signal transduction.

High-affinity α-β-γc IL-2Rs are typically found on CD4+ T regulatory cells (Tregs) as well as recently-activated T cells. Intermediate-affinity β-γc IL-2Rs are present at a low level on naïve CD8+ cells, but are prominent on antigen-experienced (memory) and memory-phenotype (MP) CD8+ T cells as well as natural killer (NK) cells. Both MPCD8+ T cells and NK cells express very high levels of IL-2Rβ and readily respond to IL-2.

Previous studies have indicated that VLS is caused by the release of proinflammatory cytokines from IL-2-activated NK cells. However, a recent study suggested that IL-2-induced pulmonary edema may result from direct binding of IL-2 to lung endothelial cells, which express functional high affinity α-β-γc IL-2Rs. This was evidenced by the observation that interaction of IL-2 with lung endothelial cells was abrogated by blocking anti-IL-2Rα monoclonal antibody (mAb), in IL-2Rα-deficient host mice, or by the use of an IL-2/anti-IL-2 mAb (IL-2/mAb) complex in which the antibody prevents IL-2/IL-2Rα interaction, thus preventing VLS.

SUMMARY OF THE INVENTION

The present invention is concerned with antibodies, or antigen binding fragments, that bind to CD122 and/or common γ chain (γc). Heavy and light chain polypeptides for CD122 and common γ chain (γc) binding antibodies are also disclosed. The antibodies, antigen binding fragments and polypeptides may be provided in isolated and/or purified form and may be formulated into compositions suitable for use in research, therapy and diagnosis.

In a first aspect, the present invention provides an antibody or antigen binding fragment, optionally isolated, which is capable of binding to CD122 and common γ chain (γc).

In some embodiments, the antibody or antigen binding fragment is a bispecific antibody or a bispecific antigen binding fragment.

In another aspect, the present invention provides an antibody or antigen binding fragment, optionally isolated, which is capable of binding to CD122, comprising the amino acid sequences i) to vi):

i) LC-CDR1:

TGTSSDIGX$_1$YDFX$_2$S (SEQ ID NO: 85)

RAGQAISSWLA; (SEQ ID NO: 6)

QASQDIGNYLN; (SEQ ID NO: 10)
or

TRSSGSIASNYVQ; (SEQ ID NO: 14)

ii) LC-CDR2:

DX$_3$NNRX$_4$S; (SEQ ID NO: 86)

KASNLES; (SEQ ID NO: 7)

DASNLET; (SEQ ID NO: 11)
or

DDNQRPT; (SEQ ID NO: 15)

iii) LC-CDR3:

SAYTSSDTX$_5$V; (SEQ ID NO: 87)

QQYQSYPYT; (SEQ ID NO: 8)

```
                                                  (SEQ ID NO: 12)
LQLYDYPLT;
or (SEQ ID NO: 16)
QSSHSTAVV;

iv) HC-CDR1:
                                                  (SEQ ID NO: 88)
NYYX6H;

(SEQ ID NO: 40)
TYAMH;

(SEQ ID NO: 44)
SYAMS;
or (SEQ ID NO: 48)
GYYWS;

v) HC-CDR2:
                                                  (SEQ ID NO: 37)
AIMPSRGGTSYPQKFQG;

(SEQ ID NO: 41)
WINTGNGNTKYSQNFQG;

(SEQ ID NO: 45)
AISGSGGSTYYADSVKG;
or (SEQ ID NO: 49)
EINHSGSTNYNPSLKS;

vi) HC-CDR3:
                                                  (SEQ ID NO: 89)
GEYYYDSSGYYX7;

(SEQ ID NO: 42)
DLGQLERLYFW;

(SEQ ID NO: 46)
DLGDY;
or (SEQ ID NO: 50)
SSSGDAFD;
``` or a variant thereof in which one or two or three amino acids in one or more of the sequences i) to vi) are replaced with another amino acid, wherein $X_1$=H or D; $X_2$=V or I; $X_3$=I, N or F; $X_4$=P or A; $X_5$=L or V; $X_6$=M or I; and $X_7$=Y or N.

In some embodiments, LC-CDR1 is one of TGTSSDIGHYDFVS (SEQ ID NO:2), TGTSSDIGDYDFVS (SEQ ID NO:18), TGTSSDIGHYDFIS (SEQ ID NO:25), RAGQAISSWLA (SEQ ID NO:6), QASQDIGNYLN (SEQ ID NO:10), or TRSSGSIASNYVQ (SEQ ID NO:14).

In some embodiments, LC-CDR2 is one of DINNRPS (SEQ ID NO:3), DNNNRPS (SEQ ID NO:20), DFNNRPS (SEQ ID NO:26), DINNRAS (SEQ ID NO:32), KASNLES (SEQ ID NO:7), DASNLET (SEQ ID NO:11), or DDNQRPT (SEQ ID NO:15).

In some embodiments, LC-CDR3 is one of SAYTSSDTLV (SEQ ID NO:4), SAYTSSDTVV (SEQ ID NO:22), QYQSYPYT (SEQ ID NO:8), LQLYDYPLT (SEQ ID NO:12), or QSSHSTAVV (SEQ ID NO:16).

In some embodiments, HC-CDR1 is one of NYYMH (SEQ ID NO:36), NYYIH (SEQ ID NO:54), TYAMH (SEQ ID NO:40), SYAMS (SEQ ID NO:44), or GYYWS (SEQ ID NO:48).

In some embodiments, HC-CDR2 is one of AIMPSRGGTSYPQKFQG (SEQ ID NO:37), WINTGNGNTKYSQNFQG (SEQ ID NO:41), AISGSGGSTYYADSVKG (SEQ ID NO:45), or EINHSGSTNYNPSLKS (SEQ ID NO:49).

In some embodiments, HC-CDR3 is one of GEYYYDSSGYYY (SEQ ID NO:38), GEYYYDSSGYYN (SEQ ID NO:52), DLGQLERLYFW (SEQ ID NO:42), DLGDY (SEQ ID NO:46), or SSSGDAFD (SEQ ID NO:50).

In some embodiments in accordance with various aspects, the present invention provides an antibody or fragment, or an isolated light chain polypeptide, having at least one light chain variable region incorporating the following CDRs:

```
LC-CDR1:
                                                  (SEQ ID NO: 2)
TGTSSDIGHYDFVS

LC-CDR2:
                                                  (SEQ ID NO: 3)
DINNRPS

LC-CDR3:
                                                  (SEQ ID NO: 4)
SAYTSSDTLV.
```

In some embodiments in accordance with various aspects, the present invention provides an antibody or fragment, or an isolated light chain polypeptide, having at least one light chain variable region incorporating the following CDRs:

```
LC-CDR1:
                                                  (SEQ ID NO: 18)
TGTSSDIGDYDFVS

LC-CDR2:
                                                  (SEQ ID NO: 3)
DINNRPS

LC-CDR3:
                                                  (SEQ ID NO: 4)
SAYTSSDTLV.
```

In some embodiments in accordance with various aspects, the present invention provides an antibody or fragment, or an isolated light chain polypeptide, having at least one light chain variable region incorporating the following CDRs:

```
LC-CDR1:
                                                  (SEQ ID NO: 2)
TGTSSDIGHYDFVS

LC-CDR2:
                                                  (SEQ ID NO: 20)
DNNNRPS

LC-CDR3:
                                                  (SEQ ID NO: 4)
SAYTSSDTLV.
```

In some embodiments in accordance with various aspects, the present invention provides an antibody or fragment, or an isolated light chain polypeptide, having at least one light chain variable region incorporating the following CDRs:

```
LC-CDR1:
                                                  (SEQ ID NO: 2)
TGTSSDIGHYDFVS

LC-CDR2:
                                                  (SEQ ID NO: 3)
DINNRPS

LC-CDR3:
                                                  (SEQ ID NO: 22)
SAYTSSDTVV.
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 25)
TGTSSDIGHYDFIS

LC-CDR2:
                              (SEQ ID NO: 26)
DFNNRPS

LC-CDR3:
                              (SEQ ID NO: 4)
SAYTSSDTLV.
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 2)
TGTSSDIGHYDFVS

LC-CDR2:
                              (SEQ ID NO: 20)
DNNNRPS

LC-CDR3:
                              (SEQ ID NO: 22)
SAYTSSDTVV.
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 2)
TGTSSDIGHYDFVS

LC-CDR2:
                              (SEQ ID NO: 32)
DNNNRAS

LC-CDR3:
                              (SEQ ID NO: 22)
SAYTSSDTVV.
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 18)
TGTSSDIGDYDFVS

LC-CDR2:
                              (SEQ ID NO: 3)
DINNRPS

LC-CDR3:
                              (SEQ ID NO: 22)
SAYTSSDTVV
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 6)
RAGQAISSWLA

LC-CDR2:
                              (SEQ ID NO: 7)
KASNLES

LC-CDR3:
                              (SEQ ID NO: 8)
QQYQSYPYT.
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 10)
QASQDIGNYLN

LC-CDR2:
                              (SEQ ID NO: 11)
DASNLET

LC-CDR3:
                              (SEQ ID NO: 12)
LQLYDYPLT
```

In some embodiments in accordance with various aspects, the present invention provides an antibody or fragment, or an isolated light chain polypeptide, having at least one light chain variable region incorporating the following CDRs:

```
LC-CDR1:
                              (SEQ ID NO: 14)
TRSSGSIASNYVQ

LC-CDR2:
                              (SEQ ID NO: 15)
DDNQRPT

LC-CDR3:
                              (SEQ ID NO: 16)
QSSHSTAVV.
```

In some embodiments in accordance with various aspects, the present invention provides an antibody or fragment, or an isolated heavy chain polypeptide, having at least one heavy chain variable region incorporating the following CDRs:

```
HC-CDR1:
                              (SEQ ID NO: 36)
NYYMH

HC-CDR2:
                              (SEQ ID NO: 37)
AIMPSRGGTSYPQKFQG

HC-CDR3:
                              (SEQ ID NO: 38)
GEYYYDSSGYYY.
```

In some embodiments in accordance with various aspects, the present invention provides an antibody or fragment, or an isolated heavy chain polypeptide, having at least one heavy chain variable region incorporating the following CDRs:

HC-CDR1:
(SEQ ID NO: 36)
NYYMH

HC-CDR2:
(SEQ ID NO: 37)
AIMPSRGGTSYPQKFQG

HC-CDR3:
(SEQ ID NO: 38)
GEYYYDSSGYYY.

In some embodiments in accordance with various aspects, the present invention provides an antibody or fragment, or an isolated heavy chain polypeptide, having at least one heavy chain variable region incorporating the following CDRs:

HC-CDR1:
(SEQ ID NO: 36)
NYYMH

HC-CDR2:
(SEQ ID NO: 37)
AIMPSRGGTSYPQKFQG

HC-CDR3:
(SEQ ID NO: 52)
GEYYYDSSGYYN.

In some embodiments in accordance with various aspects, the present invention provides an antibody or fragment, or an isolated heavy chain polypeptide, having at least one heavy chain variable region incorporating the following CDRs:

HC-CDR1:
(SEQ ID NO: 54)
NYYIH

HC-CDR2:
(SEQ ID NO: 37)
AIMPSRGGTSYPQKFQG

HC-CDR3:
(SEQ ID NO: 38)
GEYYYDSSGYYY.

In some embodiments in accordance with various aspects, the present invention provides an antibody or fragment, or an isolated heavy chain polypeptide, having at least one heavy chain variable region incorporating the following CDRs:

HC-CDR1:
(SEQ ID NO: 40)
TYAMH

HC-CDR2:
(SEQ ID NO: 41)
WINTGNGNTKYSQNFQG

HC-CDR3:
(SEQ ID NO: 42)
DLGQLERLYFW.

In some embodiments in accordance with various aspects, the present invention provides an antibody or fragment, or an isolated heavy chain polypeptide, having at least one heavy

HC-CDR1:
(SEQ ID NO: 44)
SYAMS

HC-CDR2:
(SEQ ID NO: 45)
AISGSGGSTYYADSVKG

HC-CDR3:
(SEQ ID NO: 46)
DLGDY.

In some embodiments in accordance with various aspects, the present invention provides an antibody or fragment, or an isolated heavy chain polypeptide, having at least one heavy chain variable region incorporating the following CDRs:

HC-CDR1:
(SEQ ID NO: 48)
GYYWS

HC-CDR2:
(SEQ ID NO: 49)
EINHSGSTNYNPSLKS

HC-CDR3:
(SEQ ID NO: 50)
SSSGDAFD.

In another aspect, the present invention provides an antibody or antigen binding fragment, optionally isolated, which is capable of binding to CD122, comprising a light chain and a heavy chain variable region sequence, wherein:
the light chain comprises a LC-CDR1, LC-CDR2, LC-CDR3, having at least 85% overall sequence identity to LC-CDR1: one of TGTSSDIGX$_1$YDFX$_2$S (SEQ ID NO:85), RAGQAISSWLA (SEQ ID NO:6); QASQDIGNYLN (SEQ ID NO:10); or TRSSGSIASNYVQ (SEQ ID NO:14); LC-CDR2: one of DX$_3$NNRX$_4$S (SEQ ID NO:86); KASNLES (SEQ ID NO:7); DASNLET (SEQ ID NO:11); or DDNQRPT (SEQ ID NO:15); LC-CDR3: one of SAYTSSDTX$_5$V (SEQ ID NO:87); QQYQSYPYT (SEQ ID NO:8); LQLYDYPLT (SEQ ID NO:12); or QSSHSTAW (SEQ ID NO:16); and
the heavy chain comprises a HC-CDR1, HC-CDR2, HC-CDR3, having at least 85% overall sequence identity to HC-CDR1: one of NYYX$_6$H (SEQ ID NO:88); TYAMH (SEQ ID NO:40); SYAMS (SEQ ID NO:44); or GYYWS (SEQ ID NO:48); HC-CDR2: one of AIMPSRGGTSYPQKFQG (SEQ ID NO:37); WINTGNGNTKYSQNFQG (SEQ ID NO:41); AISGSGGSTYYADSVKG (SEQ ID NO:45); or EINHSGSTNYNPSLKS (SEQ ID NO:49); HC-CDR3: one of GEYYYDSSGYYX$_7$ (SEQ ID NO:89); DLGQLERLYFW (SEQ ID NO:42); DLGDY (SEQ ID NO:46); or SSSGDAFD (SEQ ID NO:50);
wherein X$_1$=H or D; X$_2$=V or I; X$_3$=I, N or F; X$_4$=P or A; X$_5$=L or V; X$_6$=M or I; and X$_7$=Y or N.

In some embodiments the degree of sequence identity may be one of 86%, 87%, 88%, 89%, 90%, 91%, 92%, 93%, 94%, 95%, 96%, 97%, 98%, 99%, or 100%.

In another aspect, the present invention provides an antibody or antigen binding fragment, optionally isolated, which is capable of binding to CD122, comprising a light chain and a heavy chain variable region sequence, wherein:
the light chain sequence has at least 85% sequence identity to the light chain sequence of one of SEQ ID NOs:1, 17, 19, 21, 23, 24, 27, 28, 29, 30, 31, 33, 34, 148, 149, 5, 9, or 13 (FIG. 1), and;

the heavy chain sequence has at least 85% sequence identity to the heavy chain sequence of one of SEQ ID NOs:35, 51, 53, 55, 56, 57, 58, 59, 60, 61, 62, 63, 64, 65, 66, 150, 151, 39, 43, or 47 (FIG. 2).

In some embodiments the degree of sequence identity may be one of 86%, 87%, 88%, 89%, 90%, 91%, 92%, 93%, 94%, 95%, 96%, 97%, 98%, 99%, or 100%.

In another aspect, the present invention provides an antibody or antigen binding fragment, optionally isolated, which is capable of binding to CD122, which is a bispecific antibody or a bispecific antigen binding fragment comprising (i) an antigen binding fragment according to the present invention, and (ii) an antigen binding fragment capable of binding to common γ chain (γc).

In another aspect, the present invention provides an antibody or antigen binding fragment, optionally isolated, which is capable of binding to common γ chain (γc), comprising the amino acid sequences i) to vi):

```
i) LC-CDR1:
                    (SEQ ID NO: 68)
RSSQSLLHSNGYNYLD;
or
                    (SEQ ID NO: 72)
SGDALPKQFAF;

ii) LC-CDR2:
                    (SEQ ID NO: 69)
LGSNRDS;
or
                    (SEQ ID NO: 73)
KDTERPS;

iii) LC-CDR3:
                    (SEQ ID NO: 70)
MQGTHWPWT;
or
                    (SEQ ID NO: 74)
QSPDSSGTVEV;

iv) HC-CDR1:
                    (SEQ ID NO: 48)
GYYWS;
or
                    (SEQ ID NO: 79)
SSSYYWG;

v) HC-CDR2:
                    (SEQ ID NO: 90)
EINHX₈GSTNYNPSLKS;
or
                    (SEQ ID NO: 80)
SIYYSGSTYYNPSLK;

vi) HC-CDR3:
                    (SEQ ID NO: 77)
SPGGYSGGYFQH;
or
                    (SEQ ID NO: 81)
DILTGYALDY;
``` or a variant thereof in which one or two or three amino acids in one or more of the sequences i) to vi) are replaced with another amino acid, wherein $X_8$=S or F.

In some embodiments, LC-CDR1 is RSSQSLLHSNGY-NYLD (SEQ ID NO:68) or SGDALPKQFAF (SEQ ID NO:72).

In some embodiments, LC-CDR2 is LGSNRDS (SEQ ID NO:69) or KDTERPS (SEQ ID NO:73).

In some embodiments, LC-CDR3 is MQGTHWPWT (SEQ ID NO:70) or QSPDSSGTVEV (SEQ ID NO:74).

In some embodiments, HC-CDR1 is GYYWS (SEQ ID NO:48) or SSSYYWG (SEQ ID NO:79).

In some embodiments, HC-CDR2 is one of EINHSGST-NYNPSLKS (SEQ ID NO:49), EINHFGSTNYNPSLKS (SEQ ID NO:83), or SIYYSGSTYYNPSLK (SEQ ID NO:80).

In some embodiments, HC-CDR3 is SPGGYSGGYFQH (SEQ ID NO:77) or DILTGYALDY (SEQ ID NO:81).

In some embodiments in accordance with various aspects, the present invention provides an antibody or fragment, or an isolated light chain polypeptide, having at least one light chain variable region incorporating the following CDRs:

```
LC-CDR1:
                    (SEQ ID NO: 68)
RSSQSLLHSNGYNYLD

LC-CDR2:
                    (SEQ ID NO: 69)
LGSNRDS

LC-CDR3:
                    (SEQ ID NO: 70)
MQGTHWPWT.
```

In some embodiments in accordance with various aspects, the present invention provides an antibody or fragment, or an isolated light chain polypeptide, having at least one light chain variable region incorporating the following CDRs:

```
LC-CDR1:
                    (SEQ ID NO: 72)
SGDALPKQFAF

LC-CDR2:
                    (SEQ ID NO: 73)
KDTERPS

LC-CDR3:
                    (SEQ ID NO: 74)
QSPDSSGTVEV.
```

In some embodiments in accordance with various aspects, the present invention provides an antibody or fragment, or an isolated heavy chain polypeptide, having at least one heavy chain variable region incorporating the following CDRs:

```
HC-CDR1:
                    (SEQ ID NO: 48)
GYYWS

HC-CDR2:
                    (SEQ ID NO: 49)
EINHSGSTNYNPSLKS

HC-CDR3:
                    (SEQ ID NO: 77)
SPGGYSGGYFQH.
```

In some embodiments in accordance with various aspects, the present invention provides an antibody or fragment, or an isolated heavy chain polypeptide, having at least one heavy chain variable region incorporating the following CDRs:

```
HC-CDR1:
                    (SEQ ID NO: 48)
GYYWS

HC-CDR2:
                    (SEQ ID NO: 83)
EINHFGSTNYNPSLKS
```

-continued

HC-CDR3:
SPGGYSGGYFQH. (SEQ ID NO: 77)

In some embodiments in accordance with various aspects, the present invention provides an antibody or fragment, or an isolated heavy chain polypeptide, having at least one heavy chain variable region incorporating the following CDRs:

HC-CDR1:
SSSYYWG (SEQ ID NO: 79)

HC-CDR2:
SIYYSGSTYYNPSLK (SEQ ID NO: 80)

HC-CDR3:
DILTGYALDY. (SEQ ID NO: 81)

In another aspect, the present invention provides an antibody or antigen binding fragment, optionally isolated which is capable of binding to common γ chain (γc), comprising a light chain and a heavy chain variable region sequence, wherein:
the light chain comprises a LC-CDR1, LC-CDR2, LC-CDR3, having at least 85% overall sequence identity to LC-CDR1: RSSQSLLHSNGYNYLD (SEQ ID NO:68) or SGDALPKQFAF (SEQ ID NO:72); LC-CDR2: LGSNRDS (SEQ ID NO:69) or KDTERPS (SEQ ID NO:73); LC-CDR3: MQGTHWPWT (SEQ ID NO:70) or QSPDSSGTVEV (SEQ ID NO:74); and
the heavy chain comprises a HC-CDR1, HC-CDR2, HC-CDR3, having at least 85% overall sequence identity to HC-CDR1: GYYWS (SEQ ID NO:48) or SSSYYWG (SEQ ID NO:79); HC-CDR2: EINHX$_8$ GST-NYNPSLKS (SEQ ID NO:90) or SIYYSG STYYNPSLK (SEQ ID NO:80); HC-CDR3: SPG-GYSGGYFQH (SEQ ID NO:77) or DILTGYALDY (SEQ ID NO:81);
wherein X$_8$=S or F.

In some embodiments the degree of sequence identity may be one of 86%, 87%, 88%, 89%, 90%, 91%, 92%, 93%, 94%, 95%, 96%, 97%, 98%, 99%, or 100%.

In another aspect, the present invention provides an antibody or antigen binding fragment, optionally isolated, which is capable of binding to common γ chain (γc), comprising a light chain and a heavy chain variable region sequence, wherein:
the light chain sequence has at least 85% sequence identity to the light chain sequence of one of SEQ ID NOs:67, 152, 71, or 75 (FIG. 3), and;
the heavy chain sequence has at least 85% sequence identity to the heavy chain sequence of one of SEQ ID NOs:76, 153, 78, 82 or 84 (FIG. 4).

In some embodiments the degree of sequence identity may be one of 86%, 87%, 88%, 89%, 90%, 91%, 92%, 93%, 94%, 95%, 96%, 97%, 98%, 99%, or 100%.

In another aspect, the present invention provides an antibody or antigen binding fragment, optionally isolated, which is capable of binding to common γ chain (γc), which is a bispecific antibody or a bispecific antigen binding fragment comprising (i) an antigen binding fragment according to the present invention, and (ii) an antigen binding fragment capable of binding to CD122.

In another aspect, the present invention provides an antibody or antigen binding fragment, optionally isolated, which is capable of binding to common γ chain (γc) and CD122, comprising:
(i) a γc-binding antigen binding fragment according to the present invention; and
(ii) a CD122-binding antigen binding fragment according to the present invention.

In another aspect, the present invention provides an in vitro complex, optionally isolated, comprising an antibody or antigen binding fragment, according to the present invention bound to CD122, optionally wherein the antibody or antigen binding fragment is bound to common γ chain (γc).

In another aspect, the present invention provides an in vitro complex, optionally isolated, comprising an antibody or antigen binding fragment, according to the present invention bound to common γ chain (γc), optionally wherein the antibody or antigen binding fragment is bound to CD122.

In some embodiments, the antibody or antigen binding fragment according to the present invention is conjugated to a drug moiety or a detectable moiety.

In another aspect, the present invention provides a chimeric antigen receptor (CAR) comprising an antigen binding fragment, optionally a bispecific antigen binding fragment, according to the present invention.

In another aspect, the present invention provides a cell comprising a chimeric antigen receptor (CAR) according to the present invention.

In another aspect, the present invention provides a composition comprising the antibody, antigen binding fragment, conjugate, chimeric antigen receptor (CAR) or cell according to the present invention, and at least one pharmaceutically-acceptable carrier, excipient, adjuvant or diluent.

In another aspect, the present invention provides an isolated nucleic acid encoding the antibody, antigen binding fragment, conjugate, or chimeric antigen receptor (CAR) according to the present invention. The nucleic acid may have a sequence of one of SEQ ID NOs 130, 131, 132, 133, 134, 135, 136, 137, 138, 19, 140, 141, 142, 143, 144, 145, 146 or 147 (FIGS. 17 and 18), or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In another aspect, the present invention provides a vector comprising the nucleic acid according to the present invention.

In another aspect, the present invention provides a host cell comprising the vector according to the present invention. For example, the host cell may be eukaryotic, or mammalian, e.g. Chinese Hamster Ovary (CHO), or human or may be a prokaryotic cell, e.g. *E. coli*.

In another aspect, the present invention provides a method for making an antibody, antigen binding fragment, conjugate, or chimeric antigen receptor (CAR) according to the present invention, comprising culturing the host cell according to the present invention under conditions suitable for the expression of a vector encoding the antibody, antigen binding fragment, conjugate or CAR, and recovering the antibody, antigen binding fragment, polypeptide, conjugate or CAR.

In another aspect, the present invention provides an antibody, antigen binding fragment, polypeptide, conjugate, chimeric antigen receptor (CAR), cell or composition according to the present invention for use in therapy, or in a method of medical treatment.

In another aspect, the present invention provides an antibody, antigen binding fragment, polypeptide, conjugate, chimeric antigen receptor (CAR), cell or composition according to the present invention for use in the treatment of cancer.

In another aspect, the present invention provides an antibody, antigen binding fragment, polypeptide, conjugate, chimeric antigen receptor (CAR), cell or composition according to the present invention for use in the treatment of an infectious disease.

In another aspect, the present invention provides the use of an antibody, antigen binding fragment, polypeptide, conjugate, chimeric antigen receptor (CAR), cell or composition according to the present invention in the manufacture of a medicament for use in the treatment of cancer.

In another aspect, the present invention provides the use of an antibody, antigen binding fragment, polypeptide, conjugate, chimeric antigen receptor (CAR), cell or composition according to the present invention in the manufacture of a medicament for use in the treatment of an infectious disease.

In another aspect, the present invention provides a method of treating cancer comprising administering an antibody, antigen binding fragment, polypeptide, conjugate, chimeric antigen receptor (CAR), cell or composition according to the present invention to a patient suffering from a cancer.

In another aspect, the present invention provides a method of treating an infectious disease comprising administering an antibody, antigen binding fragment, polypeptide, conjugate, chimeric antigen receptor (CAR), cell or composition according to the present invention to a patient suffering from an infectious disease.

In another aspect, the present invention provides a method comprising contacting, preferably in vitro, a sample containing, or suspected to contain, CD122 and/or common γ chain (γc) with an antibody, antigen binding fragment, polypeptide, conjugate, chimeric antigen receptor (CAR), cell or composition according to the present invention and detecting the formation of a complex of the antibody, antigen binding fragment, conjugate, CAR or cell with CD122 and/or γc.

In another aspect, the present invention provides a method of diagnosing a disease or condition in a subject, the method comprising contacting, preferably in vitro, a sample from the subject with an antibody, antigen binding fragment, conjugate, chimeric antigen receptor (CAR), cell or composition according to the present invention and detecting the formation of a complex of the antibody, antigen binding fragment, conjugate, CAR or cell with CD122 and/or common γ chain (γc).

In another aspect, the present invention provides a method of selecting or stratifying a subject for treatment with an CD122 and/or common γ chain (γc)-targeted agent, the method comprising contacting, preferably in vitro, a sample from the subject with an antibody, antigen binding fragment, conjugate, chimeric antigen receptor (CAR), cell or composition according to the present invention and detecting the formation of a complex of the antibody, antigen binding fragment, conjugate, CAR or cell with CD122 and/or γc.

In another aspect, the present invention provides the use of an antibody, antigen binding fragment, conjugate, chimeric antigen receptor (CAR), cell or composition according to the present invention for the detection of CD122 and/or common γ chain (γc) in vitro or in vivo.

In another aspect, the present invention provides the use of an antibody, antigen binding fragment, conjugate, chimeric antigen receptor (CAR), cell or composition according to the present invention as an in vitro or in vive diagnostic or prognostic agent.

In another aspect, the present invention provides a method for expanding a population of T cells and/or NK cells, wherein T cells and/or NK cells are contacted in vitro, in vive or ex vivo with an antibody, antigen binding fragment, conjugate, chimeric antigen receptor (CAR), cell or composition according to the present invention.

In another aspect, the present invention provides a method of treating an infectious disease or a cancer in a subject, the method comprising culturing T cells and/or NK cells obtained from a blood sample from a subject in the presence of an antibody, antigen binding fragment, conjugate, chimeric antigen receptor (CAR), cell or composition according to the present invention so as to expand a T cell and/or NK cell population, collecting expanded T cells and/or NK cells, and administering the expanded T cells and/or NK cells to a subject in need of treatment.

In another aspect, the present invention provides a method of treating an infectious disease or a cancer in a subject, the method comprising administering an antibody, antigen binding fragment, conjugate, chimeric antigen receptor (CAR), cell or composition according to the present invention to the subject so as to expand a T cell and/or NK cell population.

The following numbered paragraphs (paras) describe further aspects of the present invention:

1. An isolated IL-2R bispecific antigen binding protein comprising:
(i) a first IL-2Rβ binding polypeptide:
(a) a binding unit VL1 consisting of an amino acid sequence of SEQ ID NO:1, 5, 9, or 13, or a variant thereof which contains at least one amino acid substitution, insertion or deletion in the binding unit VL1;
(b) a binding unit VH1 consisting of an amino acid sequence of SEQ ID NO:35, 39, 43, or 47, or a variant thereof which contains at least one amino acid substitution, insertion or deletion in the binding unit VH1;
(ii) a second IL-2Rγ binding polypeptide:
(c) a binding unit VL2 consisting of an amino acid sequence of SEQ ID NO:67 or 71, or a variant thereof which contains at least one amino acid substitution, insertion or deletion in the binding unit VL2, and
(d) a binding unit VH2 consisting of an amino acid sequence of SEQ ID NO:76 or 78, or a variant thereof which contains at least one amino acid substitution, insertion or deletion in the binding unit VH2.

2. The isolated IL-2R bispecific antigen binding protein as defined in para 1, wherein the said first IL-2Rβ binding polypeptide and said second IL-2Rγ binding polypeptide are linked by a peptide linker.

3. The isolated IL-2R bispecific antigen binding protein as defined in para 2, wherein the said peptide linker is from 5-23 amino acids in length.

4. The isolated IL-2R bispecific antigen binding protein as defined in para 1, wherein said first IL-2Rβ binding polypeptide further comprises an Fc portion comprising a CH3 domain, in which the CH3 domain comprises or consists of an amino acid sequence of SEQ ID NO:92, and wherein said second IL-2Rγ binding polypeptide further comprises an Fc portion comprising a CH3 domain, in which the CH3 domain comprises or consists of an amino acid sequence of SEQ ID NO:94.

5. The isolated IL-2R bispecific antigen binding protein as defined in para 4, wherein said first and second polypeptides meet at an engineered interface within the CH3 domains, wherein the first polypeptide comprises at least one engineered protuberance in said interface, said protuberance comprising at least one altered contact residue and the second polypeptide comprises at least one engineered cavity in its said interface, said cavity comprising at least one altered contact residue so as to form a protuberance-into-cavity pairing.

6. The isolated IL-2R bispecific antigen binding protein as defined in para 4 or para 5, wherein the said binding units are linked to said Fc portion by a linker.

7. The isolated IL-2R bispecific antigen binding protein as defined in para 6, wherein said linker is from 5-23 amino acids in length.

8. The isolated, IL-2R bispecific antigen binding protein as defined in any one of paras 4 to 7 comprising:
(i) a first IL-2Rβ binding polypeptide:
(a) a binding unit VL1 consisting of an amino acid sequence of SEQ ID NO:1, or a variant thereof which contains at least one amino acid substitution, insertion or deletion in the binding unit VL1;
(b) a binding unit VH1 consisting of an amino acid sequence of SEQ ID NO:35, or a variant thereof which contains at least one amino acid substitution, insertion or deletion in the binding unit VH1;
(c) an Fc portion comprising a CH3 domain, in which the CH3 domain comprises or consists of an amino acid sequence of SEQ ID NO:92, and
(ii) a second IL-2Rγ binding polypeptide:
(d) a binding unit VL2 consisting of an amino acid sequence of SEQ ID NO: 67, or a variant thereof which contains at least one amino acid substitution, insertion or deletion in the binding unit VL2;
(e) a binding unit VH2 consisting of an amino acid sequence of SEQ ID NO: 76, or a variant thereof which contains at least one amino acid substitution, insertion or deletion in the binding unit VH2, and
(f) an Fc portion comprising a CH3 domain, in which the CH3 domain comprises or consists of an amino acid sequence of SEQ ID NO:94.

9. The isolated IL-2R bispecific antigen binding protein as defined in para 8, wherein said binding protein has a dissociation constant ($K_D$) to human IL-2Rβ of $1.46\times10^{-7}$M and a dissociation constant ($K_D$) to human IL-2Rγ of $2.09\times10^{-8}$ M.

10. The isolated, IL-2R bispecific antigen binding protein as defined in any one of paras 4 to 7 comprising:
(i) a first IL-2Rβ binding polypeptide:
(a) a binding unit VL1 consisting of an amino acid sequence of SEQ ID NO:5, or a variant thereof which contains at least one amino acid substitution, insertion or deletion in the binding unit VL1;
(b) a binding unit VH1 consisting of an amino acid sequence of SEQ ID NO:39, or a variant thereof which contains at least one amino acid substitution, insertion or deletion in the binding unit VH1;
(c) an Fc portion comprising a CH3 domain, in which the CH3 domain comprises or consists of an amino acid sequence of SEQ ID NO:92, and
(ii) a second IL-2Rγ binding polypeptide:
(d) a binding unit VL2 consisting of an amino acid sequence of SEQ ID NO:71, or a variant thereof which contains at least one amino acid substitution, insertion or deletion in the binding unit VL2;
(e) a binding unit VH2 consisting of an amino acid sequence of SEQ ID NO:78, or a variant thereof which contains at least one amino acid substitution, insertion or deletion in the binding unit VH2, and
(f) an Fc portion comprising a CH3 domain, in which the CH3 domain comprises or consists of an amino acid sequence of SEQ ID NO:94.

11. The isolated IL-2R bispecific antigen binding protein defined in para 10, wherein said binding protein has a dissociation constant ($K_D$) to human IL-2Rβ of $1.01\times10^{-7}$M and a dissociation constant ($K_D$) to human IL-2Rγ of $7.98\times10^{-8}$M.

12. The isolated, IL-2R bispecific antigen binding protein as defined in any one of paras 4 to 7 comprising:
(i) a first IL-2Rβ binding polypeptide:
(a) a binding unit VL1 consisting of an amino acid sequence of SEQ ID NO: 9, or a variant thereof which contains at least one amino acid substitution, insertion or deletion in the binding unit VL1;
(b) a binding unit VH1 consisting of an amino acid sequence of SEQ ID NO: 43, or a variant thereof which contains at least one amino acid substitution, insertion or deletion in the binding unit VH1;
(c) an Fc portion comprising a CH3 domain, in which the CH3 domain comprises or consists of an amino acid sequence of SEQ ID NO:92, and
(ii) a second IL-2Rγ binding polypeptide:
(d) a binding unit VL2 consisting of an amino acid sequence of SEQ ID NO:67, or a variant thereof which contains at least one amino acid substitution, insertion or deletion in the binding unit VL2;
(e) a binding unit VH2 consisting of an amino acid sequence of SEQ ID NO:76, or a variant thereof which contains at least one amino acid substitution, insertion or deletion in the binding unit VH2, and
(f) an Fc portion comprising a CH3 domain, in which the CH3 domain comprises or consists of an amino acid sequence of SEQ ID NO:94.

13. The isolated IL-2R bispecific antigen binding protein defined in para 12, wherein said binding protein has a dissociation constant ($K_D$) to human IL-2Rβ of $1.81\times10^{-7}$ M and a dissociation constant (K) to human IL-2Rγ of $7.87\times10^{-8}$ M 14. The isolated, IL-2R bispecific antigen binding protein as defined in any one of paras 4 to 7 comprising:
(i) a first IL-2Rβ binding polypeptide:
(a) a binding unit VL1 consisting of an amino acid sequence of SEQ ID NO:13, or a variant thereof which contains at least one amino acid substitution, insertion or deletion in the binding unit VL1;
(b) a binding unit VH1 consisting of an amino acid sequence of SEQ ID NO:47, or a variant thereof which contains at least one amino acid substitution, insertion or deletion in the binding unit VH 1;
(c) an Fc portion comprising a CH3 domain, in which the CH3 domain comprises or consists of an amino acid sequence of SEQ ID NO:92, and
(ii) a second IL-2Rγ binding polypeptide:
(d) a binding unit VL2 consisting of an amino acid sequence of SEQ ID NO:67, or a variant thereof which contains at least one amino acid substitution, insertion or deletion in the binding unit VL2;
(e) a binding unit VH2 consisting of an amino acid sequence of SEQ ID NO:76, or a variant thereof which contains at least one amino acid substitution, insertion or deletion in the binding unit VH2, and
(f) an Fc portion comprising a CH3 domain, in which the CH3 domain comprises or consists of an amino acid sequence of SEQ ID NO:94.

15. The isolated IL-2R bispecific antigen binding protein as defined in para 14, wherein said binding protein has a dissociation constant ($K_D$) to human IL-2Rβ of $1.28 \times 10^{-7}$ M and a dissociation constant ($K_D$) to human IL-2Rγ of $3.37 \times 10^{-7}$ M.

16. The isolated IL-2R bispecific antigen binding protein as defined in any one of paras 1 to 15, wherein the IL-2R is human or simian IL-2R.

17. The isolated IL-2R bispecific antigen binding protein as defined in any one of paras 1 to 16, wherein said antigen binding protein is fully human.

18. The isolated IL-2R bispecific antigen binding protein as defined in any one of paras 1 to 17, wherein said binding protein further comprises an agent selected from the group consisting of an immunoadhesion molecule, an imaging agent, a therapeutic agent, and a cytotoxic agent.

19. The isolated IL-2R bispecific antigen binding protein of para 18, wherein said agent is an imaging agent selected from the group consisting of a radiolabel, an enzyme, a fluorescent label, a luminescent label, a bioluminescent label, a magnetic label, and biotin.

20. The isolated IL-2R bispecific antigen binding protein of para 18, wherein said agent is a therapeutic or cytotoxic agent selected from the group consisting of an antimetabolite, an alkylating agent, an antibiotic, an antiviral agent, a growth factor, a cytokine, an anti-angiogenic agent, an anti-mitotic agent, an anthracycline, toxin and an apoptotic agent.

21. The isolated IL-2R bispecific antigen binding protein as defined in any one of paras 1 to 20, wherein said binding protein is an agonist of IL-2R.

22. A method of treating an infectious disease or cancer in a subject, comprising administering the isolated antigen binding protein as defined in any one of paras 1 to 21 to a subject in need of such treatment.

23. The method as defined in para 22, wherein the cancer is melanoma, renal carcinoma cancer or bladder cancer.

24. Use of the isolated antigen binding protein as defined in any one of paras 1 to 21, in the manufacture of a medicament for treating an infectious disease or cancer.

25. The use as defined in para 24, wherein the cancer is melanoma, renal carcinoma cancer or bladder cancer.

26. A composition comprising the isolated IL-2R bispecific antigen binding protein as defined in any one of paras 1 to 21 and a pharmaceutically acceptable carrier.

27. The composition of para 26, further comprising one or more therapeutic agents.

28. The composition of para 27, wherein said one or more therapeutic agents are selected from antibiotic agents, antiviral agents, antifungal agents, chemotherapeutic agents, small molecule inhibitors, immunotherapy agents, vaccines, adoptive cell therapy agents, immune checkpoint inhibitors or antibody therapeutics.

29. An isolated cell line that is capable of producing the isolated IL-2R bispecific antigen binding protein as defined in any one of paras 1 to 21.

30. A kit comprising the isolated IL-2R bispecific antigen binding protein as defined in any one of paras 1 to 21, together with instructions for use.

DESCRIPTION

The present invention encompasses the nucleotide and amino acid sequences of a bispecific antibody with specificity for interleukin-2 receptor (IL-2R) chains β and γ, able to stimulate cells expressing the medium affinity IL-2R β-γ and not preferentially cells expressing the high affinity IL-2R α-β-γ.

This disclosure describes the design of an IL-2Rα-independent IL-2R agonist in which receptor activation is achieved through heterodimerization of the β-$γ_c$ components by bispecific antibodies (or bi-functional proteins) possessing anti-IL-2Rβ (CD122) and anti-$γ_c$ (CD132) specificities. Use of such molecules can convey desired immune stimulation by activation of immune cells, particularly the T cells, without preferential and high activation of cells expressing the high affinity α-β-$γ_c$ IL-2R. Such molecules would be useful as vaccine adjuvants.

Isolated nucleotide and amino-acid sequences for two fully human monoclonal antibodies binding to IL-2Rβ (CD122) or IL-2Rγ (CD132) are described.

Nucleotide and amino-acid sequences of the engineered antibody showing monovalent specificity for IL-2Rβ and IL-2$Rγ_c$ are described.

Bispecific antibody construct containing variable domains derived from the aforementioned isolated monoclonal antibodies and able to bind both IL-2Rβ and IL-2$Rγ_c$ are described.

Bifunctional protein containing IL-2Rβ and IL-2$Rγ_c$ binding domains derived from the sequences of the aforementioned isolated monoclonal antibodies are described.

An antibody or a bifunctional protein binding to the IL-2Rβ/$γ_c$ and triggering phosphorylation of STAT5 and/or Akt is described.

An antibody or a bifunctional protein binding to the IL-2Rβ/$γ_c$ and not binding to the IL-2Rα/β/$γ_c$ (CD25) with higher affinity is described.

An antibody or a bifunctional protein agonistically binding to the IL-2Rβ/$γ_c$ and triggering intracellular signalling, and antagonistically binding to the IL-2Rα/β/$γ_c$ (CD25) without triggering intracellular signalling is described.

The use of any of these molecules in the treatment of cancers or infectious diseases, alone or in combination with anti-cancer or anti-infectious drugs is described.

Antibodies

Antibodies according to the present invention preferably bind to CD122 (interleukin 2 receptor β (IL-2Rβ)) and/or common γ chain (γc). In some embodiments, the antibody/fragment binds to human CD122 and/or human γc. In some embodiments, the antibody/fragment binds to non-human primate CD122 and/or non-human primate γc.

By "antibody" we include a fragment or derivative thereof, or a synthetic antibody or synthetic antibody fragment. Antibodies according to the present invention may be provided in isolated form.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Antigen binding fragments of antibodies, such as Fab and $Fab_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sci. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and $F(ab')_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site.

The present invention provides an antibody or antigen binding fragment which is capable of binding to CD122 and γc. In some embodiments, the antibody/fragment is a bispecific antibody or a bispecific antigen binding fragment. In some embodiments, the bispecific antibody or bispecific antigen binding fragment may be isolated.

In some embodiments, the bispecific antibodies and bispecific antigen binding fragments comprise an antibody/fragment which is capable of binding to CD122, e.g. an antibody/fragment as described herein.

In some embodiments, the bispecific antibodies and bispecific antigen binding fragments comprise an antibody/fragment which is capable of binding to γc, e.g. an antibody/fragment as described herein.

In some embodiments, the bispecific antibodies/fragments comprise an antibody/fragment capable of binding to CD122, and an antibody/fragment capable of binding to another target protein.

In some embodiments, the bispecific antibodies/fragments comprise an antibody/fragment capable of binding to γc, and an antibody/fragment capable of binding to another target protein.

The antigen binding fragment capable of binding to another target protein may be capable of binding to another protein other than CD122 or γc.

In one aspect of the present invention a bispecific antibody is provided, which binds γc but does not bind to CD122.

An antigen-binding fragment of a bispecific antibody/fragment according to the present invention may be any fragment of a polypeptide which is capable of binding to an antigen.

In some embodiments, an antigen binding fragment comprises at least the three light chain complementarity determining regions (CDRs) (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

Bispecific antibodies and fragments according to the invention may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, $F(ab')_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tandAbs, tandem scFv (taFv), tandem dAb/VHH, triple body, triple head, Fab-scFv, or $F(ab')_2$-scFv$_2$), a bispecific Fc and CH3 fusion protein (e.g. a taFv-Fc, Di-diabody, scDb-C$_{H3}$, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

In some embodiments an scFv dimer format is preferred in which two scFv, each exhibiting specific binding for a different antigen, are connected by a linker, e.g. as illustrated in FIG. 25A, right.

A linker may be an amino acid sequence of any desired length, e.g. one of 2 to 50 amino acids, 5 to 50 amino acids, 5 to 40 amino acids, 5 to 30 amino acids, 5 to 20 amino acids, or 5 to 10 amino acids.

The skilled person is able to design and prepare bispecific antibodies and bispecific antigen binding fragments according to the present invention. Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.132.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific $F(ab)_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies:

Diabodies and Tandem scFv (Homig and Färber-Schwarz), or French, How to make bispecific antibodies, Methods Mol. Med. 2000; 40:333-339, the entire contents of both of which are hereby incorporated by reference.

For example, a DNA construct encoding the light and heavy chain variable domains for the two antigen binding fragments (i.e. the light and heavy chain variable domains for the antigen binding fragment capable of binding CD122 or γc, and the light and heavy chain variable domains for the antigen binding fragment capable of binding to another target protein), and including sequences encoding a suitable linker or dimerization domain between the antigen binding fragments can be prepared by molecular cloning techniques.

Recombinant bispecific antibody can thereafter be produced by expression (e.g. in vitro) of the construct in a suitable host cell (e.g. a mammalian host cell), and expressed recombinant bispecific antibody can then optionally be purified.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention may exhibit specific binding to CD122, and/or γc.

An antibody that specifically binds to a target molecule preferably binds the target with greater affinity, and/or with greater duration than it binds to other targets. In some embodiments the present antibodies may bind with greater affinity to CD122 and/or γc than to one or more members of the type I cytokine receptor family. In some embodiments, the extent of binding of an antibody to an unrelated target is less than about 10% of the binding of the antibody to the target as measured, e.g., by ELISA, SPR, Bio-Layer Interferometry or by a radioimmunoassay (RIA). Alternatively, the binding specificity may be reflected in terms of binding affinity where the anti-CD122 and/or γc antibody of the present invention binds to CD122 and/or γc with a $K_D$ that is at least 0.1 order of magnitude (i.e. $0.1 \times 10^n$, where n is an integer representing the order of magnitude) greater than the $K_D$ of the antibody towards another target molecule. This may optionally be one of at least 0.2, 0.3, 0.4, 0.5, 0.6, 0.7, 0.8, 0.9, 1.0, 1.5, or 2.0.

Binding affinity of an antibody for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), or by a radiolabeled antigen binding assay (RIA) performed with the Fab version of the antibody and antigen molecule.

In some embodiments, the antibody according to the present invention has a dissociation constant ($K_D$) for CD122 of one of $\leq 1\times10^{-6}$ M, $\leq 7.5\times10^{-7}$ M, $\leq 5\times10^{-7}$ M, $\leq 4.5\times10^{-7}$ M, $\leq 4\times10^{-7}$ M, $\leq \times10^{-7}$ M, $\leq 4.5\times10^{-7}$ M, $\leq 3\times10^{-7}$ M, $\leq 3.5\times10^{-7}$ M, $3\times10^{-7}$ M, $\leq 2.5\times10^{-7}$ M, $\leq 2\times10^{-7}$ M, $\leq 1.9\times10^{-7}$ M, $\leq 1.8\times10^{-7}$ M, $\leq 1.7\times10^{-7}$ M, $\leq 1.6\times10^{-7}$ M, $\leq 1.5\times10^{-7}$ M, $\leq 1.4\times10^{-7}$ M, $\leq 1.3\times10^{-7}$ M, $\leq 1.2\times10^{-7}$ M, $\leq 1.1\times10^{-7}$ M, $\leq 1\times10^{-7}$ M, $\leq 8\times10^{-8}$ M, $\leq 6\times10^{-8}$ M, $\leq 4\times10^{-8}$ M, or $\leq 2\times10^{-8}$ M.

In some embodiments, the antibody according to the present invention has a $K_D$ for γc of one of $\leq 10\times10^{-7}$ M, $\leq 7.5\times10^{-7}$ M, $\leq \times10^{-7}$ M, $\leq 2.5\times10^{-7}$ M, $\leq 1\times10^{-7}$ M, $\leq 9.5\times10^{-8}$ M, $\leq 9\times10^{-8}$ M, $\leq 8.5\times10^{-8}$ M, $\leq 8\times10^{-8}$ M, $\leq 7.5\times10^{-8}$ M, $\leq 7\times10^{-8}$ M, $\leq 6.5\times10^{-8}$ M, $\leq 6\times10^{-8}$ M, $\leq 5.5\times10^{-8}$ M, $\leq 5\times10^{-8}$ M, $\leq 4.5\times10^{-8}$ M, $\leq 4\times10^{-8}$ M, $\leq 3.5\times10^{-8}$ M, $\leq 3\times10^{-8}$ M, $\leq 2.5\times10^{-8}$ M, $\leq 2\times10^{-8}$ M, $\leq 1.5\times10^{-8}$ M, $\leq 1\times10^{-8}$ M, $\leq 8\times10^{-9}$ M, $\leq 6\times10^{-9}$ M, $\leq 4\times10^{-9}$ M or $\leq 2\times10^{-9}$ M.

In some embodiments, the antibody according to the present invention has a $K_D$ for CD122 of one of $\leq 1\times10^{-6}$ M, $\leq 7.5\times10^{-7}$ M, $\leq 5\times10^{-7}$ M, $\leq 4.5\times10^{-7}$ M, $\leq 4\times10^{-7}$ M, $\leq 5\times10^{-7}$ M, $\leq 4.5\times10^{-7}$ M, $\leq 3\times10^{-7}$ M, $\leq 3.5\times10^{-7}$ M, $\leq 3\times10^{-7}$ M, $\leq 2.5\times10^{-7}$ M, $\leq 2\times10^{-7}$ M, $\leq 1.9\times10^{-7}$ M, $\leq 1.8\times 10^{-7}$ M, $\leq 1.7\times10^{-7}$ M, $\leq 1.6\times10^{-7}$ M, $\leq 1.5\times10^{-7}$ M, $\leq 1.4\times 10^{-7}$ M, $\leq 1.3\times10^{-7}$ M, $\leq 1.2\times10^{-7}$ M, $\leq 1.1\times10^{-7}$ M, $\leq 1\times10^{-7}$ M, $\leq 8\times10^{-8}$ M, $\leq 6\times10^{-8}$ M, $\leq 4\times10^{-8}$ M, or $\leq 2\times10^{-8}$ M and a $K_D$ for γc of one of $\leq 10\times10^{-7}$ M, $\leq 7.5\times10^{-7}$ M, $\leq 5\times10^{-7}$ M, $\leq 2.5\times10^{-7}$ M, $\leq 1\times10^{-7}$ M, $\leq 9.5\times10^{-8}$ M, $\leq 9\times10^{-8}$ M, $\leq 8.5\times10^{-8}$ M, $\leq 8\times10^{-8}$ M, $\leq 7.5\times10^{-8}$ M, $\leq 7\times10^{-8}$ M, $\leq 6.5\times10^{-8}$ M, $\leq 6\times10^{-8}$ M, $\leq 5.5\times10^{-8}$ M, $\leq 5\times10^{-8}$ M, $\leq 4.5\times10^{-8}$ M, $\leq 4\times10^{-8}$ M, $\leq 3.5\times10^{-8}$ M, $\leq 3\times10^{-8}$ M, $\leq 2.5\times10^{-8}$ M, $\leq 2\times10^{-8}$ M, $\leq 1.5\times10^{-8}$ M, $\leq 1\times10^{-8}$ M, $\leq 8\times10^{-9}$ M, $\leq 6\times10^{-9}$ M, $\leq 4\times10^{-9}$ M or $2\times10^{-9}$ M.

In some embodiments, the antibody according to the present invention binds to CD122 and/or γc expressed at the cell surface of a cell expressing CD122 and/or γc. Such binding can be analysed by analysis of binding of the antibody to PBMCs incubated with the antibody, or cells transfected with constructs expressing CD122 and/or γc, and subsequent analysis of antibody binding, e.g. by flow cytometry.

In some embodiments, the antibody according to the present invention is an agonist of one or more signalling pathways which are activated by signal transduction through receptors comprising CD122 and/or γc, e.g. IL-2 receptor and/or IL-15 receptor. In some embodiments, the antibody is capable of stimulating signalling through one or more immune receptor complexes comprising CD122 and/or γc, e.g. IL-2 receptor and/or IL-15 receptor.

In some embodiments, the antibody is an IL-2 receptor agonist. Accordingly in some embodiments, the antibody is capable of activating IL-2/IL-2 receptor-mediated signalling and associated functions. For example, the in some embodiments, the antibody is capable of promoting cell division/proliferation/survival of a cell expressing the IL-2 receptor.

In some embodiments, the antibody is an IL-15 receptor agonist. Accordingly in some embodiments, the antibody is capable of activating IL-15/IL-15 receptor-mediated signalling and associated functions. For example, the in some embodiments, the antibody is capable of promoting cell division/proliferation/survival of a cell expressing the IL-15 receptor.

In some embodiments bispecific antibodies according to the present invention may preferentially bind (e.g. with greater affinity and/or specificity) receptors comprising or consisting of CD122 and γc compared to receptors that further comprise CD25. Bispecific antibodies may preferentially stimulate receptors (or cells expressing receptors) comprising or consisting of CD122 and γc, but not further comprising CD25.

In some embodiments bispecific antibodies according to the present invention that bind CD122 and γc preferably do not exhibit significant inhibition of ligand binding to receptors having the common gamma chain and not containing CD122, e.g. receptors other than IL-2R and IL-15R. For example, bispecific antibodies according to the present invention may be specific for receptors comprising both CD122 and γc over receptors that comprise γc but do not comprise CD122.

In some embodiments, the antibody according to the present invention is capable of stimulating CD122:γc mediated signalling through one of more of the following intracellular signalling pathways: STAT5, Akt, ERK. Signalling through STAT5, Akt, ERK intracellular signalling pathways can be analysed by methods well known to the skilled person, such as e.g. by detection of phosphorylated STAT5, phosphorylated Akt and optionally phosphorylated ERK, respectively following stimulation of cells expressing CD122 and/or γc with the antibody.

In some embodiments, the antibody according to the present invention is a less potent stimulator of intracellular signalling in Treg cells than IL-2. For example, treatment with the antibody may result in less phosphorylation of STAT5 as compared to treatment with IL-2.

In some embodiments, the antibody is capable of stimulating proliferation of immune cells in vitro and or in vivo. Stimulation of proliferation results in an increase in the number of the cell type whose proliferation is stimulated, effective to achieve expansion of the cell population. For example, the antibody is useful in stimulating proliferation and/or expansion of leukocytes in vitro or in vivo, preferably exhibiting reduced toxicity when compared to the effects of a corresponding amount of IL-2.

In some embodiments, the antibody is capable of stimulating proliferation of IL-2 dependent cells. In some embodiments, the antibody is capable of stimulating proliferation of CD3+ T cells (e.g. CD4+ T cells, CD8+ T cells) and/or NK cells.

Whether an antibody is capable of stimulating proliferation of cells can be analysed in vitro by methods well known in the art, such as by analysis of the number of a given cell type before and after stimulation, and/or by another assay, such as thymidine incorporation, CFSE dilution (e.g. as described in Anthony et al., 2012 Cells 1:127-140), AlamarBlue signal etc.

In some embodiments, the antibody according to the present invention is capable of binding to non-human primate (e.g. cynomolgus macaque) CD122 and/or γc. The antibody may be cross-reactive for human and non-human primate CD122 and/or γc. Accordingly, in some embodiments, the antibody is capable of stimulating IL-2/IL-2 receptor- and/or IL-15/IL-15 receptor-mediated mediated signalling in cells expressing non-human primate (e.g. cynomolgous macaque) CD122 and/or γc.

In some embodiments, the antibody of the present invention is capable of stimulating proliferation of CD3+ T cells. In some embodiments, the antibody of the present invention is capable of stimulating proliferation of CD4+ T cells. In some embodiments, the antibody of the present invention is capable of stimulating proliferation of CD8+ T cells.

In some embodiments, the antibody of the present invention is capable of increasing the ratio of CD8+ T cells to CD4+ T cells. That is, in some embodiments, following stimulation (e.g. in vitro or in vivo) of a population of cells comprising CD8+ T cells and CD4+ T cells, the ratio of CD8+ T cells to CD4+ T cells may be higher following stimulation as compared to before stimulation.

In some embodiments, the antibody of the present invention is not a potent stimulator of proliferation of CD4+ FoxP3+ cells (i.e. Tregs). In some embodiments, the antibody does not stimulate proliferation of Tregs.

In some embodiments, the antibody of the invention stimulates proliferation of Tregs to a lesser extent than IL-2.

That is, in some embodiments, the antibody of the invention is a less potent agonist of proliferation of Tregs than IL-2. In some embodiments, the antibody of the invention stimulates proliferation of Tregs to an extent which is ≤1 times, ≤0.8 times, ≤0.6 times, ≤0.4 times, ≤0.2 times, ≤0.1 times the level of proliferation of Tregs stimulated by treatment with IL-2 at a comparable concentration, in a given assay.

In some embodiments, the antibody of the present invention preferentially stimulates proliferation of the effector memory subset of CD8+ T cells over the central memory CD8+ T cell and naïve CD8+ T cell populations.

In some embodiments, the antibody of the present invention stimulates proliferation of effector memory CD8+ T cells to a greater extent than IL-2 at a comparable concentration, in a given assay.

In some embodiments, the antibody of the present invention is capable of stimulating proliferation of antigen-specific T cells, e.g. antigen-specific CD8+ T cells and/or antigen-specific CD4+ T cells. Stimulation may occur in vitro or in vivo. In some embodiments, the antibody of the present invention is capable of stimulating proliferation of antigen-specific CD8+ cytotoxic T lymphocytes (CTLs). Ability of cells to stimulate proliferation of antigen-specific T cells can be evaluated e.g. by analysis of proliferation of T cells incubated with cells presenting an antigen of interest in the presence of the antibody, e.g. as described in Examples 8 and 11 herein.

In some embodiments, the antibody of the present invention is capable of stimulating proliferation of antigen-specific T cells to a greater extent than IL-2 at a comparable concentration, in a given assay.

In some embodiments, the antibody of the present invention is capable of stimulating proliferation of antigen-specific CD8+ T cells to a greater extent than IL-2 at a comparable concentration, in a given assay.

In some embodiments, the antibody of the present invention is capable of increasing the ratio of antigen-specific CD8+ T cells to CD4+ T cells. This may occur in vitro or in vivo.

That is, in some embodiments, following stimulation (e.g. in vitro) of a population of cells comprising antigen-specific CD8+ T cells and CD4+ T cells, the ratio of CD8+ T cells to CD4+ T cells is higher following stimulation as compared to before stimulation. In some embodiments, the antibody of the invention is capable of increasing the ratio of antigen-specific CD8+ T cells to CD4+ T cells to a greater extent than IL-2 at a comparable concentration, in a given assay.

In some embodiments, the antibody of the present invention is capable of stimulating proliferation of CD8+ PD1+ T cells (e.g. antigen-specific CD8+ PD1+ T cells). In some embodiments, the antibody of the present invention is capable of stimulating proliferation of CD8+ PD1+ T cells to a greater extent than IL-2 at a comparable concentration, in a given assay.

In some embodiments, the antibody of the present invention is capable of reducing the proportion of Tregs as a proportion of CD4+ T cells. That is, in some embodiments, following treatment of a population of CD4+ T cells with the antibody, the percentage of the CD4+ T cells which are Tregs is reduced. In some embodiments, the antibody of the present invention is capable of reducing the proportion of Tregs as a proportion of CD4+ T cells to a greater extent than IL-2 at a comparable concentration, in a given assay.

In some embodiments, the antibody of the present invention is capable of stimulating CTL cytotoxicity. Ability of an antibody to stimulate CTL cytotoxicity can be measured by methods known to the skilled person. Cytotoxicity of a T cell to a given target cell can be investigated, for example, using any of the methods reviewed in Zaritskaya et al. Expert Rev Vaccines (2011), 9(6):601-616, hereby incorporated by reference in its entirety.

In some embodiments, the antibody is capable of stimulating the proliferation of immune cells in vivo. In some embodiments, the antibody is capable of stimulating the proliferation of CD3+ cells in vivo. In some embodiments, the antibody is capable of stimulating the proliferation of CD8+ T cells in vivo. In some embodiments, the antibody is capable of stimulating the proliferation of CD4+ T cells in vivo. In some embodiments, the antibody is capable of stimulating the proliferation of NK cells in vivo.

In aspects and embodiments of the present invention stimulation or expansion of cells having desired characteristics may occur in vitro or in vivo. In vitro stimulation or expansion may provide a population of cells enriched for desired characteristics that may be collected and used for a desired purpose, which may include administration to a subject. In vivo stimulation or expansion may enrich for a population of cells that are beneficial to the subject, e.g. in treating or preventing a disease. In vive stimulation or expansion may have an adjuvant effect or action.

In some aspects, the antibody of the present invention comprises the antibody/fragment of a CD122-binding antibody clone. In some aspects, the antibody comprises the antibody/fragment of clone P2C4 or a variant of P2C4. In some aspects, the antibody comprises the antibody/fragment of clone P2C4_A4 or a variant of P2C4_A4. In some aspects, the antibody comprises the antibody/fragment of clone P2C4_B1 or a variant of P2C4_B1. In some aspects, the antibody comprises the antibody/fragment of clone P2C4_B5 or a variant of P2C4_B5. In some aspects, the antibody comprises the antibody/fragment of clone P2C4_C1 or a variant of P2C4_C1. In some aspects, the antibody comprises the antibody/fragment of clone P2C4_C4 or a variant of P2C4_C4. In some aspects, the antibody comprises the antibody/fragment of clone P2C4_C7 or a variant of P2C4_C7. In some aspects, the antibody comprises the antibody/fragment of clone P2C4_D10 or a variant of P2C4_D10. In some aspects, the antibody comprises the antibody/fragment of clone P2C4_E6 or a variant of P2C4_E6. In some aspects, the antibody comprises the antibody/fragment of clone P2C4_E7 or a variant of P2C4_E7. In some aspects, the antibody comprises the antibody/fragment of clone P2C4_F8 or a variant of P2C4_F8. In some aspects, the antibody comprises the antibody/fragment of clone P2C4_C1D10 or a variant of P2C4_C1D10. In some aspects, the antibody comprises the antibody/fragment of clone P2C4_FW2 or a variant of P2C4_FW2. In some aspects, the antibody comprises the antibody/fragment of clone P2H7 or a variant of P2H7. In some aspects, the antibody comprises the antibody/fragment of clone P2D12 or a variant of P2D12. In some aspects, the antibody comprises the antibody/fragment of clone P1G11 or a variant of P1G11. In some aspects, the antibody comprises the antibody/fragment of clone P2C4_A9 or a variant of P2C4_A9. In some aspects, the antibody comprises the antibody/fragment of clone P2C4_B6 or a variant of P2C4_B6. In some aspects, the antibody comprises the antibody/fragment of clone P2C4_E9 or a variant of P2C4_E9. In some aspects, the antibody comprises the antibody/fragment of clone P2C4_B8 or a variant of P2C4_B8. In some aspects, the antibody comprises the antibody/fragment of clone P2C4_B12 or a variant of P2C4_B12. In some aspects, the antibody comprises the antibody/fragment of clone P2C4_C12 or a variant of P2C4_C12. In some aspects, the antibody comprises the antibody/fragment of clone P2C4_E2 or a variant of P2C4_E2. In some aspects, the antibody comprises the antibody/fragment of clone P2C4_E3 or a variant of P2C4_E3. In some aspects, the antibody comprises the antibody/fragment of clone P2C4_E8 or a variant of P2C4_E8. In some aspects, the antibody comprises the antibody/fragment of clone P2C4_F11 or a variant of P2C4_F11. In some aspects, the antibody comprises the antibody/fragment of clone P2C4_G2 or a variant of P2C4_G2. In some aspects, the antibody comprises the antibody/fragment of clone P2C4_G11 or a variant of P2C4_G11. In some aspects, the antibody comprises the antibody/fragment of clone P2C4_H1 or a variant of P2C4_H1. In some aspects, the antibody comprises the antibody/fragment of clone P2C4_H2 or a variant of P2C4_H2. In some aspects, the antibody comprises the antibody/fragment of clone P2C4_H3 or a variant of P2C4_H3.

The amino acid sequences of the VL domains of the CD122-binding antibody clones of the preceding paragraph are shown in FIG. 1, as are the CDRs defined according to the Kabat system. The amino acid sequences of the VH domains of the CD122-binding antibody clones of the preceding paragraph are shown in FIG. 2, as are the CDRs defined according to the Kabat system. The full amino acid sequences of the antibody constructs (including linkers) are shown in FIG. 15, and the encoding nucleotide sequences are shown in FIG. 17.

Antibodies according to the present invention may comprise the CDRs of P2C4, P2C4_A4, P2C4_B1, P2C4_B5, P2C4_C1, P2C4_C4, P2C4_C7, 2C4_D10, P2C4_E6, P2C4_E7, P2C4_F8, P2C4_C1 D10, P2C4_FW2, P2H7, P2D12, P1G11, P2C4_A9, P2C4_B6, P2C4_E9, P2C4_B8, P2C4_B12, P2C4_C12, P2C4_E2, P2C4_E3, P2C4_E8, P2C4_F11, P2C4_G2, P2C4_G11, P2C4_H1, P2C4_H2, or P2C4_H3. In an antibody according to the present invention one or two or three or four of the six CDR sequences may vary. A variant may have one or two amino acid substitutions in one or two of the six CDR sequences.

Antibodies according to the present invention may comprise VL and/or VH chains comprising an amino acid sequence that has a high percentage sequence identity to one or more of the VL and/or VH amino acid sequences shown in FIGS. 1 and 2, respectively. For example, antibodies according to the present invention include antibodies that bind CD122 and have a VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs:1, 17, 19, 21, 23, 24, 27, 28, 29, 30, 31, 33, 34, 148, 149, 5, 9, or 13 shown in FIG. 1. Antibodies according to the present invention include antibodies that bind CD122 and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs:35, 51, 53, 55, 56, 57, 58, 59, 60, 61, 62, 63, 64, 65, 66, 150, 151, 39, 43, or 47 shown in FIG. 2.

Antibodies according to the present invention include an antibody or CD122-binding fragment thereof having the amino acid sequence encoded by the nucleotide sequence of anyone of SEQ ID NOs:130, 131, 132, 133, 134, 135, 136, 137, 138, 139, 140, or 141 shown in FIG. 17. Antibodies of the present invention include an antibody comprising the VL and/or VH domain sequence of an amino acid sequence encoded by the nucleotide sequence of any one of SEQ ID NOs:130, 131, 132, 133, 134, 135, 136, 137, 138, 139, 140, or 141 shown in FIG. 17.

In some aspects, the antibody of the present invention comprises the antibody/fragment of a γc-binding antibody clone. In some aspects, the antibody comprises the antibody/fragment of clone P1A3 or a variant of P1A3. In some aspects, the antibody comprises the antibody/fragment of clone P1A3_B3 or a variant of P1A3_B3. In some aspects, the antibody comprises the antibody/fragment of clone P1A3_E8 or a variant of P1A3_E8. In some aspects, the antibody comprises the antibody/fragment of clone P1A3_E9 or a variant of P1A3_E9. In some aspects, the antibody comprises the antibody/fragment of clone P1A3_B4 or a variant of P1A3_B4. In some aspects, the antibody comprises the antibody/fragment of clone P1A3_FW2 or a variant of P1A3_FW2. In some aspects, the antibody comprises the antibody/fragment of clone P2B9 or a variant of P2B9.

The amino acid sequences of the VL domains of the γc-binding antibody clones of the preceding paragraph are shown in FIG. 3, as are the CDRs defined according to the Kabat system. The amino acid sequences of the VH domains of the γc-binding antibody clones of the preceding paragraph are shown in FIG. 4, as are the CDRs defined according to the Kabat system. The full amino acid sequences of the antibody constructs (including linkers) are shown in FIG. 16, and the encoding nucleotide sequences are shown in FIG. 18.

Antibodies according to the present invention may comprise the CDRs of P1A3, P1A3_B3 P1A3_E8, P1A3_E9, P1A3_B4, P1A3_FW2, or P2B9. In an antibody according to the present invention one or two or three or four of the six CDR sequences may vary. A variant may have one or two amino acid substitutions in one or two of the six CDR sequences.

Antibodies according to the present invention may comprise VL and/or VH chains comprising an amino acid sequence that has a high percentage sequence identity to one or more of the VL and/or VH amino acid sequences shown in FIGS. 3 and 4, respectively. For example, antibodies according to the present invention include antibodies that bind γc and have VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs:67, 152, 71, or 75 shown in FIG. 3. Antibodies according to the present invention include antibodies that bind γc and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs:76, 153, 78, 82 or 84 shown in FIG. 4.

Antibodies according to the present invention include an antibody or γc-binding fragment thereof having the amino acid sequence encoded by the nucleotide sequence of any one of SEQ ID NOs:142, 143, 144, 145, 146, or 147 shown in FIG. 18. Antibodies of the present invention include an antibody comprising the VL and/or VH domain sequence of an amino acid sequence encoded by the nucleotide sequence of any one of SEQ ID NOs:142, 143, 144, 145, 146 or 147 shown in FIG. 18.

In some aspects, the antibody of the present invention comprises the antibody/fragment of a CD122-binding antibody clone, e.g. a CD122-binding antibody clone as described, and also comprises a γc-binding clone, e.g. a γc-binding clone as described herein.

The light and heavy chain CDRs disclosed herein may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Le:franc (2001) "The Immunoglobulin FactsBook", Academic Press, incorporated herein by reference.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Chimeric Antigen Receptors

The present invention provides a chimeric antigen receptor (CAR) capable of binding to CD122 and/or γc. The CAR comprises one or more antigen binding fragments or polypeptides according to the present invention.

Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety.

Antigen-binding fragments according to the present invention are provided herein as the antigen-binding domain of a chimeric antigen receptor (CAR). In some embodiments, the CAR comprises a VL domain and a VH domain according to any embodiment of an antibody, antigen binding fragment or polypeptide described herein. Accordingly, the antigen bound by the CAR according to the present invention is CD122 and/or γc.

CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi: 10.1158/2159-8290.CD-12-0548, specifically incorporated herein by reference).

The present invention also provides a cell comprising a CAR according to the invention. The CAR according to the present invention may be used to generate T cells targeted to cells expressing CD122 and/or γc.

Engineering of CARs into T cells may be performed during culture, in vitro, for transduction and expansion, such as happens during expansion of T cells for adoptive T cell therapy. The transduction may utilize a variety of methods, but stable gene transfer is required to enable sustained CAR expression in clonally expanding and persisting T cells.

A CAR typically combines an antigen binding domain with an intracellular domain of the CD3-zeta chain or FcγRI protein in a single chimeric protein. The structural features of a CAR are described by Sjouke et al., (The pharmacology of second-generation chimeric antigen receptors. Nature Reviews Drug Discovery, 14, 499 509 (2015) doi:10.1038/nrd4597). A CAR typically has an extracellular antigen-binding domain linked to a transmembrane domain and endodomain. An optional hinge or spacer domain may provide separation between the binding moiety and transmembrane domain and may act as a flexible linker.

In accordance with the present invention, the antigen recognition domain of the CAR is, or is derived from, an antibody, antigen binding fragment or polypeptide which is capable of binding to CD122 and/or γc, as described herein.

Hinge or spacer regions of the CAR may be flexible domains allowing the binding moiety to orient in different directions. Hinge or spacer regions may be derived from IgG1 or the CH2CH3 region of immunoglobulin.

Transmembrane domains may be hydrophobic alpha helix that spans the cell membrane. The transmembrane domain associated with the endodomain is commonly used.

The endodomain is responsible for receptor clustering/dimerization after antigen binding and for initiation of signal transduction to the cell. One commonly used transmembrane domain is the CD3-zeta transmembrane and endodomain. Intracellular domains from one or more co-stimulatory protein receptors, such as CD28 4-1BB, OX40, ICOS, may optionally be incorporated into the cytoplasmic tail of the CAR to provide additional co-stimulatory signaling, which may be beneficial in terms of anti-tumor activity.

In one embodiment, a CAR comprises an extracellular domain having an antigen recognition domain, a transmembrane domain, and a cytoplasmic domain. A transmembrane domain that is naturally associated with one of the domains in the CAR may be used or the transmembrane domain can be selected or modified by amino acid substitution to avoid binding of such domains to the transmembrane domains of the same or different surface membrane proteins to minimize interactions with other members of the receptor complex.

The cytoplasmic domain may be designed to comprise the CD28 and/or 4-1BB signaling domain by itself or be combined with any other desired cytoplasmic domain(s). The cytoplasmic domain may be designed to further comprise the signaling domain of CD3-zeta. For example, the cytoplasmic domain of the CAR can include but is not limited to CD3-zeta, 4-1BB and CD28 signaling modules and combinations thereof.

The present invention also provides CAR T cells comprising as a CAR an antigen binding fragment capable of binding to CD122 and/or γc, according to the present invention.

CAR T cells of the invention can be generated by introducing a lentiviral vector in vitro comprising a desired CAR, for example a CAR comprising anti-IL2Rβ/γc, CD8a hinge and transmembrane domain, and human 4-1BB and CD3zeta signaling domains, into the cells. The CAR T cells of the invention are able to replicate in vive resulting in long-term persistence that can lead to sustained tumor control.

In one embodiment the invention relates to administering a genetically modified T cell expressing a CAR capable of binding to CD122 and/or γc for the treatment of a patient having cancer or at risk of having cancer or an infectious disease using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

Methods of Detection

Antibodies, or antigen binding fragments, described herein may be used in methods that involve the binding of the antibody or antigen binding fragment to CD122 and/or γc. Such methods may involve detection of the bound complex of antibody, or antigen binding fragment, and CD122 and/or γc. As such, in one embodiment a method is provided, the method comprising contacting a sample containing, or suspected to contain, CD122 and/or γc with an antibody or antigen binding fragment as described herein and detecting the formation of a complex of antibody, or antigen binding fragment, and CD122 and/or γc.

Suitable method formats are well known in the art, including immunoassays such as sandwich assays, e.g. ELISA. The method may involve labelling the antibody, or antigen binding fragment, or CD122 and/or γc, or both, with a detectable label, e.g. fluorescent, luminescent or radiolabel. CD122 and/or γc expression may be measured by immunohistochemistry (IHC), for example of a tissue sample obtained by biopsy.

Methods of this kind may provide the basis of a method of diagnosis of a disease or condition requiring detection and or quantitation of CD122 and/or γc. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of CD122 and/or γc present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of CD122 and/or γc present in a patient sample may be indicative that a patient may respond to treatment with an anti-CD122 and/or anti-γc antibody. The presence of a high level of CD122 and/or γc in a sample may be used to select a patient for treatment with an anti-CD122 and/or anti-γc antibody. The antibodies of the present invention may therefore be used to select a patient for treatment with anti-CD122 and/or anti-γc antibody therapy.

Detection in a sample of anti-CD122 and/or anti-γc antibody may be used for the purpose of diagnosis of an infectious disease, autoimmune disorder or a cancerous condition in the patient, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious disease, autoimmune disorder or cancerous condition.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention may preferably performed in vitro. The term "in vitro" is intended to encompass experiments with cells in culture whereas the term "in vivo" is intended to encompass experiments with and/or treatment of intact multi-cellular organisms.

Therapeutic Applications

Antibodies, antigen binding fragments and polypeptides according to the present invention and compositions comprising such agents may be provided for use in methods of medical treatment. Treatment may be provided to subjects having a disease or condition in need of treatment.

Methods of medical treatment may involve treatment of cancer by a method of ameliorating, treating, or preventing a malignancy in a human subject wherein the steps of the method assist or boost the immune system in eradicating cancerous cells. Such methods may include the administration of cells, antibodies, proteins, or nucleic acids according to the present invention that invoke an active (or achieve a passive) immune response to destroy cancerous cells. Methods of treatment may optionally include the co-administration of biological adjuvants (e.g., interleukins, cytokines, *Bacillus* Comette-Guerin, monophosphoryl lipid A, etc.) in combination with conventional therapies for treating cancer such as chemotherapy, radiation, or surgery. Methods of treatment may involve administering a composition according to the present invention as a vaccine that works by activating the immune system to prevent or destroy cancer cell growth. Methods of medical treatment may also involve in vivo, ex vivo, and adoptive immunotherapies, including those using autologous and/or heterologous cells or immortalized cell lines.

The disease or condition may be one of an infectious disease, an autoimmune disorder (e.g. e.g. Crohn's disease, Multiple Sclerosis), a cancer, an inflammatory disease (e.g. arthritis), a disease/disorder associated with deficient IL-2-mediated signalling and/or IL-15-mediated signalling, deficient T cell proliferation or T cell dysfunction.

In some embodiments, the treatment is of a disease or disorder for which increased IL-2-mediated signalling and/or IL-15-mediated signalling is therapeutic.

In some embodiments, the treatment is of a disease or disorder associated with a deficient T cell response, e.g. a deficient CD8+ T cell response.

The treatment may be aimed at preventing or treating a disease/disorder by one of more of: increasing the number of CD3+ T cells, increasing the number of CD4+ T cells, increasing the number of CD8+ T cells, increasing the number of CD8+ effector T cells (e.g. CTLs), increasing the number NK cells, increasing the ratio of CD8+ T cells to CD4+ T cells, or decreasing the proportion of Tregs.

The T-cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*. Examples of viral infections include infection with EBV, HIV, hepatitis B or hepatitis C.

The T-cell dysfunctional disorder may be associated with a cancer, such as tumor immune escape. Many human tumors express tumor-associated antigens recognised by T cells and capable of inducing an immune response.

Cancers may also be treated where there is no indication of a T-cell dysfunctional disorder but the use of an antibody, antigen binding fragment or polypeptide according to the present invention promotes an effective immune response.

The treatment may be aimed at prevention of a disease/disorder associated with deficient/reduced IL-2-mediated signalling and/or IL-15-mediated signalling. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Treatment may comprise co-therapy with a vaccine, e.g. T-cell vaccine, which may involve simultaneous, separate or sequential therapy, or combined administration of vaccine and antibody, antigen binding fragment or polypeptide in a single composition. In this context, the antibody, antigen binding fragment or polypeptide may be provided as an adjuvant to the vaccine.

Administration of an antibody, antigen binding fragment or polypeptide is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The CARs and cells comprising the CARs (i.e. CAR-T cells) of the present invention find use to treat autoimmune disorders, e.g. Crohn's disease, Multiple Sclerosis. In such treatments, the CAR-T cells are effective to kill autoimmune aggressor cells (e.g. autoreactive T cells) expressing CD122 and/or γc.

Formulating Pharmaceutically Useful Compositions and Medicaments

Antibodies, antigen binding fragments, and polypeptides, CARs and cells according to the present invention may be formulated as pharmaceutical compositions or medicaments for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment, polypeptide, CAR or cell as described herein; and/or mixing an isolated antibody, antigen binding fragment or polypeptide as described herein with a pharmaceutically acceptable carrier, adjuvant, excipient or diluent.

For example, a further aspect of the present invention relates to a method of formulating or producing a medicament or pharmaceutical composition for use in a method of medical treatment, method comprising formulating a pharmaceutical composition or medicament by mixing an antibody, antigen binding fragment, polypeptide, CAR or cell as described herein with a pharmaceutically acceptable carrier, adjuvant, excipient or diluent.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry Nature Immunology Vol. 12, No. 6, p 492-499, June 2011).

Examples of bacterial infections that may be treated include infection by *Bacillus* spp., *Bordetella pertussis*, *Clostridium* spp., *Corynebacterium* spp., *Vibrio chloerae*, *Staphylococcus* spp., *Streptococcus* spp. *Escherichia*, *Klebsiella*, *Proteus*, *Yersinia*, *Erwina*, *Salmonella*, *Listeria* sp, *Helicobacter pylori*, mycobacteria (e.g. *Mycobacterium tuberculosis*) and *Pseudomonas aeruginosa* For example, the bacterial infection may be sepsis or tuberculosis.

Examples of viral infections that may be treated include infection by Epstein-Barr virus, influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

Examples of fungal infections that may be treated include infection by *Alternaria* sp, *Aspergillus* sp, *Candida* sp and *Histoplasma* sp. The fungal infection may be fungal sepsis or histoplasmosis. Examples of parasitic infections that may be treated include infection by *Plasmodium* species (e.g. *Plasmodium falicparum*, *Plasmodium yoeli*, *Plasmodium ovale*, *Plasmodum vivax*, or *Plasmodium chabaudi chabaudi*). The parasitic infection may be a disease such as malaria, leishmaniasis and toxoplasmosis.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In particular, treatment of melanoma, kidney cancer (e.g. renal carcinoma) or bladder cancer is contemplated.

In some embodiments the cancer is an EBV or HPV positive cancer.

Adoptive Cell Transfer Therapy

Adoptive cell transfer therapy generally refers to a process in which white blood cells are removed from a subject, typically by drawing a blood sample from which white blood cells are separated, expanded in vitro or ex vivo and returned either to the same subject or to a different subject. The treatment is typically aimed at increasing the amount/concentration of an active form of the required cell population in the subject.

The antibodies/fragments of the present invention provide a means of expanding the number and/or enhancing the activity of cells expressing CD122 and/or γc. In some embodiments, the cells are T cells and/or NK cells.

Accordingly, in a further aspect of the present invention a method is provided for expanding a population of cells, wherein cells are contacted in vitro, in vivo or ex vive with an antibody, antigen binding fragment, polypeptide or composition according to the present invention. Also provided is a method for expanding a population of cells in a subject, comprising an administering an antibody/fragment an antibody, antigen binding fragment, polypeptide or composition according to the present invention to a subject.

In some embodiments, the antibodies/fragments of the present invention are capable of delivering a survival signal to cells expressing CD122 and/or γc. In some embodiments, the antibodies/fragments are useful to enhance/promote the survival of a cell or a population of cells (e.g. T cells (e.g. CD8+ T cells (e.g. CTLs), CD4+ T cells) and/or NK cells), e.g. in vitro, in vive or ex vivo.

Accordingly, in a further aspect of the present invention a method is provided for enhancing/promoting the survival of a cell or a population of cells, wherein cells are contacted in vitro, in vivo or ex vivo with an antibody, antigen binding fragment, polypeptide or composition according to the present invention. Also provided is a method for enhancing/promoting the survival of a cell or a population of cells in a subject, comprising an administering an antibody/fragment an antibody, antigen binding fragment, polypeptide or composition according to the present invention to the subject.

The methods may optionally comprise one or more of the following steps: taking a blood sample from a subject; isolating cells (e.g. one of PBMCs, T cells, NK cells etc.) from the blood sample; culturing the cells in in vitro or ex vive cell culture (where they may be contacted with the antibody, antigen binding fragment or polypeptide), collecting an expanded population of cells; mixing the cells with an adjuvant, diluent, or carrier; administering the expanded cells to a subject.

Accordingly, in some aspects of the present invention a method of treatment of a subject, e.g. a subject having a T-cell dysfunctional disorder, is provided, the method comprising obtaining a blood sample from a subject in need of treatment, culturing T cells obtained from the blood sample in the presence of an antibody, antigen binding fragment, polypeptide or composition according to the present invention so as to expand the T cell population, collecting expanded T cells, and administering the expanded T cells to a subject in need of treatment.

The T cells may be obtained from a subject requiring treatment, and may be isolated and/or purified. They may be a $CD4^+$ and/or $CD8^+$ T-cell population. They may be a CD122+ and/or γc+ population.

During culture, T cells may be contacted with the antibody, antigen binding fragment, polypeptide or composition under conditions and for a period of time suitable to allow expansion of the T cells to a desired number of cells. After a suitable period of time the T cells may be harvested, optionally concentrated, and may be mixed with a suitable carrier, adjuvant or diluent and returned to the subject's body. A subject may undergo one or more rounds of such therapy.

Methods of T cell expansion are well known in the art, such as those described in Kalamasz et al., *J Immunother* 2004 September-October; 27(5):405-18; Montes et al., *Clin Exp Immunol* 2005 November; 142(2):292-302; Wölfl and Greenburg Nature Protocols 9 p 950-966 27 Mar. 2014; Trickett and Kwan *Journal of Immunological Methods Vol.* 275, Issues 1-2, 1 Apr. 2003, p 251-255; Butler et al *PLoSONE* 7(1) 12 Jan. 2012.

Simultaneous or Sequential Administration

Compositions may be administered alone or in combination with other treatments, either simultaneously or sequentially dependent upon the condition to be treated.

In this specification an antibody, antigen binding fragment, polypeptide, CAR, cell or composition of the present invention and an anti-infective agent or chemotherapeutic agent (therapeutic agent) may be administered simultaneously or sequentially.

In some embodiments, treatment with an antibody, antigen binding fragment or polypeptide of the present invention may be accompanied by chemotherapy.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

In some embodiments, the antibody, antigen binding fragment, polypeptide, or composition of the present invention may be administered to a patient undergoing treatment by adoptive cell transfer. The administration may be aimed at stimulating proliferation of the adoptively transferred cells in the patient in vivo.

Anti-Infective Agents

In treating infection, an antibody, antigen binding fragment or polypeptide of the present invention may be administered in combination with an anti-infective agent, as described above. The anti-infective agent may be an agent known to have action against the microorganism or virus responsible for the infection.

Suitable anti-infective agents include antibiotics (such as penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins), antiviral agents (such as reverse transcriptase inhibitors, integrase inhibitors, transcription factor inhibitors, antisense and siRNA agents and protease inhibitors), anti-fungal agents (such as polyenes, imidiazoles, triazoles, thiazoles, allylamines, and echinocandins) and anti-parasitic agents (such as antinematode agents, anticestode agents, antitrematode agents, antiamoebic agents and antiprotozoal agents).

Chemotherapy

Chemotherapy and radiotherapy respectively refer to treatment of a cancer with a drug or with ionising radiation (e.g. radiotherapy using X-rays or γ-rays).

The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as *vinca* alkaloids (e.g. vincristine, vinblastine, vinorebine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (MabtheraO), palivizumab, trastuzumab, etanercept, adalimumab, nimotuzumab; EGFR inihibitors such as eriotinib, cetuximab and gefitinib; anti-angiogenic agents such as bevacizumab (Avastin®); cancer vaccines such as Sipuleucel-T (Provenge®).

In one embodiment the chemotherapeutic agent is an anti-PD-1 antibody, anti-PD-L1 antibody, anti-TIM-3 antibody, anti-LAG-3, anti-CTLA-4, anti-41BB, anti-GITR, anti-CD27, anti-BLTA, anti-OX43, anti-VEGF, anti-TNFα, anti-11L2, anti-GpIIb/IIIa, anti-CD-52, anti-CD20, anti-RSV, anti-HER2/neu(erbB2), anti-TNF receptor, anti-EGFR or other antibody. In some embodiments, the chemotherapeutic agent is an immune checkpoint inhibitor or costimulation molecule.

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aidesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDRθ, Fulvestrant, Gefitinb, Gemcitabine, Gemtuzumab ozogamicin, Gleevec™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrokl, Megace®, Megestrol, Megestrol Acetate, Melphalan, Mercaptopurine, Mesna, Mesnex™, Methotrexate, Methotrexate Sodium, Methyiprednisolone, Meticorten®, Mitomycin, Mitomycin-C, Mitoxantrone, M-Prednisol, MTC, MTX, Mustargen®, Mustine, Mutamycin®, Myleran®, MylocelT$^M$, Mylotarg®, Navebine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol, Platinol-AQ®, Prednisolone, Prednisone, Prelone®, Procarbazine, PROCRIT®, Proleukin®, Prolifeprospan 20 with Carmustine Implant Purinethokl, Raloxifene, Revlimid®, Rheumatrex®, Rituxan®, Rituximab, Roferon-AO (Interferon Alfa-2a), Rubex®, Rubidomycin hydrochloride, Sandostatin® Sandostatin LAR®, Sargramostim, Solu-Cortef®, Solu-Medrol, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Veban®, Velcade®, VePesid®, Vesanoid®, Viadur™, Vidaza®, Vinblastine, Vinblastine Sulfate, Vincasar Pfs®, Vincristine, Vinorelbine, Vinorebine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Routes of Administration

Antibodies, antigen binding fragments, polypeptides and other therapeutic agents, medicaments and pharmaceutical compositions according to aspects of the present invention may be formulated for administration by a number of routes, including but not limited to, parenteral, intravenous, intra-arterial, intramuscular, subcutaneous, intradermal, intratumoral and oral. Antibodies, antigen binding fragments, polypeptides and other therapeutic agents, may be formulated in fluid or solid form. Fluid formulations may be formulated for administration by injection to a selected region of the human or animal body.

Dosage Regime

Multiple doses of the antibody, antigen binding fragment, polypeptide, CAR, cell, or composition of the invention may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

The antibody of the present invention has favourable pharmacokinetics as compared to IL-2 as a therapeutic agent. An advantage of the antibody/fragment of the present invention is the improved half-life in vivo, e.g. in the blood or serum, as compared to IL-2, which means that administration of the antibody/fragment can be less frequent, and/or of a lower amount of the agent.

Kits

In some aspects of the present invention a kit of parts is provided. In some embodiments the kit may have at least one container having a predetermined quantity of the antibody, fragment, polypeptide, CAR, cell or composition. The kit may provide the antibody, fragment, polypeptide, CAR, or cell in the form of a medicament or pharmaceutical composition, and may be provided together with instructions for administration to a patient in order to treat a specified disease or condition. The antibody, fragment, polypeptide, CAR, cell or composition may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Protein Expression

Molecular biology techniques suitable for producing the antibody, fragment, polypeptide, or CAR according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate.

For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures, in which:

FIG. 1. Light chain variable domain sequences for anti-IL-2Rβ antibody clones. CDRs are underlined and shown separately.

FIG. 2. Heavy chain variable domain sequences for anti-IL-2Rβ antibody clones. CDRs are underlined and shown separately.

FIG. 3. Light chain variable domain sequences for anti-γc antibody clones. CDRs are underlined and shown separately.

FIG. 4. Heavy chain variable domain sequences for anti-γc antibody clones. CDRs are underlined and shown separately.

FIG. 5. Table showing light chain CDR sequences for anti-IL-2Rβ antibody clones.

FIG. 6. Table showing heavy chain CDR sequences for anti-IL-2Rβ antibody clones.

FIG. 7. Table showing light chain CDR sequences for anti-γc antibody clones.

FIG. 8. Table showing heavy chain CDR sequences for anti-γc antibody clones.

FIG. 9. Table showing light chain CDR sequences for P2C4-derived anti-IL-2Rβ antibody clones.

FIG. 10. Table showing heavy chain CDR sequences for P2C4-derived anti-IL-2Rβ antibody clones.

FIG. 11. Table showing light chain CDR sequences for P1A3-derived anti-γc antibody clones.

FIG. 12. Table showing heavy chain CDR sequences for P1A3-derived anti-γc antibody clones.

FIG. 13. CH2 and CH3 domain sequences for anti-IL-2Rβ antibody clone P2C4.

FIG. 14. CH2 and CH3 domain sequences for anti-γc antibody clone P1A3.

FIG. 15. Amino acid sequences for anti-IL-2Rβ antibody clones. $V_H$ domains are shown underlined. $(GGGS)_3$ linkers (and variants thereof) are shown in bold. $V_L$ domains are shown double underlined. Short linkers are in Italics and bold. Hinges are shown in italics. CH2 domains are shown dotted underline. CH3 domains are shown dashed underlined.

FIG. 16. Amino acid sequences for anti-γc antibody clones. $V_H$ domains are shown underlined. $(GGGS)_3$ linkers (and variants thereof) are shown in bold. $V_L$ domains are shown double underlined. Short linkers are in Italics and bold. Hinges are shown in italics. CH2 domains are shown dotted underline. CH3 domains are shown a dashed underlined.

FIG. 17. Nucleotide sequences for anti-IL-2Rβ antibody clones.

FIG. 18. Nucleotide sequences for anti-γc antibody clones.

FIG. 25A Schematic representation of antibody and scFv formats, and linkers (linkers shown in italics). FIG. 25B Graph showing proliferation of NK92 cells in response to treatment with bispecific anti-IL-2Rβ/γc antibody comprising linkers of different length. FIG. 25C Graph showing proliferation of NK92 cells in response to treatment with bispecific anti-IL-2Rβ/γc in bis-scFv format, comprising linkers of different length.

FIG. 27A CD3+ cells, FIG. 27B CD4+ cells, FIG. 27C CD8+ cells, and FIG. 27D the ratio of CD8+ to CD4+ cells.

FIG. 30A CD3+ cells, FIG. 30B CD4+ cells, FIG. 30C CD8+ cells, and FIG. 30D the ratio of CD8+ to CD4+ cells.

FIG. 31A CD8+ T cell subsets as a percentage of CD8+ cells. For each subset, from left to right, the data points are: IL-2 200 ng/ml, Mega2 3 ug/ml, Mega2 1 ug/ml, Mega2 0.3 ug/ml, Mega2 0.3 ug/ml and CD3/28. FIG. 31B CD8+ PD1+ cells as a percentage of CD8+ cells, and FIG. 31C Tregs as a percentage of CD4+ cells.

FIG. 38A Bispecific anti-IL-2Rβ/γc antibody-dependent expansion of CD8+ T cells. FIG. 38B CD8:CD4+ T cell ratio following exposure to the antibody relative to IL-2, following autologous LCL co-culture. *p value<0.05.

FIG. 41A T cells as a proportion of the total leukocyte population, FIG. 41B Ki-67+ positive CD8+ cells as a proportion of the total CD8+ T cell population. FIG. 41C Ki-67+ positive CD4+ cells as a proportion of the total CD4+ T cell population. Bispecific antibody dependent expansion is indicated by the increase in T cells relative to the total leukocyte population.

FIG. 42A NK cells as a proportion of the pre-dose total leukocyte population, FIG. 42B Ki-67+ positive NK cells as a proportion of the total NK cell population.

EXAMPLES

In the following Examples, the inventors describe the isolation of anti-IL-2Rβ and anti-γc antibodies, construction, engineering and in vitro and in vive functional characterisation of bispecific anti-IL-2Rβ/γc antibodies.

Example 1: Isolation of Anti-Human IL-2R and Anti-Human Vc Antibodies

Anti-IL-2Rβ and anti-γc antibodies were isolated from a human antibody phage display library via in vitro selection. Specific Fab antibodies were originally identified by ELISA using recombinant IL-2Rβ and γc proteins as antigens.

Figure 19:
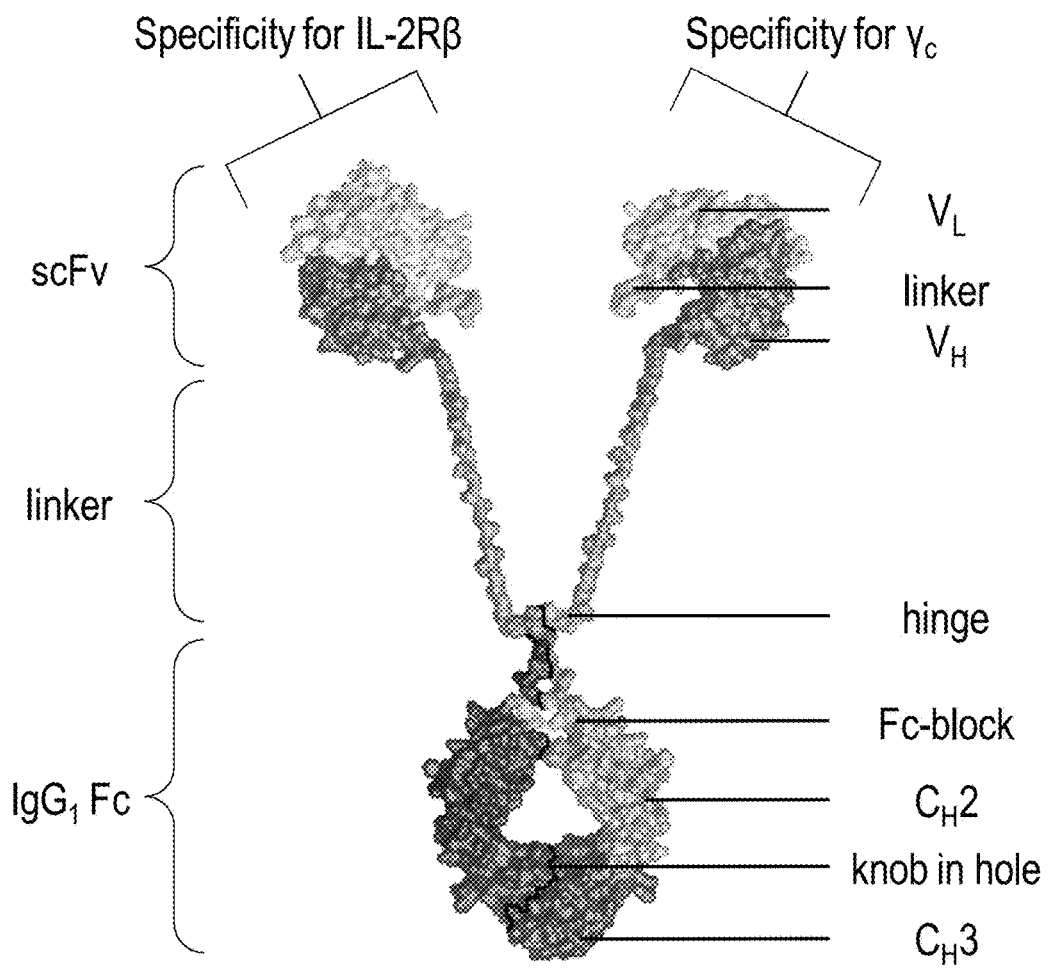
FIG. 19. Schematic representation of the bispecific anti-IL-2Rβ/γc antibody.

Example 2: Construction of a Bispecific Antibody Targeting the Medium Affinity IL-2Rβ-γc Clones showing a strong binding in ELISA (Example 1) were selected and used to construct a "knob-in-hole" monovalent, bispecific human antibody based on a single chain variable fragment (scFv) linked to a IgG1 backbone Fc region as schematised in FIG. 19.

The "knob-in-hole" format prevents homodimerisation and formation of bivalent, monospecific antibodies.

A LALA mutation (substitution of leucine residues 234 and 235 in wild type heavy chain constant domain 2 by alanine) was introduced in the Fc portion of the antibody to abrogate binding to Fc receptor.

The size of the linker between the scFv domain and the Fc domain has no effect on the function of the construct (see Example 6.2 and FIG. 25).

Figure 25A:
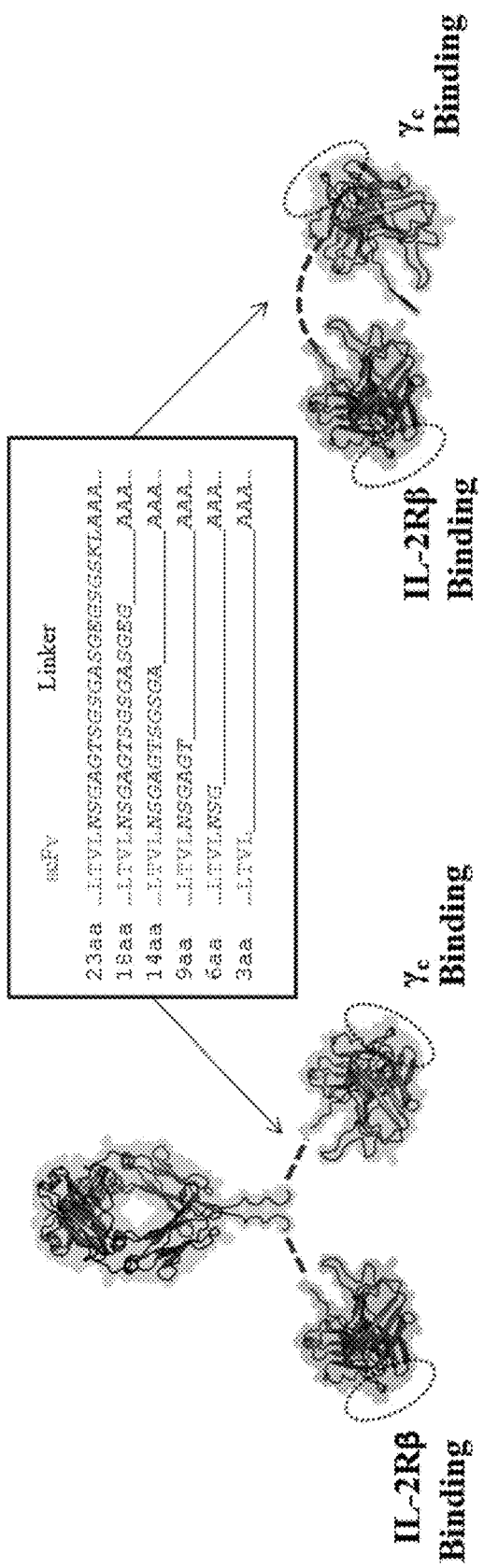
FIGS. 25A-C. Graphs and schematic showing results of analysis of linker length on binding by anti-IL-2Rβ/γc antibody.

Bispecific scFv (bis-scFv) Format:

P1A3 and P2C4 scFv were tied with a linker to form a bispecific antibody composed of two single chain variable domains connected by a linker (FIG. 25A, right). Different linker sizes were tested (FIG. 25C) and activity was tested by measuring NK92 cell growth.

Figure 25B:
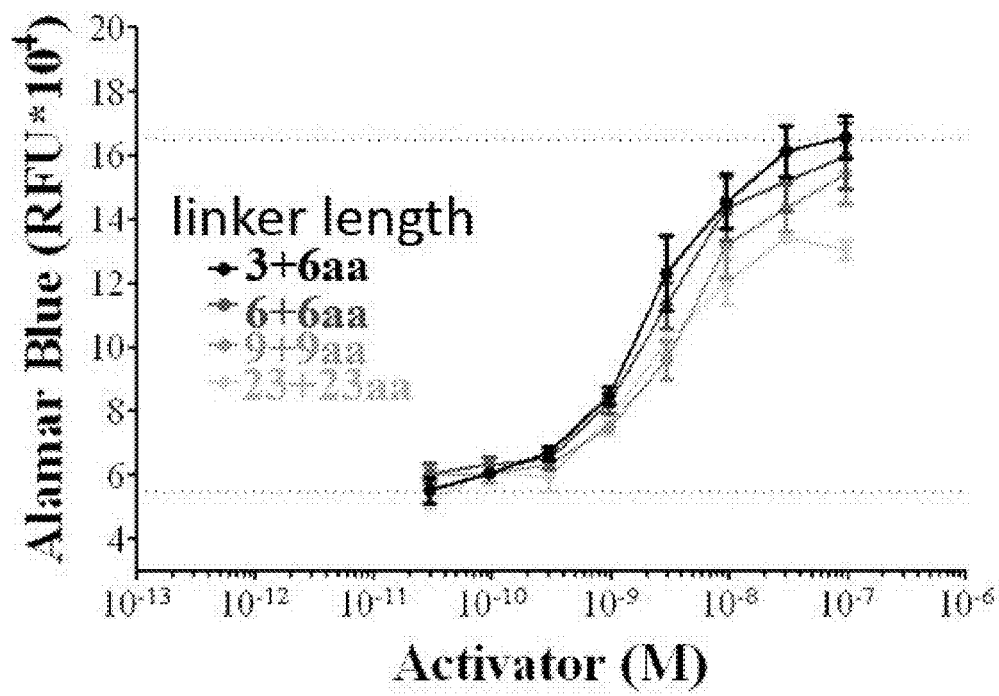
Figure 25C:
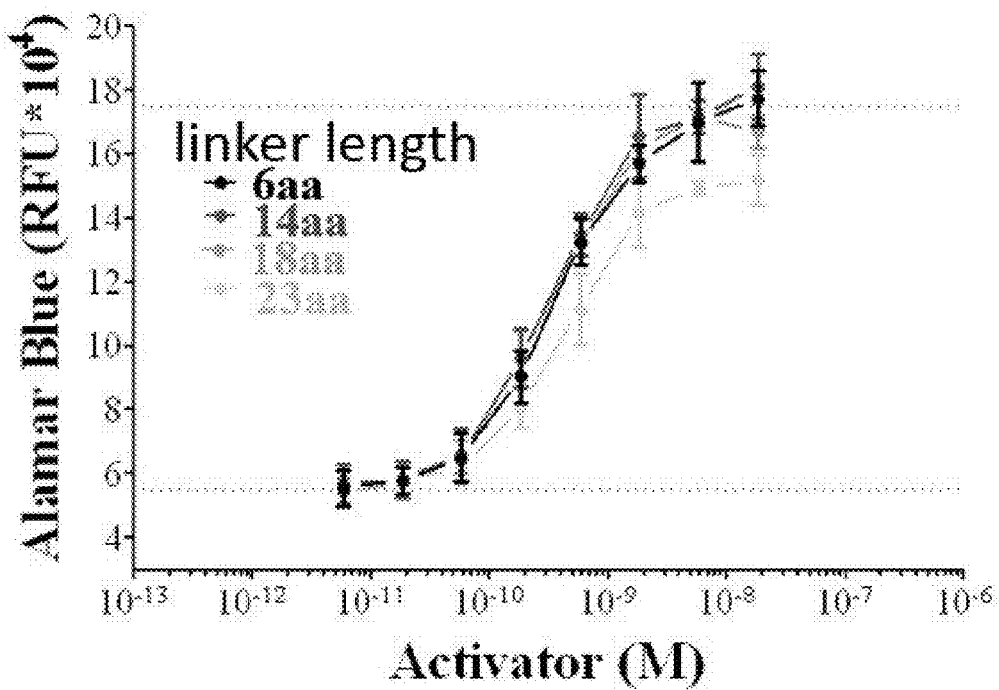

The bis-scFv was effective in maintaining proliferation of NK92 cells in the absence of IL-2. The linker size between the two single chain fragments did not affect the bispecific compound activity (FIG. 25C).

Example 3: Analysis of Binding to IL-2R Chains

The binding of the bispecific antibody to either IL-2Rβ or γc was analysed by flow cytometry.

Antibodies were incubated with HEK-293.6E cells that had previously been transfected with constructs encoding either IL-2Rβ or γc.

Binding to the cells was detected using a fluorescent-conjugated secondary antibody. An isotype IgG1 was used as a negative control. Bispecific constructs with specificity for either IL-2Rβ or γc and for an irrelevant target were also tested.

Figure 21A:
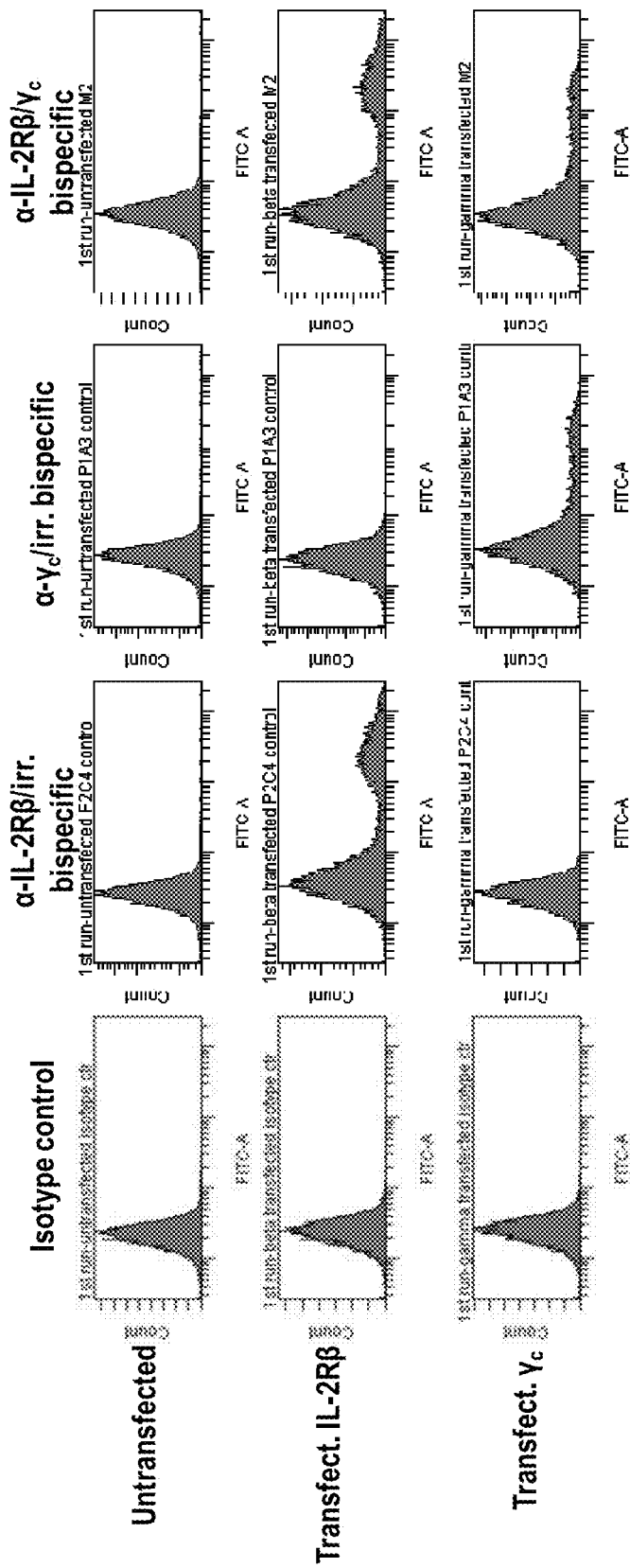
FIGS. 21A-B. Histograms showing binding of bispecific anti-IL-2Rβ/γc antibody FIG. 21A to cells expressing (and control cells not expressing) IL-2Rβ/γc, and FIG. 21B to PBMCs, as determined by flow cytometry.

The anti-IL-2Rβ/γc antibody was shown to bind to cells expressing its targets (FIG. 21A).

Example 4: Analysis of Affinity for IL-2R Chains

Association/dissociation of the anti-IL-2Rβ/γc bispecific antibody to/from the receptor chains was measured in Surface Plasmon Resonance using recombinant IL-2Rβ or γc chains immobilised on a chip, and flowing various concentrations of the antibody over the surface.

Figure 20A:
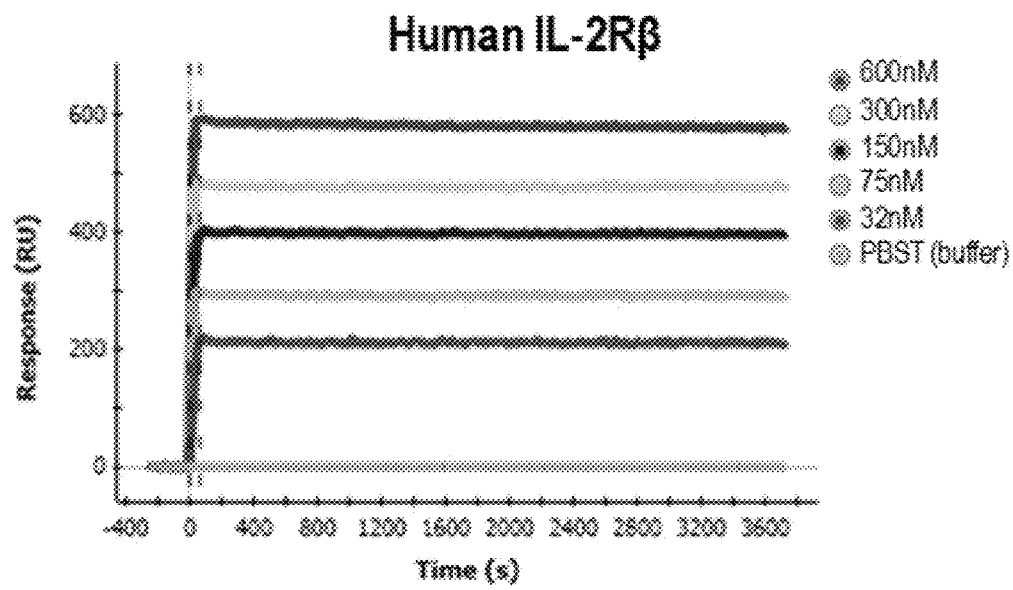
FIGS. 20A-B. Sensorgrams showing binding of the bispecific anti-IL-2Rβ/γc antibody to FIG. 20A human IL-2Rβ and FIG. 20B human γc as determined by surface plasmon resonance analysis.
Figure 20B:
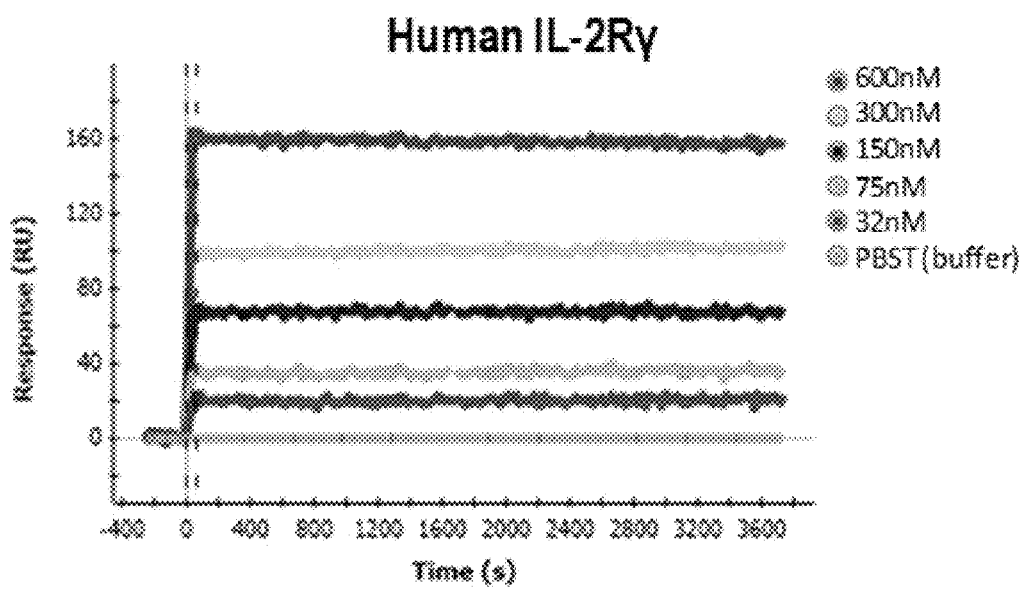

The antibody showed a very high affinity for IL-2Rβ or γc chains, with a very rapid binding and a very slow dissociation (FIG. 20).

Affinity was measured for bispecific anti-IL-2Rβ/γc antibody P2C4/P1A3, and other bispecific antibodies shown in Table 1.

TABLE 1

| Bispecific Ab | | $K_D$ (M) | |
|---|---|---|---|
| anti-IL-2Rβ clone | anti-γc clone | for IL-2Rβ | for γc |
| P2C4 | P1A3 | $1.43 \times 10^{-7}$ | $2.09 \times 10^{-8}$ |
| P2H7 | P2B9 | $1.01 \times 10^{-7}$ | $7.98 \times 10^{-8}$ |
| P2D12 | P1A3 | $1.81 \times 10^{-7}$ | $7.87 \times 10^{-8}$ |
| P1G11 | P1A3 | $1.28 \times 10^{-7}$ | $3.37 \times 10^{-7}$ |

Example 5: Binding to PBMC Subsets

The bispecific IgG anti-IL-2Rβ/γc antibody was tested on PBMCs isolated from healthy donors to check which cell subsets it binds to. Antibody or isotype IgG control were added to PBMCs and detected with a fluorescently-conjugated secondary anti-human IgG antibody in flow cytometry assays.

Figure 21B:
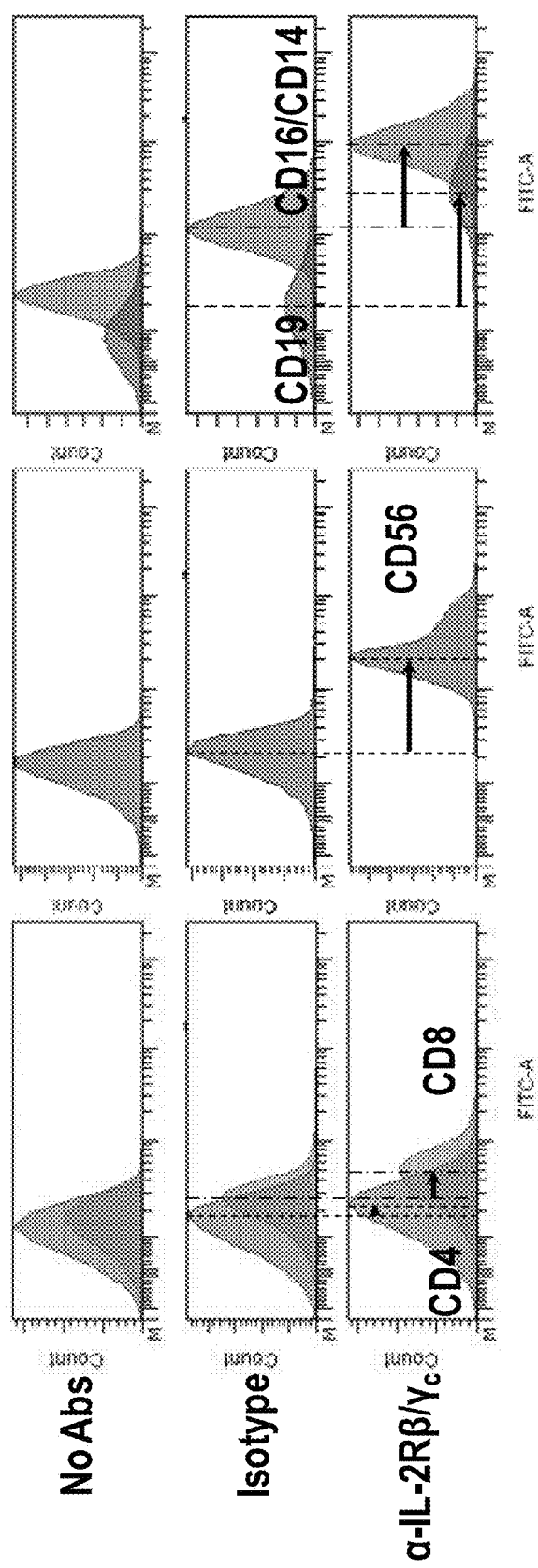

The anti-IL-2Rβ/γc bispecific antibody did not show high binding for CD4+ or CD8+ T cells. However, the antibody bound efficiently to CD56+NK cells, CD19+ B cells and CD14+/CD16+ monocytes (FIG. 21B).

Example 6: Activity/IL-2 Agonistic Effects of Anti-IL-2Rβ/γc Bispecific Antibody 6.1 Signalling Pathway Phosphorylation IL-2 is known to trigger intracellular signalling via STAT5, ERK and Akt pathways. The anti-IL-2Rβ/γc bispecific antibody was tested for its ability to induce signalling through these pathways.

IL-2-sensitive NK92 cells were deprived from serum and then stimulated either with IL-2 (100 U/ml, i.e. ~0.5 nM[1]) or the anti-IL-2Rβ/γc antibody (10 µg/ml, i.e. ~95 nM[2]) for 30 minutes, and phosphorylation of STAT5, Akt and ERK was detected using fluorescent antibodies in flow cytometry assays.

Figure 22:
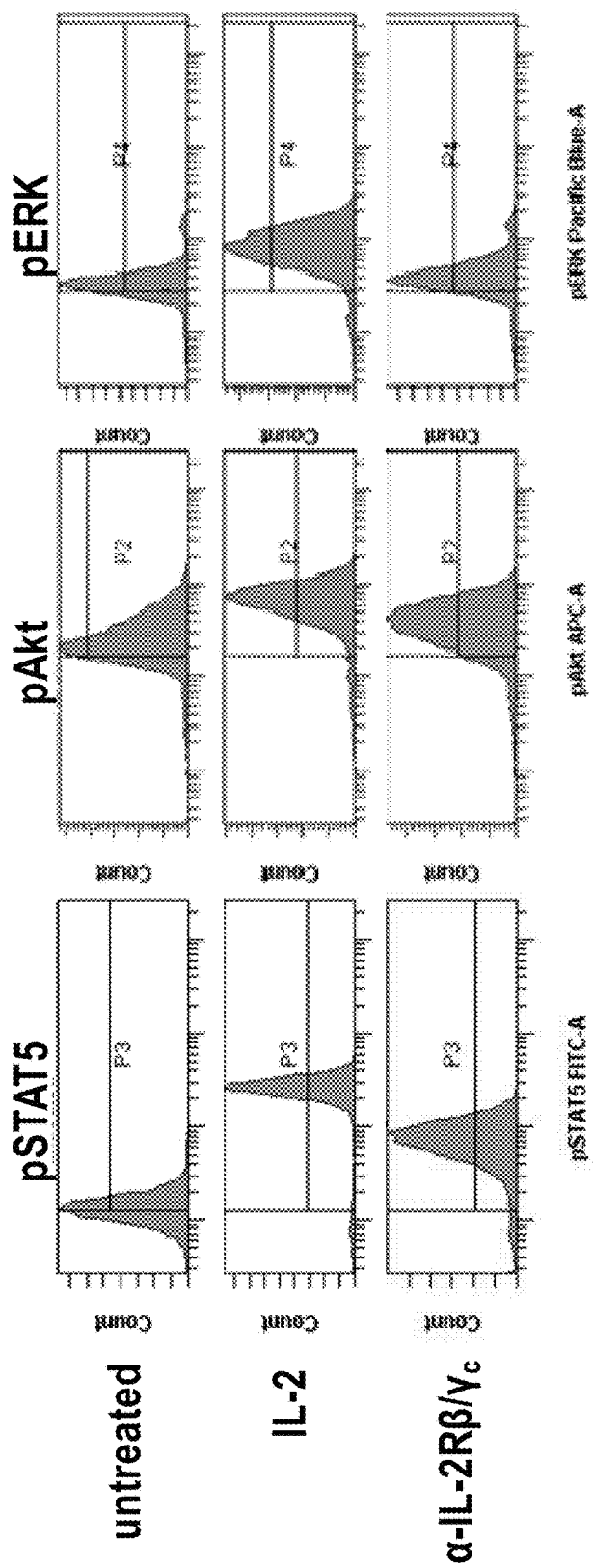
FIG. 22. Histograms showing induction of STAT5, Akt and ERK mediated signalling by treatment of NK92 cells with IL-2 or bispecific anti-IL-2Rβ/γc antibody in vitro, as determined by flow cytometry.

The anti-IL-2R γc antibody induced STAT5 and Akt phosphorylation, although in a milder way than IL-2 (FIG. 22). In this assay, the IL-2Rβ/γc antibody did not trigger phosphorylation of ERK (FIG. 22).

One of the biggest obstacles to therapeutic use of IL-2 is the preferential stimulation of cells expressing the high affinity heterotrimeric receptor CD25, e.g. regulatory T cells (Tregs), activated T cells, activated B cells, some myeloid precursor cells, and epithelial cells.

Phosphorylation of STAT5 in the presence of IL-2 or anti-IL-2Rβ/γc antibody was measured by flow cytometry in Tregs, CD8+ T cells and NK cells obtained from healthy donors.

Figure 23:
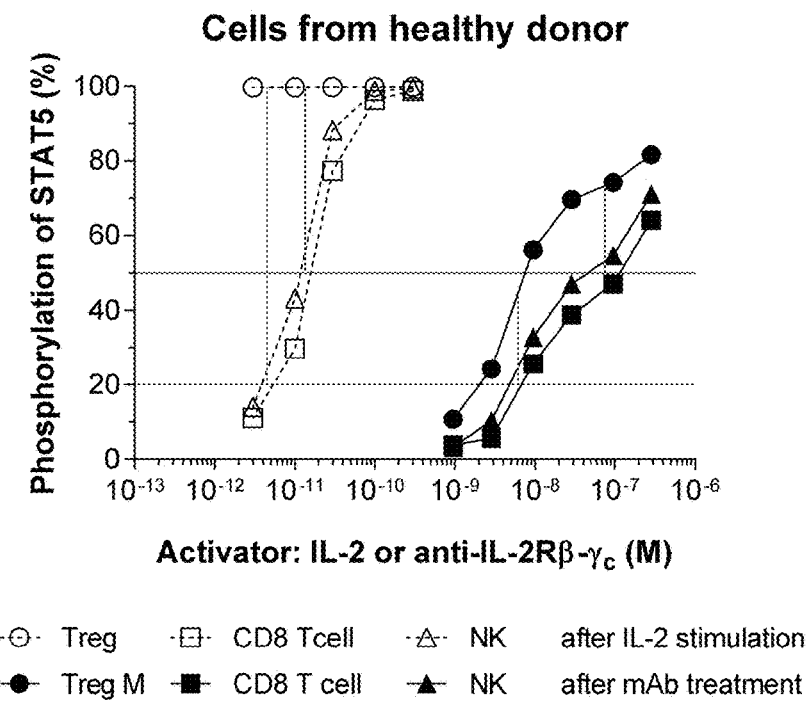
FIG. 23. Graph showing percent phosphorylation of STAT5 in response to treatment with IL-2 or bispecific anti-IL-2Rβ/γc antibody in vitro for different immune cell subsets, as determined by flow cytometry.

Small amounts of IL-2 were sufficient to activate NK or T cells, but even at low levels of IL-2 Tregs were preferentially and strongly activated. At concentrations giving less than 20% activation of the STAT5 signaling pathway in NK or CD8+ T cells, Tregs already showed 100% activation (FIG. 23).

By contrast, the bispecific antibody showed a different activation profile with a lower preferential activation of Tregs. At concentrations resulting in a 20% activation of NK and CD8+ T cells, Tregs showed between 39 and 49% STAT5 phosphorylation. At concentrations giving 50% of activation in NK and CD8+ T cells, the Treg population was still not completely activated, with 73-78% STAT5 phosphorylation (FIG. 23).

6.2 Proliferation of IL-2-Dependent Cells

Viability and growth of NK92 cells was measured with Alamar blue dye in the absence of IL-2.

Figure 24:
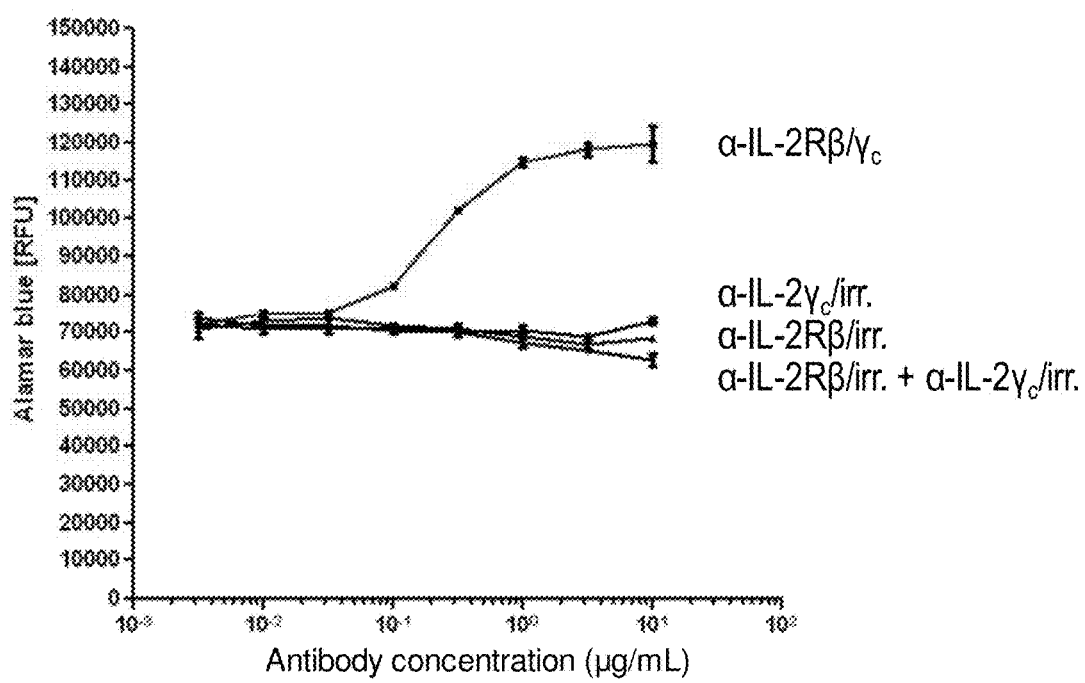
FIG. 24. Graph showing proliferation of IL-2 dependent NK92 cells in response to treatment with bispecific anti-IL-2Rβ/γc antibody or control antibodies exhibiting specificity for only IL-2Rβ or γc.

The anti-IL-2Rβ/γc antibody was able to maintain proliferation of NK92 cells in the absence of IL-2, whilst the antibody constructs binding to only one chain of the IL-2 receptor did not show any effect (FIG. 24).

To assess whether the length of the linker had an effect on the functionality of the antibody, the same assay was conducted using antibodies with different linker sizes. Growth of NK92 cells was not affected by linker size (FIG. 25B). The data in FIG. 25B were obtained using the shortest and the longest linkers (between 5 and 23 amino-acids).

Linkers of different length were analysed in the bispecific antibody format, or bispecific scFv format, as represented schematically in FIG. 25A. Briefly, P1A3 and P2C4 scFv were linked with linkers of different size, and the activity was tested by measuring NK92 cell growth.

The results are shown in FIGS. 25B and 25C. The bis-scFv is effective in maintaining proliferation of NK92 cells in the absence of IL-2, and the size of the linker between the two scFv fragments does not affect activity.

6.3 Cross-Reactivity with Cynomolgous Monkey Cells

Figure 26:
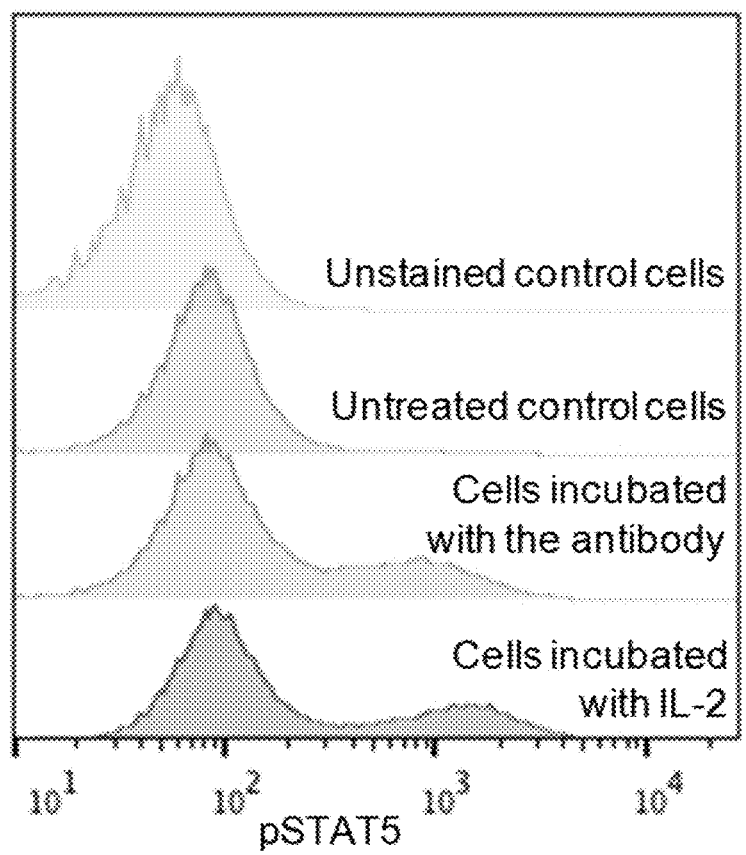
FIG. 26. Histograms showing induction of STAT5 signalling in cynomolgous macaque splenocytes by treatment with IL-2 or bispecific anti-IL-2Rβ/γc antibody in vitro, as determined by flow cytometry.

The anti-IL-2Rβ/γc antibody was also tested on Non-Human Primate cells. Briefly, Cynomolgous splenocytes were incubated in the presence of human IL-2 or the bispecific antibody and STAT5 phosphorylation was measured. The antibody was found to be cross-reactive with Cynomolgus IL-2R, and triggered phosphorylation of STAT5 as efficiently as human IL-2 (FIG. 26).

6.4 Conclusion

Taken together, these data show that the anti-IL-2Rβ/γc bispecific antibody has some agonist effects to IL-2, and that these effects are not highly preferentially directed towards CD25-expressing cells.

Example 7: Modulation of the Immune Response: Control of T Cell Expansion in a Non-Specific Stimulation Setting Peripheral blood mononuclear cells (PBMCs) were isolated from a volunteer donor and cultured for 1 week in the presence of recombinant human IL-2 (200 ng/ml), the anti-IL-2Rβ/γc bispecific antibody (3, 1, 0.3, 0.1, or 0.03 µg/ml)

or anti-CD3/CD28 beads as a positive control. After 1 week, cell expansion was assessed by measuring absolute cell counts; cell subset proportions were measured by FACS.

7.1 Expansion of T Cells

Figure 27A:
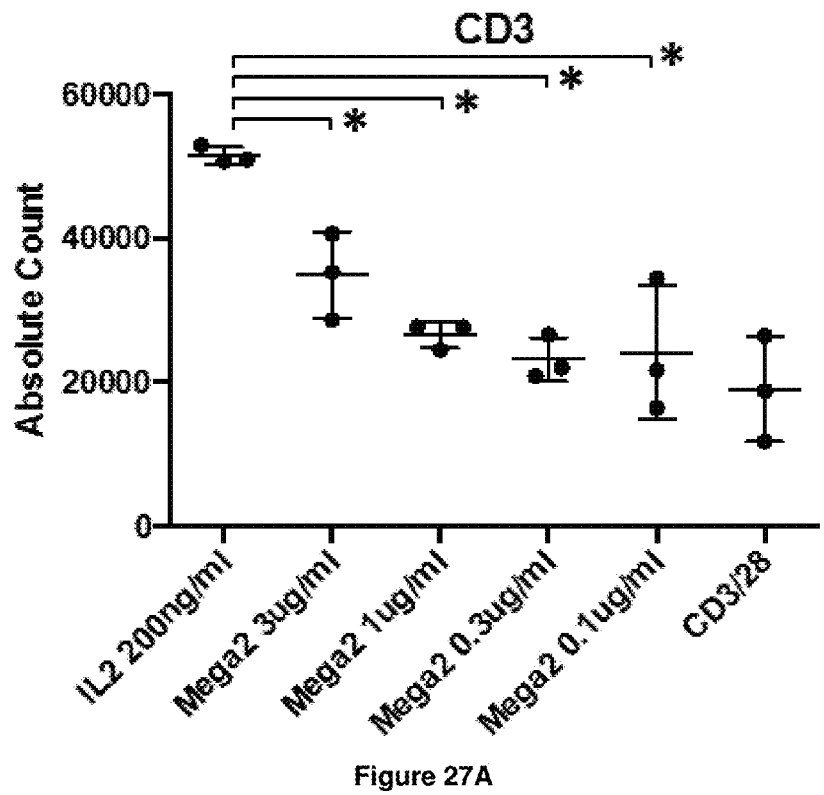
FIGS. 27A-D. Graphs showing T cell numbers and ratios following culture of PBMCs for 1 week in the presence of recombinant human IL-2 or the indicated amount of bispecific anti-IL-2Rβ/γc antibody (Mega2).
Figure 27B:
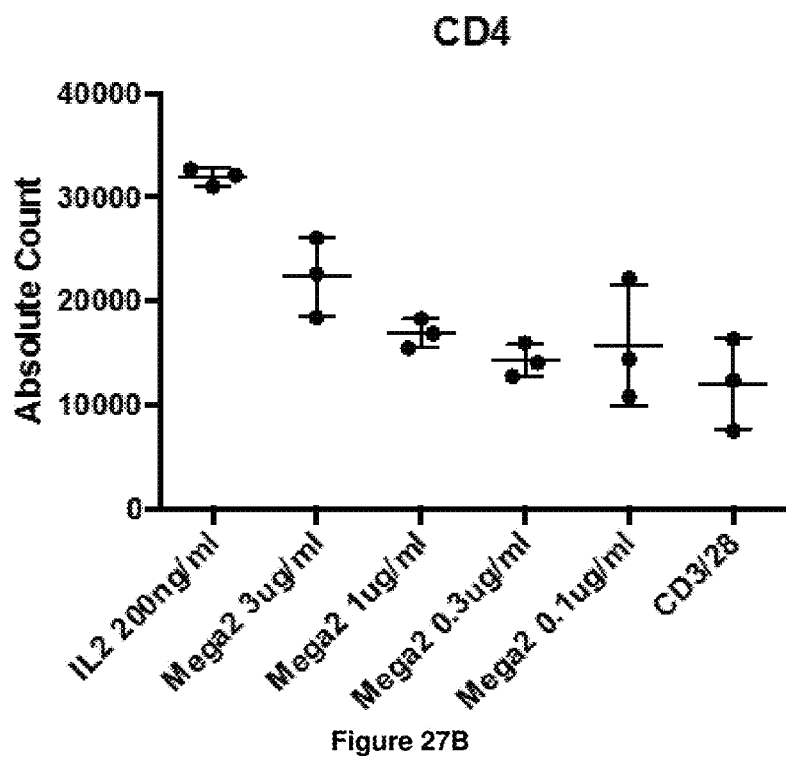
Figure 27C:
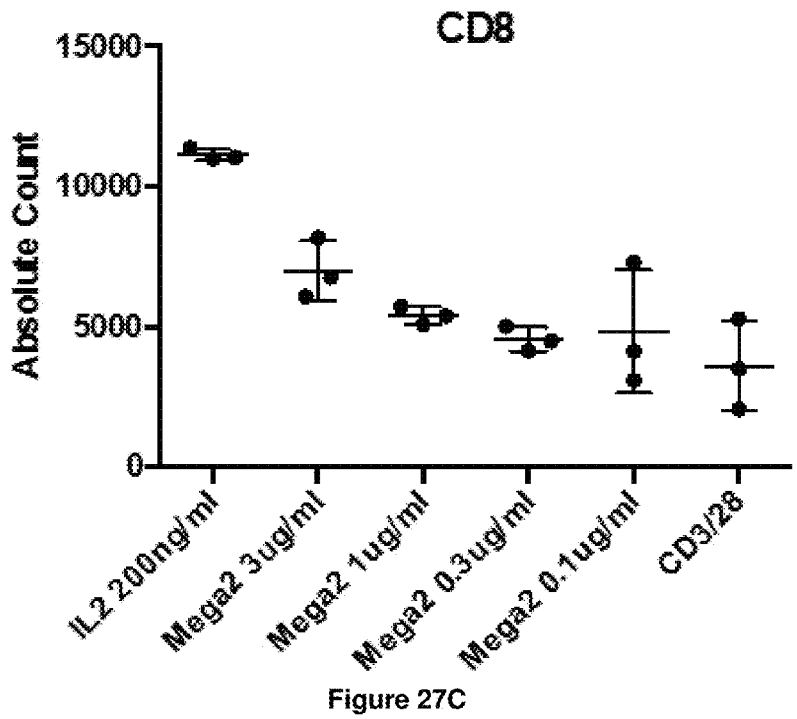
Figure 27D:
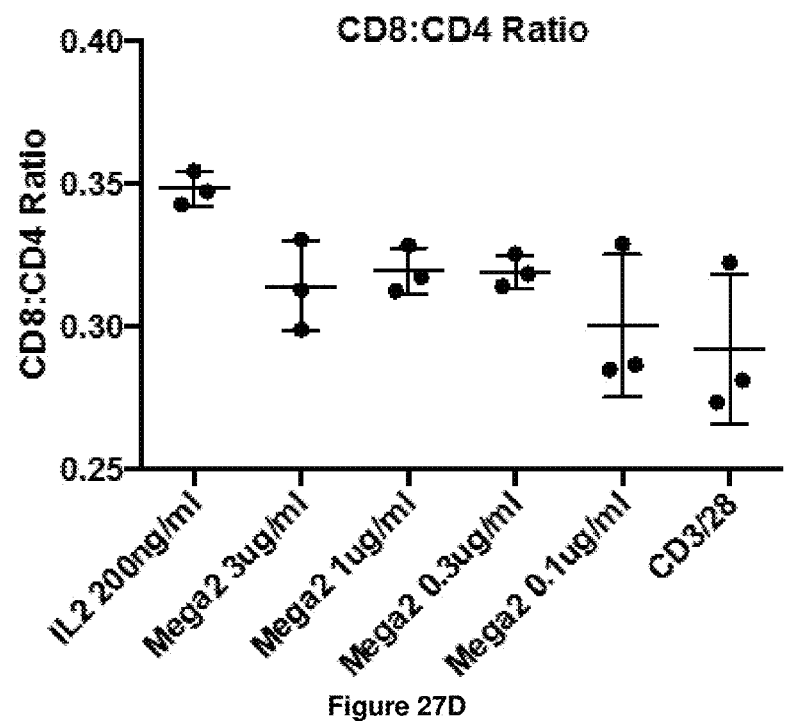

At comparable concentrations (IL-2 200 ng/ml-12 nM; Bispecific anti-IL-2Rβ/γc antibody 3 µg/ml≈20 nM), the antibody triggers T cell proliferation to a lesser extent than IL-2 (FIG. 27A to 27C). The bispecific antibody shows a dose-dependent effect on T cell proliferation (FIG. 27A to 27D). In a non-specific stimulation setting, the CD8:CD4 cell ratio was not significantly different in the presence of the anti-IL-2Rβ/γc antibody as compared to when cells were cultured with IL-2 (FIG. 27D).

7.2 Stimulation of Regulatory T Cells

Figure 28:
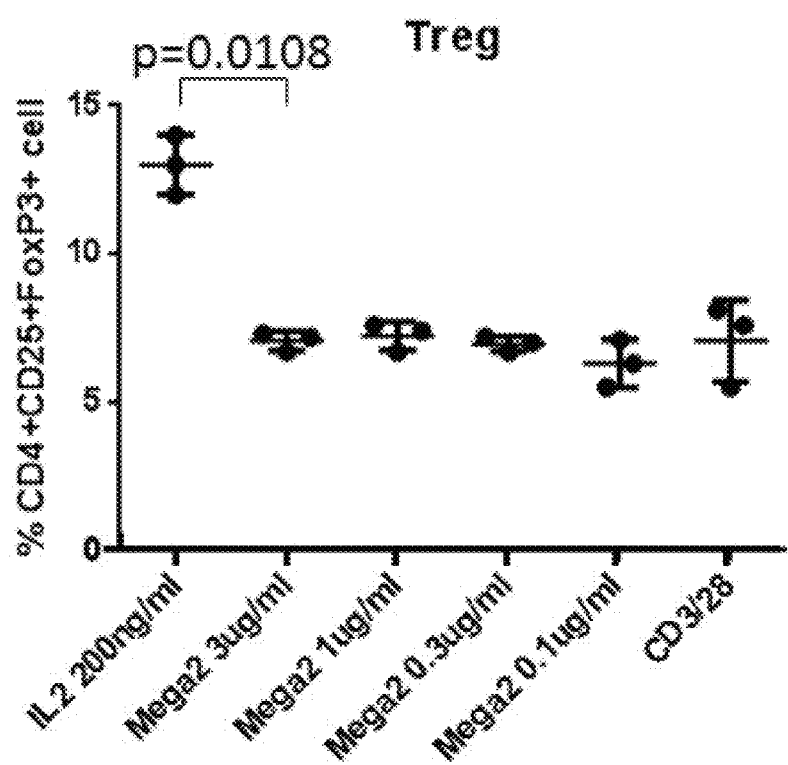
FIG. 28. Graph showing the percentage of Tregs following culture of PBMCs for 1 week in the presence of recombinant human IL-2 or the indicated amount of bispecific anti-IL-2Rβ/γc antibody (Mega2).

Regulatory T cells (Tregs) express the high affinity IL-2 receptor sub-chain IL-2Rα. In a non-specific stimulation setting, IL-2 preferentially stimulates regulatory T cells amongst CD3+CD4+ T cells; such Treg expansion was not triggered by the bispecific anti-IL-2Rβ/γc antibody (FIG. 28).

7.3 Stimulation of Effector Vs Memory Cells

Figure 29:
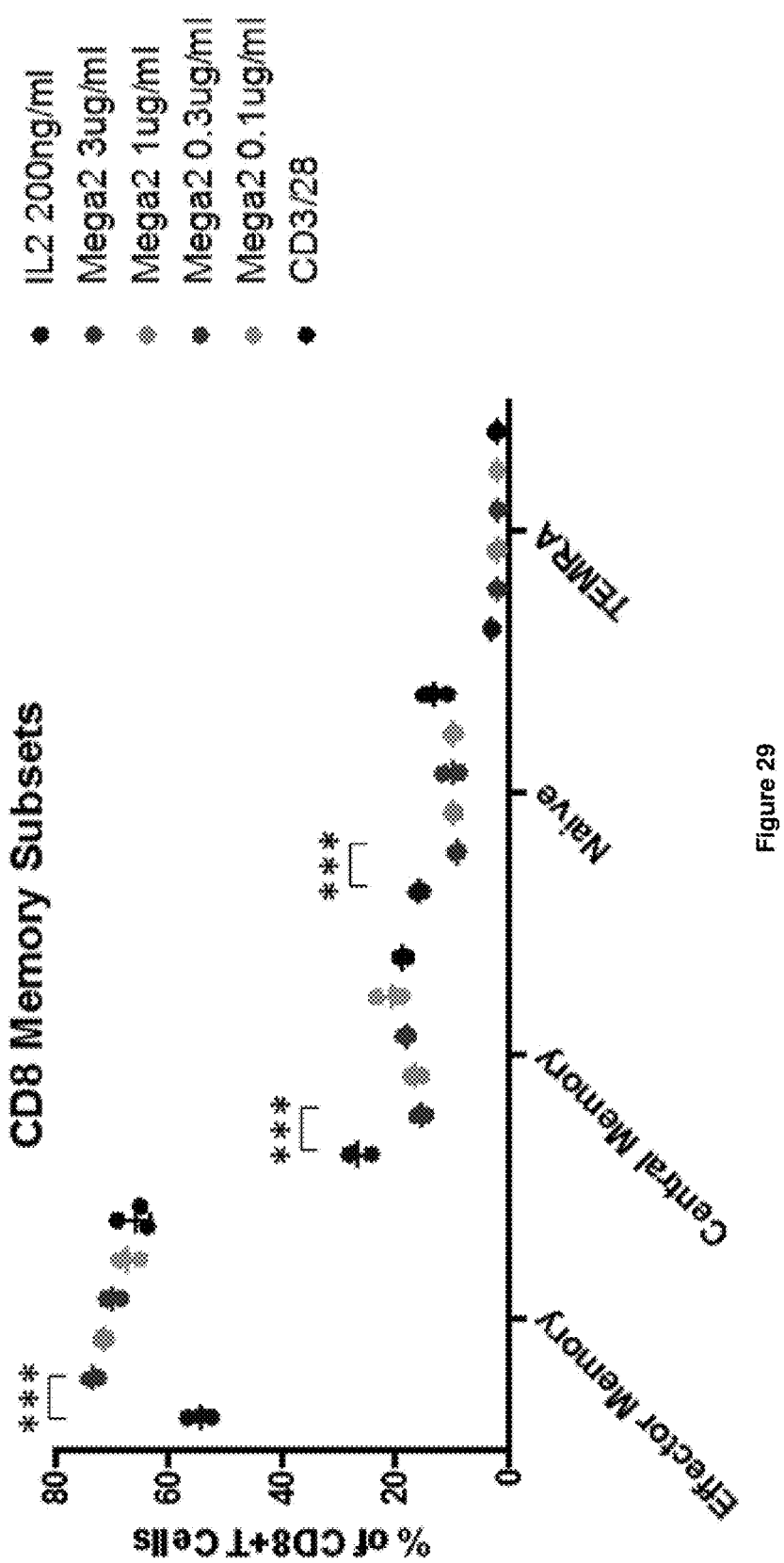
FIG. 29. Graph showing CD8+ T cell subsets as a percentage of CD8+ cells following culture of PBMCs for 1 week in the presence of recombinant human IL-2 or the indicated amount of bispecific anti-IL-2Rβ/γc antibody (Mega2). For each subset, from left to right, the data points are: IL-2 200 ng/ml, Mega2 3 ug/ml, Mega2 1 ug/ml, Mega2 0.3 ug/ml, Mega2 0.3 ug/ml and CD3/28.

With respect to memory CD8+ lymphocytes, the bispecific anti-IL-2Rβ/γc antibody triggers greater expansion of the effector memory CD8+ T cell subset, whilst triggering less expansion of the central memory and naïve CD8+ T cell subsets as compared to expansion in response to stimulation with IL-2 (FIG. 29).

Example 8: Modulation of the Immune Response: Control of T Cell Expansion in a Specific Stimulation Setting PBMCs from an Epstein-Barr virus (EBV) seropositive volunteer donor were infected with EBV to make lymphoblastoid cell lines (LCLs). LCLs were sorted and γ-irradiated in order to inhibit their subsequent proliferation. Irradiated LCLs were co-cultured at a density of $1 \times 10^5$ cells/ml with $2 \times 10^6$ autologous PBMCs/ml for 2 weeks, in the presence of IL-2, the anti-IL-2Rβ/γc bispecific antibody or anti-CD3/CD28 beads (positive control). Cells were then analysed for proliferation and the proportions of different cell subsets.

A cytotoxic killing assay was performed using a fluorescent peptide substrate for granzyme B and capsase 8. Expanded T-cells were co-incubated with live LCLs at a ratio of 2:1 for one hour. Killing was measured by analysis of peptide-fluorescent positive cells by flow cytometry, which indicated that cells were undergoing CTL-induced programmed cell death.

8.1 Expansion of T Cells

Figure 30A:
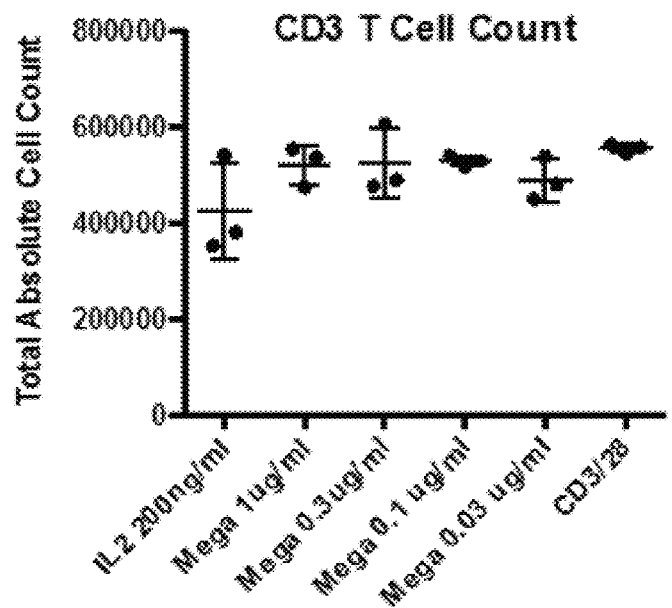
FIGS. 30A-D. Graphs showing T cell numbers and ratios following culture of PBMCs from a EBV-seropositive donor in the presence of EBV-LCLs and recombinant human IL-2 or the indicated amount of bispecific anti-IL-2Rβ/γc antibody (Mega2).
Figure 30B:
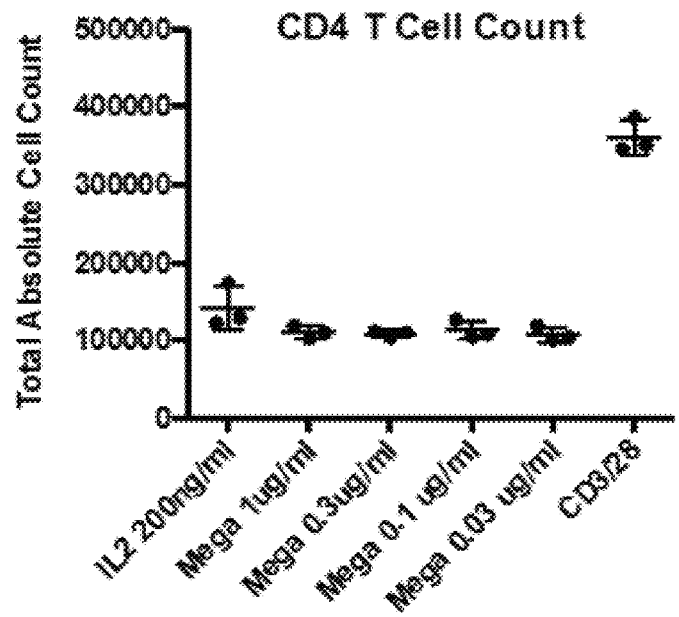
Figure 30C:
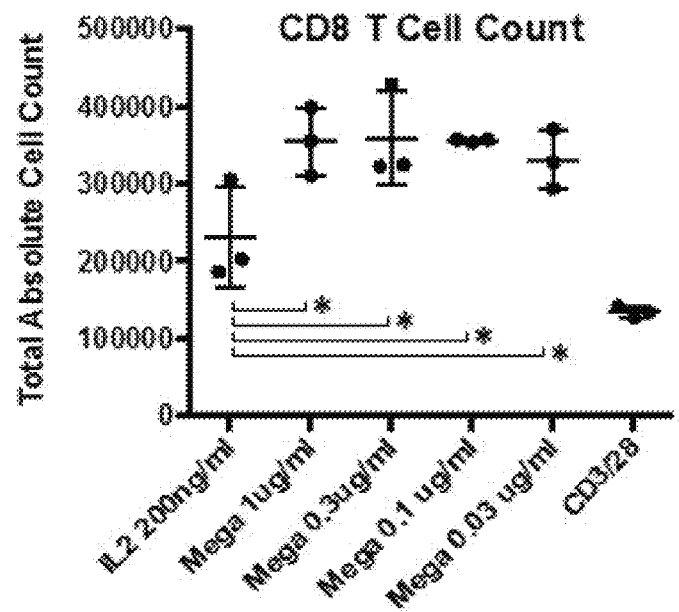
Figure 30D:
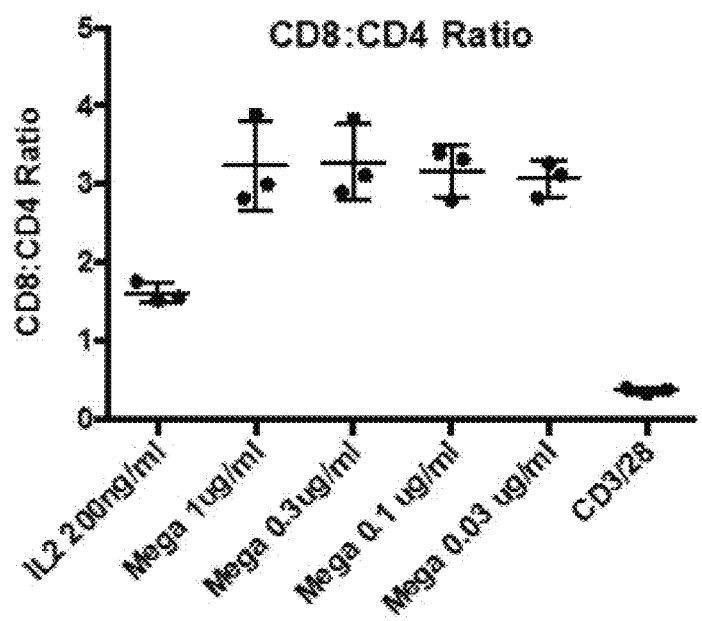

The bispecific antibody triggers expansion of T cells, even at low concentrations. Anti-IL-2Rβ/γc bispecific antibody-mediated T cell expansion is slightly greater than expansion observed following stimulation with IL-2 (FIG. 30A). Whilst the antibody does not significantly influence the number of CD4+ T cells (FIG. 30B), the antibody elicits an increase in the number of CD8+ T cells to a greater extent than IL-2 (FIG. 30C), and hence increased the CD8:CD4 cell ratio (FIG. 30D).

8.2 Effects on T Cell Subsets

Figure 31A:
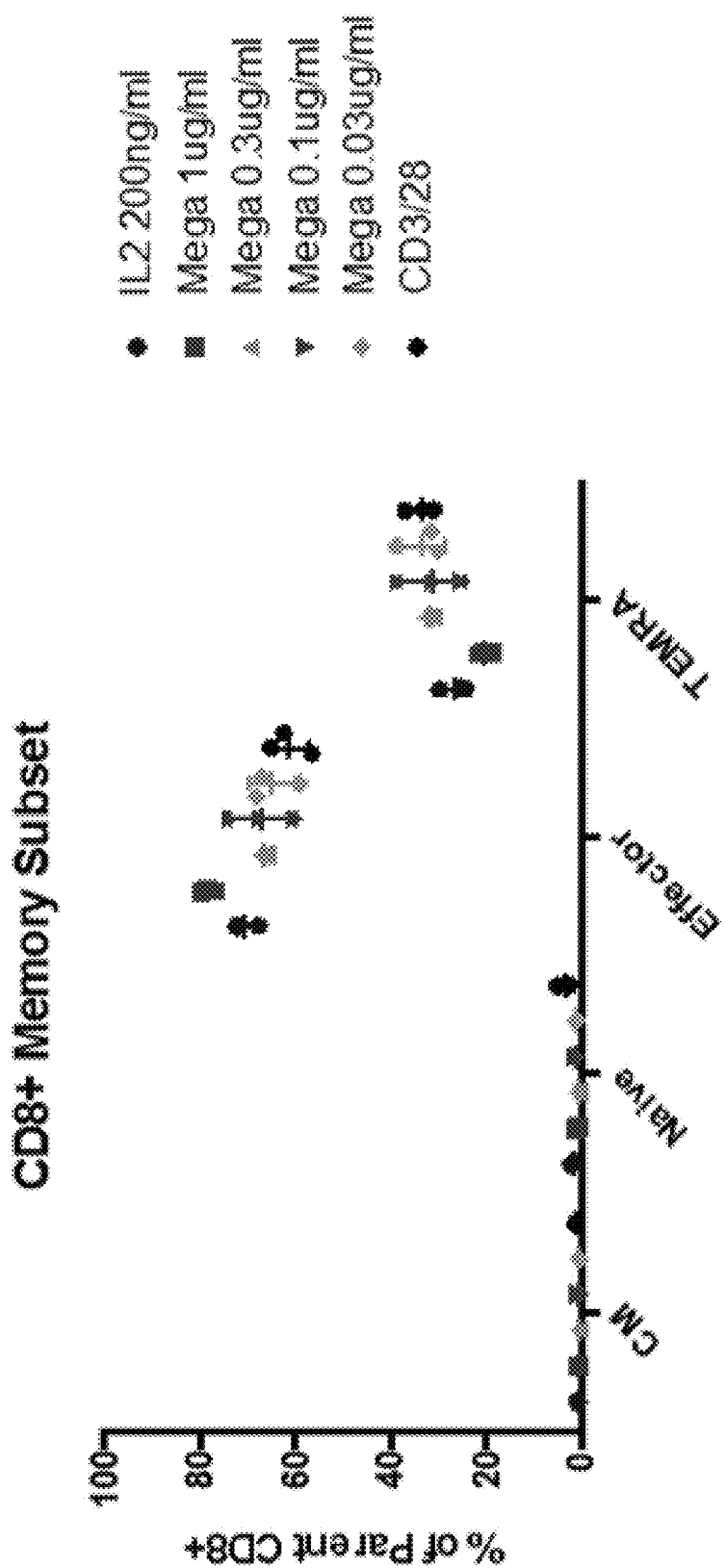
FIGS. 31A-C. Graphs showing T cell subsets following culture of PBMCs from a EBV-seropositive donor in the presence of EBV-LCLs and recombinant human IL-2 or the indicated amount of bispecific anti-IL-2Rβ/γc antibody (Mega2).
Figure 31B:
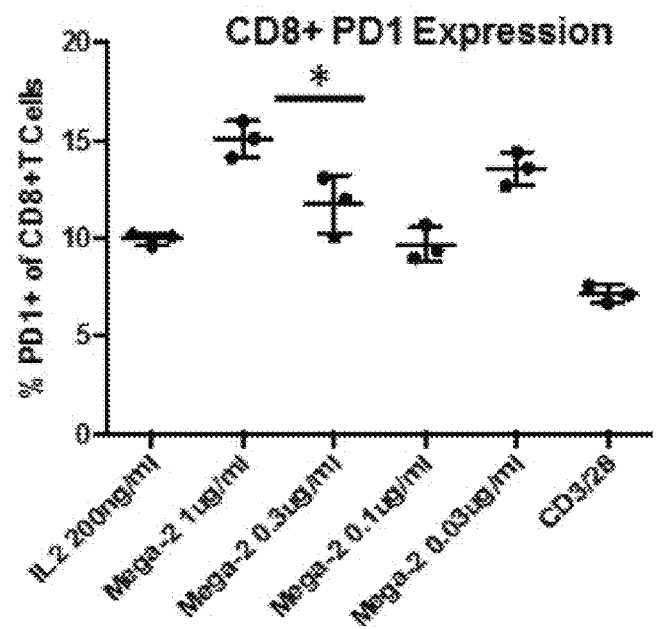
Figure 31C:
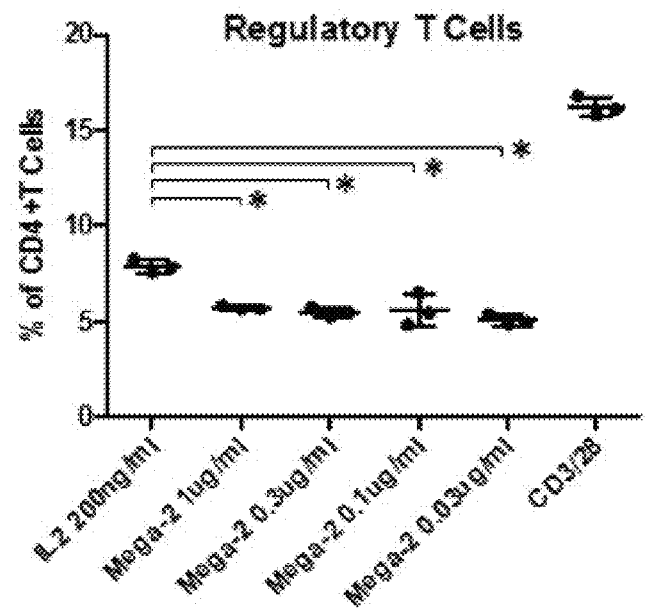

At the highest concentration (1 µg/ml), the anti-IL-2Rβ/γc antibody favours the expansion of effector CD8+ T cells over CD8+ memory cells as compared to stimulation with IL-2 (FIG. 31A). Compared to IL-2 stimulation, the anti-IL-2Rβ/γc antibody also triggers an increase in the CD8+ PD-1+ subset (FIG. 31B), whilst decreasing the proportion of Tregs (FIG. 31C).

8.3 Cytotoxic T Lymphocyte-Mediated Killing

Figure 32:
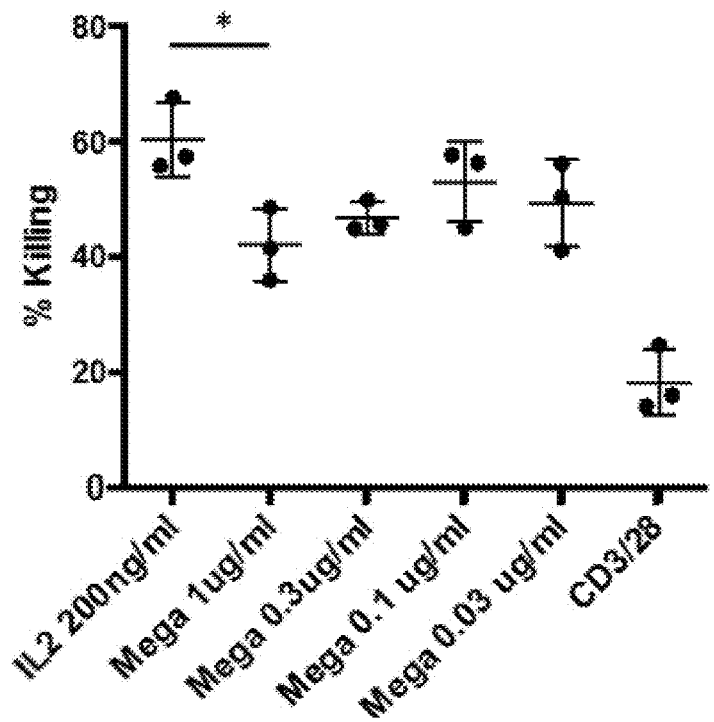
FIG. 32. Graph showing CTL cytotoxicity following culture of PBMCs from a EBV-seropositive donor in the presence of EBV-LCLs and recombinant human IL-2 or the indicated amount of bispecific anti-IL-2Rβ/γc antibody (Mega2).

The anti-IL-2Rβ/γc bispecific antibody is able to elicit CTL cytotoxicity. At comparable molarity (12 nM (200 ng/ml) for IL-2 vs. 7 nM (1 µg/mL) for the antibody), the antibody-mediated cytotoxicity is lower than cytotoxicity triggered by IL-2 (FIG. 32).

8.4 Conclusion

Taken together, the data suggest that the bispecific anti-IL-2Rβ/γc antibody triggers a different mechanism of action than that of IL-2. The antibody preferentially elicits expansion of effector CD8+ T cells. The antibody allows stimulation of cytotoxic T cells but does not preferentially stimulate Tregs as IL-2 does.

Example 9: Sequence Engineering to Improve Stability

One of the greatest challenges whilst constructing bispecific antibodies is the stability of the heterogenic construct. Unlike monospecific IgGs, the present bispecific anti-IL-2Rβ/γc antibody is an artificial assembling of two different pairs of light/heavy chains.

In order to improve the general stability of constructs, original antibody clones P2C4 and P1A3 were engineered to increase their thermostability.

9.1 Thermostable Clones

Figure 33A:
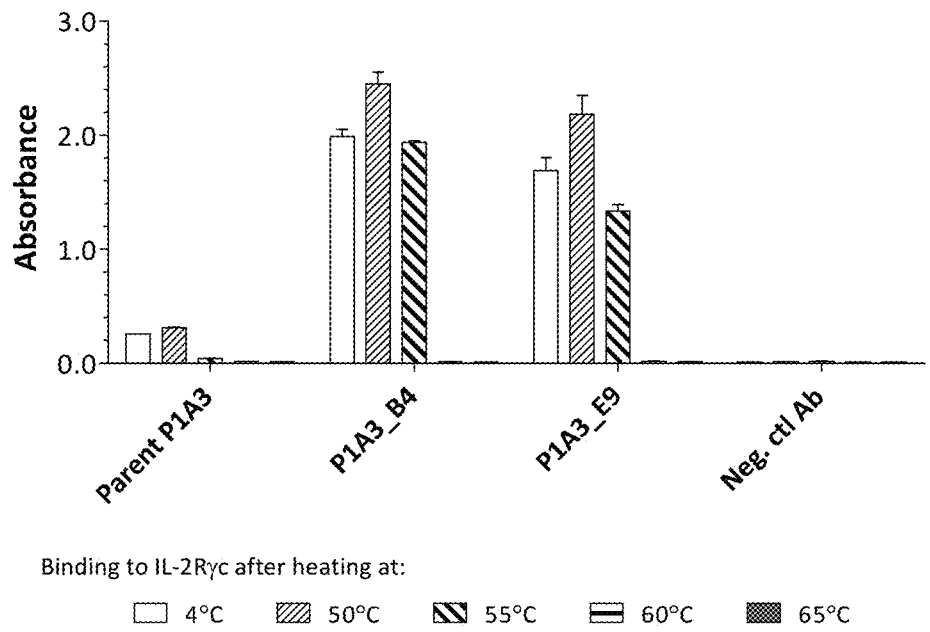
FIGS. 33A-B. Bar charts showing thermostability of P1A3 family clones. Binding of P1A3 and the mutated clones FIG. 33A B4 and E9 and FIG. 33B B3 and E8 to γc before and after heat treatment. Mean±SD on duplicates is shown.
Figure 33B:
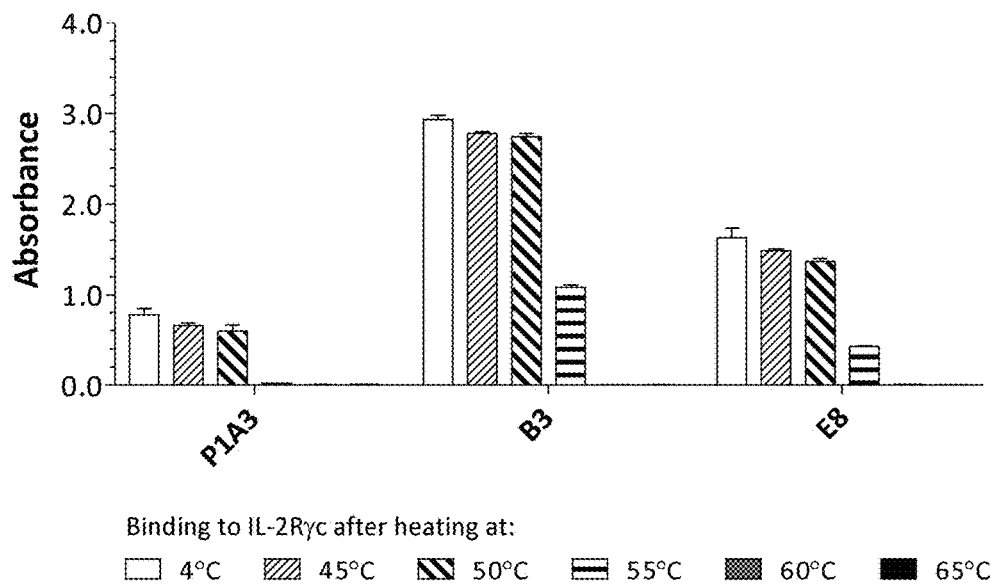
Figure 34A:
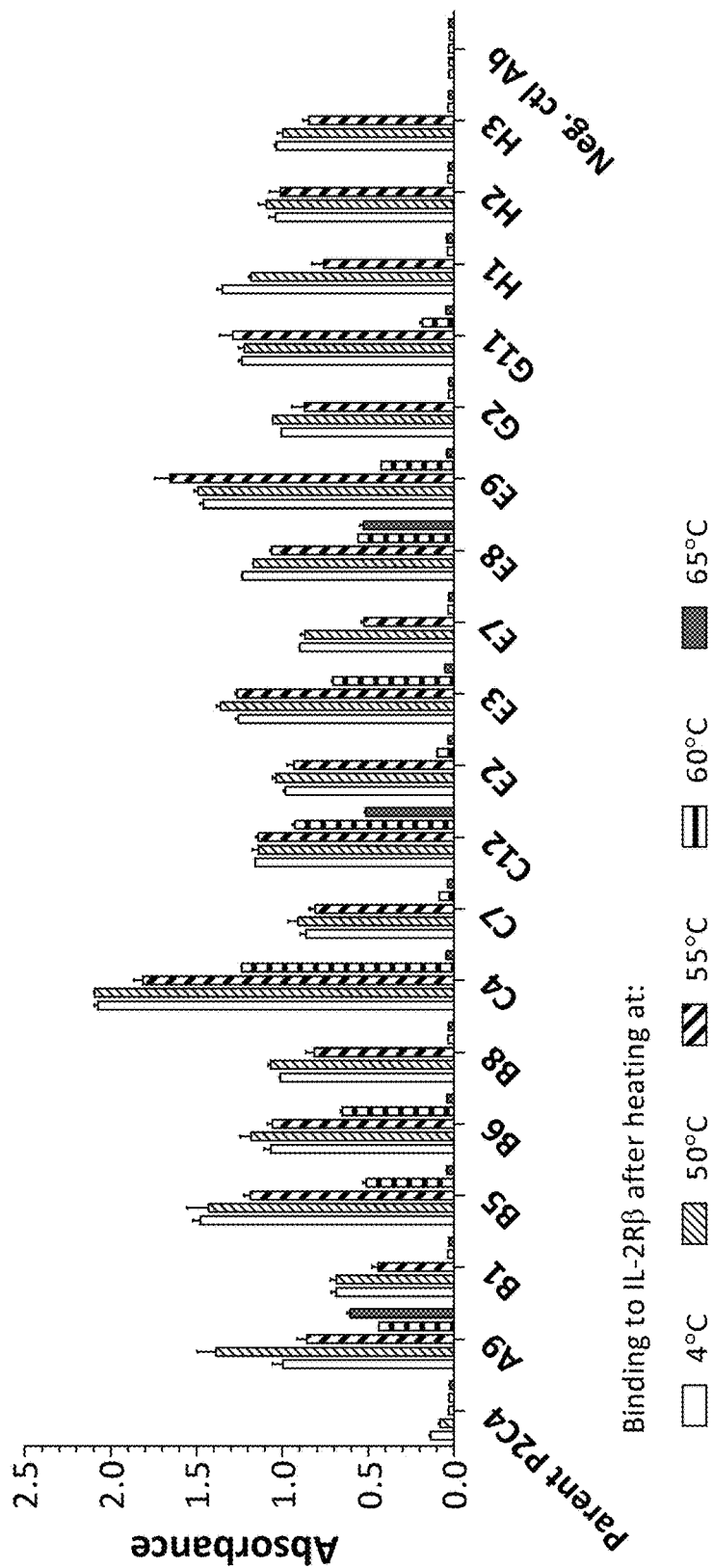
FIGS. 34A-B. Bar charts showing thermostability of P2C4 family clones. Binding of P2C4 and the mutated clones FIG. 34A A9, B1, B5, B6, B8, C4, C7, C12, E2, E3, E7, E8, E9, G2, G11, H1, H2, and H3, and FIG. 34B A4, B12, C1, D10, E6, F8, F11 and C1 D10 to IL2-Rβ before and after heat treatment. Mean±SD on duplicates is shown.
Figure 34B:
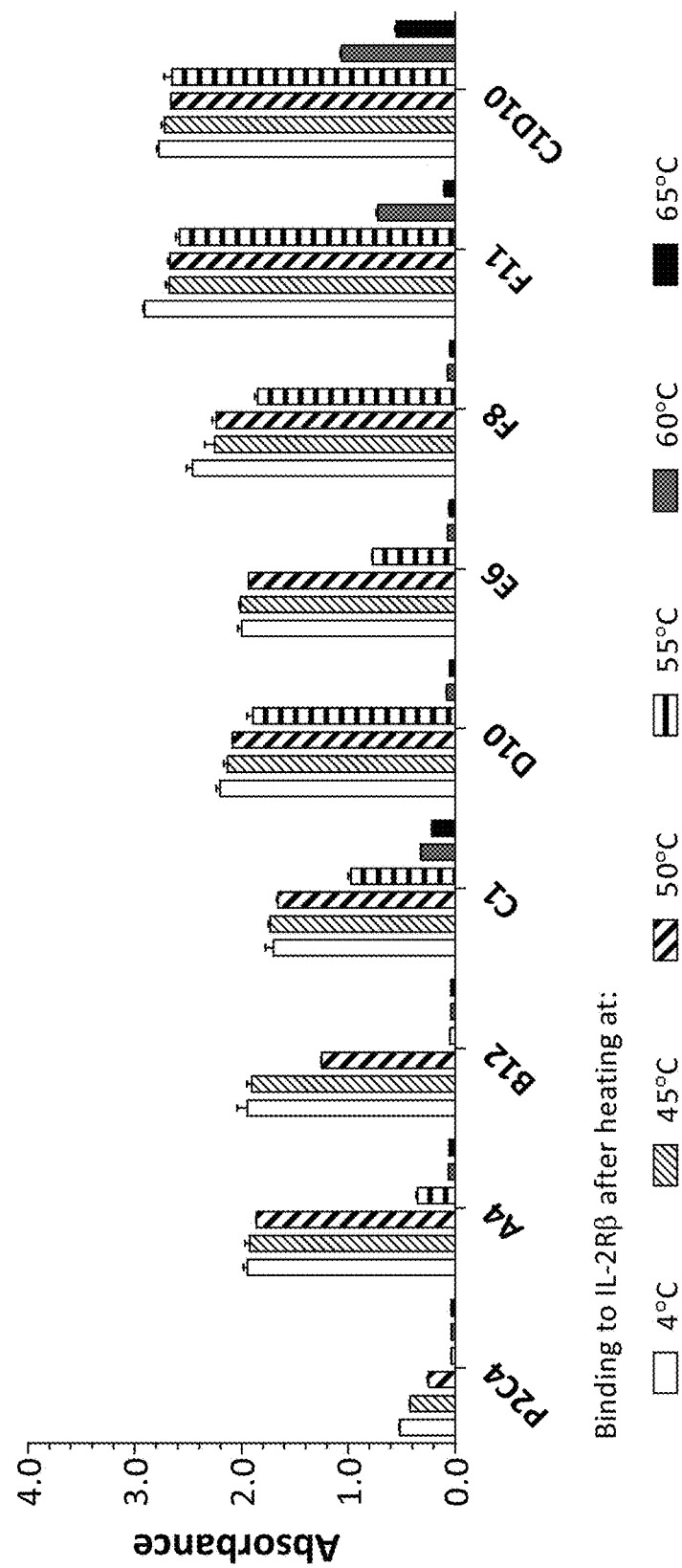

Libraries of randomly mutagenised clones were built from the parent clones P2C4 and P1A3 and mutants were screened for binding to the respective targets in a two-round panning followed by ELISA. Binders were then subjected to heating to 55° C. The mutants still binding after heating were sequenced, and unique clones were identified. Thermostability of the clones was assessed after heating for 4 hours between 45° C. and 65° C., by measuring binding to their respective target, either γc (FIGS. 33A and 33B) or IL-2Rβ (FIGS. 34A and 34B), in ELISA. The mutated clones showed higher thermal stability than the parent clones.

9.1 Engraftment of Highly Stable Framework

In order to further increase stability of the antibody, clones were engrafted in frameworks of antibodies that were known to be highly stable.

P2C4 and P1A3 were engrafted into frameworks of antibodies known to have high stability. ELISA experiments were conducted to ensure that the new clones retained the ability to bind to IL-2Rβ and γc.

Figure 35A:
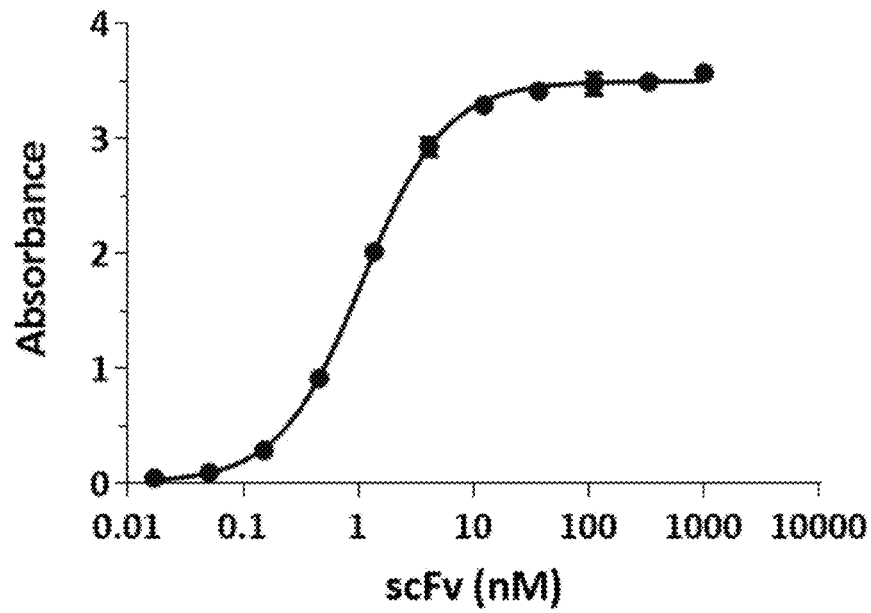
FIGS. 35A-B. Graphs showing binding of FIG. 35A P2C4_FW2 single chain antibody to IL-2Rβ, and FIG. 35B P1A3_FW2 single chain antibody to γc.
Figure 35B:
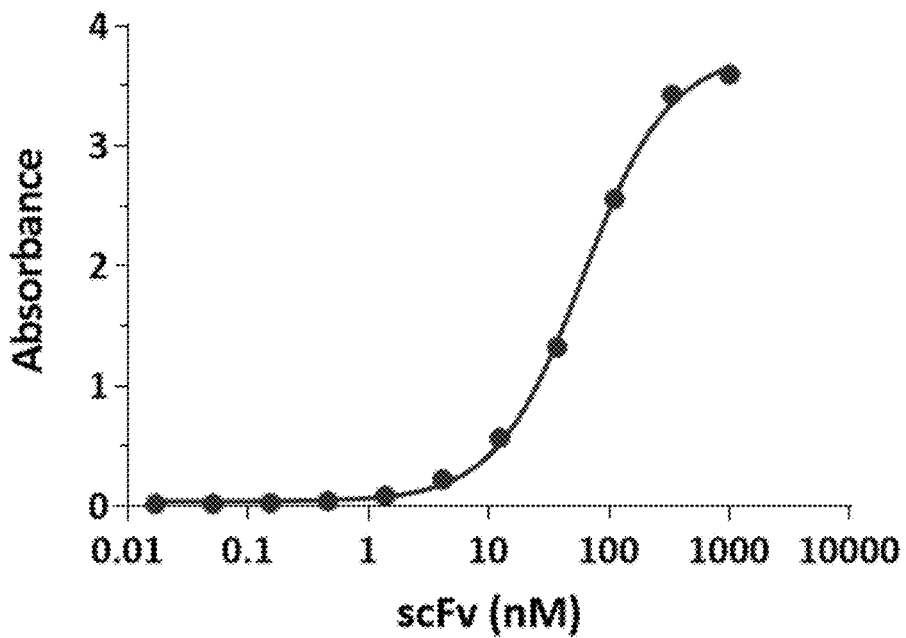

Both P2C4_FW2 and P1A3_FW2 showed a dose-dependent binding profile to IL-2Rβ and γc respectively (FIGS. 35A and 35B).

Example 10: Binding of New Bispecific Constructs to IL-2Rβ/γc 10.1 Short Linker Between Variable and Constant Domains Bispecific antibody constructs were prepared including one of the following short linkers between the scFv and constant domain (antibody format: $V_H$ domain—linker—$V_L$ domain—short linker—hinge—CH2 domain (+LALA)—CH3 domain (+knob/hole+cys)): NSGAGTAAA (SEQ ID NO:157) or GGGGSAAA (SEQ ID NO:158).

Bispecific constructs with NSGAGTAAA (SEQ ID NO:157) or GGGGSAAA (SEQ ID NO:158) short linkers were generated and tested for binding to IL-2Rβ and γc by ELISA.

Figure 36A:
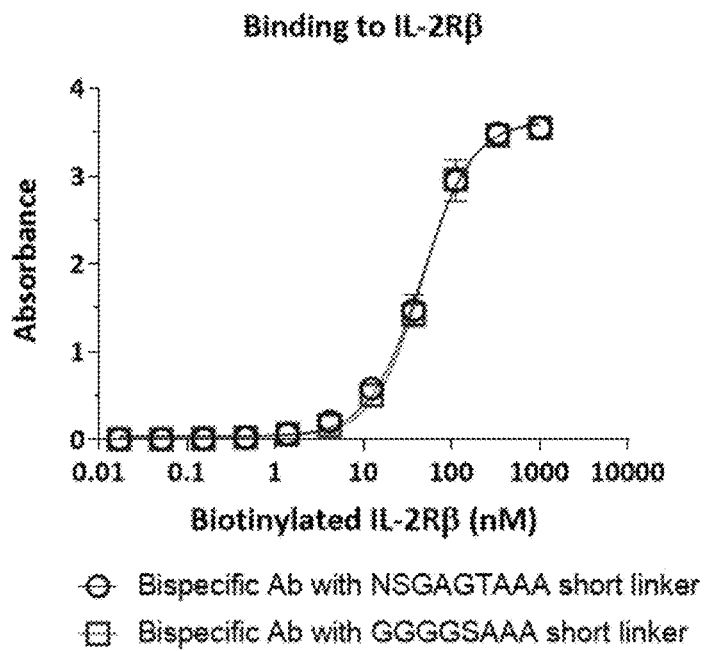
FIGS. 36A-B. Graphs showing binding of the bispecific antibody clone P2C4/P1A3 to FIG. 36A IL-2Rβ, and FIG. 36B γc, for antibodies having the NSGAGTAAA (SEQ ID NO:157) or GGGGSAAA (SEQ ID NO:158) short linkers.
Figure 36B:
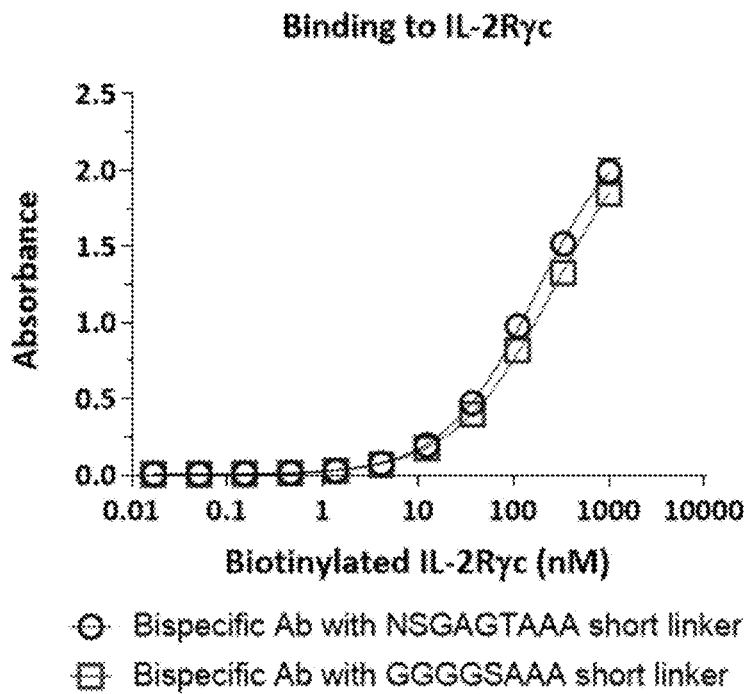

The bispecific antibodies were found to bind to with similar affinity irrespective of the identity of the short linker (FIGS. 36A and 36B).

Figure 37A:
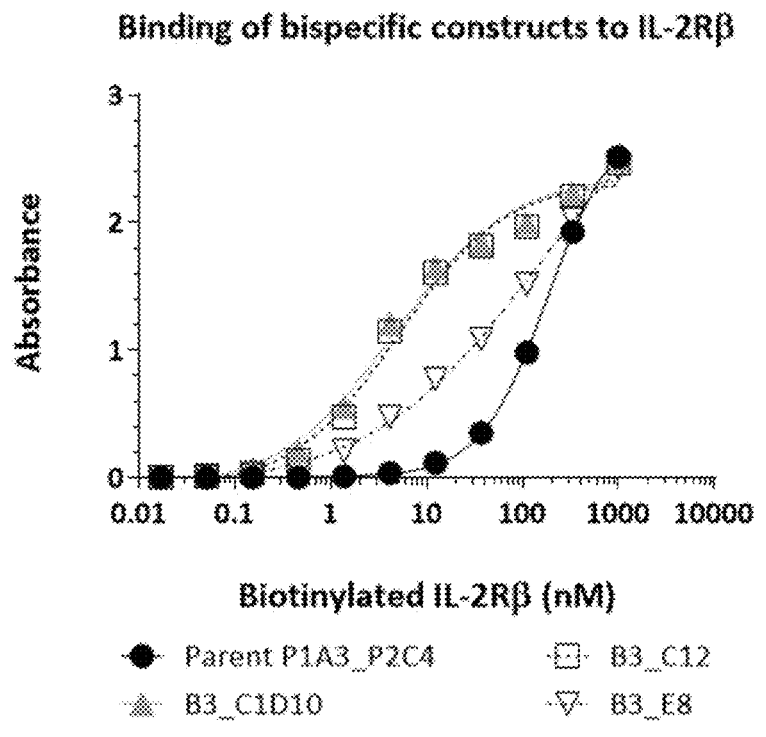
FIGS. 37A-B. Graphs showing binding of bispecific engineered antibody clones to FIG. 37A IL-2Rβ, and FIG. 37B γc.
Figure 37B:
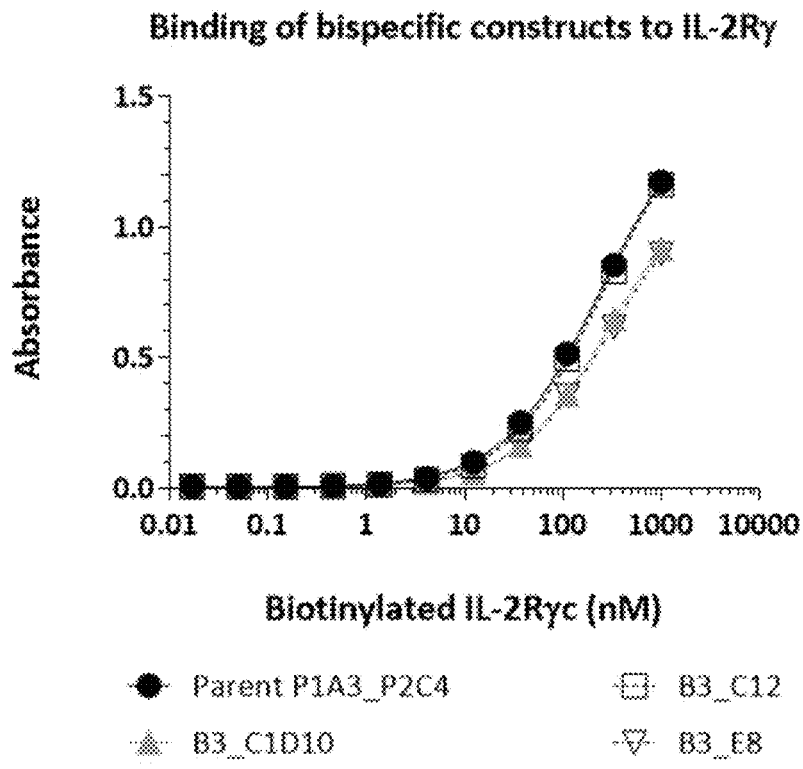

Bispecific antibodies were constructed with the new sequences and binding was assessed by ELISA on either IL-2Rβ or IL-2Rγc. The constructs were found to bind similar or better affinity than the parent bispecific antibodies to IL-2R (FIGS. 37A and 37B).

Example 11: Effects on T Cell Expansion and Polarization

Assays using T cells were performed in order to measure the effect of the anti-IL-2Rβ/γc bispecific antibody on T cell expansion in vitro and its impact on antigen specific and non-specific qualitative polarisation and subset specificity. Peripheral blood from EBV-positive individuals was used to generate both EBV-transformed lymphoblastoid B-cell lines (LCLs) and EBV-specific CTL lines.

Briefly, to generate LCLs, PBMCs were cultured for 1 week in the presence of cyclosporine and EBV, and for 2 additional weeks in refreshed media with cyclosporine but without EBV. After culture, cells were transferred to a G-Rex column and growth was monitored. For the generation of CTLs, LCLs were irradiated to act as an antigen source for CTLs. PBMCs were co-cultured with LCLs at an effector to stimulator (E:S) ratio of 40:1. Cells were stimulated by addition of IL-2, the anti-IL-2Rβ/γc bispecific antibody, or CD3/28 beads.

After 7 days, cells underwent a media change and additional stimulations. At day 10, cells were analysed for lymphocyte expansion and phenotype by flow cytometry.

Figure 38A:
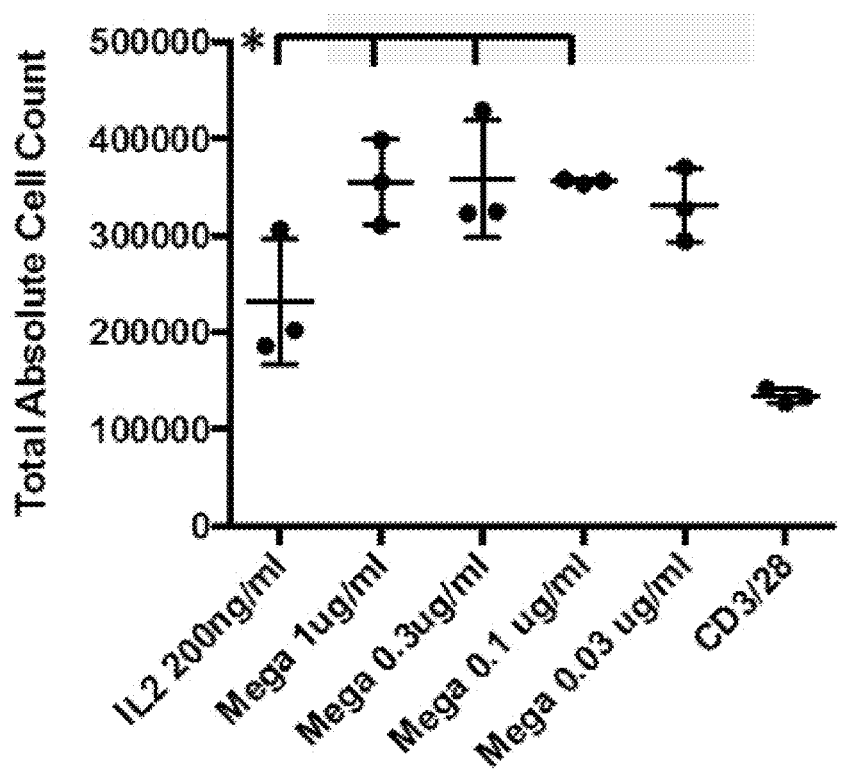
FIGS. 38A-B. Graphs showing in vitro response of antigen-specific CD8+ T cells to bispecific anti-IL-2Rβ/γc antibody exposure, as measured by flow cytometry.
Figure 38B:
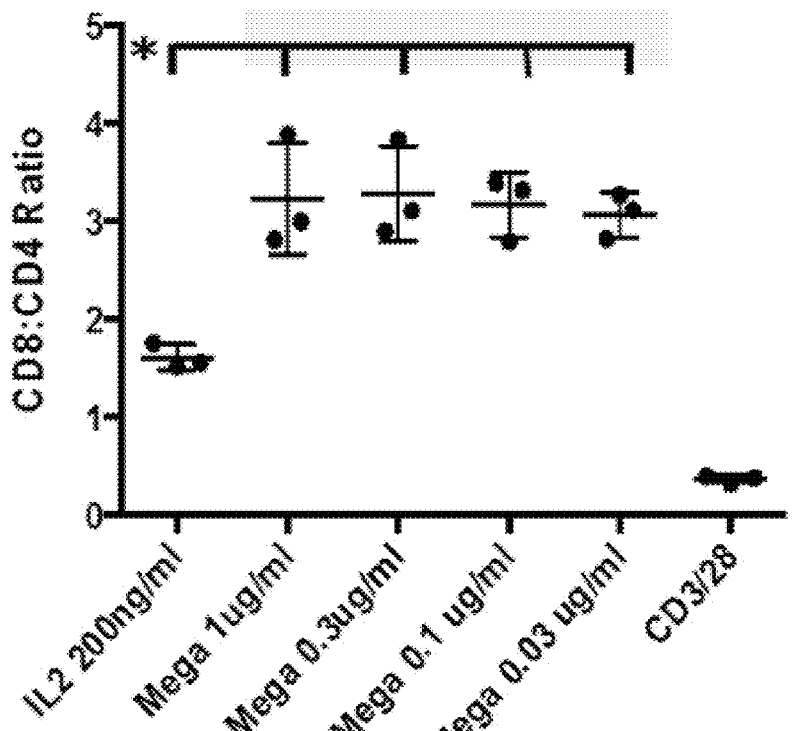

Addition of the bispecific antibody was found to result in a significant increase in antigen-specific CD8+ T cell expansion as compared to expansion in response to stimulation with IL-2 (FIG. 38A). Furthermore, in vitro cultures showed improved CD8:CD4 ratios following antibody stimulation (FIG. 38B).

Figure 39A:
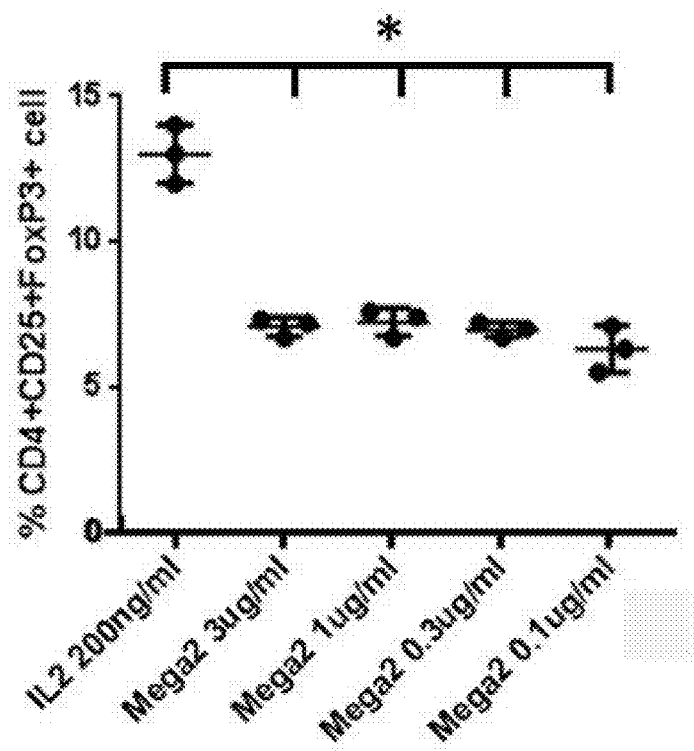
FIGS. 39A-B. Graphs showing in vitro response of Treg cells to bispecific anti-IL-2Rβ/γc antibody exposure, as measured by flow cytometry, in FIG. 39A an antigen-specific, or FIG. 39B non-specific setting. *p value<0.05.
Figure 39B:
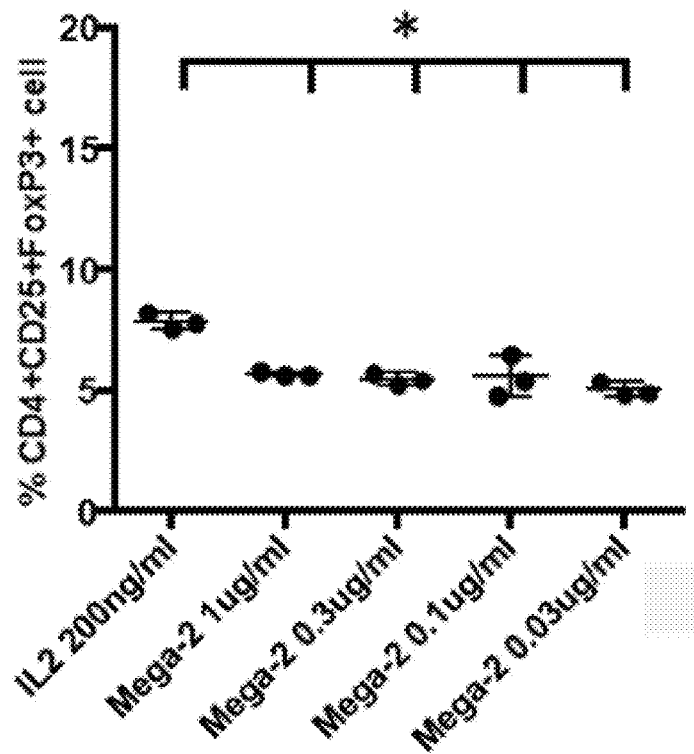
Figure 40A:
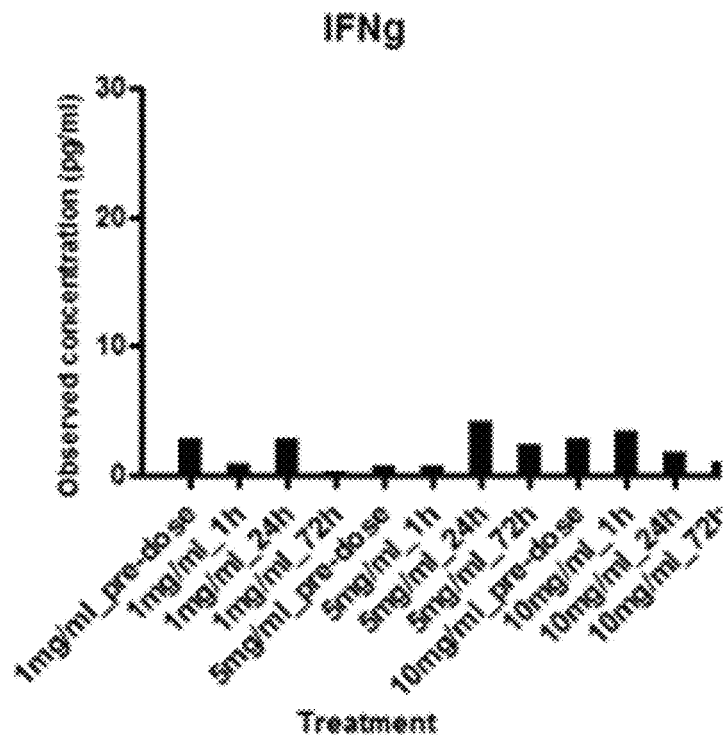
FIGS. 40A-E. Bar charts showing levels of cytokines as measured by Luminex analysis FIG. 40A IFNγ, FIG. 40B IL-15, FIG. 40C IL-1, FIG. 40D IL-6, and FIG. 40E TNFα in the plasma of non-human primates, before and after administration of anti-IL-2Rβ/γc antibody.
Figure 40B:
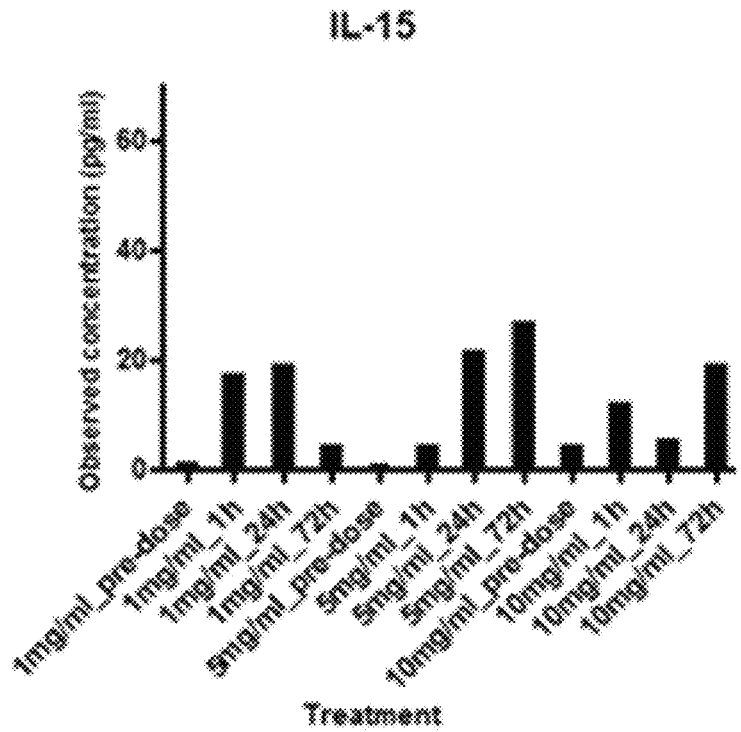
Figure 40C:
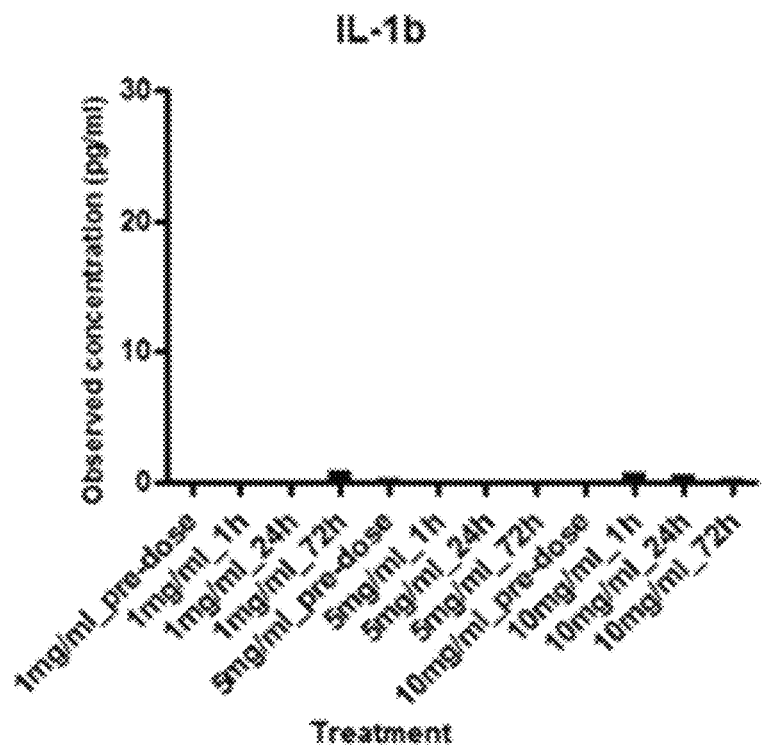
Figure 40D:
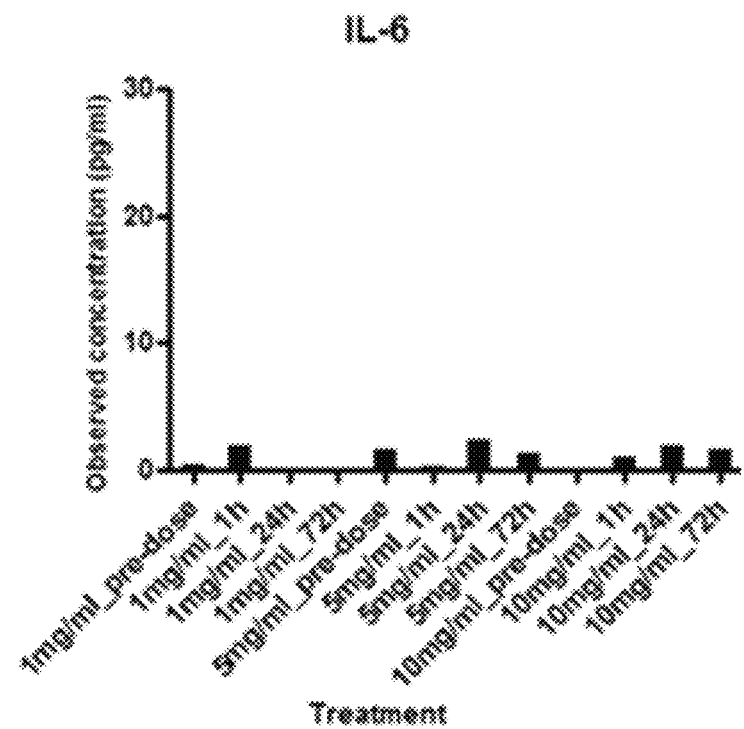
Figure 40E:
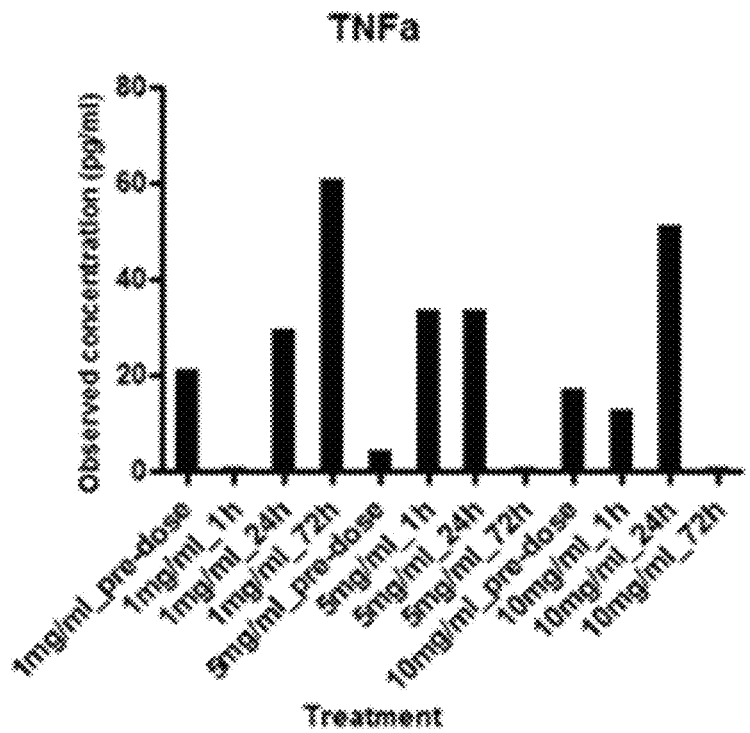

The impact of the bispecific antibody on the expansion of regulatory T cells (Tregs) was then measured and compared to expansion of Tregs in response to stimulation with IL-2, in the antigen specific (autologous LCL co-culture) and non-specific (anti-CD3/CD28 microbead) settings. Addition of the bispecific antibody results in significantly reduced expansion of Tregs as compared to Treg expansion in response to IL-2, in both the non-specific (FIG. 39A) and antigen-specific stimulation settings (FIG. 39B).

Example 12: In Vivo Data in Non-Human Primates

A dose escalating experiment was established in Cynomolgus macaques in order to measure the effects of intravenous (iv) injection of the anti-IL-2Rβ/γc bispecific antibody, its ability to drive proliferation of T cells and NK cells, and its potential toxicity through "cytokine storm".

Three macaques were administered a single dose of the anti-IL-2Rβ/γc antibody, intravenously through the femoral artery; macaque A received 1 mg/kg, macaque B received 5 mg/kg, and macaque C received 10 mg/kg. Blood was collected before antibody injection and at 1 h, 24 h, 72 h and 120 h post-injection.

Vital signs and physical examinations were performed throughout the study and then for a further 3 weeks. PBMCs were isolated at all time points, leukocyte subsets were analysed by immune-staining and flow cytometry, and cell expansion was assessed by analysis of Ki-67 expression. Plasma cytokine levels were measured by Luminex at all time points.

Veterinary physical examination indicated no abnormalities in general appearance, mucosal membranes, cardiovascular, respiratory, integumentary, alimentary, musculoskeletal, nervous, urogenital, auditory, or ocular systems. Animals displayed no clinical findings of febrile illness or depression. One animal (macaque B) showed mild weight loss from which he recovered during the course of the study. Animals showed no overt signs of toxicity commonly associated with IL-2 administration (PMID: 1418698 and 8454416).

Figure 41A:
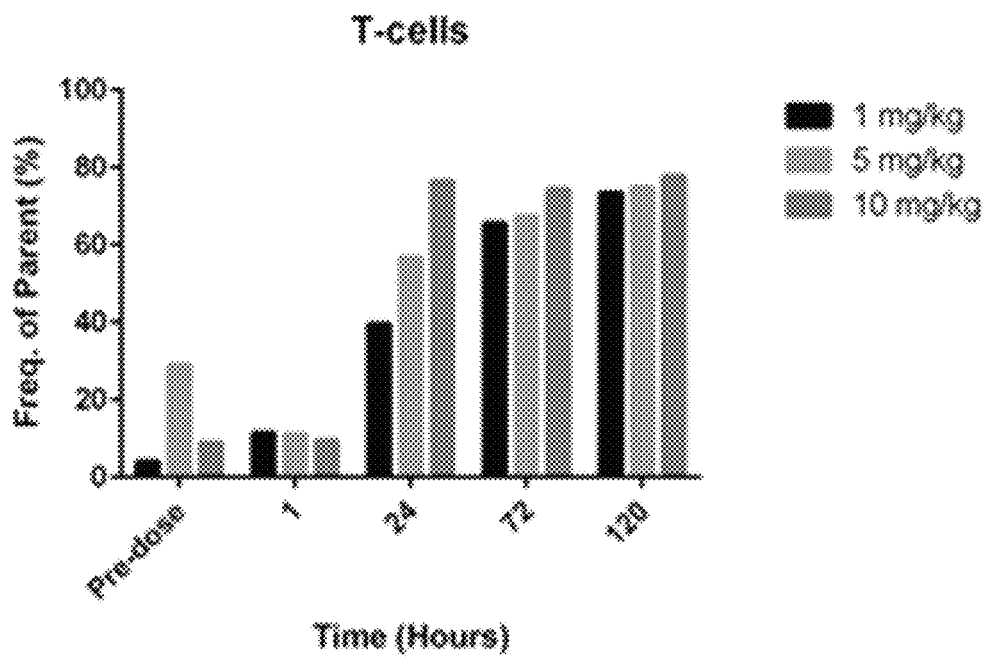
FIGS. 41A-C. Bar charts showing in vivo response of T cell subsets to bispecific anti-IL-2Rβ/γc antibody injection, as measured by flow cytometry.
Figure 41B:
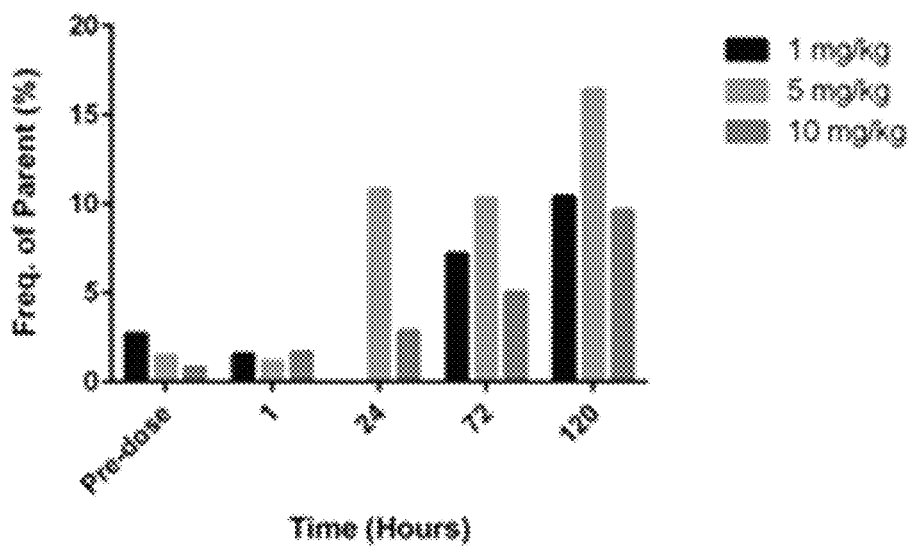
Figure 41C:
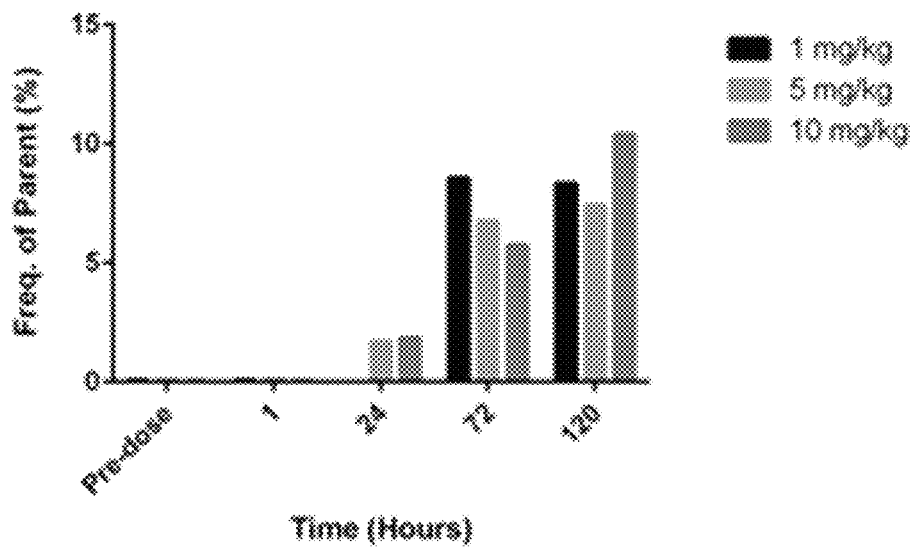

Consistent with these observations, cytokine analysis demonstrated only mild increases in inflammatory mediators post injection (FIGS. 40A to 40E). Flow cytometric analysis indicated a marked proliferation of CD4+ and CD8+ T cell populations (FIGS. 41A to 41C).

Figure 42A:
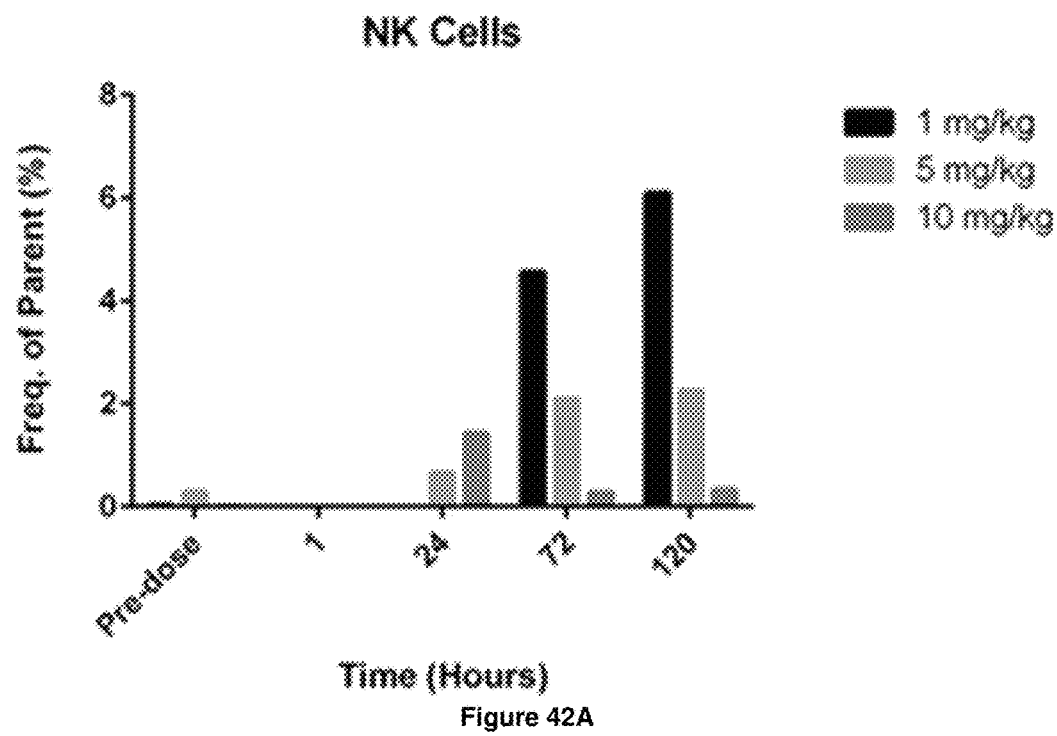
FIGS. 42A-B. Bar charts showing in vivo response of NK cells to bispecific anti-IL-2Rβ/γc antibody injection, as measured by flow cytometry.
Figure 42B:
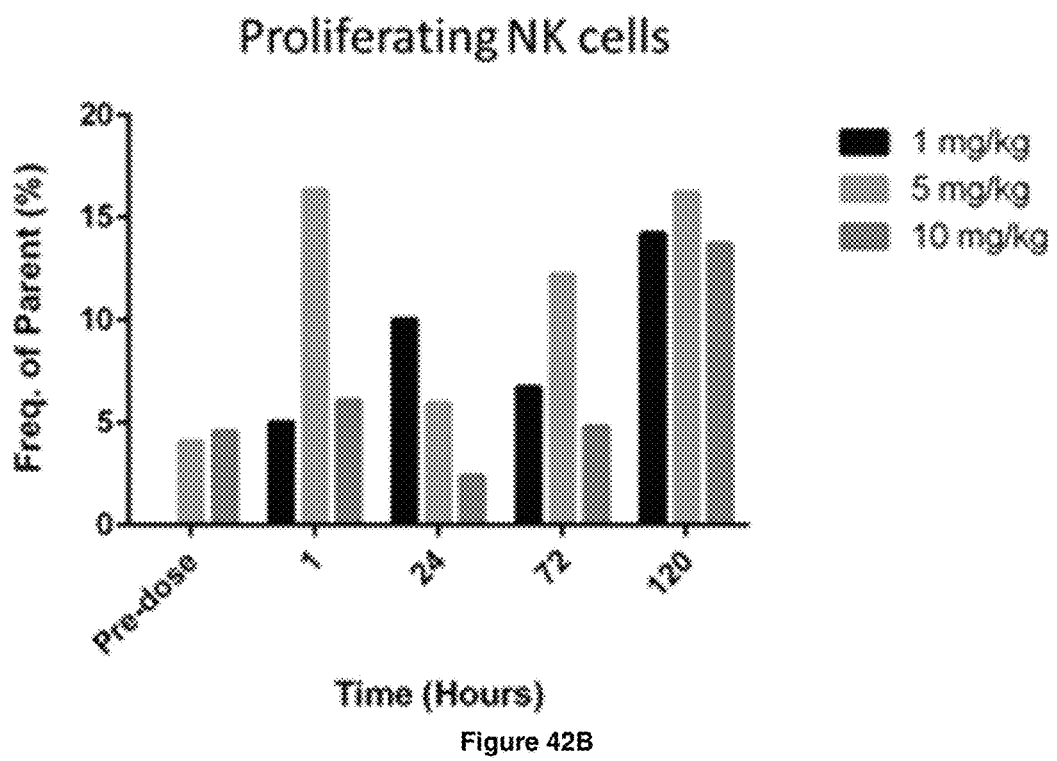

NK cell proliferation was also observed in response to the antibody treatment (FIGS. 42A and 42B). It should be noted that this expansion was observed after a single dose of antibody, compared to continuous infusion or repeated doses required for IL-2, suggesting that anti-IL-2Rβ/γc bispecific antibody has a longer half-life than IL-2.

The invention claimed is:

1. An isolated antibody or antigen binding fragment, which specifically binds to CD122 and common γ chain (γc), wherein the antibody or antigen binding fragment is an IL-2 receptor agonist, and wherein the antibody or antigen-binding fragment comprises:

(a) an antigen-binding fragment which binds to CD122, comprising:

(i) a light chain variable region comprising the following CDRs:
LC-CDR1:
(SEQ ID NO: 2)
TGTSSDIGHYDFVS

LC-CDR2:
(SEQ ID NO: 3)
DINNRPS

LC-CDR3:
(SEQ ID NO: 4)
SAYTSSDTLV;
and (ii) a heavy chain variable region comprising the following CDRs:
HC-CDR1:
(SEQ ID NO: 36)
NYYMH

HC-CDR2:
(SEQ ID NO: 37)
AIMPSRGGTSYPQKFQG

HC-CDR3:
(SEQ ID NO: 38)
GEYYYDSSGYYY;

and (b) an antigen-binding fragment which binds to common γ chain, comprising:

(i) a light chain variable region comprising the following CDRs:

LC-CDR1:
RSSQSLLHSNGYNYLD (SEQ ID NO: 68)

LC-CDR2:
LGSNRDS (SEQ ID NO: 69)

LC-CDR3:
MQGTHWPWT; (SEQ ID NO: 70)

and (ii) a heavy chain variable region comprising the following CDRs:

HC-CDR1:
GYYWS (SEQ ID NO: 48)

HC-CDR2:
EINHSGSTNYNPSLKS (SEQ ID NO: 49)

HC-CDR3:
SPGGYSGGYFQH. (SEQ ID NO: 77)

2. The isolated antibody or antigen binding fragment according to claim 1, wherein the antigen-binding fragment which binds to CD122 comprises a light chain variable region sequence and a heavy chain variable region sequence, wherein:

the light chain variable region sequence has at least 70% sequence identity to the light chain variable region sequence of SEQ ID NO:1, and the heavy chain variable region sequence has at least 70% sequence identity to the heavy chain variable region sequence of SEQ ID NO:35.

3. The isolated antibody or antigen binding fragment according to claim 1, wherein the antigen-binding fragment which binds to common γ chain comprises a light chain variable region sequence and a heavy chain variable region sequence, wherein:

the light chain variable region sequence has at least 70% sequence identity to the light chain variable region sequence of SEQ ID NO:67, and the heavy chain variable region sequence has at least 70% sequence identity to the heavy chain variable region sequence of SEQ ID NO:76.

4. The isolated antibody or antigen binding fragment according to claim 1, which binds to the IL-2 receptor comprising a complex of CD122 and common γ chain.

5. The isolated antibody or antigen binding fragment according to claim 1, provided in scFv-KiH-Fc or CrossMab format.

6. The isolated antibody or antigen binding fragment according to claim 1, conjugated to a drug moiety or a detectable moiety.

* * * * *

SEQUENCE LISTING

```
<160> NUMBER OF SEQ ID NOS: 156

<210> SEQ ID NO 1
<211> LENGTH: 108
<212> TYPE: PRT
<213> ORGANISM: Artificial Sequence
<220> FEATURE:
<223> OTHER INFORMATION: Antibody sequence

<400> SEQUENCE: 1

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60
```

```
Ser Gly Ser Lys Ser Asp Asn Met Ala Ser Leu Thr Ile Ser Gly Leu
 65                  70                  75                  80

Gln Pro Glu Asp Glu Ala Asp Tyr Tyr Cys Ser Ala Tyr Thr Ser Ser
                 85                  90                  95

Asp Thr Leu Val Phe Gly Gly Gly Thr Lys Leu Thr
            100                 105

<210> SEQ ID NO 2
<211> LENGTH: 14
<212> TYPE: PRT
<213> ORGANISM: Artificial Sequence
<220> FEATURE:
<223> OTHER INFORMATION: LC-CDR1

<400> SEQUENCE: 2

Thr Gly Thr Ser Ser Asp Ile Gly His Tyr Asp Phe Val Ser
1               5                   10

<210> SEQ ID NO 3
<211> LENGTH: 7
<212> TYPE: PRT
<213> ORGANISM: Artificial Sequence
<220> FEATURE:
<223> OTHER INFORMATION: LC-CDR2

<400> SEQUENCE: 3

Asp Ile Asn Asn Arg Pro Ser
1               5

<210> SEQ ID NO 4
<211> LENGTH: 10
<212> TYPE: PRT
<213> ORGANISM: Artificial Sequence
<220> FEATURE:
<223> OTHER INFORMATION: LC-CDR3

<400> SEQUENCE: 4

Ser Ala Tyr Thr Ser Ser Asp Thr Leu Val
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Antibody sequence

<400> SEQUENCE: 5

Asp Ile Gln Met Thr Gln Ser Pro Ser Thr Leu Ser Ala Ser Val Gly
1               5                   10                  15

Asp Arg Val Thr Leu Ser Cys Arg Ala Gly Gln Ala Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Gly Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Tyr
                85                  90                  95

Thr Phe Gly Gln Gly Thr Lys Leu Glu Ile Arg
            100                 105
```

<210> SEQ ID NO 6
<211> LENGTH: 11
<212> TYPE: PRT
<213> ORGANISM: Artificial Sequence
<220> FEATURE:
<223> OTHER INFORMATION: LC-CDR1

<400> SEQUENCE: 6

Arg Ala Gly Gln Ala Ile Ser Ser Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: LC-CDR2

<400> SEQUENCE: 7

Lys Ala Ser Asn Leu Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: LC-CDR3

<400> SEQUENCE: 8

Gln Gln Tyr Gln Ser Tyr Pro Tyr Thr
1               5

<210> SEQ ID NO 9
<211> LENGTH: 107
<212> TYPE: PRT
<213> ORGANISM: Artificial Sequence
<220> FEATURE:
<223> OTHER INFORMATION: Antibody sequence

<400> SEQUENCE: 9

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Leu Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Leu Tyr Asp Tyr Pro Leu
                85                  90                  95

Thr Phe Gly Gly Gly Thr Lys Val Glu Ile Lys
            100                 105

<210> SEQ ID NO 10
<211> LENGTH: 11
<212> TYPE: PRT
<213> ORGANISM: Artificial Sequence
<220> FEATURE:
<223> OTHER INFORMATION: LC-CDR1

<400> SEQUENCE: 10

```
Gln Ala Ser Gln Asp Ile Gly Asn Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LC-CDR2

<400> SEQUENCE: 11

Asp Ala Ser Asn Leu Glu Thr
1               5

<210> SEQ ID NO 12
<211> LENGTH: 9
<212> TYPE: PRT
<213> ORGANISM: Artificial Sequence
<220> FEATURE:
<223> OTHER INFORMATION: LC-CDR3

<400> SEQUENCE: 12

Leu Gln Leu Tyr Asp Tyr Pro Leu Thr
1               5

<210> SEQ ID NO 13
<211> LENGTH: 110
<212> TYPE: PRT
<213> ORGANISM: Artificial Sequence
<220> FEATURE:
<223> OTHER INFORMATION: Antibody sequence

<400> SEQUENCE: 13

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Phe Asp Asp Asn Gln Arg Pro Thr Gly Val Pro Asp Arg Phe Ser
    50                  55                  60

Ala Ala Ile Asp Thr Ser Ser Ser Ala Ser Leu Thr Ile Ser Gly
65                  70                  75                  80

Leu Thr Ala Glu Asp Glu Ala Asp Tyr Tyr Cys Gln Ser Ser His Ser
                85                  90                  95

Thr Ala Val Val Phe Gly Gly Gly Thr Lys Leu Thr Val Leu
            100                 105                 110

<210> SEQ ID NO 14
<211> LENGTH: 13
<212> TYPE: PRT
<213> ORGANISM: Artificial Sequence
<220> FEATURE:
<223> OTHER INFORMATION: LC-CDR1

<400> SEQUENCE: 14

Thr Arg Ser Ser Gly Ser Ile Ala Ser Asn Tyr Val Gln
1               5                   10

<210> SEQ ID NO 15
<211> LENGTH: 7
<212> TYPE: PRT
<213> ORGANISM: Artificial Sequence
```

-continued

<220> FEATURE:
<223> OTHER INFORMATION: LC-CDR2

<400> SEQUENCE: 15

Asp Asp Asn Gln Arg Pro Thr
1               5

<210> SEQ ID NO 16
<211> LENGTH: 9
<212> TYPE: PRT
<213> ORGANISM: Artificial Sequence
<220> FEATURE:
<223> OTHER INFORMATION: LC-CDR3

<400> SEQUENCE: 16

Gln Ser Ser His Ser Thr Ala Val Val
1               5

<210> SEQ ID NO 17
<211> LENGTH: 108
<212> TYPE: PRT
<213> ORGANISM: Artificial Sequence
<220> FEATURE:
<223> OTHER INFORMATION: Antibody sequence

<400> SEQUENCE: 17

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly Asp Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105

<210> SEQ ID NO 18
<211> LENGTH: 14
<212> TYPE: PRT
<213> ORGANISM: Artificial Sequence
<220> FEATURE:
<223> OTHER INFORMATION: LC-CDR1

<400> SEQUENCE: 18

Thr Gly Thr Ser Ser Asp Ile Gly Asp Tyr Asp Phe Val Ser
1               5                   10

<210> SEQ ID NO 19
<211> LENGTH: 108
<212> TYPE: PRT
<213> ORGANISM: Artificial Sequence
<220> FEATURE:
<223> OTHER INFORMATION: Antibody sequence

<400> SEQUENCE: 19

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr

```
                20                  25                  30

Asp Phe Val Ser Trp Tyr Gln Gln His Pro Gly Thr Ala Pro Lys Leu
            35                  40                  45

Ile Ile Tyr Asp Asn Asn Arg Pro Ser Gly Ile Ser Asn Arg Phe
        50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105
```

<210> SEQ ID NO 20
<211> LENGTH: 7
<212> TYPE: PRT
<213> ORGANISM: Artificial Sequence
<220> FEATURE:
<223> OTHER INFORMATION: LC-CDR2

<400> SEQUENCE: 20

```
Asp Asn Asn Asn Arg Pro Ser
1               5
```

<210> SEQ ID NO 21
<211> LENGTH: 108
<212> TYPE: PRT
<213> ORGANISM: Artificial Sequence
<220> FEATURE:
<223> OTHER INFORMATION: Antibody sequence

<400> SEQUENCE: 21

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
            35                  40                  45

Ile Ile Tyr Asp Ile Asn Arg Pro Ser Gly Ile Ser Asn Arg Phe
        50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105
```

<210> SEQ ID NO 22
<211> LENGTH: 10
<212> TYPE: PRT
<213> ORGANISM: Artificial Sequence
<220> FEATURE:
<223> OTHER INFORMATION: LC-CDR3

<400> SEQUENCE: 22

```
Ser Ala Tyr Thr Ser Ser Asp Thr Val Val
1               5                   10
```

<210> SEQ ID NO 23
<211> LENGTH: 108
<212> TYPE: PRT
<213> ORGANISM: Artificial Sequence
<220> FEATURE:
<223> OTHER INFORMATION: Antibody sequence

<400> SEQUENCE: 23

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 24
<211> LENGTH: 108
<212> TYPE: PRT
<213> ORGANISM: Artificial Sequence
<220> FEATURE:
<223> OTHER INFORMATION: Antibody sequence

<400> SEQUENCE: 24

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Ile Ser Trp Tyr Gln Gln His Pro Gly Thr Ala Pro Lys Leu
        35                  40                  45

Ile Ile Tyr Asp Phe Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105

<210> SEQ ID NO 25
<211> LENGTH: 14
<212> TYPE: PRT
<213> ORGANISM: Artificial Sequence
<220> FEATURE:
<223> OTHER INFORMATION: LC-CDR1

<400> SEQUENCE: 25

Thr Gly Thr Ser Ser Asp Ile Gly His Tyr Asp Phe Ile Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: LC-CDR2

<400> SEQUENCE: 26

Asp Phe Asn Asn Arg Pro Ser
1               5

<210> SEQ ID NO 27
<211> LENGTH: 108
<212> TYPE: PRT
<213> ORGANISM: Artificial Sequence
<220> FEATURE:
<223> OTHER INFORMATION: Antibody sequence

<400> SEQUENCE: 27

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Asn Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 28
<211> LENGTH: 108
<212> TYPE: PRT
<213> ORGANISM: Artificial Sequence
<220> FEATURE:
<223> OTHER INFORMATION: Antibody sequence

<400> SEQUENCE: 28

Gln Ser Ala Leu Thr Gln Pro Ala Ser Val Ser Gly Ser Pro Gly Gln
1               5                   10                  15

Ser Ile Val Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 29
<211> LENGTH: 108
<212> TYPE: PRT
<213> ORGANISM: Artificial Sequence
<220> FEATURE:
<223> OTHER INFORMATION: Antibody sequence

<400> SEQUENCE: 29

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly Asp Tyr
            20                  25                  30

Asp Phe Val Ser Trp Tyr Gln Gln His Pro Gly Thr Ala Pro Lys Leu
            35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Ile Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105

<210> SEQ ID NO 30
<211> LENGTH: 108
<212> TYPE: PRT
<213> ORGANISM: Artificial Sequence
<220> FEATURE:
<223> OTHER INFORMATION: Antibody sequence

<400> SEQUENCE: 30

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
            35                  40                  45

Ile Ile Tyr Asp Ile Asn Asn Arg Pro Ser Gly Ile Ser Asn Arg Phe
    50                  55                  60

Ser Gly Ser Lys Ser Asp Asp Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 31
<211> LENGTH: 108
<212> TYPE: PRT
<213> ORGANISM: Artificial Sequence
<220> FEATURE:
<223> OTHER INFORMATION: Antibody sequence

<400> SEQUENCE: 31

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
            35                  40                  45

Ile Ile Tyr Asp Ile Asn Asn Arg Ala Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 32
<211> LENGTH: 7
<212> TYPE: PRT
<213> ORGANISM: Artificial Sequence
<220> FEATURE:
<223> OTHER INFORMATION: LC-CDR2

<400> SEQUENCE: 32

Asp Ile Asn Asn Arg Ala Ser
1               5

<210> SEQ ID NO 33
<211> LENGTH: 108
<212> TYPE: PRT
<213> ORGANISM: Artificial Sequence
<220> FEATURE:
<223> OTHER INFORMATION: Antibody sequence

<400> SEQUENCE: 33

Gln Ser Ala Leu Thr Gln Pro Ala Ser Val Ser Gly Asn Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 34
<211> LENGTH: 108
<212> TYPE: PRT
<213> ORGANISM: Artificial Sequence
<220> FEATURE:
<223> OTHER INFORMATION: Antibody sequence

<400> SEQUENCE: 34

Gln Ser Thr Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105

<210> SEQ ID NO 35
<211> LENGTH: 121

```
<212> TYPE: PRT
<213> ORGANISM: Artificial Sequence
<220> FEATURE:
<223> OTHER INFORMATION: Antibody sequence

<400> SEQUENCE: 35

Glu Val Gln Leu Val Gln Ser Gly Ala Glu Val Lys Lys Pro Gly Ser
1               5                  10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 36
<211> LENGTH: 5
<212> TYPE: PRT
<213> ORGANISM: Artificial Sequence
<220> FEATURE:
<223> OTHER INFORMATION: HC-CDR1

<400> SEQUENCE: 36

Asn Tyr Tyr Met His
1               5

<210> SEQ ID NO 37
<211> LENGTH: 17
<212> TYPE: PRT
<213> ORGANISM: Artificial Sequence
<220> FEATURE:
<223> OTHER INFORMATION: HC-CDR2

<400> SEQUENCE: 37

Ala Ile Met Pro Ser Arg Gly Gly Thr Ser Tyr Pro Gln Lys Phe Gln
1               5                  10                  15

Gly

<210> SEQ ID NO 38
<211> LENGTH: 12
<212> TYPE: PRT
<213> ORGANISM: Artificial Sequence
<220> FEATURE:
<223> OTHER INFORMATION: HC-CDR3

<400> SEQUENCE: 38

Gly Glu Tyr Tyr Tyr Asp Ser Ser Gly Tyr Tyr Tyr
1               5                  10

<210> SEQ ID NO 39
<211> LENGTH: 119
<212> TYPE: PRT
<213> ORGANISM: Artificial Sequence
<220> FEATURE:
<223> OTHER INFORMATION: Antibody sequence
```

<400> SEQUENCE: 39

Glu Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Met His Trp Val Arg Gln Ala Pro Gly Gln Ser Leu Glu Trp Met
        35                  40                  45

Gly Trp Ile Asn Thr Gly Asn Gly Asn Thr Lys Tyr Ser Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Gln Leu Glu Arg Leu Tyr Phe Trp Gly Gln Gly
            100                 105                 110

Thr Leu Val Thr Val Ser Ser
            115

<210> SEQ ID NO 40
<211> LENGTH: 5
<212> TYPE: PRT
<213> ORGANISM: Artificial Sequence
<220> FEATURE:
<223> OTHER INFORMATION: HC-CDR1

<400> SEQUENCE: 40

Thr Tyr Ala Met His
1               5

<210> SEQ ID NO 41
<211> LENGTH: 17
<212> TYPE: PRT
<213> ORGANISM: Artificial Sequence
<220> FEATURE:
<223> OTHER INFORMATION: HC-CDR2

<400> SEQUENCE: 41

Trp Ile Asn Thr Gly Asn Gly Asn Thr Lys Tyr Ser Gln Asn Phe Gln
1               5                   10                  15

Gly

<210> SEQ ID NO 42
<211> LENGTH: 11
<212> TYPE: PRT
<213> ORGANISM: Artificial Sequence
<220> FEATURE:
<223> OTHER INFORMATION: HC-CDR3

<400> SEQUENCE: 42

Asp Leu Gly Gln Leu Glu Arg Leu Tyr Phe Trp
1               5                   10

<210> SEQ ID NO 43
<211> LENGTH: 114
<212> TYPE: PRT
<213> ORGANISM: Artificial Sequence
<220> FEATURE:
<223> OTHER INFORMATION: Antibody sequence

<400> SEQUENCE: 43

His Val Gln Leu Val Glu Thr Gly Gly Gly Leu Val Gln Pro Gly Gly

```
                1               5                  10                  15
             Ser Leu Arg Leu Ser Cys Ala Ala Ser Gly Phe Thr Phe Ser Ser Tyr
                            20                  25                  30

Ala Met Ser Trp Val Arg Gln Ala Pro Gly Lys Gly Leu Glu Trp Val
                            35                  40                  45

Ser Ala Ile Ser Gly Ser Gly Gly Ser Thr Tyr Tyr Ala Asp Ser Val
                            50                  55                  60

Lys Gly Arg Phe Thr Ile Ser Arg Asp Asn Ser Lys Asn Thr Leu Tyr
              65                  70                  75                  80

Leu Gln Met Asn Ser Leu Arg Ala Glu Asp Thr Ala Val Tyr Tyr Cys
                            85                  90                  95

Ala Arg Asp Leu Gly Asp Tyr Trp Gly Gln Gly Thr Leu Val Thr Val
                            100                 105                 110

Ser Ser

<210> SEQ ID NO 44
<211> LENGTH: 5
<212> TYPE: PRT
<213> ORGANISM: Artificial Sequence
<220> FEATURE:
<223> OTHER INFORMATION: HC-CDR1

<400> SEQUENCE: 44

Ser Tyr Ala Met Ser
1               5

<210> SEQ ID NO 45
<211> LENGTH: 17
<212> TYPE: PRT
<213> ORGANISM: Artificial Sequence
<220> FEATURE:
<223> OTHER INFORMATION: HC-CDR2

<400> SEQUENCE: 45

Ala Ile Ser Gly Ser Gly Gly Ser Thr Tyr Tyr Ala Asp Ser Val Lys
1               5                   10                  15

Gly

<210> SEQ ID NO 46
<211> LENGTH: 5
<212> TYPE: PRT
<213> ORGANISM: Artificial Sequence
<220> FEATURE:
<223> OTHER INFORMATION: HC-CDR3

<400> SEQUENCE: 46

Asp Leu Gly Asp Tyr
1               5

<210> SEQ ID NO 47
<211> LENGTH: 117
<212> TYPE: PRT
<213> ORGANISM: Artificial Sequence
<220> FEATURE:
<223> OTHER INFORMATION: Antibody sequence

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30
```

```
Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ser Ser Ser Gly Asp Ala Phe Asp Ile Trp Gly Gln Gly Thr Met
                100                 105                 110

Val Thr Val Ser Ser
            115

<210> SEQ ID NO 48
<211> LENGTH: 5
<212> TYPE: PRT
<213> ORGANISM: Artificial Sequence
<220> FEATURE:
<223> OTHER INFORMATION: HC-CDR1

<400> SEQUENCE: 48

Gly Tyr Tyr Trp Ser
 1               5

<210> SEQ ID NO 49
<211> LENGTH: 16
<212> TYPE: PRT
<213> ORGANISM: Artificial Sequence
<220> FEATURE:
<223> OTHER INFORMATION: HC-CDR2

<400> SEQUENCE: 49

Glu Ile Asn His Ser Gly Ser Thr Asn Tyr Asn Pro Ser Leu Lys Ser
 1               5                  10                  15

<210> SEQ ID NO 50
<211> LENGTH: 8
<212> TYPE: PRT
<213> ORGANISM: Artificial Sequence
<220> FEATURE:
<223> OTHER INFORMATION: HC-CDR3

<400> SEQUENCE: 50

Ser Ser Ser Gly Asp Ala Phe Asp
 1               5

<210> SEQ ID NO 51
<211> LENGTH: 121
<212> TYPE: PRT
<213> ORGANISM: Artificial Sequence
<220> FEATURE:
<223> OTHER INFORMATION: Antibody sequence

<400> SEQUENCE: 51

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
                 20                  25                  30

Tyr Met His Trp Val Arg Gln Ala Pro Gly Gln Gly Leu Glu Trp Met
             35                  40                  45

Gly Ala Ile Met Pro Ser Arg Gly Gly Thr Ser Tyr Pro Gln Lys Phe
 50                  55                  60
```

Gln Gly Arg Val Thr Met Thr Gly Asp Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Asn Trp Gly
            100                 105                 110

Gln Gly Thr Leu Val Thr Val Ser Ser
        115                 120

<210> SEQ ID NO 52
<211> LENGTH: 12
<212> TYPE: PRT
<213> ORGANISM: Artificial Sequence
<220> FEATURE:
<223> OTHER INFORMATION: HC-CDR3

<400> SEQUENCE: 52

Gly Glu Tyr Tyr Tyr Asp Ser Ser Gly Tyr Tyr Asn
1               5                   10

<210> SEQ ID NO 53
<211> LENGTH: 121
<212> TYPE: PRT
<213> ORGANISM: Artificial Sequence
<220> FEATURE:
<223> OTHER INFORMATION: Antibody sequence

<400> SEQUENCE: 53

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 54
<211> LENGTH: 5
<212> TYPE: PRT
<213> ORGANISM: Artificial Sequence
<220> FEATURE:
<223> OTHER INFORMATION: HC-CDR1

<400> SEQUENCE: 54

Asn Tyr Tyr Ile His
1               5

<210> SEQ ID NO 55
<211> LENGTH: 121
<212> TYPE: PRT
<213> ORGANISM: Artificial Sequence
<220> FEATURE:
<223> OTHER INFORMATION: Antibody sequence

<400> SEQUENCE: 55

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Pro Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 56
<211> LENGTH: 121
<212> TYPE: PRT
<213> ORGANISM: Artificial Sequence
<220> FEATURE:
<223> OTHER INFORMATION: Antibody sequence

<400> SEQUENCE: 56

Glu Val Gln Leu Val Gln Ser Gly Ala Glu Val Lys Lys Pro Gly Ser
1               5                   10                  15

Thr Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 57
<211> LENGTH: 121
<212> TYPE: PRT
<213> ORGANISM: Artificial Sequence
<220> FEATURE:
<223> OTHER INFORMATION: Antibody sequence

<400> SEQUENCE: 57

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

```
Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Asn
        115                 120

<210> SEQ ID NO 58
<211> LENGTH: 121
<212> TYPE: PRT
<213> ORGANISM: Artificial Sequence
<220> FEATURE:
<223> OTHER INFORMATION: Antibody sequence

<400> SEQUENCE: 58

Glu Val Gln Leu Val Gln Ser Gly Ala Glu Val Lys Glu Pro Gly Ser
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Ile Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: Antibody sequence

<400> SEQUENCE: 59

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
65                  70                  75                  80

Met Glu Leu Asn Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
```

```
                100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: Antibody sequence

<400> SEQUENCE: 60

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Pro Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Antibody sequence

<400> SEQUENCE: 61

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Met Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 62
<211> LENGTH: 121
<212> TYPE: PRT
<213> ORGANISM: Artificial Sequence
<220> FEATURE:
```

<223> OTHER INFORMATION: Antibody sequence

<400> SEQUENCE: 62

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
50                  55                  60

Gln Gly Arg Val Thr Met Thr Gly Asp Thr Ser Thr Ser Thr Val Tyr
65                  70                  75                  80

Met Glu Leu Ser Ser Leu Arg Thr Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: Antibody sequence

<400> SEQUENCE: 63

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Antibody sequence

<400> SEQUENCE: 64

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met

```
                35                  40                  45
Gly Ala Ile Met Pro Ser Arg Gly Gly Thr Ser Tyr Pro Gln Lys Phe
        50                  55                  60
Gln Gly Arg Val Thr Met Thr Gly Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
Ala Arg Gly Glu Tyr Tyr Tyr Asp Ser Ser Gly Tyr Tyr Tyr Trp Gly
                100                 105                 110
Gln Gly Thr Leu Val Asn Val Ser Ser
            115                 120

<210> SEQ ID NO 65
<211> LENGTH: 121
<212> TYPE: PRT
<213> ORGANISM: Artificial Sequence
<220> FEATURE:
<223> OTHER INFORMATION: Antibody sequence

<400> SEQUENCE: 65

Glu Val Gln Leu Val Gln Ser Gly Ala Glu Val Lys Lys Pro Gly Ser
 1               5                  10                  15
Ser Val Lys Val Ser Cys Lys Ala Ser Gly Tyr Thr Phe Ser Asn Tyr
                20                  25                  30
Tyr Met His Trp Val Arg Gln Ala Pro Gly Gln Gly Leu Glu Trp Ile
            35                  40                  45
Gly Ala Ile Met Pro Ser Arg Gly Gly Thr Ser Tyr Pro Gln Lys Phe
        50                  55                  60
Gln Gly Arg Val Thr Met Thr Gly Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
Ala Arg Gly Glu Tyr Tyr Tyr Asp Ser Ser Gly Tyr Tyr Tyr Trp Gly
                100                 105                 110
Gln Gly Thr Leu Val Thr Val Ser Ser
            115                 120

<210> SEQ ID NO 66
<211> LENGTH: 121
<212> TYPE: PRT
<213> ORGANISM: Artificial Sequence
<220> FEATURE:
<223> OTHER INFORMATION: Antibody sequence

<400> SEQUENCE: 66

Glu Val Gln Leu Val Gln Ser Gly Ala Glu Val Lys Lys Pro Gly Ser
 1               5                  10                  15
Ser Val Lys Val Ser Cys Lys Ala Thr Gly Tyr Thr Phe Thr Asn Tyr
                20                  25                  30
Tyr Met His Trp Val Arg Gln Ala Pro Gly Gln Gly Leu Glu Trp Met
            35                  40                  45
Gly Ala Ile Met Pro Ser Arg Gly Gly Thr Ser Tyr Pro Gln Lys Phe
        50                  55                  60
Gln Gly Arg Val Thr Met Thr Gly Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
```

Ala Arg Gly Glu Tyr Tyr Asp Ser Ser Gly Tyr Tyr Trp Gly
            100                 105                 110

Gln Gly Thr Leu Val Thr Val Ser Ser
        115                 120

<210> SEQ ID NO 67
<211> LENGTH: 112
<212> TYPE: PRT
<213> ORGANISM: Artificial Sequence
<220> FEATURE:
<223> OTHER INFORMATION: Antibody sequence

<400> SEQUENCE: 67

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110

<210> SEQ ID NO 68
<211> LENGTH: 16
<212> TYPE: PRT
<213> ORGANISM: Artificial Sequence
<220> FEATURE:
<223> OTHER INFORMATION: LC-CDR1

<400> SEQUENCE: 68

Arg Ser Ser Gln Ser Leu Leu His Ser Asn Gly Tyr Asn Tyr Leu Asp
1               5                   10                  15

<210> SEQ ID NO 69
<211> LENGTH: 7
<212> TYPE: PRT
<213> ORGANISM: Artificial Sequence
<220> FEATURE:
<223> OTHER INFORMATION: LC-CDR2

<400> SEQUENCE: 69

Leu Gly Ser Asn Arg Asp Ser
1               5

<210> SEQ ID NO 70
<211> LENGTH: 9
<212> TYPE: PRT
<213> ORGANISM: Artificial Sequence
<220> FEATURE:
<223> OTHER INFORMATION: LC-CDR3

<400> SEQUENCE: 70

Met Gln Gly Thr His Trp Pro Trp Thr
1               5

<210> SEQ ID NO 71
<211> LENGTH: 108

```
<212> TYPE: PRT
<213> ORGANISM: Artificial Sequence
<220> FEATURE:
<223> OTHER INFORMATION: Antibody sequence

<400> SEQUENCE: 71

Ser Tyr Glu Leu Thr Gln Pro Pro Ser Met Ser Val Ser Pro Gly Gln
1               5                   10                  15

Thr Ala Arg Ile Thr Cys Ser Gly Asp Ala Leu Pro Lys Gln Phe Ala
            20                  25                  30

Phe Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
50                  55                  60

Ser Ser Gly Thr Thr Val Thr Leu Thr Ile Thr Gly Val Gln Ala Glu
65                  70                  75                  80

Asp Glu Ala Asp Tyr Tyr Cys Gln Ser Pro Asp Ser Ser Gly Thr Val
                85                  90                  95

Glu Val Phe Gly Gly Gly Thr Lys Leu Thr Val Leu
            100                 105

<210> SEQ ID NO 72
<211> LENGTH: 11
<212> TYPE: PRT
<213> ORGANISM: Artificial Sequence
<220> FEATURE:
<223> OTHER INFORMATION: LC-CDR1

<400> SEQUENCE: 72

Ser Gly Asp Ala Leu Pro Lys Gln Phe Ala Phe
1               5                   10

<210> SEQ ID NO 73
<211> LENGTH: 7
<212> TYPE: PRT
<213> ORGANISM: Artificial Sequence
<220> FEATURE:
<223> OTHER INFORMATION: LC-CDR2

<400> SEQUENCE: 73

Lys Asp Thr Glu Arg Pro Ser
1               5

<210> SEQ ID NO 74
<211> LENGTH: 11
<212> TYPE: PRT
<213> ORGANISM: Artificial Sequence
<220> FEATURE:
<223> OTHER INFORMATION: LC-CDR3

<400> SEQUENCE: 74

Gln Ser Pro Asp Ser Ser Gly Thr Val Glu Val
1               5                   10

<210> SEQ ID NO 75
<211> LENGTH: 112
<212> TYPE: PRT
<213> ORGANISM: Artificial Sequence
<220> FEATURE:
<223> OTHER INFORMATION: Antibody sequence

<400> SEQUENCE: 75

Asp Val Val Met Thr Gln Ser Pro Leu Ser Leu Pro Val Thr Pro Gly
1               5                   10                  15
```

Glu Ser Val Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110

<210> SEQ ID NO 76
<211> LENGTH: 120
<212> TYPE: PRT
<213> ORGANISM: Artificial Sequence
<220> FEATURE:
<223> OTHER INFORMATION: Antibody sequence

<400> SEQUENCE: 76

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser
        115                 120

<210> SEQ ID NO 77
<211> LENGTH: 12
<212> TYPE: PRT
<213> ORGANISM: Artificial Sequence
<220> FEATURE:
<223> OTHER INFORMATION: HC-CDR3

<400> SEQUENCE: 77

Ser Pro Gly Gly Tyr Ser Gly Gly Tyr Phe Gln His
1               5                   10

<210> SEQ ID NO 78
<211> LENGTH: 120
<212> TYPE: PRT
<213> ORGANISM: Artificial Sequence
<220> FEATURE:
<223> OTHER INFORMATION: Antibody sequence

<400> SEQUENCE: 78

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Gly Asp Ile Leu Thr Gly Tyr Ala Leu Asp Tyr Trp Gly Gln
            100                 105                 110

Gly Thr Leu Val Thr Val Ser Ser
            115                 120

<210> SEQ ID NO 79
<211> LENGTH: 7
<212> TYPE: PRT
<213> ORGANISM: Artificial Sequence
<220> FEATURE:
<223> OTHER INFORMATION: HC-CDR1

<400> SEQUENCE: 79

Ser Ser Ser Tyr Tyr Trp Gly
1               5

<210> SEQ ID NO 80
<211> LENGTH: 15
<212> TYPE: PRT
<213> ORGANISM: Artificial Sequence
<220> FEATURE:
<223> OTHER INFORMATION: HC-CDR2

<400> SEQUENCE: 80

Ser Ile Tyr Tyr Ser Gly Ser Thr Tyr Tyr Asn Pro Ser Leu Lys
1               5                   10                  15

<210> SEQ ID NO 81
<211> LENGTH: 10
<212> TYPE: PRT
<213> ORGANISM: Artificial Sequence
<220> FEATURE:
<223> OTHER INFORMATION: HC-CDR3

<400> SEQUENCE: 81

Asp Ile Leu Thr Gly Tyr Ala Leu Asp Tyr
1               5                   10

<210> SEQ ID NO 82
<211> LENGTH: 120
<212> TYPE: PRT
<213> ORGANISM: Artificial Sequence
<220> FEATURE:
<223> OTHER INFORMATION: Antibody sequence

<400> SEQUENCE: 82

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45
```

Gly Glu Ile Asn His Phe Gly Ser Thr Asn Tyr Asn Pro Ser Leu Lys
            50                  55                  60

Ser Arg Ala Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Thr Ser Pro Gly Gly Tyr Ser Gly Gly Tyr Phe Gln His Trp Gly Gln
            100                 105                 110

Gly Thr Leu Val Thr Val Ser Ser
            115                 120

<210> SEQ ID NO 83
<211> LENGTH: 16
<212> TYPE: PRT
<213> ORGANISM: Artificial Sequence
<220> FEATURE:
<223> OTHER INFORMATION: HC-CDR2

<400> SEQUENCE: 83

Glu Ile Asn His Phe Gly Ser Thr Asn Tyr Asn Pro Ser Leu Lys Ser
 1               5                   10                  15

<210> SEQ ID NO 84
<211> LENGTH: 120
<212> TYPE: PRT
<213> ORGANISM: Artificial Sequence
<220> FEATURE:
<223> OTHER INFORMATION: Antibody sequence

<400> SEQUENCE: 84

Gln Val Gln Leu Gln Gln Trp Gly Ala Gly Met Leu Lys Pro Ser Glu
 1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Phe Gly Ser Thr Asn Tyr Asn Pro Ser Leu Lys
        50                  55                  60

Ser Arg Ala Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Thr Ser Pro Gly Gly Tyr Ser Gly Gly Tyr Phe Gln His Trp Gly Gln
            100                 105                 110

Gly Thr Leu Val Thr Val Ser Ser
            115                 120

<210> SEQ ID NO 85
<211> LENGTH: 14
<212> TYPE: PRT
<213> ORGANISM: Artificial Sequence
<220> FEATURE:
<223> OTHER INFORMATION: LC-CDR1
<220> FEATURE:
<221> NAME/KEY: VARIANT
<222> LOCATION: (9)..(9)
<223> OTHER INFORMATION: Xaa is either his or asp
<220> FEATURE:
<221> NAME/KEY: VARIANT
<222> LOCATION: (13)..(13)
<223> OTHER INFORMATION: Xaa is either val or ile

<400> SEQUENCE: 85

```
Thr Gly Thr Ser Ser Asp Ile Gly Xaa Tyr Asp Phe Xaa Ser
1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: LC-CDR2
<220> FEATURE:
<221> NAME/KEY: VARIANT
<222> LOCATION: (2)..(2)
<223> OTHER INFORMATION: Xaa is either ile, asn or phe
<220> FEATURE:
<221> NAME/KEY: VARIANT
<222> LOCATION: (6)..(6)
<223> OTHER INFORMATION: Xaa is either pro or ala

<400> SEQUENCE: 86

```
Asp Xaa Asn Asn Arg Xaa Ser
1               5
```

<210> SEQ ID NO 87
<211> LENGTH: 10
<212> TYPE: PRT
<213> ORGANISM: Artificial Sequence
<220> FEATURE:
<223> OTHER INFORMATION: LC-CDR3
<220> FEATURE:
<221> NAME/KEY: VARIANT
<222> LOCATION: (9)..(9)
<223> OTHER INFORMATION: Xaa is either leu or val

<400> SEQUENCE: 87

```
Ser Ala Tyr Thr Ser Ser Asp Thr Xaa Val
1               5                   10
```

<210> SEQ ID NO 88
<211> LENGTH: 5
<212> TYPE: PRT
<213> ORGANISM: Artificial Sequence
<220> FEATURE:
<223> OTHER INFORMATION: HC-CDR1
<220> FEATURE:
<221> NAME/KEY: VARIANT
<222> LOCATION: (4)..(4)
<223> OTHER INFORMATION: Xaa is either met or ile

<400> SEQUENCE: 88

```
Asn Tyr Tyr Xaa His
1               5
```

<210> SEQ ID NO 89
<211> LENGTH: 12
<212> TYPE: PRT
<213> ORGANISM: Artificial Sequence
<220> FEATURE:
<223> OTHER INFORMATION: HC-CDR3
<220> FEATURE:
<221> NAME/KEY: VARIANT
<222> LOCATION: (12)..(12)
<223> OTHER INFORMATION: Xaa is either tyr or asn

<400> SEQUENCE: 89

```
Gly Glu Tyr Tyr Tyr Asp Ser Ser Gly Tyr Tyr Xaa
1               5                   10
```

<210> SEQ ID NO 90
<211> LENGTH: 16

```
<212> TYPE: PRT
<213> ORGANISM: Artificial Sequence
<220> FEATURE:
<223> OTHER INFORMATION: HC-CDR2
<220> FEATURE:
<221> NAME/KEY: VARIANT
<222> LOCATION: (5)..(5)
<223> OTHER INFORMATION: Xaa is either ser or phe

<400> SEQUENCE: 90

Glu Ile Asn His Xaa Gly Ser Thr Asn Tyr Asn Pro Ser Leu Lys Ser
1               5                   10                  15

<210> SEQ ID NO 91
<211> LENGTH: 113
<212> TYPE: PRT
<213> ORGANISM: Artificial Sequence
<220> FEATURE:
<223> OTHER INFORMATION: Antibody sequence

<400> SEQUENCE: 91

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 92
<211> LENGTH: 107
<212> TYPE: PRT
<213> ORGANISM: Artificial Sequence
<220> FEATURE:
<223> OTHER INFORMATION: Antibody sequence

<400> SEQUENCE: 92

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

```
<210> SEQ ID NO 93
<211> LENGTH: 113
<212> TYPE: PRT
<213> ORGANISM: Artificial Sequence
<220> FEATURE:
<223> OTHER INFORMATION: Antibody sequence

<400> SEQUENCE: 93
```

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

```
<210> SEQ ID NO 94
<211> LENGTH: 108
<212> TYPE: PRT
<213> ORGANISM: Artificial Sequence
<220> FEATURE:
<223> OTHER INFORMATION: Antibody sequence

<400> SEQUENCE: 94
```

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Cys Val Ser Lys Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

```
<210> SEQ ID NO 95
<211> LENGTH: 480
<212> TYPE: PRT
<213> ORGANISM: Artificial Sequence
<220> FEATURE:
<223> OTHER INFORMATION: Antibody sequence

<400> SEQUENCE: 95
```

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

```
Tyr Met His Trp Val Arg Gln Ala Pro Gly Gln Gly Leu Glu Trp Met
        35                  40                  45
Gly Ala Ile Met Pro Ser Arg Gly Gly Thr Ser Tyr Pro Gln Lys Phe
 50                  55                  60
Gln Gly Arg Val Thr Met Thr Gly Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Glu Tyr Tyr Asp Ser Ser Gly Tyr Tyr Tyr Trp Gly
                100                 105                 110
Gln Gly Thr Leu Val Thr Val Ser Ser Gly Gly Gly Ser Gly Gly
            115                 120                 125
Gly Gly Ser Gly Gly Gly Ser Gln Ser Ala Leu Thr Gln Pro Ala
    130                 135                 140
Ser Val Ser Gly Ser Pro Gly Gln Ser Ile Ala Ile Ser Cys Thr Gly
145                 150                 155                 160
Thr Ser Ser Asp Ile Gly His Tyr Asp Phe Val Ser Trp Tyr Gln Gln
                165                 170                 175
His Pro Gly Thr Ala Pro Lys Leu Ile Ile Tyr Asp Ile Asn Asn Arg
            180                 185                 190
Pro Ser Gly Ile Ser Asn Arg Phe Ser Gly Ser Lys Ser Asp Asn Met
        195                 200                 205
Ala Ser Leu Thr Ile Ser Gly Leu Gln Pro Glu Asp Glu Ala Asp Tyr
210                 215                 220
Tyr Cys Ser Ala Tyr Thr Ser Ser Asp Thr Leu Val Phe Gly Gly Gly
225                 230                 235                 240
Thr Lys Leu Thr Val Leu Asn Ser Gly Ala Gly Thr Ala Ala Thr
            245                 250                 255
His Thr Cys Pro Pro Cys Pro Ala Pro Glu Ala Ala Gly Gly Pro Ser
                260                 265                 270
Val Phe Leu Phe Pro Pro Lys Pro Lys Asp Thr Leu Met Ile Ser Arg
            275                 280                 285
Thr Pro Glu Val Thr Cys Val Val Val Asp Val Ser His Glu Asp Pro
290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
370                 375                 380
Pro Pro Cys Arg Asp Glu Leu Thr Lys Asn Gln Val Ser Leu Trp Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
```

```
                    450                 455                 460
Leu His Asn His Tyr Thr Gln Lys Ser Leu Ser Leu Ser Pro Gly Lys
465                 470                 475                 480

<210> SEQ ID NO 96
<211> LENGTH: 241
<212> TYPE: PRT
<213> ORGANISM: Artificial Sequence
<220> FEATURE:
<223> OTHER INFORMATION: Antibody sequence

<400> SEQUENCE: 96

Glu Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Ala Met His Trp Val Arg Gln Ala Pro Gly Gln Ser Leu Glu Trp Met
            35                  40                  45

Gly Trp Ile Asn Thr Gly Asn Gly Asn Thr Lys Tyr Ser Gln Asn Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Leu Gly Gln Leu Glu Arg Leu Tyr Phe Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Asp Ile Gln Met Thr Gln Ser Pro Ser Thr
        130                 135                 140

Leu Ser Ala Ser Val Gly Asp Arg Val Thr Leu Ser Cys Arg Ala Gly
145                 150                 155                 160

Gln Ala Ile Ser Ser Trp Leu Ala Trp Tyr Gln Gln Lys Pro Gly Lys
                165                 170                 175

Ala Pro Lys Leu Leu Ile Tyr Lys Ala Ser Asn Leu Glu Ser Gly Val
            180                 185                 190

Pro Ser Arg Phe Ser Gly Gly Ser Gly Ala Glu Phe Thr Leu Thr
        195                 200                 205

Ile Ser Ser Leu Gln Pro Asp Asp Phe Ala Thr Tyr Tyr Cys Gln Gln
        210                 215                 220

Tyr Gln Ser Tyr Pro Tyr Thr Phe Gly Gln Gly Thr Lys Leu Glu Ile
225                 230                 235                 240

Arg

<210> SEQ ID NO 97
<211> LENGTH: 236
<212> TYPE: PRT
<213> ORGANISM: Artificial Sequence
<220> FEATURE:
<223> OTHER INFORMATION: Antibody sequence

<400> SEQUENCE: 97

His Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
```

```
            35                  40                  45
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Gly Asp Tyr Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Asp Ile Gln Leu Thr Gln Ser Pro Ser Ser Leu Ser Ala Ser Val
130                 135                 140

Gly Asp Arg Val Thr Ile Thr Cys Gln Ala Ser Gln Asp Ile Gly Asn
145                 150                 155                 160

Tyr Leu Asn Trp Tyr Gln Leu Lys Pro Gly Lys Ala Pro Lys Leu Leu
                165                 170                 175

Ile Tyr Asp Ala Ser Asn Leu Glu Thr Gly Val Pro Ser Arg Phe Ser
            180                 185                 190

Gly Ser Gly Ser Gly Thr Asp Phe Thr Phe Thr Ile Ser Ser Leu Gln
        195                 200                 205

Pro Glu Asp Ile Ala Thr Tyr Tyr Cys Leu Gln Leu Tyr Asp Tyr Pro
210                 215                 220

Leu Thr Phe Gly Gly Gly Thr Lys Val Glu Ile Lys
225                 230                 235

<210> SEQ ID NO 98
<211> LENGTH: 242
<212> TYPE: PRT
<213> ORGANISM: Artificial Sequence
<220> FEATURE:
<223> OTHER INFORMATION: Antibody sequence

<400> SEQUENCE: 98

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ser Ser Ser Gly Asp Ala Phe Asp Ile Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Asn Phe Met Leu Thr Gln Pro His Ser Val Ser Glu
        130                 135                 140

Ser Pro Gly Lys Thr Val Thr Ile Ser Cys Thr Arg Ser Ser Gly Ser
145                 150                 155                 160

Ile Ala Ser Asn Tyr Val Gln Trp Tyr Gln Gln Arg Pro Gly Ser Ser
```

```
                    165                 170                 175

Pro Thr Thr Val Ile Phe Asp Asp Asn Gln Arg Pro Thr Gly Val Pro
                180                 185                 190

Asp Arg Phe Ser Ala Ala Ile Asp Thr Ser Ser Ser Ala Ser Leu
            195                 200                 205

Thr Ile Ser Gly Leu Thr Ala Glu Asp Glu Ala Asp Tyr Tyr Cys Gln
210                 215                 220

Ser Ser His Ser Thr Ala Val Val Phe Gly Gly Gly Thr Lys Leu Thr
225                 230                 235                 240

Val Leu

<210> SEQ ID NO 99
<211> LENGTH: 255
<212> TYPE: PRT
<213> ORGANISM: Artificial Sequence
<220> FEATURE:
<223> OTHER INFORMATION: Antibody sequence

<400> SEQUENCE: 99

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu Ala Ala Ala His His His His His His
                245                 250                 255

<210> SEQ ID NO 100
<211> LENGTH: 255
<212> TYPE: PRT
<213> ORGANISM: Artificial Sequence
```

```
<220> FEATURE:
<223> OTHER INFORMATION: Antibody sequence

<400> SEQUENCE: 100

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Asn Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His
                245                 250                 255

<210> SEQ ID NO 101
<211> LENGTH: 255
<212> TYPE: PRT
<213> ORGANISM: Artificial Sequence
<220> FEATURE:
<223> OTHER INFORMATION: Antibody sequence

<400> SEQUENCE: 101

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                85                  90                  95
Ala Arg Gly Glu Tyr Tyr Tyr Asp Ser Ser Gly Tyr Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Gln Ser Ala Leu Thr Gln Pro Ala
            130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Asn Asn Asn Arg
            180                 185                 190

Pro Ser Gly Ile Ser Asn Arg Phe Ser Gly Ser Lys Ser Asp Asn Met
            195                 200                 205

Ala Ser Leu Thr Ile Ser Gly Leu Gln Pro Glu Asp Glu Ala Asp Tyr
            210                 215                 220

Tyr Cys Ser Ala Tyr Thr Ser Ser Asp Thr Leu Val Phe Gly Gly Gly
225                 230                 235                 240

Thr Lys Leu Thr Val Leu Ala Ala Ala His His His His His
            245                 250                 255

<210> SEQ ID NO 102
<211> LENGTH: 255
<212> TYPE: PRT
<213> ORGANISM: Artificial Sequence
<220> FEATURE:
<223> OTHER INFORMATION: Antibody sequence

<400> SEQUENCE: 102

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Gln Ser Ala Leu Thr Gln Pro Ala
            130                 135                 140

Ser Val Ser Gly Ser Pro Gly Gln Ser Ile Thr Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
```

```
                    195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Asp Thr Val Val Phe Gly Gly Gly
225                 230                 235                 240

Thr Lys Leu Thr Val Leu Ala Ala Ala His His His His His His
                    245                 250                 255

<210> SEQ ID NO 103
<211> LENGTH: 255
<212> TYPE: PRT
<213> ORGANISM: Artificial Sequence
<220> FEATURE:
<223> OTHER INFORMATION: Antibody sequence

<400> SEQUENCE: 103

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Met His Trp Val Arg Gln Pro Gly Gln Gly Leu Glu Trp Met
            35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Asp Thr Val Val Phe Gly Gly Gly
225                 230                 235                 240

Thr Lys Leu Thr Val Leu Ala Ala Ala His His His His His His
                    245                 250                 255

<210> SEQ ID NO 104
<211> LENGTH: 255
<212> TYPE: PRT
<213> ORGANISM: Artificial Sequence
<220> FEATURE:
<223> OTHER INFORMATION: Antibody sequence

<400> SEQUENCE: 104
```

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Pro Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Gly Gly Gly Ser Gly Gly
            115                 120                 125         Gly

Gly Gly Ser Gly Gly Gly Ser Gln Ser Ala Leu Thr Gln Pro Ala
        130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
            165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
            195                 200                 205

Ala Ser Leu Thr Ile Ser Gly Leu Gln Pro Glu Asp Glu Ala Asp Tyr
            210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
            245                 250                 255

<210> SEQ ID NO 105
<211> LENGTH: 255
<212> TYPE: PRT
<213> ORGANISM: Artificial Sequence
<220> FEATURE:
<223> OTHER INFORMATION: Antibody sequence

<400> SEQUENCE: 105

Glu Val Gln Leu Val Gln Ser Gly Ala Glu Val Lys Lys Pro Gly Ser
1               5                   10                  15

Thr Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Ala
        130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Ile Ser Trp Tyr Gln Gln
                165                 170                 175

His Pro Gly Thr Ala Pro Lys Leu Ile Ile Tyr Asp Phe Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu Ala Ala Ala His His His His His His
            245                 250                 255

<210> SEQ ID NO 106
<211> LENGTH: 255
<212> TYPE: PRT
<213> ORGANISM: Artificial Sequence
<220> FEATURE:
<223> OTHER INFORMATION: Antibody sequence

<400> SEQUENCE: 106

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Pro Val Thr Val Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

-continued

Tyr Cys Ser Ala Tyr Thr Ser Ser Asp Thr Leu Val Phe Gly Gly Gly
225                 230                 235                 240

Thr Lys Leu Thr Val Leu Ala Ala Ala His His His His His His
            245                 250                 255

<210> SEQ ID NO 107
<211> LENGTH: 255
<212> TYPE: PRT
<213> ORGANISM: Artificial Sequence
<220> FEATURE:
<223> OTHER INFORMATION: Antibody sequence

<400> SEQUENCE: 107

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Asn Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
            245                 250                 255

<210> SEQ ID NO 108
<211> LENGTH: 253
<212> TYPE: PRT
<213> ORGANISM: Artificial Sequence
<220> FEATURE:
<223> OTHER INFORMATION: Antibody sequence

<400> SEQUENCE: 108

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

```
Tyr Met His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Ala
            130                 135                 140

Ser Val Ser Gly Ser Pro Gly Gln Ser Ile Val Ile Ser Cys Thr Gly
 145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
                180                 185                 190

Pro Ser Gly Ile Ser Asn Arg Phe Ser Gly Ser Lys Ser Asp Asn Met
                195                 200                 205

Ala Ser Leu Thr Ile Ser Gly Leu Gln Pro Glu Asp Glu Ala Asp Tyr
                210                 215                 220

Tyr Cys Ser Ala Tyr Thr Ser Ser Asp Thr Val Phe Gly Gly Gly
 225                 230                 235                 240

Thr Lys Leu Thr Val Leu Ala Ala Ala His His His His
            245                 250
```

<210> SEQ ID NO 109
<211> LENGTH: 255
<212> TYPE: PRT
<213> ORGANISM: Artificial Sequence
<220> FEATURE:
<223> OTHER INFORMATION: Antibody sequence

<400> SEQUENCE: 109

```
Glu Val Gln Leu Val Gln Ser Gly Ala Glu Val Lys Lys Pro Gly Ser
 1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
 65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Asn Gly Gly Gly Ser Gly Gly
            115                 120                 125

Gly Gly Ser Gly Gly Gly Ser Gln Ser Ala Leu Thr Gln Pro Ala
            130                 135                 140
```

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
            165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 110
<211> LENGTH: 255
<212> TYPE: PRT
<213> ORGANISM: Artificial Sequence
<220> FEATURE:
<223> OTHER INFORMATION: Antibody sequence

<400> SEQUENCE: 110

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
            165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 111
<211> LENGTH: 255
<212> TYPE: PRT
<213> ORGANISM: Artificial Sequence
<220> FEATURE:
<223> OTHER INFORMATION: Antibody sequence

<400> SEQUENCE: 111

Glu Val Gln Leu Val Gln Ser Gly Ala Glu Val Lys Glu Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Ile Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His
                245                 250                 255

<210> SEQ ID NO 112
<211> LENGTH: 255
<212> TYPE: PRT
<213> ORGANISM: Artificial Sequence
<220> FEATURE:
<223> OTHER INFORMATION: Antibody sequence

<400> SEQUENCE: 112

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe

```
                50                  55                  60
Gln Gly Arg Val Thr Met Thr Gly Asp Thr Ser Thr Ser Thr Val Tyr
 65                  70                  75                  80

Met Glu Leu Asn Ser Leu Arg Ser Glu Asp Thr Ala Val Tyr Tyr Cys
                 85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Gln Ser Ala Leu Thr Gln Pro Ala
            130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
                180                 185                 190

Pro Ser Gly Ile Ser Asn Arg Phe Ser Gly Ser Lys Ser Asp Asn Met
                195                 200                 205

Ala Ser Leu Thr Ile Ser Gly Leu Gln Pro Glu Asp Glu Ala Asp Tyr
                210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255
```

<210> SEQ ID NO 113
<211> LENGTH: 255
<212> TYPE: PRT
<213> ORGANISM: Artificial Sequence
<220> FEATURE:
<223> OTHER INFORMATION: Antibody sequence

<400> SEQUENCE: 113

```
Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
                35                  40                  45

Gly Ala Ile Met Pro Ser Arg Gly Gly Thr Ser Tyr Pro Gln Lys Phe
 50                  55                  60

Gln Gly Arg Val Thr Met Thr Gly Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Tyr Tyr Tyr Asp Ser Ser Gly Tyr Tyr Tyr Trp Gly
                100                 105                 110

Gln Gly Thr Leu Val Thr Val Ser Ser Gly Gly Gly Gly Ser Gly Gly
                115                 120                 125

Gly Gly Ser Gly Gly Gly Gly Ser Gln Ser Ala Leu Thr Gln Pro Ala
            130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
```

```
                165                 170                 175
His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
            195                 200                 205

Ala Ser Leu Ile Ile Ser Gly Leu Gln Pro Glu Asp Glu Ala Asp Tyr
            210                 215                 220

Tyr Cys Ser Ala Tyr Thr Ser Ser Asp Thr Leu Val Phe Gly Gly Gly
225                 230                 235                 240

Thr Lys Leu Thr Val Leu Ala Ala Ala His His His His His His
                245                 250                 255

<210> SEQ ID NO 114
<211> LENGTH: 255
<212> TYPE: PRT
<213> ORGANISM: Artificial Sequence
<220> FEATURE:
<223> OTHER INFORMATION: Antibody sequence

<400> SEQUENCE: 114

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asp Met
            195                 200                 205

Ala Ser Leu Thr Ile Ser Gly Leu Gln Pro Glu Asp Glu Ala Asp Tyr
            210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 115
<211> LENGTH: 255
<212> TYPE: PRT
```

<213> ORGANISM: Artificial Sequence
<220> FEATURE:
<223> OTHER INFORMATION: Antibody sequence

<400> SEQUENCE: 115

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Tyr | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Ala | Ile | Met | Pro | Ser | Arg | Gly | Gly | Thr | Ser | Tyr | Pro | Gln | Lys | Phe |
| 50 | | | | | 55 | | | | | 60 | | | | | |
| Gln | Gly | Arg | Val | Thr | Met | Thr | Gly | Asp | Thr | Ser | Thr | Ser | Thr | Val | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Glu | Tyr | Tyr | Asp | Ser | Ser | Gly | Tyr | Tyr | Tyr | Trp | Gly |
| | | | 100 | | | | | 105 | | | | | 110 | | |
| Pro | Gly | Thr | Leu | Val | Thr | Val | Ser | Ser | Gly | Gly | Gly | Ser | Gly | Gly |
| | | | 115 | | | | | 120 | | | | | 125 | | |
| Gly | Gly | Ser | Gly | Gly | Gly | Ser | Gln | Ser | Ala | Leu | Thr | Gln | Pro | Ala |
| | 130 | | | | | 135 | | | | | 140 | | | | |
| Ser | Val | Ser | Gly | Ser | Pro | Gly | Gln | Ser | Ile | Ala | Ile | Ser | Cys | Thr | Gly |
| 145 | | | | | 150 | | | | | 155 | | | | | 160 |
| Thr | Ser | Ser | Asp | Ile | Gly | His | Tyr | Asp | Phe | Val | Ser | Trp | Tyr | Gln | Gln |
| | | | | 165 | | | | | 170 | | | | | 175 | |
| His | Pro | Gly | Thr | Ala | Pro | Lys | Leu | Ile | Ile | Tyr | Asp | Ile | Asn | Asn | Arg |
| | | | 180 | | | | | 185 | | | | | 190 | | |
| Pro | Ser | Gly | Ile | Ser | Asn | Arg | Phe | Ser | Gly | Ser | Lys | Ser | Asp | Asn | Met |
| | | | 195 | | | | | 200 | | | | | 205 | | |
| Ala | Ser | Leu | Thr | Ile | Ser | Gly | Leu | Gln | Pro | Glu | Asp | Glu | Ala | Asp | Tyr |
| | | 210 | | | | | 215 | | | | | 220 | | | |
| Tyr | Cys | Ser | Ala | Tyr | Thr | Ser | Ser | Asp | Thr | Val | Val | Phe | Gly | Gly | Gly |
| 225 | | | | | 230 | | | | | 235 | | | | | 240 |
| Thr | Lys | Leu | Thr | Val | Leu | Ala | Ala | Ala | His | His | His | His | His |
| | | | 245 | | | | | 250 | | | | | 255 | |

<210> SEQ ID NO 116
<211> LENGTH: 255
<212> TYPE: PRT
<213> ORGANISM: Artificial Sequence
<220> FEATURE:
<223> OTHER INFORMATION: Antibody sequence

<400> SEQUENCE: 116

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Tyr | Ile | His | Trp | Val | Arg | Gln | Ala | Pro | Gly | Gln | Gly | Leu | Glu | Trp | Met |
| | | 35 | | | | | 40 | | | | | 45 | | | |
| Gly | Ala | Ile | Met | Pro | Ser | Arg | Gly | Gly | Thr | Ser | Tyr | Pro | Gln | Lys | Phe |
| 50 | | | | | 55 | | | | | 60 | | | | | |
| Gln | Gly | Arg | Val | Thr | Met | Thr | Gly | Asp | Thr | Ser | Thr | Ser | Thr | Val | Tyr |
| 65 | | | | | 70 | | | | | 75 | | | | | 80 |

```
Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Ala Ser Gly Ile Ser Asn Arg Phe Ser Gly Ser Lys Ser Asp Asn Met
            195                 200                 205

Ala Ser Leu Thr Ile Ser Gly Leu Gln Pro Glu Asp Glu Ala Asp Tyr
        210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 117
<211> LENGTH: 255
<212> TYPE: PRT
<213> ORGANISM: Artificial Sequence
<220> FEATURE:
<223> OTHER INFORMATION: Antibody sequence

<400> SEQUENCE: 117

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
        50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Asn Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190
```

```
Pro Ser Gly Ile Ser Asn Arg Phe Ser Gly Ser Lys Ser Asp Asn Met
            195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 118
<211> LENGTH: 255
<212> TYPE: PRT
<213> ORGANISM: Artificial Sequence
<220> FEATURE:
<223> OTHER INFORMATION: Antibody sequence

<400> SEQUENCE: 118

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ala Ile Met Pro Ser Arg Gly Gly Thr Ser Tyr Pro Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Met Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Thr Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
    195                 200                 205

Ala Ser Leu Thr Ile Ser Gly Leu Gln Pro Glu Asp Glu Ala Asp Tyr
210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 119
<211> LENGTH: 255
<212> TYPE: PRT
<213> ORGANISM: Artificial Sequence
<220> FEATURE:
<223> OTHER INFORMATION: Antibody sequence

<400> SEQUENCE: 119
```

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Thr Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Val Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255
```

<210> SEQ ID NO 120
<211> LENGTH: 255
<212> TYPE: PRT
<213> ORGANISM: Artificial Sequence
<220> FEATURE:
<223> OTHER INFORMATION: Antibody sequence

<400> SEQUENCE: 120

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110
```

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Ala
        130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 121
<211> LENGTH: 255
<212> TYPE: PRT
<213> ORGANISM: Artificial Sequence
<220> FEATURE:
<223> OTHER INFORMATION: Antibody sequence

<400> SEQUENCE: 121

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Asn Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

```
Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 122
<211> LENGTH: 255
<212> TYPE: PRT
<213> ORGANISM: Artificial Sequence
<220> FEATURE:
<223> OTHER INFORMATION: Antibody sequence

<400> SEQUENCE: 122

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
                20                  25                  30

Tyr Met His Trp Val Arg Gln Ala Pro Gly Gln Gly Leu Glu Trp Ile
            35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 123
<211> LENGTH: 255
<212> TYPE: PRT
<213> ORGANISM: Artificial Sequence
<220> FEATURE:
<223> OTHER INFORMATION: Antibody sequence

<400> SEQUENCE: 123

Glu Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Thr Asn Tyr
```

```
                 20                  25                  30
Tyr Met His Trp Val Arg Gln Ala Pro Gly Gln Gly Leu Glu Trp Met
             35                  40                  45

Gly Ala Ile Met Pro Ser Arg Gly Gly Thr Ser Tyr Pro Gln Lys Phe
         50                  55                  60

Gln Gly Arg Val Thr Met Thr Gly Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Tyr Tyr Tyr Asp Ser Ser Gly Tyr Tyr Trp Gly
                100                 105                 110

Gln Gly Thr Leu Val Thr Val Ser Gly Gly Gly Ser Gly Gly
            115                 120                 125

Gly Gly Ser Gly Gly Gly Ser Gln Ser Ala Leu Thr Gln Pro Ala
        130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Asp Thr Val Val Phe Gly Gly Gly
225                 230                 235                 240

Thr Lys Leu Thr Val Leu Ala Ala Ala His His His His His His
                245                 250                 255

<210> SEQ ID NO 124
<211> LENGTH: 482
<212> TYPE: PRT
<213> ORGANISM: Artificial Sequence
<220> FEATURE:
<223> OTHER INFORMATION: Antibody sequence

<400> SEQUENCE: 124

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Ala Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly
        115                 120                 125

Gly Ser Gly Gly Gly Gly Ser Asp Val Val Met Thr Gln Ser Pro Leu
```

```
            130                 135                 140
Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
                195                 200                 205

Thr Asp Phe Thr Leu Lys Ile Ser Arg Val Glu Ala Glu Asp Val Gly
210                 215                 220

Val Tyr Tyr Cys Met Gln Gly Thr His Trp Pro Trp Thr Phe Gly Gln
225                 230                 235                 240

Gly Thr Lys Val Glu Ile Lys Asn Ser Gly Ala Gly Thr Ala Ala Ala
                245                 250                 255

Thr His Thr Cys Pro Pro Cys Pro Ala Pro Glu Ala Ala Gly Gly Pro
                260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Cys Thr
            370                 375                 380

Leu Pro Pro Ser Arg Asp Glu Leu Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Cys Val Ser Lys Leu Thr Val Asp
            435                 440                 445

Lys Ser Arg Trp Gln Gln Gly Asn Val Phe Ser Cys Ser Val Met His
            450                 455                 460

Glu Ala Leu His Asn His Tyr Thr Gln Lys Ser Leu Ser Leu Ser Pro
465                 470                 475                 480

Gly Lys

<210> SEQ ID NO 125
<211> LENGTH: 243
<212> TYPE: PRT
<213> ORGANISM: Artificial Sequence
<220> FEATURE:
<223> OTHER INFORMATION: Antibody sequence

<400> SEQUENCE: 125

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Asp Ile Leu Thr Gly Tyr Ala Leu Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Ser Tyr Glu Leu Thr Gln Pro Pro Ser
130                 135                 140

Met Ser Val Ser Pro Gly Gln Thr Ala Arg Ile Thr Cys Ser Gly Asp
145                 150                 155                 160

Ala Leu Pro Lys Gln Phe Ala Phe Trp Tyr Gln Gln Lys Pro Gly Gln
                165                 170                 175

Ala Pro Val Leu Val Ile Tyr Lys Asp Thr Glu Arg Pro Ser Gly Ile
                180                 185                 190

Pro Glu Arg Phe Ser Gly Ser Ser Gly Thr Thr Val Thr Leu Thr
                195                 200                 205

Ile Thr Gly Val Gln Ala Glu Asp Glu Ala Asp Tyr Tyr Cys Gln Ser
    210                 215                 220

Pro Asp Ser Ser Gly Thr Val Glu Val Phe Gly Gly Gly Thr Lys Leu
225                 230                 235                 240

Thr Val Leu

<210> SEQ ID NO 126
<211> LENGTH: 256
<212> TYPE: PRT
<213> ORGANISM: Artificial Sequence
<220> FEATURE:
<223> OTHER INFORMATION: Antibody sequence

<400> SEQUENCE: 126

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
                100                 105                 110

Gly Thr Leu Val Thr Val Ser Ser Gly Gly Gly Gly Ser Gly Gly Gly
            115                 120                 125
```

```
Gly Ser Gly Gly Gly Ser Asp Val Val Met Thr Gln Ser Pro Leu
    130             135                 140
Ser Leu Pro Val Thr Pro Gly Glu Pro Ala Ser Ile Ser Cys Arg Ser
145             150                 155                 160
Ser Gln Ser Leu Leu His Ser Asn Gly Tyr Asn Tyr Leu Asp Trp Tyr
                165                 170                 175
Leu Gln Lys Pro Gly Gln Ser Pro Gln Leu Leu Ile Tyr Leu Gly Ser
            180                 185                 190
Asn Arg Asp Ser Gly Val Pro Asp Arg Phe Ser Gly Ser Gly Ser Gly
        195                 200                 205
Thr Asp Phe Thr Leu Lys Ile Ser Arg Val Glu Ala Glu Asp Val Gly
    210                 215                 220
Val Tyr Tyr Cys Met Gln Gly Thr His Trp Pro Trp Thr Phe Gly Gln
225                 230                 235                 240
Gly Thr Lys Val Glu Ile Lys Ala Ala Ala His His His His His His
                245                 250                 255

<210> SEQ ID NO 127
<211> LENGTH: 256
<212> TYPE: PRT
<213> ORGANISM: Artificial Sequence
<220> FEATURE:
<223> OTHER INFORMATION: Antibody sequence

<400> SEQUENCE: 127

Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
                20                  25                  30
Tyr Trp Ser Trp Ile Arg Gln Pro Pro Gly Lys Gly Leu Glu Trp Ile
            35                  40                  45
Gly Glu Ile Asn His Phe Gly Ser Thr Asn Tyr Asn Pro Ser Leu Lys
        50                  55                  60
Ser Arg Ala Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Thr Ser Pro Gly Gly Tyr Ser Gly Gly Tyr Phe Gln His Trp Gly Gln
                100                 105                 110
Gly Thr Leu Val Thr Val Ser Ser Gly Gly Gly Gly Ser Gly Gly Gly
            115                 120                 125
Gly Ser Gly Gly Gly Gly Ser Asp Val Val Met Thr Gln Ser Pro Leu
    130             135                 140
Ser Leu Pro Val Thr Pro Gly Glu Pro Ala Ser Ile Ser Cys Arg Ser
145             150                 155                 160
Ser Gln Ser Leu Leu His Ser Asn Gly Tyr Asn Tyr Leu Asp Trp Tyr
                165                 170                 175
Leu Gln Lys Pro Gly Gln Ser Pro Gln Leu Leu Ile Tyr Leu Gly Ser
            180                 185                 190
Asn Arg Asp Ser Gly Val Pro Asp Arg Phe Ser Gly Ser Gly Ser Gly
        195                 200                 205
Thr Asp Phe Thr Leu Lys Ile Ser Arg Val Glu Ala Glu Asp Val Gly
    210                 215                 220
Val Tyr Tyr Cys Met Gln Gly Thr His Trp Pro Trp Thr Phe Gly Gln
225                 230                 235                 240
```

Gly Thr Lys Val Glu Ile Lys Ala Ala Ala His His His His His
              245                 250                 255

<210> SEQ ID NO 128
<211> LENGTH: 256
<212> TYPE: PRT
<213> ORGANISM: Artificial Sequence
<220> FEATURE:
<223> OTHER INFORMATION: Antibody sequence

<400> SEQUENCE: 128

Gln Val Gln Leu Gln Gln Trp Gly Ala Gly Met Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240

Gly Thr Lys Val Glu Ile Lys Ala Ala Ala His His His His His
                245                 250                 255

<210> SEQ ID NO 129
<211> LENGTH: 255
<212> TYPE: PRT
<213> ORGANISM: Artificial Sequence
<220> FEATURE:
<223> OTHER INFORMATION: Antibody sequence

<400> SEQUENCE: 129

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

```
Gly Glu Ile Asn His Phe Gly Ser Thr Asn Tyr Asn Pro Ser Leu Lys
            50                  55                  60
Ser Arg Ala Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                85                  90                  95
Thr Ser Pro Gly Gly Tyr Ser Gly Tyr Phe Gln His Trp Gly Gln
            100                 105                 110
Gly Thr Leu Val Thr Val Ser Ser Gly Gly Gly Ser Gly Glu Gly
            115                 120                 125
Gly Ser Gly Gly Gly Ser Asp Val Val Met Thr Gln Ser Pro Leu
            130                 135                 140
Ser Leu Pro Val Thr Pro Gly Glu Pro Ala Ser Ile Ser Cys Arg Ser
145                 150                 155                 160
Ser Gln Ser Leu Leu His Ser Asn Gly Tyr Asn Tyr Leu Asp Trp Tyr
                165                 170                 175
Leu Gln Lys Pro Gly Gln Ser Pro Gln Leu Leu Ile Tyr Leu Gly Ser
            180                 185                 190
Asn Arg Asp Ser Gly Val Pro Asp Arg Phe Ser Gly Ser Gly Ser Gly
            195                 200                 205
Thr Asp Phe Thr Leu Lys Ile Ser Arg Val Glu Ala Glu Asp Val Gly
            210                 215                 220
Val Tyr Tyr Cys Met Gln Gly Thr His Trp Pro Trp Thr Phe Gly Gln
225                 230                 235                 240
Gly Thr Lys Val Glu Ile Lys Ala Ala Ala His His His His
            245                 250                 255

<210> SEQ ID NO 130
<211> LENGTH: 648
<212> TYPE: DNA
<213> ORGANISM: Artificial Sequence
<220> FEATURE:
<223> OTHER INFORMATION: P2C4 Fab Light Chain ntd (VL, joint, CL)

<400> SEQUENCE: 130
cagtctgccc tgactcagcc tgcctccgtg tctgggtctc ctggacagtc gatcgccatt      60
tcctgcactg gaaccagcag tgacattggt cattatgact ttgtctcctg gtaccaacag     120
cacccaggca cagcccccaa actcataatt tatgatatca ataatcggcc ctcagggatt     180
tctaatcgct tctctggctc caagtctgac aatatggcct ccctgaccat ctctgggctc     240
cagcctgagg acgaggctga ttattactgc agtgcatata caagcagcga cactctggtc     300
ttcggcggag ggaccaagtt gaccgtcctc agtcagccca aggctgcccc ctcggtcact     360
ctgttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac acctccaaa  caaagcaaca caagtacgc  ggccagcagc     540 tacctgagcc tgacgcctga gcagtggaag tcccacaaaa gctacagctg ccaggtcacg     600
catgaaggga gcaccgtgga gaagacagtg gcccctacag aatgttca                  648

<210> SEQ ID NO 131
<211> LENGTH: 672
<212> TYPE: DNA
<213> ORGANISM: Artificial Sequence
<220> FEATURE:
<223> OTHER INFORMATION: P2C4 Fab Heavy Chain ntd (VH, joint, CH)
```

<400> SEQUENCE: 131

```
gaggtccagc tggtacagtc tggggctgag gtgaagaagc ctgggtcctc agtgaaggtt      60
tcctgcaagg catctggata caccttcacc aactactata tgcactgggt gcgacaggcc     120
cctggacaag gcttgagtg gatgggggca atcatgccta gtcgtggtgg cacaagttac     180
ccacagaagt tccagggcag agtcaccatg accggggaca cgtccacgag cacagtctac     240
atggagctga gcagcctgag atctgaggac acggccgtgt attactgtgc gagaggggag     300
tattactatg atagtagtgg ttattactac tggggccagg gcaccctggt caccgtctca     360
agcgcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtccacacct tcccggctgt cctacagtcc     540
tcaggactct actccctcag cagcgtagtg accgtgccct ccagcagctt gggcacccag     600
acctacatct gcaacgtgaa tcacaagccc agcaacacca aggtggacaa gaaagttgag     660
cccaaatctt gt                                                         672
```

<210> SEQ ID NO 132
<211> LENGTH: 1440
<212> TYPE: DNA
<213> ORGANISM: Artificial Sequence
<220> FEATURE:
<223> OTHER INFORMATION: P2C4 scFv ntd (scFv and Fc with knob
      modification)

<400> SEQUENCE: 132

```
gaagtgcagc tggtgcagag cggggcagaa gtgaaaaagc ctgggtcaag cgtgaaggtc      60
tcctgtaaag caagcggata cacattcaca aactactata tgcactgggt gcggcaggcc     120
cccggacagg gcctggagtg gatgggcgct atcatgcctt cccgaggcgg gacttcttac     180
ccacagaagt tccagggaag agtgaccatg acaggcgaca ctagcacctc cacagtctat     240
atggagctga gcagcctgag gagcgaagac actgccgtgt actattgcgc tcgcggagaa     300
tactattacg attctagtgg ctattactat tgggggcagg gaacactggt gactgtctca     360
agcggaggag gaggaagtgg cggaggaggc tccggaggag gcgggtctca gagtgcactg     420
acccagccag catcagtgag cggcagcccc ggccagtcta tcgcaattag ttgtactggg     480
acctcctctg acatcggaca ctacgatttc gtctcttggt atcagcagca ccccggcacc     540
gctcctaagc tgatcatcta cgacatcaac aatcggccca gcggcatttc caacagattt     600
tctggagta atcagataa tatggcctca ctgacaatta gcggcctcca gcctgaggac     660
gaagctgatt actattgctc cgcatacact agttcagata ccctggtgtt tggaggcggg     720
accaaactga cagtcctgaa cagcggcgcg ggcaccgcgg ccgcgactca cacatgccca     780
ccgtgcccag cacctgaagc cgcggggga ccgtcagtct tcctcttccc cccaaaaccc     840
aaggacaccc tcatgatctc ccggacccct gaggtcacat gcgtggtggt ggacgtgagc     900
cacgaagacc ctgaggtcaa gttcaactgg tacgtggacg gcgtggaggt gcataatgcc     960
aagacaaagc cgcgggagga gcagtacaac agcacgtacc gtgtggtcag cgtcctcacc    1020
gtcctgcacc aggactggct gaatggcaag gagtacaagt gcaaggtctc caacaaagcc    1080
ctcccagccc ccatcgagaa aaccatctcc aaagccaaag gcagccccg agaaccacag    1140
gtgtacaccc tgccccatg ccgggatgag ctgaccaaga accaggtcag cctgtggtgc    1200
ctggtcaaag gcttctatcc cagcgacatc gccgtggagt gggagagcaa tgggcagccg    1260
```

```
gagaacaact acaagaccac gcctcccgtg ctggactccg acggctcctt cttcctctac   1320
agcaagctca ccgtggacaa gagcaggtgg cagcagggga acgtcttctc atgctccgtg   1380
atgcatgagg ctctgcacaa ccactacacg cagaagagcc tctccctgtc tccgggtaaa   1440
```

<210> SEQ ID NO 133
<211> LENGTH: 642
<212> TYPE: DNA
<213> ORGANISM: Artificial Sequence
<220> FEATURE:
<223> OTHER INFORMATION: P2H7 Fab Light Chain ntd (VL, joint, CL)

<400> SEQUENCE: 133

```
gacatccaga tgacccagtc tccttccaca ttgtctgcat ctgtaggaga cagagtcaca     60
ctctcttgcc gggccggtca ggctattagt agttggttgg cctggtatca acagaaacca    120
ggtaaagccc caaagcttct gatctataag gcatctaatt tagaaagtgg agtcccatca    180
aggttcagcg gcggtggatc tggggcagaa ttcactctca ccatcagcag cctgcagcct    240
gatgattttg caacttatta ctgccaacag tatcagagct acccttacac ttttggccag    300
gggaccaagc tggagatcag acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 134
<211> LENGTH: 666
<212> TYPE: DNA
<213> ORGANISM: Artificial Sequence
<220> FEATURE:
<223> OTHER INFORMATION: P2H7 Fab Heavy Chain ntd (VH, joint, CH)

<400> SEQUENCE: 134

```
gaggtgcagc tggtgcagtc tgggactgag gtgaagaagc ctggggcctc agtgaaggtt     60
tcctgcaagg cttctggata caccttcact acctatgcta tgcattgggt gcgccaggcc    120
cccggacaaa gccttgagtg gatgggatgg atcaacactg gcaatggtaa cacaaaatat    180
tcacagaact tccagggcag agtcaccatg accagggaca cgtccatcag cacagcctac    240
atggagctga gcaggctgag atctgacgac acggccgtgt attactgtgc gagagatctc    300 ggcaactgg aacgactcta cttctggggc cagggcaccc tggtcaccgt ctcaagcgcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtccac accttcccgg ctgtcctaca gtcctcagga    540
ctctactccc tcagcagcgt agtgaccgtg ccctccagca gcttgggcac ccagacctac    600
atctgcaacg tgaatcacaa gcccagcaac accaaggtgg acaagaaagt tgagcccaaa    660
tcttgt                                                              666
```

<210> SEQ ID NO 135
<211> LENGTH: 1428
<212> TYPE: DNA
<213> ORGANISM: Artificial Sequence
<220> FEATURE:

<223> OTHER INFORMATION: P2H7 scFv ntd (scFv and Fc with knob modification)

<400> SEQUENCE: 135

```
gaggtgcagc tggtgcagtc tgggactgag gtgaagaagc ctggggcctc agtgaaggtt      60
tcctgcaagg cttctggata caccttcact acctatgcta tgcattgggt gcgccaggcc     120
cccggacaaa gccttgagtg gatgggatgg atcaacactg caatggtaa cacaaaatat     180
tcacagaact tccagggcag agtcaccatg accaggggaca cgtccatcag cacagcctac     240
atggagctga gcaggctgag atctgacgac acggccgtgt attactgtgc gagagatctc     300
gggcaactgg aacgactcta cttctggggc cagggcaccc tggtcaccgt ctcaagcgga     360
ggaggaggat ctggcggagg aggcagtgga ggaggagggt cacttgacat ccagatgacc     420
cagtctcctt ccacattgtc tgcatctgta ggagacagag tcacactctc ttgccgggcc     480
ggtcaggcta ttagtagttg gttggcctgg tatcaacaga accaggtaa agccccaaag     540
cttctgatct ataaggcatc taatttagaa agtggagtcc catcaaggtt cagcggcggt     600
ggatctgggg cagaattcac tctcaccatc agcagcctgc agcctgatga ttttgcaact     660
tattactgcc aacagtatca gagctaccct tacacttttg gccaggggac caagctggag     720
atcagaaaca gcggcgcggg caccgcggcc gcgactcaca catgcccacc gtgcccagca     780
cctgaagccg cggggggacc gtcagtcttc ctcttccccc caaaacccaa ggacaccctc     840
atgatctccc ggacccctga ggtcacatgc gtggtggtgg acgtgagcca cgaagaccct     900
gaggtcaagt tcaactggta cgtggacggc gtggaggtgc ataatgccaa gacaaagccg     960
cgggaggagc agtacaacag cacgtaccgt gtggtcagcg tcctcaccgt cctgcaccag    1020
gactggctga atggcaagga gtacaagtgc aaggtctcca acaaagccct cccagccccc    1080
atcgagaaaa ccatctccaa agccaaaggg cagccccgag aaccacaggt gtacaccctg    1140
cccccatgcc gggatgagct gaccaagaac caggtcagcc tgtggtgcct ggtcaaaggc    1200
ttctatccca gcgacatcgc cgtggagtgg gagagcaatg ggcagccgga gaacaactac    1260
aagaccacgc ctcccgtgct ggactccgac ggctccttct tcctctacag caagctcacc    1320
gtggacaaga gcaggtggca gcaggggaac gtcttctcat gctccgtgat gcatgaggct    1380
ctgcacaacc actacacgca gaagagcctc tccctgtctc cgggtaaa              1428
```

<210> SEQ ID NO 136
<211> LENGTH: 642
<212> TYPE: DNA
<213> ORGANISM: Artificial Sequence
<220> FEATURE:
<223> OTHER INFORMATION: P2D12 Fab Light Chain ntd (VL, joint, CL)

<400> SEQUENCE: 136

```
gacatccagt tgacccagtc tccatcctcc ctgtctgcat ctgtaggaga cagagtcacc      60
atcacttgcc aggcgagtca ggacattggc aactatttaa attggtatca gcttaaacca     120
gggaaagccc ctaagctcct gatctacgat gcatccaatt ggaaacagg ggtcccatca     180
aggttcagtg aagtggatc tgggacagat tttactttca ccatcagcag cctgcagcct     240
gaagatattg caacatatta ctgtctacaa ctttatgatt accccctcac tttcggcgga     300
gggaccaagg tggagatcaa acgaactgtg gctgcaccat ctgtcttcat cttccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 137
<211> LENGTH: 651
<212> TYPE: DNA
<213> ORGANISM: Artificial Sequence
<220> FEATURE:
<223> OTHER INFORMATION: P2D12 Fab Heavy Chain ntd (VH, joint, CH)

<400> SEQUENCE: 137

| cacgtgcagc tggtggagac tgggggaggc ttggtgcagc ctggggggtc cctgagactc | 60 |
| tcctgtgcag cctctggatt cacctttagc agctatgcca tgagctgggt ccgccaggct | 120 |
| ccagggaagg gctggagtg gtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtat attactgtgc gagagatctc | 300 |
| ggggattatt ggggccaggg aaccctggtc accgtctcaa gcgcctccac caagggccca | 360 |
| tcggtcttcc ccctggcacc ctcctccaag agcacctctg gggcacagc ggccctgggc | 420 |
| tgcctggtca aggactactt ccccgaaccg gtgacggtgt cgtggaactc aggcgccctg | 480 |
| accagcggcg tccacacctt cccggctgtc ctacagtcct caggactcta ctccctcagc | 540 |
| agcgtagtga ccgtgccctc agcagcttg ggcacccaga cctacatctg caacgtgaat | 600 |
| cacaagccca gcaacaccaa ggtggacaag aaagttgagc ccaaatcttg t | 651 |

<210> SEQ ID NO 138
<211> LENGTH: 1452
<212> TYPE: DNA
<213> ORGANISM: Artificial Sequence
<220> FEATURE:
<223> OTHER INFORMATION: P2D12 scFv ntd (scFv and Fc with knob
      modification)

<400> SEQUENCE: 138

| caggtccagc tgcaggagtc cgggccaggg ctggtgaaac caagcgaaac actgagtctg | 60 |
| acatgtaccg tgagtgggg gtccattaac aatagtaact actattggtc atggatcaga | 120 |
| cagagccctg gaagaggcct ggagtggatc ggcgggatct acttcagcgg caccacatac | 180 |
| tataacccat cactgcagag ccgggtgact atctccattg acacctctaa gaatcagttc | 240 |
| agcctgaagc tgagcagcgt gaccgccgct gatacagcca tctactattg cgtccggcag | 300 |
| atgaattact atcacctggg ctctagtgtg gggttcgacc cctggggaca gggagcactg | 360 |
| gccaccgtgt caagcgtctc ctctggagga ggaggcagcg gcgaggagg ctctggagga | 420 |
| ggcgggagtg atgtggtcat gacacagagc ccagctactc tgtctgtgag tccggcgaa | 480 |
| agggccacac tgagctgtcg cgcttcacag agcgtcagtt caaacctggc atggtaccag | 540 |
| cagaagccag acaggcacc ttccctgctg atctatgagg cttctacacg agcaactggc | 600 |
| attcctgcta gattctccgg ctctgggagt ggaaccgact ttactctgac catcagctcc | 660 |
| ctgcagagcg aagattttgc aatctactat tgtcagcagt ataacgattg gctgtggacc | 720 |
| ttcgggcagg ggactaaagt ggagattcgg aacagcggcg cgggcaccgc ggccgcgact | 780 |
| cacacatgcc caccgtgccc agcacctgaa gccgcgggg gaccgtcagt cttcctcttc | 840 |
| cccccaaaac ccaaggacac cctcatgatc tcccggaccc ctgaggtcac atgcgtggtg | 900 |

| | |
|---|---|
| gtggacgtga gccacgaaga ccctgaggtc aagttcaact ggtacgtgga cggcgtggag | 960 |
| gtgcataatg ccaagacaaa gccgcgggag gagcagtaca acagcacgta ccgtgtggtc | 1020 |
| agcgtcctca ccgtcctgca ccaggactgg ctgaatggca aggagtacaa gtgcaaggtc | 1080 |
| tccaacaaag ccctcccagc ccccatcgag aaaaccatct ccaaagccaa agggcagccc | 1140 |
| cgagaaccac aggtgtacac cctgccccca tgccgggatg agctgaccaa gaaccaggtc | 1200 |
| agcctgtggt gcctggtcaa aggcttctat cccagcgaca tcgccgtgga gtgggagagc | 1260 |
| aatgggcagc cggagaacaa ctacaagacc acgcctcccg tgctggactc cgacggctcc | 1320 |
| ttcttcctct acagcaagct caccgtggac aagagcaggt ggcagcaggg gaacgtcttc | 1380 |
| tcatgctccg tgatgcatga ggctctgcac aaccactaca cgcagaagag cctctccctg | 1440 |
| tctccgggta aa | 1452 |

<210> SEQ ID NO 139
<211> LENGTH: 648
<212> TYPE: DNA
<213> ORGANISM: Artificial Sequence
<220> FEATURE:
<223> OTHER INFORMATION: P1G11 Fab Light Chain ntd (VL, joint, CL)

<400> SEQUENCE: 139

| | |
|---|---|
| aattttatgc tgactcagcc ccactctgtg tcggagtctc cggggaagac ggtaaccatc | 60 |
| tcctgcaccc gcagcagtgg cagcattgcc agcaactatg tgcagtggta ccagcagcgc | 120 |
| ccgggcagtt cccccaccac ggtcatttt gacgacaatc aaagaccac tggtgtccct | 180 |
| gatcgcttct ctgccgccat cgacacctcc tccagttctg cctccctcac catctctgga | 240 |
| ctgacggctg aggacgaggc cgattactat tgtcagtcgt tcatagcacc gctgtcgtc | 300 |
| tttggcggag ggaccaagct gaccgtccta agtcagccca aggctgcccc ctcggtcact | 360 |
| ctgttcccgc cctcctctga ggagcttcaa gccaacaagg ccacactggt gtgtctcata | 420 |
| agtgacttct acccgggagc cgtgacagtg gcctggaagg cagatagcag ccccgtcaag | 480 |
| gcgggagtgg agaccaccac accctccaaa caaagcaaca acaagtacgc ggccagcagc | 540 |
| tacctgagcc tgacgcctga gcagtggaag tcccacaaaa gctacagctg ccaggtcacg | 600 |
| catgaaggga gcaccgtgga agacagtgtg gcccctacag aatgttca | 648 |

<210> SEQ ID NO 140
<211> LENGTH: 660
<212> TYPE: DNA
<213> ORGANISM: Artificial Sequence
<220> FEATURE:
<223> OTHER INFORMATION: P1G11 Fab Heavy Chain ntd (VH, joint, CH)

<400> SEQUENCE: 140

| | |
|---|---|
| caggtgcagc tacagcagtg gggcgcagga ctgttgaagc cttcggagac cctgtccctc | 60 |
| acctgcgctg tctatggtgg gtccttcagt ggttactact ggagctggat ccgccagccc | 120 |
| ccagggaagg ggctggagtg gattgggaa atcaatcata gtggaagcac caactacaac | 180 |
| ccgtccctca gagtcgagt caccatatca gtagacacgt ccaagaacca gttctccctg | 240 |
| aagctgagct ctgtgaccgc cgcggacacg gctgtgtatt actgtgcgag aagctcgtcc | 300 |
| ggggatgctt ttgatatctg gggccaaggg acaatggtca ccgtctcaag cgcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt ccacaccttc ccggctgtcc tacagtcctc aggactctac | 540 |

| tccctcagca gcgtagtgac cgtgccctcc agcagcttgg gcacccagac ctacatctgc | 600 |
| aacgtgaatc acaagcccag caacaccaag gtggacaaga agttgagcc caaatcttgt | 660 |

<210> SEQ ID NO 141
<211> LENGTH: 1431
<212> TYPE: DNA
<213> ORGANISM: Artificial Sequence
<220> FEATURE:
<223> OTHER INFORMATION: P1G11 scFv ntd (scFv and Fc with knob modification)

<400> SEQUENCE: 141

| caggtgcagc tacagcagtg gggcgcagga ctgttgaagc cttcggagac cctgtccctc | 60 |
| acctgcgctg tctatggtgg gtccttcagt ggttactact ggagctggat ccgccagccc | 120 |
| ccagggaagg ggctggagtg gattgggaa atcaatcata gtggaagcac caactacaac | 180 |
| ccgtccctca gagtcgagt caccatatca gtagacacgt ccaagaacca gttctccctg | 240 |
| aagctgagct ctgtgaccgc cgcggacacg gctgtgtatt actgtgcgag aagctcgtcc | 300 |
| ggggatgctt ttgatatctg gggccaaggg acaatggtca ccgtctcaag cggaggagga | 360 |
| ggatctggcg gaggaggcag tggaggagga gggtcactta ttttatgct gactcagccc | 420 |
| cactctgtgt cggagtctcc ggggaagacg gtaaccatct cctgcacccg cagcagtggc | 480 |
| agcattgcca gcaactatgt gcagtggtac cagcagcgcc cgggcagttc ccccaccacg | 540 |
| gtcattttg acgacaatca agacccact ggtgtccctg atcgcttctc tgccgccatc | 600 |
| gacacctcct ccagttctgc ctccctcacc atctctggac tgacggctga ggacgaggcc | 660 |
| gattactatt gtcagtcgtc tcatagcacc gctgtcgtct tggcggagg gaccaagctg | 720 |
| accgtcctaa cagcggcgc gggcaccgcg gccgcgactc acacatgccc accgtgccca | 780 |
| gcacctgaag ccgcgggggg accgtcagtc ttcctcttcc cccaaaaacc caaggacacc | 840 |
| ctcatgatct cccggacccc tgaggtcaca tgcgtggtgg tggacgtgag ccacgaagac | 900 |
| cctgaggtca agttcaactg gtacgtggac ggcgtggagg tgcataatgc caagacaaag | 960 |
| ccgcgggagg agcagtacaa cagcacgtac cgtgtggtca gcgtcctcac cgtcctgcac | 1020 |
| caggactggc tgaatggcaa ggagtacaag tgcaaggtct ccaacaaagc cctcccagcc | 1080 |
| cccatcgaga aaaccatctc caaagccaaa gggcagcccc gagaaccaca ggtgtacacc | 1140 |
| ctgcccccat gccgggatga gctgaccaag aaccaggtca gcctgtggtg cctggtcaaa | 1200 |
| ggcttctatc ccagcgacat cgccgtggag tgggagagca atgggcagcc ggagaacaac | 1260 |
| tacaagacca cgcctcccgt gctggactcc gacggctcct tcttcctcta cagcaagctc | 1320 |
| accgtggaca gagcaggtg gcagcagggg aacgtcttct catgctccgt gatgcatgag | 1380 |
| gctctgcaca accactacac gcagaagagc ctctccctgt ctccgggtaa a | 1431 |

<210> SEQ ID NO 142
<211> LENGTH: 657
<212> TYPE: DNA
<213> ORGANISM: Artificial Sequence
<220> FEATURE:
<223> OTHER INFORMATION: P1A3 Fab Light Chain ntd (VL, joint, CL)

<400> SEQUENCE: 142

| gatgttgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgcaga agccagggca gtctccacag ctcctgatct atttgggttc taaccgggac | 180 |

```
tctgggtcc cagacagatt cagcggcagt gggtcaggca ctgatttcac actgaaaatc      240
agcagggtgg aggctgagga tgttggggtt tattactgca tgcaaggtac acactggccg      300
tggacgttcg gccaagggac caaggtggaa atcaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt       657
```

<210> SEQ ID NO 143
<211> LENGTH: 669
<212> TYPE: DNA
<213> ORGANISM: Artificial Sequence
<220> FEATURE:
<223> OTHER INFORMATION: P1A3 Fab Heavy Chain ntd (VH, joint, CH)

<400> SEQUENCE: 143

```
caggtgcagc tacagcagtg gggcgcagga ctgttgaagc cttcggagac cctgtccctc       60
acctgcgctg tctatggtgg gtccttcagt ggttactact ggagctggat ccgccagccc      120
ccagggaagg gctggagtg gattggggaa atcaatcata gtggaagcac caactacaac      180
ccgtccctca gagtcgagc caccatatca gtagacacgt ccaagaacca gttctccctg      240
aagctgagct ctgtgaccgc cgcggacacg gctgtgtatt actgtgcgac cagcccggga      300
ggctattccg ggggatactt ccagcactgg ggccagggaa ccctggtcac cgtctcaagc      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtc cacaccttcc cggctgtcct acagtcctca      540
ggactctact ccctcagcag cgtagtgacc gtgccctcca gcagcttggg cacccagacc      600
tacatctgca acgtgaatca caagcccagc aacaccaagg tggacaagaa agttgagccc      660
aaatcttgt                                                            669
```

<210> SEQ ID NO 144
<211> LENGTH: 1443
<212> TYPE: DNA
<213> ORGANISM: Artificial Sequence
<220> FEATURE:
<223> OTHER INFORMATION: P1A3 scFv ntd (scFv and Fc with hole
      modification)

<400> SEQUENCE: 144

```
caggtccagc tgcagcagtg gggagccggc ctgctgaaac catctgaaac tctgagcctg       60
acttgcgctg tctacggggg gtccttcagt ggctactatt ggtcatggat caggcagccc      120
cctgggaagg gactggagtg gatcgggaa attaaccact ccggatctac aaactacaat      180
cccagtctga atcacgcgc caccattct gtggacacca gtaagaatca gttcagcctg      240
aagctgagca gcgtgacagc cgctgatacc gccgtgtact attgcgcaac cagccctggc      300
ggatactccg gaggctattt tcagcattgg ggccagggga ccctggtgac agtctctagt      360
gggggaggag gtctggagg aggaggaagt ggaggaggag gctccgacgt ggtcatgact      420
cagagcccac tgtccctgcc agtgacccc ggcgagcctg ctagtatctc atgtcgatca      480
agccagtcac tgctgcacag caacgggtac aattatctgg attggtactt gcagaagcca      540
```

```
ggccagtctc cccagctgct gatctatctg ggctccaacc gggactctgg ggtgcctgat    600
agattcagcg gcagcggctc tgggactgac tttaccctga aaatttccag agtcgaggca    660
gaagatgtgg gagtctacta ttgcatgcag ggcactcatt ggccctggac cttcggacag    720
ggcacaaagg tggagatcaa aacagcggc gcgggcaccg cggccgcgac tcacacatgc    780
ccaccgtgcc cagcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca gtgcaaggt ctccaacaaa    1080 gccctcccag cccccatcga gaaaaccatc tccaaagcca aagggcagcc ccgagaacca   1140
caggtgtgca ccctgccccc atcccgggat gagctgacca agaaccaggt cagcctgtcc   1200
tgcgccgtca aaggcttcta tcccagcgac atcgccgtgg agtgggagag caatgggcag   1260
ccggagaaca actacaagac cacgcctccc gtgctggact ccgacggctc cttcttcctc   1320
gtgagcaagc tcaccgtgga caagagcagg tggcagcagg ggaacgtctt ctcatgctcc   1380
gtgatgcatg aggctctgca caaccactac acgcagaaga gcctctccct gtctccgggt   1440
aaa                                                                  1443

<210> SEQ ID NO 145
<211> LENGTH: 642
<212> TYPE: DNA
<213> ORGANISM: Artificial Sequence
<220> FEATURE:
<223> OTHER INFORMATION: P2B9 Fab Light Chain ntd (VL, joint, CL)

<400> SEQUENCE: 145
tcctatgagc tgactcagcc accctcgatg tcagtgtccc caggacagac ggccaggatc     60
acctgctctg gagatgcatt gccaaaacaa tttgcttttt ggtaccagca gaagccaggc    120
caggcccctg tgttggtgat ttataaagac actgagaggc cctcagggat ccctgagcga    180
ttctctggct ccagctcagg gacaacagtc acgttgacca tcactggagt ccaggcagaa    240
gatgaggctg actattactg tcaatctcca gacagcagtg gtaccgtcga agtgttcggc    300
ggagggacca agctgaccgt cctaggtcag cccaaggctg cccccctcggt cactctgttc    360 ccgccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctacctg    540
agcctgacgc ctgagcagtg gaagtccac agaagctaca ctgccaggt cacgcatgaa    600 gggagcaccg tggagaagac agtggccct gcagaatgtt ca                        642

<210> SEQ ID NO 146
<211> LENGTH: 669
<212> TYPE: DNA
<213> ORGANISM: Artificial Sequence
<220> FEATURE:
<223> OTHER INFORMATION: P2B9 Fab Heavy Chain ntd (VH, joint, CH)

<400> SEQUENCE: 146
caggtgcagc tgcaggagtc gggcccagga ctggtgaagc cttcggagac cctgtccctc     60
acctgcactg tctctggtgg ctccatcagc agtagtagtt actactgggg ctggatccgc    120
```

| | |
|---|---:|
| cagcccccag ggaagggggct ggagtggatt gggagtatct attatagtgg gagcacctac | 180 |
| tacaacccgt ccctcaagag tcgagtcacc atatccgtag acacgtccaa gaaccagttc | 240 |
| tccctgaagc tgagctctgt gaccgccgca gacacggctg tgtattactg cgggcgat | 300 |
| attttgactg gttatgccct tgactactgg ggccagggaa ccctggtcac cgtctcaagc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag cgccctgac cagcggcgtc cacaccttcc cggctgtcct acagtcctca | 540 |
| ggactctact ccctcagcag cgtagtgacc gtgccctcca gcagcttggg cacccagacc | 600 |
| tacatctgca acgtgaatca caagcccagc aacaccaagg tggacaagaa agttgagccc | 660 |
| aaatcttgt | 669 |

<210> SEQ ID NO 147
<211> LENGTH: 1431
<212> TYPE: DNA
<213> ORGANISM: Artificial Sequence
<220> FEATURE:
<223> OTHER INFORMATION: P2B9 scFv ntd (scFv and Fc with hole modification)

<400> SEQUENCE: 147

| | |
|---|---:|
| caggtgcagc tgcaggaaag cggacccgga ctggtgaagc catctgaaac actgagcctg | 60 |
| acttgtaccg tgagcggcgg aagcatcagc tcctctagtt actattgggg atggatcagg | 120 |
| cagcccccctg caaggggct ggagtggatc ggcagcatct actatagcgg ctccacatac | 180 |
| tataacccta gcctgaaatc ccgcgtgaca atctctgtgg acactagtaa gaatcagttc | 240 |
| tctctgaaac tgtcaagcgt gaccgccgct gatacagctg tctactattg cgcaggcgac | 300 |
| attctgaccg gtacgcccct ggattattgg gacagggca ctctggtgac cgtctcctct | 360 |
| ggaggaggag gctcaggagg aggagggtcc ggaggcgggg gaagttcata cgaactgaca | 420 |
| cagccaccct ctatgagtgt gtcaccaggg cagactgcac gaatcacctg tagcggagac | 480 |
| gccctgccca gcagttcgc ttttggtat cagcagaaac ctggccaggc tccagtgctg | 540 |
| gtcatctata aggatactga gcggccctct gggattcctg aaagattcag tggcagcagc | 600 |
| agcggaacca cagtgactct gaccattaca ggcgtgcagg cagaggacga agccgattac | 660 |
| tattgccagt cccccgacag ttcaggcacc gtggaggtct ttggcggggg aacaaaactg | 720 |
| actgtgctga cagcggcgc gggcaccgcg ccgcgactc acacatgccc accgtgccca | 780 |
| gcacctgaac tcctgggggg accgtcagtc ttcctcttcc ccccaaaacc caaggacacc | 840 |
| ctcatgatct cccggacccc tgaggtcaca tgcgtggtgg tggacgtgag ccacgaagac | 900 |
| cctgaggtca agttcaactg gtacgtggac ggcgtggagg tgcataatgc caagacaaag | 960 |
| ccgcgggagg agcagtacaa cagcacgtac cgtgtggtca gcgtcctcac cgtcctgcac | 1020 |
| caggactggc tgaatggcaa ggagtacaag tgcaaggtct ccaacaaagc cctcccagcc | 1080 |
| cccatcgaga aaaccatctc caaagccaaa gggcagcccc gagaaccaca ggtgtgcacc | 1140 |
| ctgcccccat cccgggatga gctgaccaag aaccaggtca gcctgtcctg cgccgtcaaa | 1200 |
| ggcttctatc ccagcgacat cgccgtggag tgggagagca tgggcagcc ggagaacaac | 1260 |
| tacaagacca cgcctcccgt gctggactcc gacggctcct tcttcctcgt gagcaagctc | 1320 |
| accgtggaca gagcaggtg gcagcagggg aacgtcttct catgctccgt gatgcatgag | 1380 |
| gctctgcaca accactacac gcagaagagc ctctccctgt ctccgggtaa a | 1431 |

<210> SEQ ID NO 148
<211> LENGTH: 108
<212> TYPE: PRT
<213> ORGANISM: Artificial Sequence
<220> FEATURE:
<223> OTHER INFORMATION: Antibody sequence

<400> SEQUENCE: 148

```
Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly Asp Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105
```

<210> SEQ ID NO 149
<211> LENGTH: 108
<212> TYPE: PRT
<213> ORGANISM: Artificial Sequence
<220> FEATURE:
<223> OTHER INFORMATION: Antibody sequence

<400> SEQUENCE: 149

```
Gln Ser Val Leu Thr Gln Pro Pro Ser Val Ser Gly Ala Pro Gly Gln
1               5                   10                  15

Arg Val Thr Ile Ser Cys Thr Gly Thr Ser Ser Asp Ile Gly His Tyr
            20                  25                  30

Asp Phe Val Ser Trp Tyr Gln Gln Leu Pro Gly Thr Ala Pro Lys Leu
        35                  40                  45

Leu Ile Tyr Asp Ile Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105
```

<210> SEQ ID NO 150
<211> LENGTH: 121
<212> TYPE: PRT
<213> ORGANISM: Artificial Sequence
<220> FEATURE:
<223> OTHER INFORMATION: Antibody sequence

<400> SEQUENCE: 150

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
```

```
                35                  40                  45
Gly Ala Ile Met Pro Ser Arg Gly Gly Thr Ser Tyr Pro Gln Lys Phe
        50                  55                  60
Gln Gly Arg Val Thr Met Thr Gly Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Glu Tyr Tyr Tyr Asp Ser Ser Gly Tyr Tyr Tyr Trp Gly
            100                 105                 110
Gln Gly Thr Pro Val Thr Val Ser Ser
        115                 120

<210> SEQ ID NO 151
<211> LENGTH: 121
<212> TYPE: PRT
<213> ORGANISM: Artificial Sequence
<220> FEATURE:
<223> OTHER INFORMATION: Antibody sequence

<400> SEQUENCE: 151

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Tyr Met His Trp Val Arg Gln Ala Pro Gly Gln Gly Leu Glu Trp Met
            35                  40                  45
Gly Ala Ile Met Pro Ser Arg Gly Gly Thr Ser Tyr Pro Gln Lys Phe
        50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Glu Tyr Tyr Tyr Asp Ser Ser Gly Tyr Tyr Tyr Trp Gly
            100                 105                 110
Gln Gly Thr Leu Val Thr Val Ser Ser
        115                 120

<210> SEQ ID NO 152
<211> LENGTH: 112
<212> TYPE: PRT
<213> ORGANISM: Artificial Sequence
<220> FEATURE:
<223> OTHER INFORMATION: Antibody sequence

<400> SEQUENCE: 152

Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Ser Leu Leu His Ser
                20                  25                  30
Asn Gly Tyr Asn Tyr Leu Asp Trp Tyr Gln Gln Lys Pro Gly Lys Ala
            35                  40                  45
Pro Lys Leu Leu Ile Tyr Leu Gly Ser Asn Arg Asp Ser Gly Val Pro
        50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Met Gln Gly
                85                  90                  95
```

```
Thr His Trp Pro Trp Thr Phe Gly Gln Gly Thr Lys Val Glu Ile Lys
            100                 105                 110
```

<210> SEQ ID NO 153
<211> LENGTH: 120
<212> TYPE: PRT
<213> ORGANISM: Artificial Sequence
<220> FEATURE:
<223> OTHER INFORMATION: Antibody sequence

<400> SEQUENCE: 153

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Ser Trp Val Arg Gln Ala Pro Gly Lys Gly Leu Glu Trp Val
        35                  40                  45

Ser Glu Ile Asn His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Pro Gly Gly Tyr Ser Gly Gly Tyr Phe Gln His Trp Gly Gln
            100                 105                 110

Gly Thr Leu Val Thr Val Ser Ser
        115                 120
```

<210> SEQ ID NO 154
<211> LENGTH: 246
<212> TYPE: PRT
<213> ORGANISM: Artificial Sequence
<220> FEATURE:
<223> OTHER INFORMATION: Antibody sequence

<400> SEQUENCE: 154

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Pro Val Thr Val Ser Gly Gly Gly Gly Ser Gly Gly
        115                 120                 125

Gly Gly Ser Gly Gly Gly Ser Gln Ser Ala Leu Thr Gln Pro Ala
            130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175
```

-continued

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
            195                 200                 205

Ala Ser Leu Thr Ile Ser Gly Leu Gln Pro Glu Asp Glu Ala Asp Tyr
210                 215                 220

Tyr Cys Ser Ala Tyr Thr Ser Ser Asp Thr Val Val Phe Gly Gly Gly
225                 230                 235                 240

Thr Lys Leu Thr Val Leu
                245

<210> SEQ ID NO 155
<211> LENGTH: 246
<212> TYPE: PRT
<213> ORGANISM: Artificial Sequence
<220> FEATURE:
<223> OTHER INFORMATION: Antibody sequence

<400> SEQUENCE: 155

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Val Ser Gly Ala Pro Gly Gln Arg Val Thr Ile Ser Cys Thr Gly
145                 150                 155                 160

Thr Ser Ser Asp Ile Gly His Tyr Asp Phe Val Ser Trp Tyr Gln Gln
                165                 170                 175

Leu Pro Gly Thr Ala Pro Lys Leu Leu Ile Tyr Asp Ile Asn Asn Arg
            180                 185                 190

Pro Ser Gly Val Pro Asp Arg Phe Ser Gly Ser Lys Ser Gly Thr Ser
            195                 200                 205

Ala Ser Leu Ala Ile Thr Gly Leu Gln Ala Glu Asp Glu Ala Asp Tyr
210                 215                 220

Tyr Cys Ser Ala Tyr Thr Ser Ser Asp Thr Leu Val Phe Gly Gly Gly
225                 230                 235                 240

Thr Lys Leu Thr Val Leu
                245

<210> SEQ ID NO 156
<211> LENGTH: 247
<212> TYPE: PRT
<213> ORGANISM: Artificial Sequence
<220> FEATURE:
<223> OTHER INFORMATION: Antibody sequence

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Ser Trp Val Arg Gln Ala Pro Gly Lys Gly Leu Glu Trp Val
        35                  40                  45

Ser Glu Ile Asn His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Arg Ser Pro Gly Gly Tyr Ser Gly Gly Tyr Phe Gln His Trp Gly Gln
            100                 105                 110

Gly Thr Leu Val Thr Val Ser Ser Gly Gly Gly Ser Gly Gly Gly
            115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ser
145                 150                 155                 160

Ser Gln Ser Leu Leu His Ser Asn Gly Tyr Asn Tyr Leu Asp Trp Tyr
                165                 170                 175

Gln Gln Lys Pro Gly Lys Ala Pro Lys Leu Leu Ile Tyr Leu Gly Ser
            180                 185                 190

Asn Arg Asp Ser Gly Val Pro Ser Arg Phe Ser Gly Ser Gly Ser Gly
            195                 200                 205

Thr Asp Phe Thr Leu Thr Ile Ser Ser Leu Gln Pro Glu Asp Phe Ala
    210                 215                 220

Thr Tyr Tyr Cys Met Gln Gly Thr His Trp Pro Trp Thr Phe Gly Gln
225                 230                 235                 240

Gly Thr Lys Val Glu Ile Lys
                245